(12) United States Patent
St. George-Hyslop et al.

(10) Patent No.: US 6,210,919 B1
(45) Date of Patent: Apr. 3, 2001

(54) GENETIC SEQUENCES AND PROTEINS RELATED TO ALZHEIMER'S DISEASE

(75) Inventors: Peter H. St. George-Hyslop; Johanna M. Rommens; Paul E. Fraser, all of Toronto (CA)

(73) Assignee: HSC Research and Development Limited Partnership, Toronto (CA)

( * ) Notice: Subject to any disclaimer, the term of this patent is extended or adjusted under 35 U.S.C. 154(b) by 0 days.

(21) Appl. No.: 08/496,841

(22) Filed: Jun. 28, 1995

Related U.S. Application Data

(63) Continuation-in-part of application No. 08/431,048, filed on Apr. 28, 1995.

(51) Int. Cl.$^7$ ............................ C12N 15/63; C07H 21/04; C07K 14/47

(52) U.S. Cl. ...................... 435/69.1; 536/23.5; 536/23.1; 435/320.1; 435/325; 435/455; 530/350

(58) Field of Search ................................ 536/23.5; 435/6, 435/69.1, 172.1, 172.3, 325, 375, 320.1, 455; 800/2, DIG. 1; 530/350

(56) References Cited

U.S. PATENT DOCUMENTS

| | | | |
|---|---|---|---|
| 5,297,562 | 3/1994 | Potter | 128/898 |
| 5,449,604 | 9/1995 | Schellenberg et al. | 435/6 |
| 5,545,808 | * 8/1996 | Hew et al. | 800/2 |
| 5,668,006 | 9/1997 | Hadcock et al. | 435/252.3 |

FOREIGN PATENT DOCUMENTS

| | | | |
|---|---|---|---|
| 2054302 | 4/1992 | (CA) . | |
| 2071105 | 12/1992 | (CA) . | |
| 2096911 | 11/1993 | (CA) . | |
| 94/00569 | 1/1994 | (WO) . | |
| 94/23049 | 10/1994 | (WO) . | |
| WO 97/03086 | 1/1997 | (WO) | C07H/21/04 |
| WO 97/03192 | 1/1997 | (WO) | C12N/15/12 |
| WO 97/03999 | 2/1997 | (WO) | C07H/21/04 |

OTHER PUBLICATIONS

Mullins et al. Transgenesis in Nonmurine Species. Hypertension, vol. 22, No. 4, pp. 630–633, Oct. 1993.*
Pursel et al. Genetic Engineering of Livestock. Science, vol. 244, pp. 1281–1288, Jun. 16, 1989.*
Salter et al. Transgenic Chickens: Insertion of Retroviral Genes into the Chicken Germ Line. Virology, vol. 157, pp. 236–240, 1987.*
J. Li et al. PNAS 92:12180–4, Dec. 1995.*
J. Morrell et al. Science 254:97–99, Oct. 4, 1995.*
T. Yamada et al. Biochem. Biophys. Res. Comm. 149(2):665–71, 1987.*
Chartier–Harlin, et al., "Early onset Alzheimer's disease caused by mutations at codon 717 of the β–amyloid precursor protein gene," Nature, vol. 353:844–846 (1991).

Foncin, et al., "Alzheimer's Presenile dementia transmitted in an extended kindred," Rev. Neurol (Paris), vol. 141:194–202 (1985).
Goate, et al., "Segregation of a missense mutation in the amyloid precursor protein gene with familial Alzheimer's disease," Nature, vol. 349:704–706 (1991).
Goudsmit, et al., "Familial Alzheimer's Disease in two kindreds of the same geographic and ethnic origin: a clinical and genetic study," J. Neurol. Sci., vol. 49:79–89 (1981).
Gyapay, et al., "The 1993–1994 Genethon human genetic linkage map," Nature Genetics, vol. 7:246–311 (1994).
Karlinsky, et al., "Molecular and prospective phenotypic characterization of a pedigree with familial Alzheimer's disease and a missense mutation in codon 717 of the β–amyloid precursor protein (APP) gene," Neurology, vol. 42:1445–1453 (1992).
Katzman, R., "Alzheimer's Disease," N.Eng.J.Med., vol. 314:964–973, (1986).
Mullan, et al., "A pathogenic mutation for probable Alzheimer's disease in the APP gene at the N–terminus of β–amyloid", Nature Genetics, vol. 1:345–347 (1992).
Mullan, et al., "A locus for familial early–onset Alzheimer's disease on the long arm of chromosome 14, proximal to the α1–antichymotrypsin gene," Nature Genetics, vol. 2:340–342 (1992).
Murrell, et al., "A mutation in the amyloid precursor protein associated with hereditary Alzheimer's Disease," Science, vol. 254:97–99 (1991).
Nee, et al., "A family with histologically confirmed Alzheimer's Disease," Arch Neurol, vol. 40:203–208 (1983).
Pericak–Vance, et al., "Genetic linkage studies in Alzheimer's Disease families," Exp. Neurol, vol. 102:271–279 (1988).
Rogaev, et al., "Analysis of the c–FOS gene on chromosome 14 and the promoter of the amyloid precursor protein gene in familial Alzheimer's disease," Neurology, vol. 43:2275–2279 (1993).
Rommens, et al., "A transcription map of the region containing the Huntington disease gene," Hum. Molec. Genet., vol. 2:901–907 (1993).
St. George–Hyslop, et al., "Genetic linkage studies suggest that Alzheimer's disease is not a single homogeneous disorder," Nature, vol. 347:194–197 (1990).

(List continued on next page.)

Primary Examiner—Deborah J. Clark
(74) Attorney, Agent, or Firm—Darby & Darby

(57) ABSTRACT

The present invention describes the identification, isolation, cloning, and sequencing of the Alzheimer Related Membrane Protein (ARMP) gene for both normal and mutant forms. An analogous mouse gene, mARMP gene, has also been isolated, cloned, and sequenced. The gene transcript and gene products are used in developing DNA diagnosis for and detection of carriers of the gene, Alzheimer's Disease diagnosis, gene therapy, protein therapy, immunotherapy, as well as the isolation and manufacture of the protein and the development of transgenic animals carrying mutations in the ARMP gene.

30 Claims, 9 Drawing Sheets

OTHER PUBLICATIONS

St. George–Hyslop, et al., "Genetic evidence for a novel familial Alzheimer's disease locus on chromosome 14," *Nature Genetics*, vol. :2:330–334 (1992).

St. George–Hyslop, et al., "Alzheimer's Disease and Possible Gene Interaction," *Science*, vol. 263:537 (1994).

Saunders, et al., "Association of apolipoprotein E allele e4 with the late–onset familial and sporadic Alzheimer's disease," *Neurology*, vol. 43:1467–1472 (1993).

Schellenberg, et al., "Genetic Linkage Evidence for a Familial Alzheimer's Disease Locus on Chromosome 14," *Science*, vol. 258:668–670 (1992).

Schellenberg, et al., "Chromosome 14 and Late–Onset Familial Alzheimer Disease (FAD)," *Am. J. Hum. Genet.*, vol. 53:619–628 (1993).

Strittmatter, et al., "Apolipoprotein E: high avidity binding to β–amyloid and increased frequency of type 4 allele in late–onset familial Alzheimer's disease," *Proc. Nat'l. Acad. Sci. USA*, vol. 90:1977–1981 (1993).

Van Broeckhoven, et al., "Mapping of a gene predisposing to early–onset Alzheimer's disease to chromosome 14q24.3," *Nature Genetics*, vol. 2:335–339 (1992).

Wong, et al., "Mutation of the gene for the human lysosomal serine protease Cathespin G is not the cause of aberrant APP processing in familial Alzheimer disease," *Neurosci. Lett*, vol. 152:96–98 (1993).

Citron et al., "Mutant Presenilins of Alzheimer's Disease Increase Production of 42–residue Amyloid β–protein in Both Transfected Cells and Transgenic Mice," Nat. Med., 3:67–72 (1997).

Felsenstein et al., "Transgenic Rat and In–Vitro Studies of β–Amyloid Precursor Protein Processing," Alzheimer's and Parkinson's Diseases, pp. 401–409 (Hanin, et al., Plenum Press, NY) (1995).

Selkoe, "In the Beginning . . . ," Nature, 354: 532–433 (1991).

Lannfelt, et al., "Alzheimer's disease: molecular genetics and transgenic animal models," Behav. Brain Res. 57: 207–213 (1993).

Porteous, "How relevant are mouse models for human diseases to somatic gene therapy?" *Tibtech*, II:173–181(1993).

Ledley, "Clinical Considerations in the Design of Protocols for Somatic Gene Therapy," *Human Gene Therapy*, 2:77–83(1991).

Cameron et al., "Transgenic Science," *British Veterinary Journal*, 150:9–24(1994).

L'Hernault et al., "Mutation of a Putative Sperm Membrane Protein in *Caenorhabditis elegans* Prevents Sperm Differentiation but Not Its Associated Meiotic Divisions," *J. Cell Biol.*, 119(1):55–68 (1992).

Johansson, E., et al., The Journal of Biological Chemistry, 270(35):20615–20620 (1995).

Pawlak, A., et al., EMBL Sequence Data Library, Dec. 20, 1994, Accession No. T18858.

Auffray, C., et al., EMBL Sequence Data Library, Feb. 17, 1995, Accession No. F08730.

Zahraoui, A., et al., EMBL Sequence Data Library, Jul. 22, 1994, Accession No. X56740.

Drivas, G.T., et al., EMBL Sequence Data Library, Feb. 19, 1991, Accession No. X53143.

Chambon, P., et al., EMBL Sequence Data Library, Feb. 7, 1992, Accession No. M84820.

Fleischhauer, K., et al., EMBL Sequence Data Library, Mar. 31, 1992, Accession No. X63522.

Yu, V.C., et al., EMBL Sequence Data Library, Dec. 10, 1991, Accession No. M81766.

Sevigny, G., et al., EMBL Sequence Data Library, Jan. 7, 1995, Accession No. U17104.

Walkley, N.A., et al., EMBL Sequence Data Library, Jan. 1, 1994, Accession No. X74801.

Hillier, L., et al., EMBL Sequence Data Library, Apr. 22, 1995, Accession No. R12984.

Fujiwara, T., et al., EMBL Sequence Data Library, Aug. 25, 1995, Accession No. D55326.

Hillier, L., et al., EMBL Sequence Data Library, Mar. 6, 1995, Accession No. T64843.

* cited by examiner

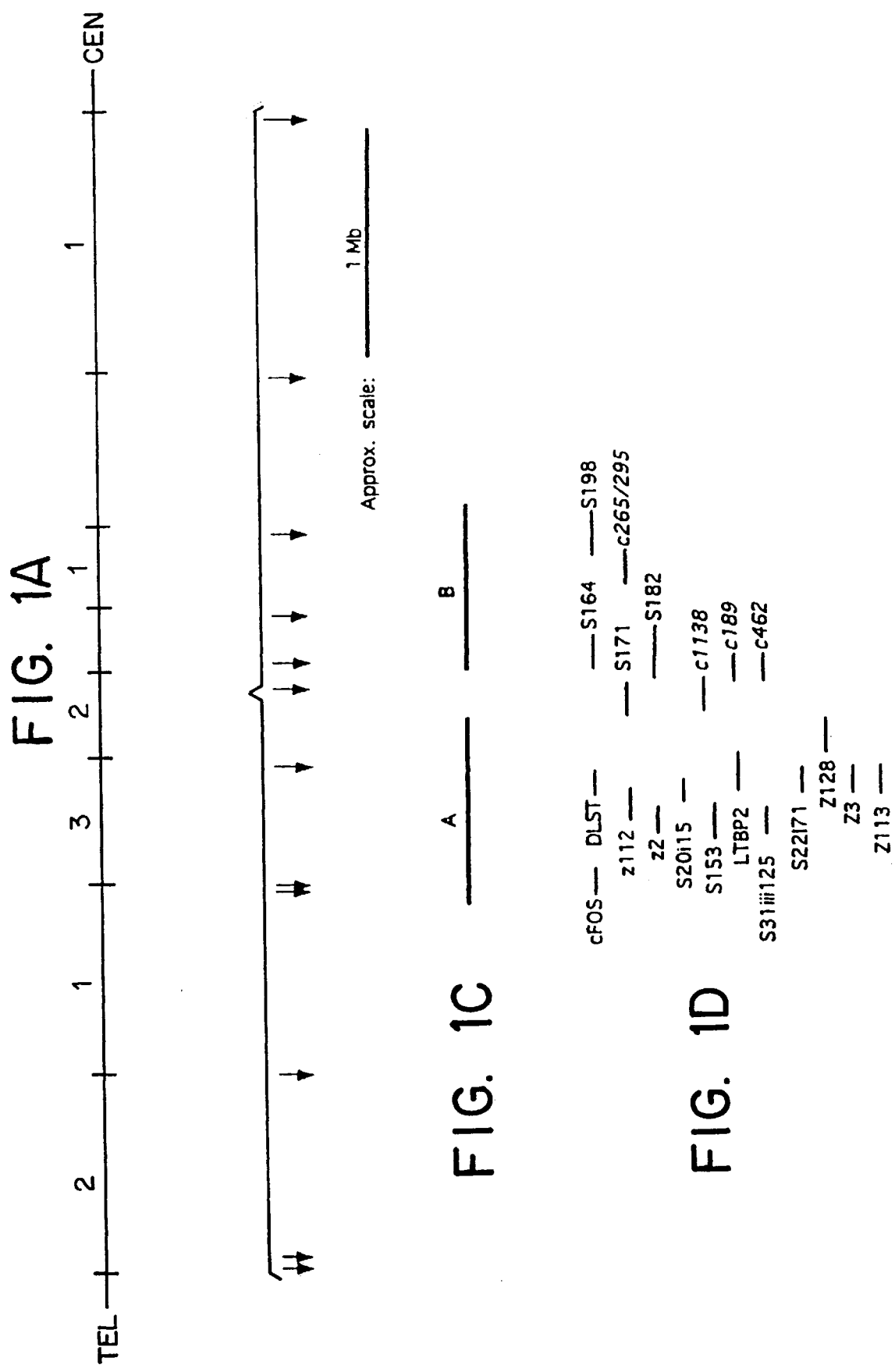

Approx. Scale: 1 Mb

Met    146    Leu

His 163 Arg

Ala  246  Glu

Leu     286     Val

Cys   410   Tyr

SEQUENCE LISTING (1) GENERAL INFORMATION:

(iii) NUMBER OF SEQUENCES: 175

(2) INFORMATION FOR SEQ ID NO: 1:

(i) SEQUENCE CHARACTERISTICS:
      (A) LENGTH: 2791 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 1:

```
TGGGACAGGC AGCTCCGGGG TCCGCGGTTT CACATCGGAA ACAAAACAGC GGCTGGTCTG      60

GAAGGAACCT GAGCTACGAG CCGCGGCGGC AGCGGGGCGG CGGGGNAAGC GTATACCTAA     120

TCTGGGAGCC TGCAAGTGAC AACAGCCTTT GCGGTCCTTA GACAGCTTGG CCTGGAGGAG     180

AACACATGAA AGAAAGAACC TCAAGAGGCT TTGTTTTCTG TGAAACAGTA TTTCTATACA     240

GTTGCTCCAA TGACAGAGTT ACCTGCACCG TTGTCCTACT TCCAGAATGC ACAGATGTCT     300

GAGGACAACC ACCTGAGCAA TACTGTACGT AGCCAGAATG ACAATAGAGA ACGGCAGGAG     360

CACAACGACA GACGGAGCCT TGGCCACCCT GAGCCATTAT CTAATGGACG ACCCCAGGGT     420

AACTCCCGGC AGGTGGTGGA GCAAGATGAG GAAGAAGATG AGGAGCTGAC ATTGAAATAT     480

GGCGCCAAGC ATGTGATCAT GCTCTTTGTC CCTGTGACTC TCTGCATGGT GGTGGTCGTG     540

GCTACCATTA AGTCAGTCAG CTTTTATACC CGGAAGGATG GGCAGCTAAT CTATACCCCA     600

TTCACAGAAG ATACCGAGAC TGTGGGCCAG AGAGCCCTGC ACTCAATTCT GAATGCTGCC     660

ATCATGATCA GTGTCATTGT TGTCATGACT ATCCTCCTGG TGGTTCTGTA TAAATACAGG     720

TGCTATAAGG TCATCCATGC CTGGCTTATT ATATCATCTC TATTGTTGCT GTTCTTTTTT     780

TCATTCATTT ACTTGGGGGA AGTGTTTAAA ACCTATAACG TTGCTGTGGA CTACATTACT     840

GTTGCACTCC TGATCTGGAA TTTGGGTGTG GTGGGAATGA TTTCCATTCA CTGGAAAGGT     900

CCACTTCGAC TCCAGCAGGC ATATCTCATT ATGATTAGTG CCCTCATGGC CCTGGTGTTT     960

ATCAAGTACC TCCCTGAATG GACTGCGTGG CTCATCTTGG CTGTGATTTC AGTATATGAT    1020
```

-continued

```
TTAGTGGCTG TTTTGTGTCC GAAAGGTCCA CTTCGTATGC TGGTTGAAAC AGCTCAGGAG    1080

AGAAATGAAA CGCTTTTTCC AGCTCTCATT TACTCCTCAA CAATGGTGTG GTTGGTGAAT    1140

ATGGCAGAAG GAGACCCGGA AGCTCAAAGG AGAGTATCCA AAAATTCCAA GTATAATGCA    1200

GAAAGCACAG AAAGGGAGTC ACAAGACACT GTTGCAGAGA ATGATGATGG CGGGTTCAGT    1260

GAGGAATGGG AAGCCCAGAG GGACAGTCAT CTAGGGCCTC ATCGCTCTAC ACCTGAGTCA    1320

CGAGCTGCTG TCCAGGAACT TTCCAGCAGT ATCCTCGCTG GTGAAGACCC AGAGGAAAGG    1380

GGAGTAAAAC TTGGATTGGG AGATTTCATT TTCTACAGTG TTCTGGTTGG TAAAGCCTCA    1440

GCAACAGCCA GTGGAGACTG GAACACAACC ATAGCCTGTT TCGTAGCCAT ATTAATTGGT    1500

TTGTGCCTTA CATTATTACT CCTTGCCATT TTCAAGAAAG CATTGCCAGC TCTTCCAATC    1560

TCCATCACCT TTGGGCTTGT TTTCTACTTT GCCACAGATT ATCTTGTACA GCCTTTTATG    1620

GACCAATTAG CATTCCATCA ATTTTATATC TAGCATATTT GCGGTTAGAA TCCCATGGAT    1680

GTTTCTTCTT TGACTATAAC CAAATCTGGG GAGGACAAAG GTGATTTTCC TGTGTCCACA    1740

TCTAACAAAG TCAAGATTCC CGGCTGGACT TTTGCAGCTT CCTTCCAAGT CTTCCTGACC    1800

ACCTTGCACT ATTGGACTTT GGAAGGAGGT GCCTATAGAA AACGATTTTG AACATACTTC    1860

ATCGCAGTGG ACTGTGTCCT CGGTGCAGAA ACTACCAGAT TTGAGGGACG AGGTCAAGGA    1920

GATATGATAG GCCCGGAAGT TGCTGTGCCC CATCAGCAGC TTGACGCGTG GTCACAGGAC    1980

GATTTCACTG CACACTGCGAA CTCTCAGGAC TACCGGTTAC AAGAGGTTA GGTGAAGTGG    2040

TTTAAACCAA ACGGAACTCT TCATCTTAAA CTACACGTTG AAAATCAACC CAATAATTCT    2100

GTATTAACTG AATTCTGAAC TTTTCAGGAG GTACTGTGAG GAAGAGCAGG CACCAGCAGC    2160

AGAATGGGGA ATGGAGAGGT GGGCAGGGGT TCCAGCTTCC CTTTGATTTT TTGCTGCAGA    2220

CTCATCCTTT TTAAATGAGA CTTGTTTTCC CCTCTCTTTG AGTCAAGTCA AATATGTAGA    2280

TGCCTTTGGC AATTCTTCTT CTCAAGCACT GACACTCATT ACCGTCTGTG ATTGCCATTT    2340

CTTCCCAAGG CCAGTCTGAA CCTGAGGTTG CTTTATCCTA AAAGTTTTAA CCTCAGGTTC    2400

CAAATTCAGT AAATTTTGGA AACAGTACAG CTATTTCTCA TCAATTCTCT ATCATGTTGA    2460

AGTCAAATTT GGATTTTCCA CCAAATTCTG AATTTGTAGA CATACTTGTA CGCTCACTTG    2520

CCCCAGATGC CTCCTCTGTC CTCATTCTTC TCTCCCACAC AAGCAGTCTT TTTCTACAGC    2580

CAGTAAGGCA GCTCTGTCGT GGTAGCAGAT GGTCCCACTT ATTCTAGGGT CTTACTCTTT    2640

GTATGATGAA AAGAATGTGT TATGAATCGG TGCTGTCAGC CCTGCTGTCA GACCTTCTTC    2700

CACAGCAAAT GAGATGTATG CCCAAAGCGG TAGAATTAAA GAAGAGTAAA ATGGCTGTTG    2760

AAGCAAAAAA AAAAAAAAA AAAAAAAAAA A                                   2791
```

(2) INFORMATION FOR SEQ ID NO: 2:

(i) SEQUENCE CHARACTERISTICS:
  (A) LENGTH: 467 amino acids
  (B) TYPE: amino acid
  (C) STRANDEDNESS: single
  (D) TOPOLOGY: linear (ii) MOLECULE TYPE: protein (xi) SEQUENCE DESCRIPTION: SEQ ID NO: 2:

```
Met Thr Glu Leu Pro Ala Pro Leu Ser Tyr Phe Gln Asn Ala Gln Met
 1               5                  10                  15

Ser Glu Asp Asn His Leu Ser Asn Thr Val Arg Ser Gln Asn Asp Asn
            20                  25                  30
```

-continued

```
Arg Glu Arg Gln Glu His Asn Asp Arg Arg Ser Leu Gly His Pro Glu
         35                  40                  45

Pro Leu Ser Asn Gly Arg Pro Gln Gly Asn Ser Arg Gln Val Val Glu
     50                  55                  60

Gln Asp Glu Glu Asp Glu Glu Leu Thr Leu Lys Tyr Gly Ala Lys
 65              70              75                      80

His Val Ile Met Leu Phe Val Pro Val Thr Leu Cys Met Val Val Val
                 85              90                  95

Val Ala Thr Ile Lys Ser Val Ser Phe Tyr Thr Arg Lys Asp Gly Gln
             100             105             110

Leu Ile Tyr Thr Pro Phe Thr Glu Asp Thr Glu Thr Val Gly Gln Arg
             115             120             125

Ala Leu His Ser Ile Leu Asn Ala Ala Ile Met Ile Ser Val Ile Val
             130             135             140

Val Met Thr Ile Leu Leu Val Val Leu Tyr Lys Tyr Arg Cys Tyr Lys
145                 150             155                     160

Val Ile His Ala Trp Leu Ile Ile Ser Ser Leu Leu Leu Phe Phe
                 165             170             175

Phe Ser Phe Ile Tyr Leu Gly Glu Val Phe Lys Thr Tyr Asn Val Ala
             180             185             190

Val Asp Tyr Ile Thr Val Ala Leu Leu Ile Trp Asn Leu Gly Val Val
         195             200             205

Gly Met Ile Ser Ile His Trp Lys Gly Pro Leu Arg Leu Gln Gln Ala
         210             215             220

Tyr Leu Ile Met Ile Ser Ala Leu Met Ala Leu Val Phe Ile Lys Tyr
225             230             235                     240

Leu Pro Glu Trp Thr Ala Trp Leu Ile Leu Ala Val Ile Ser Val Tyr
             245             250             255

Asp Leu Val Ala Val Leu Cys Pro Lys Gly Pro Leu Arg Met Leu Val
             260             265             270

Glu Thr Ala Gln Glu Arg Asn Glu Thr Leu Phe Pro Ala Leu Ile Tyr
             275             280             285

Ser Ser Thr Met Val Trp Leu Val Asn Met Ala Glu Gly Asp Pro Glu
     290             295             300

Ala Gln Arg Arg Val Ser Lys Asn Ser Lys Tyr Asn Ala Glu Ser Thr
305             310             315                     320

Glu Arg Glu Ser Gln Asp Thr Val Ala Glu Asn Asp Asp Gly Gly Phe
             325             330             335

Ser Glu Glu Trp Glu Ala Gln Arg Asp Ser His Leu Gly Pro His Arg
             340             345             350

Ser Thr Pro Glu Ser Arg Ala Ala Val Gln Glu Leu Ser Ser Ser Ile
             355             360             365

Leu Ala Gly Glu Asp Pro Glu Glu Arg Gly Val Lys Leu Gly Leu Gly
             370             375             380

Asp Phe Ile Phe Tyr Ser Val Leu Val Gly Lys Ala Ser Ala Thr Ala
385             390             395                     400

Ser Gly Asp Trp Asn Thr Thr Ile Ala Cys Phe Val Ala Ile Leu Ile
                 405             410             415

Gly Leu Cys Leu Thr Leu Leu Leu Ala Ile Phe Lys Lys Ala Leu
             420             425             430

Pro Ala Leu Pro Ile Ser Ile Thr Phe Gly Leu Val Phe Tyr Phe Ala
             435             440             445
```

```
Thr Asp Tyr Leu Val Gln Pro Phe Met Asp Gln Leu Ala Phe His Gln
    450                 455                 460

Phe Tyr Ile
465

(2) INFORMATION FOR SEQ ID NO: 3:

(i) SEQUENCE CHARACTERISTICS:
        (A) LENGTH: 1929 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 3:

ACCANACANC GGCAGCTGAG GCGGAAACCT AGGCTGCGAG CCGGCCGCCC GGGCGCGGAG      60

AGAGAAGGAA CCAACACAAG ACAGCAGCCC TTCGAGGTCT TTAGGCAGCT TGGAGGAGAA     120

CACATGAGAG AAAGAATCCC AAGAGGTTTT GTTTTCTTTG AGAAGGTATT TCTGTCCAGC     180

TGCTCCAATG ACAGAGATAC CTGCACCTTT GTCCTACTTC CAGAATGCCC AGATGTCTGA     240

GGACAGCCAC TCCAGCAGCG CCATCCGGAG CCAGAATGAC AGCCAAGAAC GGCAGCAGCA     300

GCATGACAGG CAGAGACTTG ACAACCCTGA GCCAATATCT AATGGGCGGC CCAGAGTAA      360

CTCAAGACAG GTGGTGGAAC AAGATGAGGA GGAAGACGAA GAGCTGACAT TGAAATATGG     420

AGCCAAGCAT GTCATCATGC TCTTTGTCCC CGTGACCCTC TGCATGGTCG TCGTCGTGGC     480

CACCATCAAA TCAGTCAGCT TCTATACCCG GAAGGACGGT CAGCTAATCT ACACCCCATT     540

CACAGAAGAC ACTGAGACTG TAGGCCAAAG AGCCCTGCAC TCGATCCTGA ATGCGGCCAT     600

CATGATCAGT GTCATTGTCA TTATGACCAT CCTCCTGGTG GTCCTGTATA AATACAGGTG     660

CTACAAGGTC ATCCACGCCT GGCTTATTAT TTCATCTCTG TTGTTGCTGT TCTTTTTTTC     720

GTTCATTTAC TTAGGGGAAG TATTTAAGAC CTACAATGTC KCCGTGGACT ACGTTACAGT     780

AGCACTCCTA ATCTGGAATT GGGGTGTGGT CGGGATGATT GCCATCCACT GGAAAGGCCC     840

CCTTCGACTG CAGCAGGCGT ATCTCATTAT GATCAGTGCC CTCATGGCCC TGGTATTTAT     900

CAAGTACCTC CCCGAATGGA CCGCATGGCT CATCTTGGCT GTGATTTCAG TATATGATTT     960

GGTGGCTGTT TTATGTCCCA AGGCCCACT TCGTATGCTG GTTGAAACAG CTCAGGAAAG    1020

AAATGAGACT CTCTTTCCAG CTCTTATCTA TTCCTCAACA ATGGTGTGGT TGGTGAATAT    1080

GGCTGAAGGA GACCCAGAAG CCCAAAGGAG GGTACCCAAG AACCCCAAGT ATAACACACA    1140

AAGAGCGGAG AGAGAGACAC AGGACAGTGG TTCTGGGAAC GATGATGGTG GCTTCAGTGA    1200

GGAGTGGGAG GCCCAAAGAG ACAGTCACCT GGGGCCTCAT CGCTCCACTC CCGAGTCAAG    1260

AGCTGCTGTC CAGGAACTTT CTGGGAGCAT TCTAACGAGT GAAGACCCGG AGGAAAGAGG    1320

AGTAAAACTT GGACTGGGAG ATTTCATTTT CTACAGTGTT CTGGTTGGTA AGGCCTCAGC    1380

AACCGCCAGT GGAGACTGGA ACACAACCAT AGCCTGCTTK GTAGCCATAC TGATCGGCCT    1440

GTGCCTTANA TTACTCCTGC TCGCCATTTA CAAGAAAGGG TNGCCAGCCC NCCCCATCTC    1500

CATCACCTTC GGGTTCGTGT TCTNCTTCGC CACGGATTAC CTTGTGCAGC CCTTCATGGA    1560

CCAACTTGCA TTCCATCAGT TTTATATCTA GCCTTTCTGC AGTTAGAACA TGGATGTTTC    1620

TTCTTTGATT ATCAAAAACA CAAAAACAGA GAGCAAGCCC GAGGAGGAGA CTGGTGACTT    1680

TCCTGTGTCC TCAGCTAACA AAGGCAGGAC TCCAGCTGGA CTTCTGCAGC TTCCTTCCGA    1740

GTCTCCCTAG CCACCCGCAC TACTGGACTG TGGAAGGAAG CGTCTACAGA GGAACGGTTT    1800
```

-continued

```
CCAACATCCA TCGCTGCAGC AGACGGTGTC CCTCAGTGAC TTGAGAGACA AGGACAAGGA    1860

AATGTGCTGG GCCAAGGAGC TGCCGTGCTC TGCTAGCTTT GGMCCGTGGG CATGGAGATT    1920

TACCCGCAC                                                              1929
```

(2) INFORMATION FOR SEQ ID NO: 4:

(i) SEQUENCE CHARACTERISTICS:
        (A) LENGTH: 467 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 4:

```
Met Thr Glu Ile Pro Ala Pro Leu Ser Tyr Phe Gln Asn Ala Gln Met
 1               5                  10                  15

Ser Glu Asp Ser His Ser Ser Ala Ile Arg Ser Gln Asn Asp Ser
             20                  25                  30

Gln Glu Arg Gln Gln Gln His Asp Arg Gln Arg Leu Asp Asn Pro Glu
             35                  40                  45

Pro Ile Ser Asn Gly Arg Pro Gln Ser Asn Ser Arg Gln Val Val Glu
 50                  55                  60

Gln Asp Glu Glu Glu Asp Glu Glu Leu Thr Leu Lys Tyr Gly Ala Lys
 65                  70                  75                  80

His Val Ile Met Leu Phe Val Pro Val Thr Leu Cys Met Val Val Val
                 85                  90                  95

Val Ala Thr Ile Lys Ser Val Ser Phe Tyr Thr Arg Lys Asp Gly Gln
                100                 105                 110

Leu Ile Tyr Thr Pro Phe Thr Glu Asp Thr Glu Thr Val Gly Gln Arg
            115                 120                 125

Ala Leu His Ser Ile Leu Asn Ala Ala Ile Met Ile Ser Val Ile Val
            130                 135                 140

Ile Met Thr Ile Leu Leu Val Val Leu Tyr Lys Tyr Arg Cys Tyr Lys
145                 150                 155                 160

Val Ile His Ala Trp Leu Ile Ile Ser Ser Leu Leu Leu Leu Phe Phe
                165                 170                 175

Phe Ser Phe Ile Tyr Leu Gly Glu Val Phe Lys Thr Tyr Asn Val Xaa
                180                 185                 190

Val Asp Tyr Val Thr Val Ala Leu Leu Ile Trp Asn Trp Gly Val Val
            195                 200                 205

Gly Met Ile Ala Ile His Trp Lys Gly Pro Leu Arg Leu Gln Gln Ala
210                 215                 220

Tyr Leu Ile Met Ile Ser Ala Leu Met Ala Leu Val Phe Ile Lys Tyr
225                 230                 235                 240

Leu Pro Glu Trp Thr Ala Trp Leu Ile Leu Ala Val Ile Ser Val Tyr
                245                 250                 255

Asp Leu Val Ala Val Leu Cys Pro Lys Gly Pro Leu Arg Met Leu Val
            260                 265                 270

Glu Thr Ala Gln Glu Arg Asn Glu Thr Leu Phe Pro Ala Leu Ile Tyr
            275                 280                 285

Ser Ser Thr Met Val Trp Leu Val Asn Met Ala Glu Gly Asp Pro Glu
            290                 295                 300

Ala Gln Arg Arg Val Pro Lys Asn Pro Lys Tyr Asn Thr Gln Arg Ala
305                 310                 315                 320
```

```
Glu Arg Glu Thr Gln Asp Ser Gly Ser Gly Asn Asp Asp Gly Gly Phe
            325                 330                 335

Ser Glu Glu Trp Glu Ala Gln Arg Asp Ser His Leu Gly Pro His Arg
            340                 345                 350

Ser Thr Pro Glu Ser Arg Ala Ala Val Gln Glu Leu Ser Gly Ser Ile
            355                 360                 365

Leu Thr Ser Glu Asp Pro Glu Arg Gly Val Lys Leu Gly Leu Gly
            370                 375             380

Asp Phe Ile Phe Tyr Ser Val Leu Val Gly Lys Ala Ser Ala Thr Ala
385                 390                 395                 400

Ser Gly Asp Trp Asn Thr Thr Ile Ala Cys Xaa Val Ala Ile Leu Ile
                405                 410                 415

Gly Leu Cys Leu Xaa Leu Leu Leu Leu Ala Ile Tyr Lys Lys Gly Xaa
                420                 425                 430

Pro Ala Xaa Pro Ile Ser Ile Thr Phe Gly Phe Val Phe Xaa Phe Ala
            435                 440                 445

Thr Asp Tyr Leu Val Gln Pro Phe Met Asp Gln Leu Ala Phe His Gln
            450                 455                 460

Phe Tyr Ile
465

(2) INFORMATION FOR SEQ ID NO: 5:

(i) SEQUENCE CHARACTERISTICS:
        (A) LENGTH: 3087 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 5:

GAATTCGGCA CGAGGGAAAT GCTGTTTGCT CGAAGACGTC TCAGGGCGCA GGTGCCTTGG      60

GCCGGGATTA GTAGCCGTCT GAACTGGAGT GGAGTAGGAG AAAGAGGAAG CGTCTTGGGC     120

TGGGTCTGCT TGAGCAACTG GTGAAACTCC GCGCCTCACG CCCCGGGTGT GTCCTTGTCC     180

AGGGGCGACG AGCATTCTGG GCGAAGTCCG CACSCCTCTT GTTCGAGGCG AAGACGGGG      240

TCTGATSCTT TCTCCTTGGT CGGGMCTGTC TCGAGGCATG CATGTCCAGT GACTCTTGTG     300

TTTGCTGCTG CTTCCCTCTC AGATTCTTCT CACCGTTGTG GTCAGCTCTG CTTTAGGCAN     360

TATTAATCCA TAGTGGAGGC TGGGATGGGT GAGAGAATTG AGGTGACTTT TCCATAATTC     420

AGACCTAATC TGGAGCCTG CAAGTGACAA CAGCCTTTGC GGTCCTTAGA CAGCTTGGCC      480

TGGAGGAGAA CACATGAAAG AAAGAACCTC AAGAGGCTTT GTTTTCTGTG AAACAGTATT     540

TCTATACAGT TGCTCCAATG ACAGAGTTAC CTGCACCGTT GTCCTACTTC AGAATGCAC      600

AGATGTCTGA GGACAACCAC CTGAGCAATA CTAATGACAA TAGAGAACGG CAGGAGCACA     660

ACGACAGACG GAGCCTTGGC CACCCTGAGC CATTATCTAA TGGACGACCC CAGGGTAACT     720

CCCGGCAGGT GGTGGAGCAA GATGAGGAAG AAGATGAGGA GCTGACATTG AAATATGGCG     780

CCAAGCATGT GATCATGCTC TTTGTCCCTG TGACTCTCTG CATGGTGGTG GTCGTGGCTA     840

CCATTAAGTC AGTCAGCTTT TATACCCGGA AGGATGGGCA GCTAATCTAT ACCCCATTCA     900

CAGAAGATAC CGAGACTGTG GGCCAGAGAG CCCTGCACTC AATTCTGAAT GCTGCCATCA     960

TGATCAGTGT CATTGTTGTC ATGACTATCC TCCTGGTGGT TCTGTATAAA TACAGGTGCT    1020

ATAAGGTCAT CCATGCCTGG CTTATTATAT CATCTCTATT GTTGCTGTTC TTTTTTTCAT    1080
```

| | | | |
|---|---|---|---|
| TCATTTACTT | GGGGGAAGTG | TTTAAAACCT ATAACGTTGC | TGTGGACTAC ATTACTGTTG | 1140 |
| CACTCCTGAT | CTGGAATTTG | GGTGTGGTGG GAATGATTTC | CATTCACTGG AAAGGTCCAC | 1200 |
| TTCGACTCCA | GCAGGCATAT | CTCATTATGA TTAGTGCCCT | CATGGCCCTG GTGTTTATCA | 1260 |
| AGTACCTCCC | TGAATGGACT | GCGTGGCTCA TCTTGGCTGT | GATTTCAGTA TATGATTTAG | 1320 |
| TGGCTGTTTT | GTGTCCGAAA | GGTCCACTTC GTATGCTGG | TGAAACAGCT CAGGAGAGAA | 1380 |
| ATGAAACGCT | TTTTCCAGCT | CTCATTTACT CCTCAACAAT | GGTGTGGTTG GTGAATATGG | 1440 |
| CAGAAGGAGA | CCCGGAAGCT | CAAAGGAGAG TATCCAAAAA | TTCCAAGTAT AATGCAGAAA | 1500 |
| GCACAGAAAG | GGAGTCACAA | GACACTGTTG CAGAGAATGA | TGATGGCGGG TTCAGTGAGG | 1560 |
| AATGGGAAGC | CCAGAGGGAC | AGTCATCTAG GGCCTCATCG | CTCTACACCT GAGTCACGAG | 1620 |
| CTGCTGTCCA | GGAACTTTCC | AGCAGTATCC TCGCTGGTGA | AGACCCAGAG GAAAGGGGAG | 1680 |
| TAAAACTTGG | ATTGGGAGAT | TTCATTTTCT ACAGTGTTCT | GGTTGGTAAA GCCTCAGCAA | 1740 |
| CAGCCAGTGG | AGACTGGAAC | ACAACCATAG CCTGTTTCGT | AGCCATATTA ATTGGTTTGT | 1800 |
| GCCTTACATT | ATTACTCCTT | GCCATTTTCA AGAAAGCATT | GCCAGCTCTT CCAATCTCCA | 1860 |
| TCACCTTTGG | GCTTGTTTTC | TACTTTGCCA CAGATTATCT | TGTACAGCCT TTTATGGACC | 1920 |
| AATTAGCATT | CCATCAATTT | TATATCTAGC ATATTTGCGG | TTAGAATCCC ATGGATGTTT | 1980 |
| CTTCTTTGAC | TATAACCAAA | TCTGGGGAGG ACAAAGGTGA | TTTTCCTGTG TCCACATCTA | 2040 |
| ACAAAGTCAA | GATTCCCGGC | TGGACTTTTG CAGCTTCCTT | CCAAGTCTTC CTGACCACCT | 2100 |
| TGCACTATTG | GACTTTGGAA | GGAGGTGCCT ATAGAAAACG | ATTTTGAACA TACTTCATCG | 2160 |
| CAGTGGACTG | TGTCCTCGGT | GCAGAAACTA CCAGATTTGA | GGGACGAGGT CAAGGAGATA | 2220 |
| TGATAGGCCC | GGAAGTTGCT | GTGCCCCATC AGCAGCTTGA | CGCGTGGTCA CAGGACGATT | 2280 |
| TCACTGACAC | TGCGAACTCT | CAGGACTACC GGTTACCAAG | AGGTTAGGTG AAGTGGTTTA | 2340 |
| AACCAAACGG | AACTCTTCAT | CTTAAACTAC ACGTTGAAAA | TCAACCCAAT AATTCTGTAT | 2400 |
| TAACTGAATT | CTGAACTTTT | CAGGAGGTAC TGTGAGGAAG | AGCAGGCACC AGCAGCAGAA | 2460 |
| TGGGGAATGG | AGAGGTGGGC | AGGGGTTCCA GCTTCCCTTT | GATTTTTTGC TGCAGACTCA | 2520 |
| TCCTTTTTAA | ATGAGACTTG | TTTTCCCCTC TCTTTGAGTC | AAGTCAAATA TGTAGATGCC | 2580 |
| TTTGGCAATT | CTTCTTCTCA | AGCACTGACA CTCATTACCG | TCTGTGATTG CCATTTCTTC | 2640 |
| CCAAGGCCAG | TCTGAACCTG | AGGTTGCTTT ATCCTAAAAG | TTTTAACCTC AGGTTCCAAA | 2700 |
| TTCAGTAAAT | TTTGGAAACA | GTACAGCTAT TTCTCATCAA | TTCTCTATCA TGTTGAAGTC | 2760 |
| AAATTTGGAT | TTTCCACCAA | ATTCTGAATT TGTAGACATA | CTTGTACGCT CACTTGCCCC | 2820 |
| AGATGCCTCC | TCTGTCCTCA | TTCTTCTCTC CCACACAAGC | AGTCTTTTTC TACAGCCAGT | 2880 |
| AAGGCAGCTC | TGTCGTGGTA | GCAGATGGTC CCACTTATTC | TAGGGTCTTA CTCTTTGTAT | 2940 |
| GATGAAAAGA | ATGTGTTATG | AATCGGTGCT GTCAGCCCTG | CTGTCAGACC TTCTTCCACA | 3000 |
| GCAAATGAGA | TGTATGCCCA | AAGCGGTAGA ATTAAAGAAG | AGTAAAATGG CTGTTGAAGC | 3060 |
| AAAAAAAAAA | AAAAAAAAAA | AAAAAA | | 3087 |

(2) INFORMATION FOR SEQ ID NO: 6:

(i) SEQUENCE CHARACTERISTICS:
        (A) LENGTH: 945 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 6:

```
GTTNTCCNAA CCAACTTAGG AGNTTGGACC TGGGRAAGAC CNACNTGATC TCCGGGAGGN      60
AAAGACTNCA GTTGAGCCGT GATTGCACCC ACTTTACTCC AAGCCTGGGC AACCAAAATG     120
AGACACTGGC TCCAAACACA AAAACAAAAA CAAAAAAAGA GTAAATTAAT TTANAGGGAA     180
GNATTAAATA AATAATAGCA CAGTTGATAT AGGTTATGGT AAAATTATAA AGGTGGGANA     240
TTAATATCTA ATGTTTGGGA GCCATCACAT TATTCTAAAT AATGTTTTGG TGGAAATTAT     300
TGTACATCTT TTAAAATCTG TGTAATTTTT TTTCAGGGAA GTGTTTAAAA CCTATAACGT     360
TGCTGTGGAC TACATTACTG TTNCACTCCT GATCTGGAAT TTTGGTGTGG TGGGAATGAT     420
TTCCATTCAC TGGAAAGGTC CACTTCGACT CCAGCAGGCA TATCTCATTA TGATTAGTGC     480
CCTCATGNCC CTGKTGTTTA TCAAGTACCT CCCTGAATGG ACTGNGTGGC TCATCTTGGC     540
TGTGATTTCA GTATATGGTA AAACCCAAGA CTGATAATTT GTTTGTCACA GGAATGCCCC     600
ACTGGAGTGT TTTCTTTCCT CATCTCTTTA TCTTGATTTA GAGAAAATGG TAACGTGTAC     660
ATCCCATAAC TCTTCAGTAA ATCATTAATT AGCTATAGTA ACTTTTTCAT TTGAAGATTT     720
CGGCTGGGCA TGGTAGCTCA TGCCTGTAAT CTTAGCACTT TGGGAGGCTG AGGCGGGCAG     780
ATCACCTAAG CCCAGAGTTC AAGACCAGCC TGGGCAACAT GGCAAAACCT CGTATCTACA     840
GAAAATACAA AAATTAGCCG GGCATGGTGG TGCACACCTG TAGTTCCAGC TACTTAGGAG     900
GCTGAGGTGG GAGGATCGAT TGATCCCAGG AGGTCAAGNC TGCAG                    945
```

(2) INFORMATION FOR SEQ ID NO: 7:

(i) SEQUENCE CHARACTERISTICS:
        (A) LENGTH: 450 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 7:

```
GTTGCAAAGT CATGGATTCC TTTAGGTAGC TACATTATCA ACCTTTTTGA GAATAAAATG      60
AATTGAGAGT GTTACAGTCT AATTCTATAT CACATGTAAC TTTTATTTGG ATATATCAGT     120
AATAGTGCTT TTTTTTTTTT TTTTTTTTTT TTTTTTTTTT TTTGGGGANA GAGTCTCGCT     180
CTGTCGCCAG GTTGGAGTGC AATGGTGCGA TCTTGGCTCA CTGAAAGCTC CACCNCCCGG     240
GTTCAAGTGA TTCTCCTGCC TCAGCCNCCC AAGTAGNTGG GACTACAGGG GTGCGCCACC     300
ACGCCTGGGA TAATTTTGGG NTTTTTAGTA GAGATGGCGT TTCACCANCT TGGNGCAGGC     360
TGGTCTTGGA ACTCCTGANA TCATGATCTG CCTGCCTTAG CCTCCCCAAA GTGCTGGGAT     420
TNCAGGGGTG AGCCACTGTT CCTGGGCCTC                                     450
```

(2) INFORMATION FOR SEQ ID NO: 8:

(i) SEQUENCE CHARACTERISTICS:
        (A) LENGTH: 516 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 8:

```
GCTCATCATG CTTCACGGGG GAGGCTGTGC GGGAAGAATG CTCCCACACA GNATAAAGAA      60
TGCTCCCGCA CAGGATAGAG AATGCCCCCG CACAGCATAG AGAAGCCCCC GCACAGCATA     120
```

```
GAGAATGCCC CCNCACAGCA TAGAGAAGCC CCCGCACAGC ATAGAGAATG CTCTTCACCT      180

CTGGGTTTTT AACCAGCCAA ACTAAAATCA CAGAGGSCMA CACATCATTT AAGATAGAAA      240

TTTCTGTATC TTTTAATTTY TTTCMAAGTA GTTTTACTTA TTTTCAGATT CTATTTCTTT      300

ACTAGAATTA AGGGATAAAA TAACAATGTG TGCATAATGA ACCCTATGAA ACMAACMMAA      360

GCTAGGTTTT TTTCATAGST CTTCTTCCAG ATTGAATGAA CGTCTGTTCT AAAATTTAAC      420

CCCCCAGGGA AATATTCAGT TAACTATGTT AAAAACCCAG ACTTGTGATT GAGTTTTGCC      480

TGAAAATGCT TTCATAATTA TGTGTGAATG TGTGTC                                516

(2) INFORMATION FOR SEQ ID NO: 9:

(i) SEQUENCE CHARACTERISTICS:
        (A) LENGTH: 1726 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 9:

GGATCCCTCC CCTTTTTAGA CCATACAAGG TAACTTCCGG ACGTTGCCAT GGCATCTGTA       60

AACTGTCATG GTGTTGGCGG GGAGTGTCTT TTAGCATGCT AATGTATTAT AATTAGCGTA      120

TAGTGAGCAG TGAGGATAAC CAGAGGTCAC TCTCCTCACC ATCTTGGTTT TGGTGGGTTT      180

TGGCCAGCTT CTTTATTGCA ACCAGTTTTA TCAGCAAGAT CTTTATGAGC TGTATCTTGT      240

GCTGACTTCC TATCTCATCC CGNAACTAAG AGTACCTAAC CTCCTGCAAA TTGMAGNCCA      300

GNAGGTCTTG GNCTTATTTN ACCCAGCCCC TATTCAARAT AGAGTNGYTC TTGGNCCAAA      360

CGCCYCTGAC ACAAGGATTT TAAAGTCTTA TTAATTAAGG TAAGATAGKT CCTTGSATAT      420

GTGGTCTGAA ATCACAGAAA GCTGAATTTG GAAAAAGGTG CTTGGASCTG CAGCCAGTAA      480

ACAAGTTTTC ATGCAGGTGT CAGTATTTAA GGTACATCTC AAAGGATAAG TACAATTGTG      540

TATGTTGGGA TGAACAGAGA GAATGGAGCA ANCCAAGACC CAGGTAAAAG AGAGGACCTG      600

AATGCCTTCA GTGAACAATG ATAGATAATC TAGACTTTTA AACTGCATAC TTCCTGTACA      660

TTGTTTTTTC TTGCTTCAGG TTTTTAGAAC TCATAGTGAC GGGTCTGTTG TTAATCCCAG      720

GTCTAACCGT TACCTTGATT CTGCTGAGAA TCTGATTTAC TGAAAATGTT TTTCTTGTGC      780

TTATAGAATG ACAATAGAGA ACGGCAGGAG CACAACGACA GACGGAGCCT TGGCCACCCT      840

GANCCATTAT CTAATGGACG ACCCAGGGTA ACTCCCGGCA GGTGGTGGAN CAAGATGAGG      900

AAGAAGATGA GGANCTGACA TTGAAATATG NCGSCAAGCA TGTGATCATG CTCTTTGKCC      960

CTGTGACTCT CTGCATGGTG GTGGTCGTGG NTACCATTAA GTCAGTCAGC TTTTATACCC     1020

GGAAGGATGG GCAGCTGTAC GTATGAGTTT KGTTTTATTA TTCTCAAASC CAGTGTGGCT     1080

TTTCTTTACA GCATGTCATC ATCACCTTGA AGGCCTCTNC ATTGAAGGGG CATGACTTAG     1140

CTGGAGAGCC CATCCTCTGT GATGGTCAGG AGCAGTTGAG AGANCGAGGG GTTATTACTT     1200

CATGTTTTAA GTGGAGAAAA GGAACACTGC AGAAGTATGT TCCTGTATG GTATTACTGG      1260

ATAGGGCTGA AGTTATGCTG AATTGAACAC ATAAATTCTT TTCCACCTCA GGGNCATTTT     1320

GCGCCCATTG NTCTTCTGCC TAGAATATTC TTTCCTTTNC TNACTTKGGN GGATTAAAGC     1380

CCTGTCATCC CCCTCCTCTT GGTGTTATAT ATAAAGTNTT GGTGCCGCAA AGAAGTAGC      1440

ACTCGAATAT AAAATTTTCC TTTTAATTCT CAGCAAGGNA AGTTACTTCT ATATAGAAGG     1500

GTGCACCCNT ACAGATGGAA CAATGGCAAG CGCACATTTG GGACAAGGGA GGGGAAAGGG     1560
```

-continued

| | | |
|---|---|---|
| TTCTTATCCC TGACACACGT GGTCCCNGCT GNTGTGTNCT NCCCCCACTG ANTAGGGTTA | 1620 | |
| GACTGGACAG GCTTAAACTA ATTCCAATTG GNTAATTTAA AGAGAATNAT GGGGTGAATG | 1680 | |
| CTTTGGGAGG AGTCAAGGAA GAGNAGGTAG NAGGTAACTT GAATGA | 1726 | |

(2) INFORMATION FOR SEQ ID NO: 10:

(i) SEQUENCE CHARACTERISTICS:
        (A) LENGTH: 1883 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 10:

| | |
|---|---|
| CNCGTATAAA AGACCAACAT TGCCANCNAC AACCACAGGC AAGATCTTCT CCTACCTTCC | 60 |
| CCCNNGGTGT AATACCAAGT ATTCNCCAAT TTGTGATAAA CTTTCATTGG AAAGTGACCA | 120 |
| CCCTCCTTGG TTAATACATT GTCTGTGCCT GCTTTCACAC TACAGTAGCA CAGTTGAGTG | 180 |
| TTTGCCCTGG AGACCATATG ACCCATAGAG CTTAAAATAT TCAGTCTGGC TTTTTACAGA | 240 |
| GATGTTTCTG ACTTTGTTAA TAGAAAATCA ACCCAACTGG TTTAAATAAT GCACATACTT | 300 |
| TCTCTCTCAT AGAGTAGTGC AGAGGTAGNC AGTCCAGATT AGTASGGTGG CTTCACGTTC | 360 |
| ATCCAAGGAC TCAATCTCCT TCTTTCTTCT TTAGCTTCTA ACCTCTAGCT TACTTCAGGG | 420 |
| TCCAGGCTGG AGCCCTASCC TTCATTTCTG ACAGTAGGAA GGAGTAGGGG AGAAAAGAAC | 480 |
| ATAGGACATG TCAGCAGAAT TCTCTCCTTA GAAGTTCCAT ACACAACACA TCTCCCTAGA | 540 |
| AGTCATTGCC CTTACTTGTT CTCATAGCCA TCCTAAATAT AAGGGAGTCA GAAGTAAAGT | 600 |
| CTKKNTGGCT GGGAATATTG GCACCTGGAA TAAAAATGTT TTTCTGTGAA TGAGAAACAA | 660 |
| GGGGAAGATG GATATGTGAC ATTATCTTAA GACAACTCCA GTTGCAATTA CTCTGCAGAT | 720 |
| GAGAGGCACT AATTATAAGC CATATTACCT TTCTTCTGAC AACCACTTGT CAGCCCNCGT | 780 |
| GGTTTCTGTG GCAGAATCTG GTTCYATAMC AAGTTCCTAA TAANCTGTAS CCNAAAAAAT | 840 |
| TTGATGAGGT ATTATAATTA TTTCAATATA AAGCACCCAC TAGATGGAGC CAGTGTCTGC | 900 |
| TTCACATGTT AAGTCCTTCT TTCCATATGT TAGACATTTT CTTTGAAGCA ATTTTAGAGT | 960 |
| GTAGCTGTTT TTCTCAGGTT AAAAATTCTT AGCTAGGATT GGTGAGTTGG GGAAAAGTGA | 1020 |
| CTTATAAGAT NCGAATTGAA TTAAGAAAAA GAAAATTCTG TGTTGGAGGT GGTAATGTGG | 1080 |
| KTGGTGATCT YCATTAACAC TGANCTAGGG CTTTKGKGTT TGKTTTATTG TAGAATCTAT | 1140 |
| ACCCCATTCA NAGAAGATAC CGAGACTGTG GGCCAGAGAG CCCTGCACTC AATTCTGAAT | 1200 |
| GCTGCCATCA TGATCAGNGT CATTGTWGTC ATGACTANNC TCCTGGTGGT TCWGTATAAA | 1260 |
| TACAGGTGCT ATAAGGTGAG CATGAGACAC AGATCTTTGN TTTCCACCCT GTTCTTCTTA | 1320 |
| TGGTTGGGTA TTCTTGTCAC AGTAACTTAA CTGATCTAGG AAAGAAAAAA TGTTTTGTCT | 1380 |
| TCTAGAGATA AGTTAATTTT TAGTTTTCTT CCTCCTCACT GTGGAACATT CAAAAAATAC | 1440 |
| AAAAAGGAAG CCAGGTGCAT GTGTAATGCC AGGCTCAGAG GCTGAGGCAG GAGGATCGCT | 1500 |
| TGGGCCCAGG AGTTCACAAG CAGCTTGGGC AACGTAGCAA GACCCTGCCT CTATTAAAGA | 1560 |
| AAACAAAAAA CAAATATTGG AAGTATTTTA TATGCATGGA ATCTATATGT CATGAAAAAA | 1620 |
| TTAGTGTAAA ATATATATAT TATGATTAGN TATCAAGATT TAGTGATAAT TTATGTTATT | 1680 |
| TTGGGATTTC AATGCCTTTT TAGGCCATTG TCTCAAMAAA TAAAAGCAGA AAACAAAAAA | 1740 |
| AGTTGTAACT GAAAAATAAA CATTTCCATA TAATAGCACA ATCTAAGTGG GTTTTTGNTT | 1800 |

```
GTTTGTTTGN TTGTTGAAGC AGGGCCTTGC CCTNYCACCC AGGNTGGAGT GAAGTGCAGT      1860

GGCACGATTT TGGCTCACTG CAG                                             1883

(2) INFORMATION FOR SEQ ID NO: 11:

(i) SEQUENCE CHARACTERISTICS:
        (A) LENGTH: 823 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 11:

CAGGAGTGGA CTAGGTAAAT GNAAGNTGTT TTAAAGAGAG ATGNGGNCNG GGACATAGTG       60

GTACACANCT GTAATGCTCA NCACTKATGG GGAGTACTGA AGGNGGNSGG ATCACTTGNG      120

GGTCNGGAAT NTGAGANCAG CCTGGGCAAN ATGGCGAAAC CCTGTCTCTA CTAAAAATAG     180

CCANAAWNWA GCCTAGCGTG GTGGCGCRCA CGCGTGGTTC CACCTACTCA GGAGGCNTAA     240

GCACGAGNAN TNCTTGAACC CAGGAGGCAG AGGNTGTGGT GARCTGAGAT CGTGCCACTG     300

CACTCCAGTC TGGGCGACMA AGTGAGACCC TGTCTCCNNN AAGAAAAAAA AAATCTGTAC     360

TTTTTAAGGG TTGTGGGACC TGTTAATTAT ATTGAAATGC TTCTYTTCTA GGTCATCCAT     420

GCCTGGCTTA TTATATCATC TCTATTGTTG CTGCTCTTTT TTACATTCAT TTACTTGGGG     480

TAAGTTGTGA AATTTGGGGT CTGTCTTTCA GAATTAACTA CCTNNGTGCT GTGTAGCTAT     540

CATTTAAAGC CATGTACTTT GNTGATGAAT TACTCTGAAG TTTTAATTGT NTCCACATAT     600

AGGTCATACT TGGTATATAA AAGACTAGNC AGTATTACTA ATTGAGACAT TCTTCTGTNG     660

CTCCTNGCTT ATAATAAGTA GAACTGAAAG NAACTTAAGA CTACAGTTAA TTCTAAGCCT     720

TTGGGGAAGG ATTATATAGC CTTCTAGTAG GAAGTCTTGT GCNATCAGAA TGTTTNTAAA     780

GAAAGGGTNT CAAGGAATNG TATAAANACC AAAAATAATT GAT                      823

(2) INFORMATION FOR SEQ ID NO: 12:

(i) SEQUENCE CHARACTERISTICS:
        (A) LENGTH: 736 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 12:

GTCTTTCCCA TCTTCTCCAC AGAGTTTGTG CCTTACATTA TTACTCCTTG CCATTTTCAA      60

GAAAGCATTG TCAGCTCTTC CAATCTCCAT CACCTTTGGG CTTGTTTTCT ACTTTGCCAC     120

AGATTATCTT GTACAGCCTT TTATGGACCA ATTAGCATTC CATCAATTTT ATATCTAGCA     180

TATTTGCGGT TAGAATCCCA TGGATGTTTC TTCTTTGACT ATAACAAAAT CTGGGGAGGA     240

CAAAGGTGAT TTCCTGTGTC CACATCTAAC AAATCAAGAT CCCCGGCTGG ACTTTTGGAG     300

GTTCCTTCCA AGTCTTCCTG ACCACCTTGC ACTATTGGAC TTTGGAAGGA GGTGCCTATA     360

GAAAACGATT TTGAACATAC TTCATCGCAG TGGACTGTGT CCTCGGTGCA GAAACTACCA     420

GATTTGAGGG ACGAGGTCAA GGAGATATGA TAGGCCCGGA AGTTGCTGTG CCCCATCAGC     480

AGCTTGACGC GTGGTCACAG GACGATTTTC ACTGACACTG CGAACTCTCA GGACTACCGT     540

TACCAAGAGG TTAGGTGAAG TGGTTTAAAC CAAACGGAAC TCTTCATCTT AAACTACACG     600
```

```
TTGAAAATCA ACCCAATAAT TCTGTATTAA CTGAATTCTG AACTTTTCAG GAGGTACTGT        660

GAGGAAGAGC AGGCACCACC AGCAGAATGG GGAATGGAGA GGTGGGCAGG GGTTCCAGCT        720

TCCCTTTGAT TTTTTG                                                        736

(2) INFORMATION FOR SEQ ID NO: 13:

(i) SEQUENCE CHARACTERISTICS:
        (A) LENGTH: 893 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 13:

GGATCCGCCC GCCTTGGCCT CCCAAAGTGC TGGGATTACA GGCATGAGCC ACCGCTCCTG         60

GCTGAGTCTG CGATTTCTTG CCAGCTCTAC CCAGTTGTGT CATCTTAAGC AAGTCACTGA        120

ACTTCTCTGG ATTCCCTTCT CCTNNWGTAA AATAAGNATG TTATCTGNCC NNCCTGCCTT        180

GGGCATTGTG ATAAGGATAA GATGACATTA TAGAATNTNG CAAAATTAAA AGCGCTAGAC        240

AAATGATTTT ATGAAAATAT AAAGATTAGN TTGAGTTTGG GCCAGCATAG AAAAAGGAAT        300

GTTGAGAACA TTCCNTTAAG GATTACTCAA GCYCCCCTTT TGSTGKNWAA TCAGANNGTC        360

ATNNAMNTAT CNTNTGTGGG YTGAAAATGT TTGGTTGTCT CAGGCGGTTC CTACTTATTG        420

CTAAAGAGTC CTACCTTGAG CTTATAGTAA ATTTGTCAGT TAGTTGAAAG TCGTGACAAA        480

TTAATACATT CCTGGTTTAC AAATTGGTCT TATAAGTATT TGATTGGTNT AAATGNATTT        540

ACTAGGATTT AACTAACAAT GGATGACCTG GTGAAATCCT ATTTCAGACC TAATCTGGGA        600

GCCTGCAAGT GACAACAGCC TTTGCGGTCC TTAGACAGCT TGGCCTGGAG GAGAACACAT        660

GAAAGAAAGG TTTGTTTCTG CTTAATGTAA TCTATGGAAG TGTTTTTTAT AACAGTATAA        720

TTGTAGTGCA CAAAGTTCTG TTTTTCTTTC CCTTTTCAGA ACCTCAAGAG GCTTTGTTTT        780

CTGTGAAACA GTATTTCTAT ACAGTNTGCT CCAANTGNAC AGAGTTACCT GCACNNCGTT        840

GTCCNTACTT CCAGAATGCA CAGATGTCTG AGGACAACCA CCTGAGCAAT ACT              893

(2) INFORMATION FOR SEQ ID NO: 14:

(i) SEQUENCE CHARACTERISTICS:
        (A) LENGTH: 475 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 14:

TCAGAAAATA CTTTNGGGCA CATGAGAATC ACATGAGAAC AAGCTGATGC ATAATTCCTC         60

CTGTGATGGA ATGTAATAGT AATTTAACAG TGTCCTTTCT TTTTAACTGC CTCAAGGATA        120

CAGCAAAATA AACAAAAGC AATATGAAGG CTGAGAATAG GTATCAGATT ATCATAAAAA        180

GTATAGATCA AAAGGAATCT GGTKCTNAGG TTGGCGCAGC AGCCTCTAGA AGCGACNAGG        240

GAGACTTTTA GAACTACCAT TCTCCTCTAT AAGTGGATCC NANGCCCAGG RAAACTTGAT        300

ATTGAGNACA ATGGCCTTAC TGAAATAACC TGTGATCCAC TCGGNCTCAT CATCTCCACC        360

ACCACCATAA ATTTGATGAG TNCCTATAAT ATTCCANCCA GNGGAAATAC CTGGRAGGTT        420

ACTGAAAGGC NACNATCAGA CNAAAATAAA GNATACCGTA GGTAAATTCT ACAGT            475
```

(2) INFORMATION FOR SEQ ID NO: 15:

(i) SEQUENCE CHARACTERISTICS:
        (A) LENGTH: 180 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 15:

```
GTTCTCNAGA TCTCTTCAAA ATTCATTNTG CGCTATAGGA GCTGGGATTA CCGCGGGTGC    60
TGGAACCAGA CTTGCNCTCC AATGGATCCT CCANACNGGA NGGGGGGTGG ACTCACACCA   120
TTTACAGGGG GCTCGTAAAG AATCCTGTTT TGANTATTNT NCCGTCAATT ACCNCCCCAA   180
```

(2) INFORMATION FOR SEQ ID NO: 16:

(i) SEQUENCE CHARACTERISTICS:
        (A) LENGTH: 457 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 16:

```
AATGTAACMA CMAAACCYCA AACTCCTGNA AGAANATGGT TACTTATNGA TNCCATTTNC    60
TTTTTNCACT CTCAGACATA AATATAAACM MANTTTCTAC TGTGGRAAAA CATCTNCAGG   120
GGNCNTTTAN CCATGATCTC TAGNACNANG GGCTNGTGGN TNGTTTTAAT GTCTCTAAGC   180
NACTNGACTA GTTTCTCTTN CACTGAGNAA ACTGCNACAA GTNNTTNCTN CTGNATCTGN   240
ACTGNAATGC TAAGTTNCAA GTNCCAATGA GCTNGTGANT TANYCTTTAT TTNAMCNAAA   300
GTNNTTAATC ANCCNCAGTG TTACTTTGNA AAGCTNCTCC CTGGACAGGC GGCCCNACTT   360
CTAATGTTAT GAATGGGCTG GAGNANCCTC NACNTGAGTT TNNWAAGGNT CAACANCCAA   420
TRGNAANTGT AMCCGACTCT AAATTCCAAC CNATAAT                            457
```

(2) INFORMATION FOR SEQ ID NO: 17:

(i) SEQUENCE CHARACTERISTICS:
        (A) LENGTH: 373 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 17:

```
ATCTGTGCTA GGTAGTGTAC TAATCATTCA GTTTATCTCA TTTAATCTNN ATGNAACTCT    60
AAGTCATTCG CTNTGANCNA CACATAACAG ATCTCGCAAC TGNAGTTTAG CGAGGCCAGT   120
TAATTTKCCA AAGNTCATAA TNCTAAGNAG TTCTAGNATG GAGATTCMAA GTCCNACTGT   180
TTAGTCAAGA GACCCTACTG TTAACTAGTA CCTTTACACT ACTAACTGGG TAANCCATAA   240
NCAATTAATG ATAAAGATTG AGATTACTKC CACATTCTCA CTGGTTATAA ATTAAAACNT   300
CAAATAAAAA NTCTTGGCAC TTCTATGGTA ATATTTTTAT TAGGATAAAC TTTCAAGNAG   360
TGGATNCTAG GTG                                                      373
```

(2) INFORMATION FOR SEQ ID NO: 18:

(i) SEQUENCE CHARACTERISTICS:
        (A) LENGTH: 422 base pairs

```
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 18:

CCCACACTGN TGGGCCATGG AAGCCATGAG TGTACCACAT GGCCCTGTCC CACTGGCCAC      60

AGTNGATTGG TTGGNTCGGG AGTAGTCACC TGATTCAAGN TGGGCCAATC AGATCCTACC     120

TCCANGGGGT TNGGAATTAG AAAACAGTGA CCCTAGYTAG TNTAGGCNAC TTGAACTGGA     180

GGGCCCATAC ATTCAGGAGC CTTATGGGGC CATGTACACA TGGAAGCAGG AAGANTGAAG     240

GAGGGAGAAG TAGAGGCCAG AAACCCACCT GGGTTCCTGT TTCCCAATGN TAAGTCCCTG     300

CCATGTYCCT GCTCTTCCTG TGGTTNGGAT CTTCAAAGGT TGCTCAAATT NGGGGCAGTG     360

GCCCTGGCAG CTTTTCAAAT CCTYCCCATT TTTATTGAAG CTGAAAGACC CTTGACTAGA     420

AC                                                                   422

(2) INFORMATION FOR SEQ ID NO: 19:

(i) SEQUENCE CHARACTERISTICS:
        (A) LENGTH: 395 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 19:

ATTGTTATTT TTCGTCACTA CCTCCCCGGG TCGGGAGTGG GTAATTTGCG CGCCTGCTGC      60

CTTCCTTGGA TGTGGTAGCC GTTTCTCAGG CTCCCTCTCC GGAATCGAAC CCTGATTCCC     120

CGTCACCCGT GGTCACCATG GTTAGGCACG GCGACTACCA TCGAAAGTTA ATAGGGCAGA     180

TCTCGAGAAT TCTCGAGATC TCCNTCMAAT TATTACTTCA NTTKCGGTAG TGATCAGNAC     240

NAGGCAGTTC TATTGATTTC TCTCCTTTCA TTCTGAGTTT CTCCATAAAT TAATTGGACC     300

TAATCATGTT TKNAATCCTG TCTTTTAGGG GGNANTTGNA CTNTCAAGTG TTTAAAGGGA     360

GGGNCGGAGN ATGATTNTGG ATTGGAGTGA GAGCA                               395

(2) INFORMATION FOR SEQ ID NO: 20:

(i) SEQUENCE CHARACTERISTICS:
        (A) LENGTH: 487 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 20:

CAGANTTTCT GGGTNAAAAG GACCTNANAC ATAATATAGT GGACTTNCAA TAAACACTTA      60

CCAAATGGAN AAATGAACCC CTGGTCACCC CGATCTCACT AGTNCCTNCC CTGAAACCCG     120

ANANATCTGA GTCCTTTTCT CCTTTACTAA CCCTTNCTCC AATCCTGCTC ATGGGAATTA     180

ANGNTGTAAA ATANGCCTGG GGNACCTCGG RCCTCTNCCC TGGGNTCTGT GGGTGGGAGN     240

ACTGTGGAAG CCGTWTCAAT CGCCCCCACC TATGAGAGCC TTTCTNCAGG GCCAGCCATG     300

AACGTCCCCC ATGTNATCAG NATCTNCAGG CTACTGCTGT CCTTCYTGGA TWTTTAACCT     360

GGRGGCGGGC CAGGGACAGA AAARGGAGGT GGCAAGATCC TTGAACAAAA GGAGCTATAA     420

AAGGGCGTTG GGGGAAGCAA GGCAAACGGC AGATTAAACA AGCAGGCACC TCAAGGAAAC     480
```

GTGACGC                                                                      487

(2) INFORMATION FOR SEQ ID NO: 21:

(i) SEQUENCE CHARACTERISTICS:
        (A) LENGTH: 500 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 21:

CTCGAGATCT GGCCCATCAT TTAGTTTTAT NGCTTGNAGT NTNTAGNAGA TAAAACATCC      60

ACGTGGATCT NCTCTTAGAG AAATCAANTA CTTTAGGNAT NTGATAGTCA GAGANTGGNT     120

ATCAAATNGA AAGGNATNTN GGTNGANCAG TTAGTTNGYN CCNTTNGNNG AGACCACTGG     180

GNTGTNGASA CCAGATTCMK GGGTNCNAAT CTTANGGTAA TCTNAGAGCC AACACATGGG     240

TCATNTTATS CCCCAAACTT AGCCACATCT BGTGGGGYTA TGGNGTCACC CCAAGAGCAG     300

GAGGAGCATG GNTGGATGGA AATCCATCTC CACCACTGGA ACCCCAAWTT CTGAATGNAT     360

CACCTGTTAG AGTTTCTTGT YCATAAAATA GCAGGGAATT TAGGAATTTA GTTTTTTTTT     420

AATAGTTTGG GCCTTTTATC CACACTCTCA GGAGCTTAGG ATACTTTTCT CCTTCAGCTC     480

ACTCTGAAAC TCCCTCTGGA                                                 500

(2) INFORMATION FOR SEQ ID NO: 22:

(i) SEQUENCE CHARACTERISTICS:
        (A) LENGTH: 406 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 22:

TCGAGATCTG TGGTAGTNAC ATGATATTCT GGCAMCTACT TTCATTATCA CCTTTATTAA      60

AATAAATTTA AGAAAAAATG GCAGTATGTT TCTGTGRAGN CCACGAGTAC TCATTTTAAA     120

GGACTCMAGA GTTNCAGRNA AGTAAAAAGR AAAGAGTAAA ATCATTTTCT AANTYTYWYY     180

TTCCAGAAAT AACGATGTTG AGCATTAAGT GGACTTCATT TCATACTCTT TCMMAGNTTA     240

TGTAGGCATA WAWATGTGTG TGTATATACA TATATATGGG TACATCCTTA GAGAAGTTGG     300

CTGGCTAGAT AGACACACNT NAAAAATGGR ATCATACTCT AATKCCATTT NNANTTTANA     360

AAATACATAT TCAGANCCNC TGTNCTTATA NACAGAGTAA NTGAAA                    406

(2) INFORMATION FOR SEQ ID NO: 23:

(i) SEQUENCE CHARACTERISTICS:
        (A) LENGTH: 289 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 23:

GACCCAGTAA AACTTATCTC ATGAGCATAA GGCTGAATGG GATTGACAGC CTACAGAACC      60

CGGATTTTAT CATGAGGGCA TTAGTGGGGG TTGGGGGTTA GGTACTGAAA GTTTAAGGAG     120

GTGAAAGGAA AGCAACTTGT GCCTTACAGG GTCAAGCTAG GTCAAGGAAA TTCCCAGGAG     180

```
CGTGTGGAAG CTCTCTACCT GATAGGTGAG CTCAAGCTTA TGACCGCCCA AGCTTCTCCC      240

CAAGCTTCCC TTCCACTGCT TCCTCTTGAT TGACTTCCAC AGCAAGGTC                 289
```

(2) INFORMATION FOR SEQ ID NO: 24:

(i) SEQUENCE CHARACTERISTICS:
        (A) LENGTH: 367 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 24:

```
CCATCAGGAT TTACTGAGTA AAAATCTCAG GTNTTAACCA TGCCCCTAAA ATGTGCTATN       60

CCAAAGAGGA ACAGGTTACT TGGGAGGAAA AAAGCTGCCT GGGNAACTCC CCNCAAATGT      120

TTATTTTAAA TAAAAATGGT NGATGGAAAT ATTTTNTAAA AGAACTTGGG GTNTAATATG      180

GNATACTGCC CATCAAACAA AAAAGGAAAT AAAACTTCNT TCCCATTTAT AATAAGTTNC      240

CCACCCTTTA CTATCAAGAT TACAACTTAT TGACCTTTTA TGCTNGCTNG GTTTTTTTGG      300

GACTGCCTAA TCCAATGTTT AAATTTTCTA NGTCTGNATT TCAATGTGGG TAGGAGTNAT      360

TTTTCAA                                                                367
```

(2) INFORMATION FOR SEQ ID NO: 25:

(i) SEQUENCE CHARACTERISTICS:
        (A) LENGTH: 425 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 25:

```
GAGTATCTGA CAGGTAAGAT TGCTTTTTAA AGTTGTTTTA AATGCATTAC ATGACTGAGA       60

AAAGAAAAAT GCACATTTTA TTGTTGCAGT TTAAAATTTC ATTTNGNGTG AAACTAAACG      120

TGAAACAAAA GGGATAAATG TGTTTTGNTT TTGTTTTGGT TTTACCTGTT TGGGGTATTT      180

TTTTCTGAGT TTGTGTAGAA ACCCGTGTGG NTACACTGGG TAATCTTGTC AGGGNTACMA      240

AMCTTGGGTC TTGANTTTGG TTANTTGGNT TTANTTGGTG NACCCATGTA CTTGCTCTTC      300

CNTCCCAGAA ACATAGCTTG GTAGGCNAGG GTTAANCCAG TGTCGGCGAN CCCATGTCCC      360

TANCACAGCA TCTTGTAAGT TTAATGCACA ATCGTTCCNT CCCAGGATGG ANTTATCATT      420

ATAAA                                                                  425
```

(2) INFORMATION FOR SEQ ID NO: 26:

(i) SEQUENCE CHARACTERISTICS:
        (A) LENGTH: 2377 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 26:

```
GAGAGGCGCA GGAGCCACAA ATAAAGCAAG AGCCAGAATC AGAAGNGGAG GAAGAAGAAA       60

AGCAAGAAAA AGRAGRAANA CGAGAAGAAC CCATGGRAGA GGAAGAGGAN CCAGANCMAA      120

AGCCTTGTCT GAAACCTACT CTGAGGCCCA TCAGCTCTGC TCCATCTGTT TCCTCTGCCA      180
```

```
GTGGNAATGC NACACCTAAC ACTCCTGGGG ATGAGTCTCC CTGTGGTATT ATTATTCCTC        240

ATGRAAACTC ACCAGATCAA CAGCAACCTG AGGAGCATAG GCCMAAAATA GGACTAAGTC        300

TTAAACTGGG TGCTTCCAAT AGTCCTGGTC AGCCTAATTC TGTGAAGAGA AAGAAACTAC        360

CTGTAGATAG TGTCTTTAAC AAATTTGAGG ATGAAGACAG TGATGACGTA CCCCGAAAAA        420

GGAAACTGGT TCCCTTGGAT TATGGTGAAG ATGATAAAAA TNCAACCAAA GGCACTGTAA        480

ACACTGAAGA AAAGCGTAAA CACATTAAGA GTCTCATTGA GAAATCCCT ACAGCCAAAC         540

CTGAGCTCTT CGCTTATCCC CTGGATTGGT CTATTGTGGA TTCTATACTG ATGGAACGTC        600

GAATTAGACC ATGGATTAAT AAGAAAATCA TAGAATATAT AGGTGAAGAA GAAGCTACAT        660

TAGTTGATTT NGTTTGTTCT AAGGTTATGG CTCATAGTNC ACCCCAGAGC ATTTTAGATG        720

ATGTTGCCAT GGTACTTGAT GAAGAAGCAG AAGTTTTTAT AGTCAAAATG TGGAGATTAT        780

TGATATATGA AACAGAAGCC AAGAAAATTG GTCTTGTGAA GTAAAACTTT TTATATTTAG        840

AGTTCCATTT CAGATTTCTT CTTTGCCACC CTTTTAAGGA CTTKGAATTT TTCTTTGTCT        900

TKGAAGACAT TGTGAGATCT GTAATTTTTT TTTTTTGTAG AAAATGTGAA TTTTTTGGTC        960

CTCTAATTTG TTGTTGCCCT GTGTACTCCC TTGGTTGTAA AGTCATCTGA ATCCTTGGTT       1020

CTCTTTATAC TCACCAGGTA CAAATTACTG GTATGTTTTA TAAGCCGCAG CTACTGTACA       1080

CAGCCTATCT GATATAATCT TGTTCTGCTG ATTTGTTTCT TGTAAATATT AAAACGACTC       1140

CCCAATTATT TTGCAGAATT GCACTTAATA TTGAAATGTA CTGTATAGGA ACCAACATGA       1200

ACAATTTTAA TTGAAAACAC CAGTCATCAA CTATTACCAC CCCCACTCTC TTTTCATCAG       1260

AAATGGCAAG CCCTTGTGAA GGCATGGAGT TTAAAATTGG AATGCAAAAA TTAGCAGACA       1320

ATCCATTCCT ACTGTATTTC TGTATGAATG TGTTTGTGAA TGTATGTGTA AAAGTCTTTC       1380

TTTTCCCTAA TTTGCTTTGG TGGGGTCCTT AAAACATTTC CCAACTAAAG AATAGAATTG       1440

TAAAGGAAAA GTGGTACTGT TCCAACCTGA AATGTCTGTT ATAATTAGGT TATTAGTTTC       1500

CCAGAGCATG GTGTTCTCGT GTCGTGAGCA ATGTGGGTTG CTAACTGTAT GGGGTTTTCT       1560

TATTAATAAG ATGGCTGCTT CAGCTTCTCT TTTAAAGGAA TGTGGATCAT AGTGATTTTT       1620

CCTTTTAATT TTATTGCTCA GAAATGAGGC ATATCCCTAA AAATCTCGGA GAGCTGTATT       1680

TAATGCATTT TTGCACTAAT TGGTCCTTAG TTTAATTCTA TTGTATCTGT TTATTTAACA       1740

AAAAATTCAT CATATCAAAA AGTGTAAGTG AAAACCCCCT TTAAAACAAA ACAAAAAAAT       1800

GAAATAAAAT TAGGCAAATT GACAGACAGT GAGAGTTTTA CAAACATGAT AGGTATTCTG       1860

CTCGGCAATT TGTAAGTTTA CATGTTATTT AAGGATAAAG GTAAATCATT CAAGGCAGTT       1920

ACCAACCACT AACTATTTGT TTTCATTTTT GTCTTGTAGA AGGTTTATAT CTTGTTTTAC       1980

CTTGGCTCAT TAGTGTTTAA AAATGTACTG ATGATGTGCT TAGAGAAATT CCTGGGGCTT       2040

TCTTCGTTGT AGATCAGAAT TTCACCAGGG AGTAAAATTA CCTGAAAACG TAAGAAGTTT       2100

TAAACAGCTT TCCACACAAA TTAGATGCAA CTGTTCCCAT GTCTGAGGTA CTTATTTAAA       2160

AGAAAGGTAA AGATTGGCCT GTTAGAAAAA GCATAATGTG AGCTTTGGAT TACTGGATTT       2220

TTTTTTTTTT TAAACACACC TGGAGAGGAC ATTTGAAAAC ACTGTTCTTA CCCTCGAACC       2280

CTGATGTGGT TCCATTATGT AAATATTTCA AATATTAAAA ATGTATATAT TTGAAAAAAA       2340

AAAAAAAAAA AAAATTCCTG CGGCCGCAAG GGAATTC                              2377
```

(2) INFORMATION FOR SEQ ID NO: 27:

(i) SEQUENCE CHARACTERISTICS:

```
        (A) LENGTH: 489 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 27:

ATTGGAGCTC CACCGCGGTG GCGGCCGCTC TAGNAACTAG TGGATCCCCC GGGCTGCAGG      60

AATTCTCGAG ATCTCCCCCA AGTAAATGAA TGAAAAAAAG AACAGCAACA ATAGAGATGA     120

TATAATAAGC CAGGCATGGA TGACCTTATA GCACCCTGTA TTTATACAGA ACCACCAGGA     180

GGATAGTCAT GACAACNATG ACACTGATCA TGATNCCAGC ATTCAGAATT GAGTNCAGGG     240

CTCTCTGGCC CACAGTCTCG GTATCTTCTG TGNATGGGGT ATAGATTARC TGTCCATCCT     300

TCCGGGNATA AAANCTGACT GACTTAATGG TANCCACGAC CACCACCCAT KCAGAGAGTC     360

ACAGGGACMA AAGAGCATGA TCAACATGCT TGGCNCCATA TTTCAATNTC ANCTCCTCAT     420

CTTCTTCCTC ATCTTNCTCC ACCACCTNCC GGGAGTTAAC CCTGGGGTCG TCCATTAGAT     480

AATGGCTCA                                                             489

(2) INFORMATION FOR SEQ ID NO: 28:

(i) SEQUENCE CHARACTERISTICS:
        (A) LENGTH: 2307 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 28:

AGGGTGCTTC AGTGTGGCTG ACACAGCAGC ATGGTCTTGA CAAGTTTTCT TCATCCTACC      60

ACAAAATCCC AGTTGGTAAT AGAGACTTTA CTCCTACCTA TCAAAACCAC AAAATGTCCC     120

ATTAGGGGGG GACATGTTGT ACATGTTAGG ATCATTCAAA TAACCAAGAT TATAAGGTGA     180

GGAAAGATGC CCCTAACTGA TTCTTTTGTC TCTCATCTTG TTGGTTCCAG GGACCGAGTG     240

GGGTCAATCT TCTGGTSSTG CCTCTCCAGG TCTCTTCCAG GCCGGTCATA GACGTACTCC     300

CTCTGAGGCC GACCGATGGT TAGAAGAGGT GTCTAAGAGC GTCCGGGCTC AGCAGCCCCA     360

GGCCTCAGCT GCTCCTCTGC AGCCAGTTCT CCAGCCTCCT CCACCCACTG CCATCTCCCA     420

GCCAGCATCA CCTTTCCAAG GGAATGCATT CCTCACCTCT CAGCCTGTGC AGTGGGTGT     480

GGTCCCAGCC CTGCAACCAG CCTTTGTCCC TGCCCAGTCC TATCCTGTGG CCAATGGAAT     540

GCCCTATCCA GCCCCTAATG TGCCTGTGGT GGGCATCACT CCCTCCCAGA TGGTGGCCAA     600

CGTWTTTGGC ACTGCAGGCC ACCCTCAGGC TGCCCATCCC CATCAGTCAC CCAGCCTGGT     660

CAGGCAGCAG ACATTCCCTC ACTACGAGGC AAGCAGTGCT ACCACCAGTC CCTTCTTTAA     720

GCCTCCTGCT CAGCACCTCA ACGGTTCTGC AGCTTTCAAT GGTGTAGATG ATGGCAGGTT     780

GGCCTCAGCA GACAGGCATA CAGAGGTTCC TACAGGCACC TGCCCAGTGG ATCCTTTTGA     840

AGCCCAGTGG GCTGCATTAG AAAATAAGTC CAAGCAGCGT ACTAATCCCT CCCCTACCAA     900

CCCTTTCTCC AGTGACTTAC AGAAGACGTT TGAAATTGAA CTTTAAGCAA TCATTATGGC     960

TATGTATCTT GTCCATACCA GACAGGGAGC AGGGGGTAGC GGTCAAAGGA GCMAAACAGA    1020

YTTTGTCTCC TGATTAGTAC TCTTTTCACT AATCCCAAAG GTCCCAAGGA ACAAGTCCAG    1080

GCCCAGAGTA CTGTGAGGGG TGATTTTGAA AGACATGGGA AAAAGCATTC CTAGAGAAAA    1140

GCTGCCTTGC AATTAGGCTA AAGAAGTCAA GGAAATGTTG CTTTCTGTAC TCCCTCTTCC    1200
```

```
CTTACCCCCT TACAAATCTC TGGCAACAGA GAGGCAAAGT ATCTGAACAA GAATCTATAT    1260

TCCAAGCACA TTTACTGAAA TGTAAAACAC AACAGGAAGC AAAGCAATGT CCCTTTGTTT    1320

TTCAGGCCAT TCACCTGCCT CCTGTCAGTA GTGGCCTGTA TTAGAGATCA AGAAGAGTGG    1380

TTTGTGCTCA GGCTGGGAAC AGAGAGGCAC GCTATGCTGC CAGAATTCCC AGGAGGGCAT    1440

ATCAGCAACT GCCCAGCAGA GCTATATTTT GGGGGAGAAG TTGAGCTTCC ATTTTGAGTA    1500

ACAGAATAAA TATTATATAT ATCAAAAGCC AAAATCTTTA TTTTTATGCA TTTAGAATAT    1560

TTTAAATAGT TCTCAGATAT TAAGAAGTTG TATGAGTTGT AAGTAATCTT GCCAAAGGTA    1620

AAGGGGCTAG TTGTAAGAAA TTGTACATRA GATTGATTTA TCATTGATGC CTACTGAAAT    1680

AAAAAGAGGA AAGGCTGGAA GCATGCAGAC AGGATCCCTA GCTTGTTTTC TGTCAGTCAT    1740

TCATTGTAAG TAGCACATTG CAACAACAAT CATGCTTATG ACCAATACAG TCACTAGGTT    1800

GTAGTTTTTT TTAAATAAAG GAAAAGCAGT ATTGTCCTGG TTTTAAACCT ATGATGGAAT    1860

TCTAATGTCA TTATTTTAAT GGAATCAATC GAAATATGCT CTATAGAGAA TATATCTTTT    1920

ATATATTGCT GCAGTTTCCT TATGTTAATC CTTTAACACT AAGGTAACAT GACATAATCA    1980

TACCATAGAA GGGAACACAG GTTACCATAT TGGTTTGTAA TATGGGTCTT GGTGGGTTTT    2040

GTTTTATCCT TTAAATTTTG TTCCCATGAG TTTTGTGGGG ATGGGGATTC TGGTTTTATT    2100

AGCTTTGTGT GTGTCCTCTT CCCCCAAACC CCCTTTTGGT GAGAACATCC CCTTGACAGT    2160

TGCAGCCTCT TGACCTCGGA TAACAATAAG AGAGCTCATC TCATTTTTAC TTTTGAACGT    2220

TGGCGCTTAC AATCAAATGT AAGTTATATA TATTTGTACT GATGAAAATT TATAATCTGC    2280

TTTAACAAAA ATAAATGTTC ATGGTAG                                       2307

(2) INFORMATION FOR SEQ ID NO: 29:

(i) SEQUENCE CHARACTERISTICS:
         (A) LENGTH: 343 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 29:

GGCAGCTATT TACATGGCCT CACAGGCATC AGCTGAAAAG AGGACCCMAA AAGAAATTGG      60

AGATATTGCT GGTGTTGCTG ATGTTACAAT CAGRCAGTTC TATAGACTGA TCTATCCTCG     120

AGCCCCAGAT CTGTTCCTTA CAGACTTCMA ATTKGACACC CCAGTGGACA AACTACCACA    180

GCTATAAATT GAGGCAGYTA ACGTCMAATT CTTGANNACM AAACTTKNCC TGTTGTACAT    240

AGCCTATACM AAATGCTGGG TTGAGCCTTT CATAAGGNAA AACMNAAGAC ATGGNTACGC    300

ATTCCAGGGC TKGANTACTT ATTGCTTGGC ATTCTTGTAT GTA                      343

(2) INFORMATION FOR SEQ ID NO: 30:

(i) SEQUENCE CHARACTERISTICS:
         (A) LENGTH: 363 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 30:

AAAGGGCTAA CCAGCCACTG CACCAAAATT AGTCCTTACA TTATAATACT CTGGCCATTG      60
```

-continued

```
GAAGAGAAAA ATGGGAAAAT TCAACAATTT GAAAGACTAT GATCCCTCTG GCTCATGATC      120

TACTGACCAG AATGAAGTCC TGAAGGATTT CCTTCTGTTA TGTTATCTAC CCAGCTAATC      180

TCAAACAAGA GGAGCTGGAA AGAACAAAGC CCCATGAAGC TACCCCTAGA CCCAGAAAGC      240

CAAGAACAGG GCCAAGAAAA TGAACAGCAG ACAAGCCTGA ATAGAAGTG GNACAGACAT       300

GTGGNAAGAC CAAGTACACC CAGTTNGGTG GTAAAGATTC CGATATCAAG CTTATCGATA      360

CCG                                                                   363
```

(2) INFORMATION FOR SEQ ID NO: 31:

(i) SEQUENCE CHARACTERISTICS:
  (A) LENGTH: 362 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO: 31:

```
AGTACATGGT TTCTTGNCCA CCCCASCCAC CTTTCCCCAT CTCTACCGGY TGATAGTCTC      60

TCAGNTAGTA GACCTTTTCT NGTTTAGRCA GGGCCACNTT TTTAAAAACT CCAGACGGGT     120

ACCCTCCATG TKGMAGGCGA CGTGGCCCTG GATCACTCAA CTGANTGTCA TNKGANTGGT     180

GCCCCCAGAG TGAGGACAAT GGTGNAGCCC TCCTAAGGCC CTNCCTGAGT GTCCCTCCTT     240

CATGAAGATG ATTCTGAGGN TTCCCAGGCC TNCACCCTTC TTKGAAARCC CATAGNAGTT     300

CATATGNACT NCTCTNCTAT GCTCACCAAA CTCTNCCTTC ATCATACTTG GGGATGTGT      360

GT                                                                   362
```

(2) INFORMATION FOR SEQ ID NO: 32:

(i) SEQUENCE CHARACTERISTICS:
  (A) LENGTH: 475 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO: 32:

```
GTGCATGTAA TTACAGTTAC GATATATGAA ACGTACAAAA TATTATGAGT ATATAATATG      60

GGGAGACTTA ATCTAGTTTG GGGGATCAGG GCACATTTCT CTAAGAAAGT GACATTTGAA     120

TTGAGCTCTG AAGGATAAAT AGACATTACC CAGAAGAATA AAATGATGGG GAAGAAGGAG     180

GACATTTTCC GTAGATTTCC AGTGGCCCCN CTTGATCCCT TATCCACTCA TCACTNAGGA     240

GGATATTAAA TKCTATAGAA ATGGRAGRAA GACMMAAAGA GACCCTNATA TCTCGAGAGG     300

ATCCAGCMAA ATTCCAAGAG ACACAACAWT AAGAAACTNG GAAGGAAGAG AAAAGGCMMN     360

NNAGGNAAAA GAAAGACAAG GAAATTNWNN NAGNACGGAG AGAAAGAGAG AGGGAGCGTN     420

NAAGGGNACG AGAAAGGCGA GNACGGGGAC GAGAAAGGGN AAGAGNACGT AAACG          475
```

(2) INFORMATION FOR SEQ ID NO: 33:

(i) SEQUENCE CHARACTERISTICS:
  (A) LENGTH: 346 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO: 33:

```
GGAAATAAAT GAGATCTCAG TGGTGGTATG GATTGGACTG ATCTCTGTAA CTGTGTNTGG      60
AAAAAGGACC GGAAAATGAA AGCCAGATCC CAGTAAGGGG TAGAGAGGGG CCAAGAGAAC     120
TGAACATCTG GGCTGCCGGA GAAATCAAAG TCTAGGAAGT AAGAGGTAAG AGTGTACTAC     180
AGGGGACATA CCCCAATCTC TTGGTTCCCT CCCTCTNCCT TCCTCTCCCA GAGACCCAGG     240
TCCCTGGGAC TATNTTGGAT CTGTCTCTGA AGCTGAAAAA CAAAAGGCAG AGGAGACAGT     300
CGGNTCTAAG TGACCAATCT CAAGCCAGCT TGGTCAGAAN TCCTAA                    346
```

(2) INFORMATION FOR SEQ ID NO: 34:

(i) SEQUENCE CHARACTERISTICS:
        (A) LENGTH: 433 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 34:

```
AAATCCAGTG CAGGCAACAT TATGTGGAAA TAGAAACAGG GCTCCTGCTA GGAGATTGAN      60
ATTCTGGCTT TCCTTTGGAA CCCCTCACTG ACTCATCGCC CCTGAANCAG GANCCANCAG     120
GTNCCAAGGC TCCCCTGCTC CTNTCCCTNC CCCAGGGCGA GATAGGAARC CGGAARCCTG     180
GGCAGGCTGA RCCCANCCGA CTGGAACCAG GGNAGANCCT GTGGGTGGGT GGNAGGGAGG     240
GAAGGAGGCC AGATTCCTCC AGAACTGGGG RAGAGAACAG GTTTTGGAAG TTGGGGGAGG     300
GTTTGGGTTT CACAGTGATG GTTTCATGAN ACCCTGGAGG GTTNCACACT CCTGGTKCAN     360
TTTTGNTANT CGTNCTTTGA ANACARNCCG CTTCCTTTCA ACCCTCCNCN TAAAAAGTTT     420
TGATNTTTTA AGG                                                        433
```

(2) INFORMATION FOR SEQ ID NO: 35:

(i) SEQUENCE CHARACTERISTICS:
        (A) LENGTH: 350 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 35:

```
ACCAAGAGCC CCCAGTTTAT GNTAACTCTC ATGACAAACA CAATTTTAGT ACCTCTCACT      60
ACCAACTATC CAGGAACCAG GANTCACCTA TTACTACGGT TCCAGCAGAA TGGGAATCCC     120
ATTCTCGGAT ATCCAGGGTA AATCCCTGAC CATGTGAGAG GAATCCTAGT GCCCCAACAA     180
CCTCACCCCC TGACTCCTCC TCAANGGCTC TGCCAAGTCA ACAAAAAAAT CCTCTACATT     240
TACACTATCT GTAAAGCCAA AGACCAGCGT CAACCTAAAT GTCCATCAAT AAGGGAATGG     300
TTGGATAAGT AAAAATTATG CAGCTGTAGG AAGGAATGAA GAATGTCTAT                350
```

(2) INFORMATION FOR SEQ ID NO: 36:

(i) SEQUENCE CHARACTERISTICS:
        (A) LENGTH: 512 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 36:

```
AAAGGGAACA AAAGCTGGTA CCGGGCCCCC CCTCGAGGTC GACGGTATCG ATAAGCTGGA      60

TATCGAATCC TCGAGATCTA CCTAAAAAAA AAAAATTAAC TTCCCAAATG TGGGAGTCTA     120

CTCTGTTCCC TCCTNGTNTT TATTNCTGTN TACTTTYCTA ANATGGTTAA AATGTGTAAN     180

CAATATGTGT CCTTTNACTN KGGKGTGAAC ATTTTTYCTA TTATAAATYC TWAGAAAATA     240

TTNCTATGGN TATGAGATAT TKGATTCCAA GTGCCTKGTA ATTTACTYCT CAAATGTCCC     300

TGATGTKGGA NATTKGTTNC TAGTGTTYCA CTATTTAAAA AAACAGNAAT ATCTGTCTNT     360

ATGCTNAGAG CTTNTYCAGT TTYCAAATTA TTNCCTTAGG GTAAAATCCT AGAAGTAGAA     420

TTTTTGGGGC AAATTATCTA CATATTTATA ATTGTCTTGG TATTCCAAAT CTCGTTTTCC     480

AAAAGCTTAT ATCAATTTGT ACTTAACACC AG                                   512
```

(2) INFORMATION FOR SEQ ID NO: 37:

(i) SEQUENCE CHARACTERISTICS:
    (A) LENGTH: 450 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO: 37:

```
ATTTAAGATG ACTGGGGGTC TCTNCCTAAT CCCATACTCC ACTGGAGAGG ANAAGTGGGA      60

AAGGTTGGTC TAGTTARGGT NGNTGGGGAC CCTCCCAAGA GCTGNAGAAG CAGAGATAAG     120

NAGAGCCTNC TNCTAAATCC ACATGGNCCT YCCAAGGNTC TCATCCTCTA GGACCTACCA     180

CTNCTCAGTC TACTTACTTG TCTYCTGANA TGCTTTCTNG AGGGGNAGAA AACAAAGGAA     240

GAGTAATAAC AAGCAGNAGA AACTGCAGAG AATGNAAAAT AAGTCCATAG GAGAATGTTG     300

NAAATAGAAT CATCCNCCTT TACATATTGT CACTCCAGGA AAACTGCCAA GAACCACTCA     360

TTCCTCTAGA TACAMTTCCT GTAGGATCCY CCCAGACTTC CTCCCTTAAG CACGTCAGTA     420

TTCTCCTTAT TCTCCCTTCA TTTCAACCCT                                      450
```

(2) INFORMATION FOR SEQ ID NO: 38:

(i) SEQUENCE CHARACTERISTICS:
    (A) LENGTH: 766 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO: 38:

```
CGAGATCTGC CCCAGCCCAC ATTTCCTTTG TTGAATGAGT AGAGAAGACT GAGAAGTATC      60

ACTCACCCGT GATGTGGTTT GTCCCTTTTC CAGCCAGTGT GTTGGTAATA AAAGTCACCT     120

TTCAGAGCTT TGGTCCCCGT AATGCCCGTC TTTCCTGTGT CCAGGAATAA CCTTTGNTAC     180

TAGGCAGTCC TCTGAAAGAT TTGTAGAAGG TTAAAGTGGA AAGGGACTTG GAAGCTCATA     240

GAATCCATGC CTCTTCTTTT AGCATCAAGG AATTAGAAGT CCTGAGAGAT GAAGAATGTT     300

GTCTTCCCAA CTCAAACCCA TTTCTTGAAG CCATTTCCCT GGTTACTGNA TTGGCCACAA     360

CCCTTCCCCC TTGNTATCCT CATCCTGCTA ATGCTGTTTT TAATGGCCTG CCAGTCTGGA     420

TTTGTCTTTG GCAACCAAAC AATTTTGCTT CACAAGATTC CTACTTAAGG GAAGAGAGGG     480

GCTCCTCATT TNTCACTTGT ACAAGAGCAG GGCTGGTCAG CTTTACACAG GTGTCAGATG     540
```

```
AACCGTCACA ANCCAGANTT NCATGTTGGC CTCAGGAGGG CTTCNAGGTC CAACATCTCG      600

ACGTAAGGAG CGTTCCCAGT TCTTTCATGC TCAGATAACA GTNCTAACTN CAGCTGTTTC      660

ATCCCNAATC CCTANTTGAG GTCTTAACAT CTATTCCATT TTKCCNACMA GGGTTATNCT      720

GTTAACCCTC TNCACCAGAN TTAGANCTGA CTGATNCACT TCCTAG                     766

(2) INFORMATION FOR SEQ ID NO: 39:

(i) SEQUENCE CHARACTERISTICS:
        (A) LENGTH: 327 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 39:

TCATACTTGT ATAGTTCKNT AAGATAATCA CTCTCTCACT CAGACATNNG GNGRARNGCC       60

CNTCGATCAC TTGGGANAGG NGACTTGCMA TGTTTAATGA TTGTCANCCM NANAANTAAG      120

CTNACAGGGC AAAAACAGCC TYANGTCAGT TCTNTCTCCC TAATCCTCTA GRAKNAAATC      180

NNAWRNTRNN ACTCTGNNTC TGTGCCATNA NANATNTTNC ANTTGTATTT ATGNACTCCA      240

CATNGAGTAC ACCTCACTAA WTNTNCTNCT GGGNAACNCC CSCMCCANTT TTTNNTTGNT      300

GANANACARC AATGCTGGCA TACNGTG                                          327

(2) INFORMATION FOR SEQ ID NO: 40:

(i) SEQUENCE CHARACTERISTICS:
        (A) LENGTH: 431 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 40:

CCAGACTTTC ATAACTNGTG TTATTATGAA GATTAGAGTN CTGAAGCTTA CTGGATTAGA       60

AGAGNACGAG GGGGTAGCTG CCCCAATATA TTCTAATTTC TCTKGAGGAC CACCAAATNG      120

GMAGAGTGTC TCTGATAGGG AAAAGGAAGA GTTGGAAGGN ATCTTAGCCT CTAGGANAAA      180

AGAACCATTT TTATTGGCCA CCAAAGTTAC ATCTAGTKGC CTACAAATTT ATNTCCAAAC      240

TCCTTATCCT GCCAATTCAG GGTCCTGNAA ACTGATGCCA AACTATAGTT TAGTCTNCTA      300

TCACATGACT GCATTATACA TACCCAATTA TCTGGGMAAA CAGACCTGAT CCAAACACAG      360

TTKGGTNCTT TCCTTNCCTT NCCTTKGTTT AGCCTGTYCC GTCTACTNGG GGTGTCTTKG      420

ATTTGCTCCA G                                                           431

(2) INFORMATION FOR SEQ ID NO: 41:

(i) SEQUENCE CHARACTERISTICS:
        (A) LENGTH: 276 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 41:

TTTTTTTCCA CCAGACTTAC CAAATTTTAG ATGNATGGAA GAACTGTAAA TNCCCATAAA       60

GNTAATCTAT NCATNGACCC CCACCATTAT GATAGAGATC ATNTGGTGAN TAATGAAAGA      120
```

```
TGAAACTCTC AGCTGGGAAA GTAANAAGGA ATAGGATGTA AGTATGAGCT CCTGTTTTTT      180

ATTATNTTTA TGGATGCCCC CTCAGAAAAA TATGNAANGG GGTAACTGAC TNGGAAATGG      240

GTNTTTTATG NATAGTAAGT CCCACTCACG AGGTTT                                276

(2) INFORMATION FOR SEQ ID NO: 42:

(i) SEQUENCE CHARACTERISTICS:
        (A) LENGTH: 270 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 42:

TCGAGATCTA AAGCAGATGN AGACTTTNCA CNAAATAAAT TTACTGCTTT TTTYCTGTGA       60

NATAAGTTNC GAGAAGGAAA GCTTTKGATT NCTRNATGAG TYCAGTGGAT TATYCTNAGN      120

ACTAGAGTKG NKGTKGAAGN CATGGNACAT TTATATAGWT YWTTCAGTTC TACACTAAAT      180

GATGGAAGAA TGAGAAATCC TATATGACAA ATAGAAAAGT YCATYCTYCA TAATTGAGAA      240

CATTGAGCAG TTGGATTACC AAGATCTCGA                                       270

(2) INFORMATION FOR SEQ ID NO: 43:

(i) SEQUENCE CHARACTERISTICS:
        (A) LENGTH: 580 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 43:

CTTAGTTTTA GACTAGTTTC ATTATACTAC CAGTTTCTAA TATGTTGGTT TTTTATTCAC       60

TATTTGATAT ATTTGTTTTA ATATATGTTC TTGTTTTAGC AGGTAAAAGA ATCATAACAA      120

ATGTTTTTAA AAGAACATTA TTATTCTTTA ATAACTGTCT TTTTATGCAT TTGGCATGCC      180

AACTTTTTTC ATTAACATCT TGGGTATTTT ATAAAAAGAG GGAAAGCTCA ATGTTTAACA      240

GGTAGCTTTT CTTAGGAGCT AAATTAAATA TTTAACAAAT CTCCTTCCCT TCNCCCTTCC      300

CCATCCCTCA AAGNATGGGT GNANTTATCT TTAACTTTTG GGCTNGCATC CNTGNAAGCT      360

TATGGNTANT CATAGTCTNA CMAAACTAGG GTCACCNAAC TTGGCAGCAG AAATAATCTA      420

GTCTTACTGT GATAACTACC CAATTACTTT ATTATTTTTC CAGTTNCAGT TCCAAATGTT      480

TTGTGGNAAN AATTTTTNCT GTTTGTGATT TTCCAAGCTT AGAGGGGGAA ACCAACTTTC      540

CAGTGTTGGA GAGCACTGNA TAGTTTATGN ATTGTGTAAA                            580

(2) INFORMATION FOR SEQ ID NO: 44:

(i) SEQUENCE CHARACTERISTICS:
        (A) LENGTH: 347 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 44:

TGTTTCTTAA NACAGAAAAA AATTTACTGA TNGGACATTG TTCTAAGTGT ATTATTGTAT       60

TAAATGGATC ATTTAATTTA ATCTTCATAA CTGACATAGG AGTTGAGTAA CTTGTGTGGT      120
```

| | |
|---|---|
| CAAATAGCTA GTAAGTGATG AGTAGGCTGG GCGCAGTGGC TCAAGCCTGT AATCCCAGCA | 180 |
| CTCTGGGAGG CTGAGGCAGG CAGATCACTT GAGGTCAGGA GTTTGAGACC AGCCTGGNCA | 240 |
| ACATGGNAAA ACCTCGTCTC TACTAAAAAT ACAAAAATTA GCTGGGCGTG GTGGGNGCGC | 300 |
| ACTTGTAGNC CCAGNTACTC GGAAGGCTGA GGCAGGAGGA ATCGCTT | 347 |

(2) INFORMATION FOR SEQ ID NO: 45:

(i) SEQUENCE CHARACTERISTICS:
        (A) LENGTH: 430 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 45:

| | |
|---|---|
| GCTCATCATG CTTCACGGGG GAGGCTGTGC GGGAAGAATG CTCCCACACA GNATAAAGAA | 60 |
| TGCTCCCGCA CAGGATAGAG AATGCCCCCG CACAGCATAG AGAAGCCCCC GCACAGCATA | 120 |
| GAGAATGCCC CCNCACAGCA TAGAGAAGCC CCCGCACAGN ATAGAGAATG CTCTTCACCT | 180 |
| CTGGGTTTTT AACCAGCCAA ACTAAAATCA CAGAGGGCAA CACATCATTT AAGATAGAAA | 240 |
| TTTCTGTATC TTTTAATTTC TTTCAAAGTA GTTTTACTTA TTTNCAGATT CTATTTCTTT | 300 |
| ACTAGAATTA AGGGATAAAA TAACAATGTG TGCATAATGA ACCCTATGAA ACAAACAAAA | 360 |
| GCTAGGTTTT NTNCATAGGT CTNCTTCCNN ATTGAATGAA CGTCTNTCCT CAAATTTANC | 420 |
| CCCCCAGGGA | 430 |

(2) INFORMATION FOR SEQ ID NO: 46:

(i) SEQUENCE CHARACTERISTICS:
        (A) LENGTH: 400 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 46:

| | |
|---|---|
| CAAACCCTAT GNGAAATGGA AAGGAAACTA TTCTAAAGCA TAAAAGGTAG AAATATATAT | 60 |
| ACCACCCATC AAGAAAGATT ATTTTTGNTG AACTCAAGTC ACCAGAGTGG CTAAAGCCCA | 120 |
| GTAGAATGGA AATGATTATA TGGAAGGTGA GGCCAACGGG ACCAGAACAT ACTGTGATAG | 180 |
| ACAGNAAGGA GCTGTCTATC TTCTATTCTC CCACAGAAGG AGGTGACTAA GTCANCTGCC | 240 |
| CAAGCAATGT TATATCTGCA ATTGATGTNC AGCAGTACAA GTCTGAACAA CTTGGATTGG | 300 |
| NTGATTAATG TCCACANTAA ACATACAAGT CNTAATAGCT ATCTCTATAT AGTCTTTGGG | 360 |
| TNTTTACAAG GCACTGNCAC ATNATCTCAC CTATTCCTCC | 400 |

(2) INFORMATION FOR SEQ ID NO: 47:

(i) SEQUENCE CHARACTERISTICS:
        (A) LENGTH: 500 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 47:

| | |
|---|---|
| AGNATCCAGA ATTGAGTGNA GNGTTCTCTG GNCCACAGTC TCGGTATCTN CTGTGAAATG | 60 |

```
GGGTATAGAT TCTACAATAA AACAAACACA NNGGCCCTAG GTCAGTGTTA ATGGAGATCA         120

CCANCCACAT TACCACCTCC AACACAGAAT TTTCTTTTTC TTAATNCAAT NCGTNTCTTA         180

TAAGTCACTT TNCCCCAACT CACCAATCTA GNTAAGAATT TTTACCCTGA GAAAAACAGC         240

TACACTCTAA AATTGCTNCA AGAAAATGT CTAACATNTG GAAAGAAGGA CTTAACATGT          300

GANGNAGACA CTGGCTCCAT CTAGNGGGTG CTTTNTTTTG AAATAATTAT AATNCCNCAT         360

CAAATTTTNG GGGGNTACAG CTTATTAGGA ACTTGTTATA GAACCAGATT CTGCCACAGA         420

ANCCACGTGG GTTGACAAGT GGTTGNCAGA AGAAAGGTAA TATGGCTTAT NATTAGGGNC         480

TCNCATCTGC AGAGTAATTG                                                    500
```

(2) INFORMATION FOR SEQ ID NO: 48:

(i) SEQUENCE CHARACTERISTICS:
        (A) LENGTH: 460 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 48:

```
AAAATGCTTG ANNCAAATGT CATCTAGTTC CATCTCTACG ACTCTCATGG GGTCCAAAGA          60

AGAGTTTTAN TTGAGTTTTA GAATGTGAAG TTGTGAAGTG TCTGAAAAAC TACATGGTGN         120

TCTGAAAGNC AAACTTTTAG CCTTGGGGGA GAGCATCTAA GACAGNAGGT GAAGGGNAGG         180

GGTTAGAACT AGAGGGATTG AAGAATATTA TCCATATAGG TTAGGGTTAG GTNNGGCAAC         240

GTTTTATAGA ACAAACATTG GCAAGCTACA GCCACAGGCC AGATCTGTCT NCTACCTTCC         300

CACAAAGGTG TAATAACAAA GTTATTCACA AATGTGTGAA TAAACTNNCA TTGGAAAGTG         360

CCCACGCTCC TNGGTTTATA CATTGTCTGT GGCTGCTTTC ACACTACAGT AGCACAGGTG         420

AGTGTNTGCA CTGGAGACCA TATGCCCCAT AGAGCTTTAA                              460
```

(2) INFORMATION FOR SEQ ID NO: 49:

(i) SEQUENCE CHARACTERISTICS:
        (A) LENGTH: 370 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 49:

```
ATCAAGCAAC AGTGTGTTAT GCCTATACTC CATGTTTATA TGTGTGTATT AAAAAATGTA          60

TTTGTATATA TGTGTATGTA TAAGTGTGTG TGTGTGTATG ATGATTCTNC TCCCGNTTTG         120

AAGGTGAAAG AAAGCACACC TTTATTTAAG CATAAACTTT GGGTTTCAGA TACTGTCTGG         180

AAAAATGATT TATCTCCCAC TTTGAAATTC CAAAATACGT ACATATATTT TTTTTTTCTT         240

TTCTTTTTTA GTTTNAGGGT CTTGCTGTGT TGCCCAGGCT GGAGTGCAGT AGTGTGATCA         300

TAGNTCACAC AGNCTCTAAC TCCCAGGNTC AAGNTATCTT CCTGCCCCAG NCTCCTGAGT         360

AGNTGGGACT                                                               370
```

(2) INFORMATION FOR SEQ ID NO: 50:

(i) SEQUENCE CHARACTERISTICS:
        (A) LENGTH: 500 base pairs
        (B) TYPE: nucleic acid (C) STRANDEDNESS: single
            (D) TOPOLOGY: linear (ii) MOLECULE TYPE: DNA (genomic)

(xi) SEQUENCE DESCRIPTION: SEQ ID NO: 50:

```
CAAAAAATCA AAGGGAAGNT GGAACCCCTG CCCACCTCTC CATTCCCCAT TCTGCTGGTG      60

GTGNCTGCTC TTCCTCACAG TACCTCCTGA AAAGTTCAGA ATTCAGTTAA TACAGAATTA     120

TTGGGTTGAT TTTCAACGTG TAGTTTAAGA TGAAGAGTTC CGNTTGGTTT AAACCACTTC     180

ACCTAACCTC TTGGTAACGG TAGTCCTGAG AGTTCGCAGT GTCANTGAAA ATCGTCCTGT     240

GACCACGCGT CAAGCTGCTG ATGGGGGACA GAAACTTCCG GGNCTATCAT ATCTCCTTGA     300

NCTCGGCCCT CAAATCTGGT AGTTTCTGCA CCGAGGGACA CAGTCCACTG CGATGAAGTA     360

TGTTCAAAAT CGNTTTCTTT AGGGAACTCC TTCCAAAGTC CAATAGTGNA AGGTGGTCAA     420

GGAAGGATTT GGAAGGAAGN TGNAAAAGTC AGNCGGGAAT CTTGATTTGG NTAGNTGTGG     480

ANANAGGAAA TCACTTGGCC                                                500
```

(2) INFORMATION FOR SEQ ID NO: 51:

(i) SEQUENCE CHARACTERISTICS:
        (A) LENGTH: 105 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 51:

```
GGAAAGAGGT CTCCTAACAC CCAGACAGTG TAAAAATCCA GTTTTTCTTC CTTTTGGNNG      60

GAGACAGAGT CTCGCACTGT AGCTCAGGCT GGAGTGCAGT GGCAC                    105
```

(2) INFORMATION FOR SEQ ID NO: 52:

(i) SEQUENCE CHARACTERISTICS:
        (A) LENGTH: 386 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 52:

```
AGTCCCAGCT ACTCAGGAGG CTGGGGCAGG AAGATAGCTT GAGCCTGGGA GTTAGAGGCT      60

GTGTGAGCTA TGATCACACT ACTGCACTCC AGCCTGGGCA ACACAGCAAG ACCCTAAAAC     120

TAAAAAAGAA AAGAAAAAAA AAATATATGT ACGTATTTTG GAATTTCAAA GTGGGAGATA     180

AATCATTTTT CCAGACAGTA TCTGAAACCC AAAGTTTATG CTTAAATAAA GGTGTGCTTT     240

CTTTCACCTT CAAAGCGGGA GAAGAATCAT CATACACACA CACACACTTA TACATACACA     300

TATATACAAA ATACATTTTT TAATACACAC ATATAAACAT GGAGTATAGG CATAACACAC     360

TGTTGCTTGA TAAAATATAG GGATCC                                         386
```

(2) INFORMATION FOR SEQ ID NO: 53:

(i) SEQUENCE CHARACTERISTICS:
        (A) LENGTH: 377 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 53:

```
TATATTTNAT CAAGCAACAG TGTGTTATGC CTATACTCCA TGTTTATATG TGTGTATTAA      60
AAAATGTATT TGTATATATG TGTATGTATA AGTGTGTGTG TGTGTATGAT GATTCTCCTC     120
CCGNTTGAAG GTGAAAGAAA GCACACCTTT ATTTAAGCAT AAACTTTGGG TTTCAGATAC     180
TGTCTGGAAA AATGATTTAT CTCCCACTTT GAAATTCCAA AATACGTACA TATATTTTTT     240
TTTTCTTTTC TTTTTTAGTT TNAGGGTCTT GCTGTGTTGC CCAGGCTGGA GTGCAGTAGT     300
GTGATCATAG NTCACACAGG CTCTAACTCC CAGGNTCAAG CTATCTTCCT GCCCCAGNCT     360
CCTGAGTAGG TGGGACT                                                    377
```

(2) INFORMATION FOR SEQ ID NO: 54:

(i) SEQUENCE CHARACTERISTICS:
        (A) LENGTH: 521 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 54:

```
CTGCAGTAAG CCACGTTCAT GCCACTGTAC TCTAGCGTGG ATGACAGAGA GAGATCCTGT      60
CTTTGGAAGA AAAAAACAAA AGAAAAAAA AAAGAGTATG GCCATGGCCT TATAATATAG      120
AAGGGGTCAC ATATTAATCT CTGAAAATGG ATCTCTTGTG GGCTTTCATA CAAGGCAACA     180
GCCACAGAGT ACGTACCTGA AAGCTGCCTG GGNTTAATGG CTGGNAGTAT GTTCTAACTN     240
GTTCAGGNAC CCATGTCACN ACTGGTGGTT ACAGAATGTG AATCTCACAC TGTCCNAAAT     300
CGGTTTTATT TTTAAAANGA ATAATTCTAN TACATTACCT TATAAAAAGT AGGTAACCTA     360
ATTTTGGNTT TTAAAAGTGA ATTGAGGGCA GATGCAAGTG GNTCACACCT ATTAATCCCA     420
AATACCTTGG AGAGGGCAAG GTAGGAGGAT TGGTTGGAGC CCAGGAGTCC AAAGACCAGG     480
CTAGGGAATA TTGNAAGAAN GTCCTCTCTA CAANAAANAA T                         521
```

(2) INFORMATION FOR SEQ ID NO: 55:

(i) SEQUENCE CHARACTERISTICS:
        (A) LENGTH: 516 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 55:

```
CTGCANGAAG CTTTTNTTNC TTTTNGGNGG AGACAGAGTC TTGCTGTGTC ANCCCAGGCT      60
GGGGTGCAGT GGNACAGTCA TAGCTCACTG CAACCTTGAA CTCCCTGGNT CATGCGATCC     120
TCCCACTTCA GCCTCTCAAG TAGCTAGAAC TACAGGTGTG CACCACCATG CCTGACTAAC     180
TTGTTTATTN GNGGGAGAGA GAACGNTCTT GCTATATTGC CTAGGCTGGT CNTTGAACTC     240
TTGGGNTNCA AGCAATCCTC CTACCTTGGC CTCTNCAAGG TANTTGGGAT TNATAGGTGT     300
GAGCCACNTG CATCTGGCCT CAATTCACTT TTAAAATNCA AAATTAGGTT ACCTACTTTT     360
TATAAGGTAA TGTATTAGAA TTATTCTTNN NAAAAATAAA ACCGATTTGG GAAAGNGTGA     420
GANTCACATT CTGTAACCAC CAGTGGTGAA ATGGGTCCCC GAACAAGGTA GAACATACTC     480
CCAGCCATTA ACCCCAGGGA GNGTTCAAGT CCGTNC                               516
```

(2) INFORMATION FOR SEQ ID NO: 56:

(i) SEQUENCE CHARACTERISTICS:
        (A) LENGTH: 505 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 56:

```
GGATCCTGTT TCTTAAAACA GAAAAAAATT TACTGATAGN ACATTGTTCT AAGTGTATTA      60

TTGTATTAAA TGGATCATTT AATTTAATCT TCATAACTGA CATAGGAGTT GAGTAACTTG     120

TGTGGTCAAA TAGCTAGTAA GTGATGAGTA GGCTGGGCGC AGTGGNTCAA GCCTGTAATC     180

CCAGCACTCT GGGAGGCTGA GGCAGGCAGA TCACTTGAGG TCAGGAGTTT GAGACCAGCC     240

TGGCCAACAT GGNAAAACCT CGTCTCTACT AAAAATACAA AAATTAGCTG GGCGTGGTGG     300

GTGCGCACTT GTAGTCCCAG CTACTCGGAA GGGTTGAGGC AGGAGGAATC GCTTGGTCCC     360

CGGGAGGGAG AGGTTGNTNG TGNAGCTGAG ATCACGCCAC TNGCACTCCA GGCTGGGNAA     420

CAAAAGGGAG ACCTTTNCTC AAAAAAAAAT NAAAATAAAA AGTGATGAGT AGGATTGGGA     480

CCCNAGACAT CTTTTCTCCA AGACC                                          505
```

(2) INFORMATION FOR SEQ ID NO: 57:

(i) SEQUENCE CHARACTERISTICS:
        (A) LENGTH: 500 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 57:

```
CTGCAGNCTC AAACCCTTGT CCTGGGATCA ACAATCCTC CCACCTCAGC CTTCAAAGTA      60

GATAGAACTA CAGGCATGCA CTACCATGCC TAATTTTTTA AAAAAAAATT TTTTTTCAGA    120

GATGAGATCT CACTGTGTTT CCCAGGNTTG TCCGGAACTC CTGGACTCAA GCGATCCTCC    180

CACCTTGGGC TGCCAAAGTG TTGGGATTAC AGGCATGAGC CACCATGCCT GGCCATACAC    240

TTTTTTTTTT TTTTTAANCA AGACGGAGTC TNGTTCTGTC GCCCAGACTG GAGTGCAGGG    300

GCGTNNATCT TGGCTCACTT GAAAGCTTCG CCTCCCAGGG TTCATGCCGT TCTCCTGNCT    360

CAGCCTCCCA AGTNGGTGGG ACTACAGGNA TCTGCACCAC GNCCGGTTAT TTNTTGGGTT    420

TGNNGNAGGG ACGGGGTTTC ACCATGTTAG GCAGGATGAC TTCGGACTTC CNGACCCAAG    480

ATCACCCTGC TCGGCTCCCA                                               500
```

(2) INFORMATION FOR SEQ ID NO: 58:

(i) SEQUENCE CHARACTERISTICS:
        (A) LENGTH: 440 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 58:

```
GAATTCCAGA CGAGCCTGGG CAACACAGTG AGACTCTATC ACTACAAAAA AATTTTAAAA     60

TTAGCTAAAG TTGATGGNAC ATGCCTGCAG TCCCAGCTAC TCAGGAGGCT GGGGCAGGAA    120
```

-continued

```
GATAGCTTGA GCCTGGGAGT TAGAGGCTGT GTGAGCTATG ATCACACTAC TGCACTCCAG      180

CCTGGGCAAC ACAGCAAGAC CCTAAAACTA AAAAGAAAA GAAAAAAAAA ATATATGTAC      240

GTNTTTGGGG AATTTCAAAG TGGGAGATAA ATCATTTTTC CAGACAGTNT CTTGAAACCC      300

AAAGTTTATG CTTAAATAAA GGTGTGCTTT CTTTCACCTT CAAANGCGGG AGAAGGATCA      360

TCATNCACAC ACACACACTN ATCATNCACA TTTTTACAAA TNCAATTNNN NAATACAACA      420

CATTTTAACA TGGGGTTTTG                                                 440
```

(2) INFORMATION FOR SEQ ID NO: 59:

(i) SEQUENCE CHARACTERISTICS:
        (A) LENGTH: 513 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 59:

```
GGATCCTGTT TCTTAAAACA GAAAAAAATT TACTGATAGN ACATTGTTCT AAGTGTATTA       60

TTGTATTAAA TGGATCATTT AATTTAATCT TCATAACTGA CATAGGAGTT GAGTAACTTG      120

TGTGGTCAAA TAGCTAGTAA GTGATGAGTA GGCTGGGCGC AGTGGCTCAA GCCTGTAATC      180

CCAGCACTCT GGGAGGCTGA GGCAGGCAGA TCACTTGAGG TCAGGAGTTT GAGACCAGCC      240

TGGCCAACAT GGNAAAACCT CGTCTCTACT AAAAATACAA AAATTAGCTG GGCGTGGTGG      300

NTGCGCACTT GTAGTCCCAG CTACTCGGAA GGCTNGAGGC AGGAGGAATC GCTTGATCCC      360

NGGGAGGGAG AGGTTGGTNG TGANGCTGAG ATCACGNCAC TTGNACTCCA GNCTGGGNAA      420

CAAANGNGAG ATCTTNTCTC AAAAAAAAAT AAAANTAAAA NGTGATGAGT AGGATTTGGA      480

CCCCAGACAT CCTNTCTCCA GGACCTGGNA TTC                                  513
```

(2) INFORMATION FOR SEQ ID NO: 60:

(i) SEQUENCE CHARACTERISTICS:
        (A) LENGTH: 390 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 60:

```
GAATTCCTGG NCTCAAGTGA TCCTCTCACC TCAGCCTCCC AAATTGCTGG GATTAGAGTG       60

TGAGCCACTG TGCCTAGCCT GCATATATCT ATTTTTAATG ACTGCTAAAT CTCATTGTAT      120

GAAAATTTAT GTCCTAGCTA TAAAATTTGN TAGCACATGT TTAATTTTTT CTAATTTCAG      180

ATGTTTTAAA CTAATATTTC CCAAAGTATA GTATGGCATT TTAGGTATGA TATGATCTTT      240

NNTCCTCTTC GTACTCATTT TTATAGTTAT GGCCTGTGCA ACTGGTTTCC CATTTATATG      300

AATGATACAG AGCTTCCTAT TAAGAAAAAG TTCAGCTTGG GGAAAAAAAA AGTGAATTGT      360

CAACTTNGAG GGAAAAAAGT GAATTATTGG                                      390
```

(2) INFORMATION FOR SEQ ID NO: 61:

(i) SEQUENCE CHARACTERISTICS:
        (A) LENGTH: 366 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 61:

| | | | | | |
|---|---|---|---|---|---|
| TCAAGTACCT | CCCTGAATGG | ACTGCGTGGC | TCATCTTGGC | TGTGATTTCA | GTATATGGTA | 60
| AAACCCAAGA | CTGATAATTT | GTTTGTCACA | GGAATGCCCC | ACTGGAGTGT | TTTCTTTCCT | 120
| CATCTCTTTA | TCTTGATTTA | GAGAAAATGG | TAACGTGTAC | ATCCCATAAC | TCTTCAGTAA | 180
| ATCATTAATT | AGCTATAGTA | ACTTTTTCAT | TTGAAGATTT | CGGCTGGGCA | TGGTAGCTCA | 240
| TGCCTGTAAT | CTTAGCACTT | TGGGAGGCTG | AGGCGGGCAG | ATCACCTAAG | CCCAGAGTTC | 300
| AAGACCAGCC | TGGGCAACAT | GGCAAAACCT | CGTATCTACA | GAAAATACAA | AAATTNGNCG | 360
| GGNATG     |            |            |            |            |            | 366

(2) INFORMATION FOR SEQ ID NO: 62:

(i) SEQUENCE CHARACTERISTICS:
        (A) LENGTH: 498 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 62:

| | | | | | |
|---|---|---|---|---|---|
| AACACCAGGG | NCATGAGGGC | ACTAATCATA | ATGAGATATG | CCTGCTGGAG | TCGAAGTGGA | 60
| CCTTTCCAGT | GAATGGAAAT | CATTCCCACC | ACACCAAAAT | TCCAGATCAG | GAGTGNAACA | 120
| GTAATGTAGT | CCACAGCAAC | GTTATAGGTT | TTAAACACTT | CCCTGAAAAA | AAATTACACA | 180
| GATTTTAAAA | GATGTACAAT | AATTTCCACC | AAAACATTAT | TTAGAATAAT | GTGATGGCTC | 240
| CCAAACATTA | GATATTAATN | TCCCACCTTT | ATAATTTTAC | CATAACCTAT | ATCAACTGTG | 300
| CTATTATTTA | TTTAATNCTT | CCCTNTAAAT | TAATTTACTC | TTTTTTTGTT | TTTGTTTTTG | 360
| NGTTTGGAGC | CAGTGTCTCA | TTTTGGTTGC | CCAGGCTTGG | AGTAAAGTGG | GTGCAATCAC | 420
| GGCTCAACTG | NAGTCTTTNC | CTCCNGGAGA | TCAGGTNGGT | CTTCCCCAGG | TCCAANCTCC | 480
| TAAGTTGGTT | NGGANAAC   |            |            |            |            | 498

(2) INFORMATION FOR SEQ ID NO: 63:

(i) SEQUENCE CHARACTERISTICS:
        (A) LENGTH: 469 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 63:

| | | | | | |
|---|---|---|---|---|---|
| TAAACAACAG | GGNCATGAGG | GCACTAATCA | TAATGAGATA | TGCCTGCTGG | AGTCGAAGTG | 60
| GACCTTTCCA | GTGAATGGAA | ATCATTCCCA | CCACACCAAA | ATTCCAGATC | AGGAGTGAAA | 120
| CAGTAATGTA | GTCCACAGCA | ACGTTATAGG | TTTTAAACAC | TTCCCTGAAA | AAAAATTACA | 180
| CAGATTTTAA | AAGATGTACA | ATAATTTCCA | CCAAAACATT | ATTTAGAATA | ATGTGATGGC | 240
| TCCCAAACAT | TAGATATTAA | TNTCCCACCT | TTATAATTTT | ACCATAACCT | ATATCAACTG | 300
| TGCTATTATT | TATTTAATNC | TTCCCTCTAA | ATTAATTTAC | TCTTTTTTTG | TTTTTGTTTT | 360
| TGTGTTTGGA | GCCAGTGTCT | CATTTTGGTT | GCCCAGGCTT | GGAGTAAAGT | GGGTGCAATC | 420
| ACGGCTCAAC | TGNAGTCTTT | ACCTCCCGGA | GATCANGTTG | GTCTTTCCC  |            | 469

(2) INFORMATION FOR SEQ ID NO: 64:

(i) SEQUENCE CHARACTERISTICS:
        (A) LENGTH: 370 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 64:

```
GTTTATCAAG TACCTCCCTG AATGGACTGN GTGGCTCATC TTGGCTGTGA TTTCAGTATA      60

TGGTAAAACC CAAGACTGAT AATTTGTTTG TCACAGGAAT GCCCCACTGG AGTGTTTTCT     120

TTCCTCATCT CTTTATCTTG ATTTAGAGAA AATGGTAACG TGTACATCCC ATAACTCTTC     180

AGTAAATCAT TAATTAGCTA TAGTAACTTT TTCATTTGAA GATTTCGGCT GGGCATGGTA     240

GCTCATGCCT GTAATCTTAG CACTTTGGGA GGCTGAGGCG GGCAGATCAC CTAAGCCCAG     300

AGTTCAAGAC CAGCCTGGGC AACATGGCAA AACCTCGTAT CTACAGAAAA TACAAAAATT     360

AGCCNGGNAT                                                           370
```

(2) INFORMATION FOR SEQ ID NO: 65:

(i) SEQUENCE CHARACTERISTICS:
        (A) LENGTH: 316 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 65:

```
GTCATGGTGT TGGCGGGGAG TGTCTTTTAG CATGCTAATG TATTATAATT AGCGTATAGT      60

GAGCAGTGAG GATAACCAGA GGTCACTCTC CTCACCATCT TGGTTTTGGT GGGTTTTGGC     120

CAGCTTCTTT ATTGCAACCA GTTTTATCAG CAAGATCTTT ATGAGCTGTA TCTTGTGCTG     180

ACTTCCTATC TCATCCCGNA ACTAAGAGTA CCTAACCTCC TGNAAATTGA AGNCCAGNAG     240

GTCTTGGCCT TATTTNACCC AGCCCCTATT CAAAATAGAG TNGTTCTTGG NCCAAACGCC     300

CCTGACACAA GGATTT                                                    316
```

(2) INFORMATION FOR SEQ ID NO: 66:

(i) SEQUENCE CHARACTERISTICS:
        (A) LENGTH: 448 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 66:

```
CTGCAGNCCG GGGGATCCTG GTAAAAGTCA CAAGGTCAGC CTACTAAAGC AGGGAAAACT      60

AAAGGCAAGT AAACACGTGC AGACAAAAAA AGGGATAAAG AAAAGGAATT AAGAAACTAG     120

CATTTTTAAN GTGGGGGAGG TGAATGCTTC CCAGAATGGG TTTATATCAC TTGCTTGNGG     180

GCCTTCTGAG TGTTGGNAAC AACCTGTCAT CATCACACAT ACCTGTCATC TTTAATGGTC     240

TCCATACATT ACTAATAGAT TATACAGATG GCCATCACTT AACACTTCCA CTCACTCAAT     300

TTGTNCAACA TGCAAGGTTA CCCTCTTTTT TNGCTTACNG CCACAAAGCA TTGGANAAGG     360

TTTGTGATTT TTACTAGCCN CCACTTCATC AAATTTAAGC ATTTTCTTTT TCCTNTTAAC     420

ANCCAGGACA GGNTTNAACN AAGGAAAT                                       448
```

(2) INFORMATION FOR SEQ ID NO: 67:

(i) SEQUENCE CHARACTERISTICS:
        (A) LENGTH: 450 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 67:

```
CTGCAGCTCC AAGCACCTTT TTCAAATTCA GCTTTCTGTG ATTTCAGACC ACATATGCAA      60
GGAACTATCT TACCTTAATT AATAAGACTT TAAAATCCTT GTGTCAGAGG CGTTTGGACC     120
AGAGCAACTC TATCTTGAAT AGGGGCTGGG TAAAATAAGG CCAAGACCTA CTGGGCTGCA     180
TTTGCAGGAG GTTAGGTACT CTTAGTTACG GGATGAGATA GGAAGTCAGC ACAAGATACA     240
GCTCATAAAG GATCTTGCTG ATAAAACTGG TTGCAATAAA GAAGCTGGNC AAAACCCACC     300
AAAACCAAGA TGGTGAGGAG AGTGACCTCT GGTTATCCTC ACTGNTCACT ATACGNTAAT     360
TATTATACAT TAGCATGCTA AAAGACACTC CCCGCAACAA CCATGANAGG TTTACAAGTT     420
NCCATGGNAA CGNNCCCGGA NGNTANCTTG                                      450
```

(2) INFORMATION FOR SEQ ID NO: 68:

(i) SEQUENCE CHARACTERISTICS:
        (A) LENGTH: 388 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 68:

```
CTGNAGCCTC CACCACCCAG GTTCAGGTGA TTCTCCTGCC GTAGNCTCAT GAGTAGNTGG      60
GATTACAGGC ATGTGCCACC ATGCCCGACT AATTTTTATA TTTTTAGTAG AGACGGGGTT     120
TCACCATGTT GGGCAGGCTG GTCTCAAACT CCTGACCTCA AGTGATCTGC CCACCTTGGC     180
CTCCCAAAGT GCTGGGATTT CAGGCGCCTG GCCTGTTACT TGATTATATG CTAAACAAGG     240
GGTGGATTAT TCATGAGTTT TCTGGGAAAG AGGTGGGCAA TTCCCGGAAC TGAGGGATCC     300
CTCCCCTTNN NAGACCATAC AAGGTAACTT CCGGACGTTG GCATGGNATC TTGTTAAACT     360
TGTCATGGNG TTGGGGGGA GTGTCTTT                                         388
```

(2) INFORMATION FOR SEQ ID NO: 69:

(i) SEQUENCE CHARACTERISTICS:
        (A) LENGTH: 500 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 69:

```
CTGCAGAAGT ATGTTTCCTG TATGGTATTA CTGGATAGGG CTGAAGTTAT GCTGAATTGA      60
ACACATAAAT TCTTTTCCAC CTCAGGGNCA TTGGGCGCCC ATTGCTCTTC TGCCTAGAAT     120
ATTCTTTCCT TTTCTAACTT TGGTGGATTA AATTCCTGTC ATCCCCCTCC TCTTGGTGTT     180
ATATATAAAG TNTTGGTGCC GCAAAAGAAG TAGCACTCGA ATATAAAATT TTCCTTTTAA     240
TTCTCAGCAA GGNAAGTTAC TTCTATATAG AAGGGTGCAC CCNTACAGAT GGAACAATGG     300
```

```
CAAGCGCACA TTTGGGACAA GGGAGGGGAA AGGGTTCTTA TCCCTGACAC ACGTGGTCCC        360

NGCTGNTGTG TNCTNCCCCC ACTGANTAGG GTTAGACTGG ACAGGCTTAA ACTAATTCCA        420

ATTGGNTAAT TTAAAGAGAA TNATGGGGTG AATGCTTTGG GAGGAGTCAA GGAAGAGNAG        480

GTAGNAGGTA ACTTGAATGA                                                    500
```

(2) INFORMATION FOR SEQ ID NO: 70:

(i) SEQUENCE CHARACTERISTICS:
        (A) LENGTH: 435 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 70:

```
CTGCAGAGTA ATTGCAACTG GAGTTGTCTT AAGATAATGT CACATATCCA TCTTCCCCTT         60

GTTTCTCATT CACAGAAAAA CATTTTTATT CCAGGTGCCA ATATTCCCAG CCAAAAAGAC        120

TTTACTTCTG ACTCCCTTAT ATTTAGGATG GCTATGAGAA CAAGTAAGGG CAATGACTTC        180

TAGGGAGATG TGTTGTGTAT GGAACTTCTA AGGAGAGAAT TCTGCTGACA TGTCCTATGT        240

TCTTTTCTCC CCTACTCCTT CCTACTGTCA GAAATGAAGG CTAGGGCTCC AGCCTGGACC        300

CTGAAGTAAG CTAGAGGTTA GAAGCTAAAG AAGAAAGAAG GAGATTGAGT CCTTGGATGA        360

ACGTGAAGCC ACCCTACTAA TCTGGACTGN CTACCTCTGN ACTACTCTAT GAGAGAGAAA        420

GTATGTGCAT TATTT                                                         435
```

(2) INFORMATION FOR SEQ ID NO: 71:

(i) SEQUENCE CHARACTERISTICS:
        (A) LENGTH: 439 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 71:

```
CATGCTCTTT GTCCCTGTGA CTCTCTGCAT GGTGGTGGTC GTGGNTACCA TTAAGTCAGT         60

CAGCTTTTAT ACCCGGAAGG ATGGGCAGCT GTACGTATGA GTTTGGTTTT ATTATTCTCA        120

AAGCCAGTGT GGCTTTTCTT TACAGCATGT CATCATCACC TTGAAGGCCT CTGCATTGAA        180

GGGGCATGAC TTAGCTGGAG AGCCCATCCT CTGTGATGGT CAGGAGCAGT TGAGAGAGCG        240

AGGGGTTATT ACTTCATGTT TTAAGTGGAG AAAAGGAACA CTGCAGAAGT ATGTTTCCTG        300

TATGGTATTA CTGGATAGGG CTGAAGTTAT GCTGAATTGA ACACATAAAT TCTTTTCCAC        360

CTCAGGGGCA TTGGGCGCCC ATTGNTCTTC TGCCTAGAAT ATTCTTTCCT TTNCTNACTT        420

GGGNGGATTA AATTCCTGT                                                     439
```

(2) INFORMATION FOR SEQ ID NO: 72:

(i) SEQUENCE CHARACTERISTICS:
        (A) LENGTH: 318 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 72:

```
TCCATCTCTA CGACTCTCAT GGGGTCCAAA GAAGAGTTTT AATTGAGTTT TAGAATGTGN        60

AGTTGTGAAG TGTCTGAAAA ACTACATGGT GNTCTGAAAG NCAAACTTTT AGCCTTGGGG       120

GAGAGCATCT AAGACAGNAG GTGAAGGGGA GGGGTTAGAN CTAGAGGGAT TGAAGAATAT       180

TATCCATATA GGTTAGGGTT AGGTGTGGCA ACGTTTTATA GAACAAACAT TGGNAAGCTA       240

CAGACACAGG CCAGNTCTGT CTNCTACCTN TCCACAAAGG TGTNATAACA AAGTTANNCA       300

CAAATGTGTG AATAAACT                                                    318
```

(2) INFORMATION FOR SEQ ID NO: 73:

(i) SEQUENCE CHARACTERISTICS:
        (A) LENGTH: 450 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 73:

```
GTTGCAAAGT CATGGATTCC TTTAGGTAGC TACATTATCA ACCTTTTTGA GAATAAAATG        60

AATTGAGAGT GTTACAGTCT AATTCTATAT CACATGTAAC TTTTATTTGG ATATATCAGT       120

AATAGTGCTT TTTCNTTTTT TTTTTTTNTT TTTTTTNNTT TTNGGGGANA GAGTCTCGCT       180

CTGTCGCCAG GTTGGAGTGC AATGGTGCGA TCTTGGCTCA CTGAAAGCTC CACCNCCCGG       240

GTTCAAGTGA TTCTCCTGCC TCAGCCNCCC AAGTAGNTGG GACTACAGGG GTGCGCCACC       300

ACGCCTGGGA TAATTTTGGG NTTTTTAGTA GAGATGGCGT TTCACCANCT TGGNGCAGGC       360

TGGTCTTGGA ACTCCTGANA TCATGATCTG CCTGCCTTAG CCTCCCCAAA GTGCTGGGAT       420

TNCAGGGGTG AGCCACTGTT CCTGGGCCTC                                       450
```

(2) INFORMATION FOR SEQ ID NO: 74:

(i) SEQUENCE CHARACTERISTICS:
        (A) LENGTH: 489 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 74:

```
CTGCAGNTGA GCCGTGATTG CANCCACTTT ACTCCNAGCC TGGGCAANCA AAATGAGACA        60

CTGGCTNCAA ACACAAAAAC AAAAACAAAA AAAGAGTAAA TTAATTTAAA GGGAAGTATT       120

AAATAAATAA TAGCACAGTT GATATAGGTT ATGGTAAAAT TATAAAGGTG GGATATTAAT       180

ATCTAATGTT TGGGAGCCAT CACATTATTC TAAATAATGT TTTGGTGGAA ATTATTGTAC       240

ATCTTTTAAA ATCTGTGTAA TTTTTTTTCA GGGAAGTGTT TAAAACCTAT AACGTTGCTG       300

TGGACTACAT TACTGTTGCA CTCCTGATCT GGAATTTTGG TGTGGTGGGA ATGATTTCCA       360

TTCACTGGAA AGGTCCACTT CGACTCCAGC AGGCATATCT CATTATGATT AGTGCCCTCA       420

TGGCCCTGGT GTTTATCAAG TACCNCCCTG AATGGACTGG GTGGCTCATC TTGGCTGTGA       480

TTTCAGTAT                                                              489
```

(2) INFORMATION FOR SEQ ID NO: 75:

(i) SEQUENCE CHARACTERISTICS:
        (A) LENGTH: 449 base pairs
        (B) TYPE: nucleic acid (C) STRANDEDNESS: single
        (D) TOPOLOGY: linear (ii) MOLECULE TYPE: DNA (genomic)

(xi) SEQUENCE DESCRIPTION: SEQ ID NO: 75:

| | | |
|---|---|---|
| CTGCAGNCTT GACCTCCTGG GATCAATCGA TCCTCCCACC TCAGCCTCCT AAGTAGCTGG | 60 |
| AACTACAGGT GTGCACCACC ATGCCCGGCT AATTTTTGTA TTTTCTGTAG ATACGAGGTT | 120 |
| TTGCCATGTT GCCCAGGCTG GTCTTGAACT CTGGGCTTAG GTGATCTGCC CGCCTCAGCC | 180 |
| TCCCAAAGTG CTAAGATTAC AGGCATGAGC TACCATGCCC AGCCGAAATC TTCAAATGAA | 240 |
| AAAGTTACTA TAGCTAATTA ATGATTTACT GAAGAGTTAT GGGATGTACA CGTTACCATT | 300 |
| TTCTCTAAAT CAAGATAAAG AGATGAGGAA AGAAAACACT CCAGTGGGGC ATTCCTGTGA | 360 |
| CAAACAAATT ATCAGTCTTG GGTTTTACNA TATACTGAAA TCACAGCCAA GATGAGCCAC | 420 |
| GCAGTCCATT CAGGGAGGTA CTTGATAAA | 449 |

(2) INFORMATION FOR SEQ ID NO: 76:

(i) SEQUENCE CHARACTERISTICS:
        (A) LENGTH: 490 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 76:

| | | |
|---|---|---|
| TTCTTGCCGT TCCCGACCCG AGCCTGGTGC CCCTTCCCCA TTATGATCCT TNTCGCTTCC | 60 |
| GGCGGCATCG GGATGCCCCG CGTTGCAGGC CATNCTGTCC CAGNCAGGTA GATGACGACC | 120 |
| ATCAGGGACA GCTTCAAGGA TCGCTCGCGG CTCTTACCAG CCTAACTTCG ATCATTGGAC | 180 |
| CGCTGATCGT CACGGCGATT TATCCCGCCT CGGCGAGCAC ATGGAACGGG TTGGCATGGA | 240 |
| TTGTAGGCGC CGCCCTATAC CTTGTCTGCC TCCCCCGCGT TGCGTCGCGG TGCATGGAGC | 300 |
| CGGNCCACCT CGACCTGAAT GGAANCCGGC GGCACCTCGC TAACGGATTC ACCACTCCAA | 360 |
| GAATTGGAGC CAATCAATTC TTGCGGAGAA CTGTGAATGC NCAAACCAAC CCTTGGCAGA | 420 |
| ACATATCCAT CGCGTCCGCC ATCTCCANCA GCCGCACGCG GCGCATCTCG GGCAGCGTTG | 480 |
| GGTCCTGCAG | 490 |

(2) INFORMATION FOR SEQ ID NO: 77:

(i) SEQUENCE CHARACTERISTICS:
        (A) LENGTH: 470 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 77:

| | | |
|---|---|---|
| CTGCAGTGTT TAAAAAATAA AATAAACTAA AAGTTTATTT ATGAGGAGTA CACTGCTTTC | 60 |
| TTGTAAACAC ATGTACAAGC CATATAATAG AGTTCATTTC NNACCCTAGT TACGGAAACA | 120 |
| CTAGAAAGTC TNCACCCGGC CAAGATAACA CATCTTTAGG TAAAAATAGC AAGAAATATT | 180 |
| TTATGGGTTG TTTACTTAAA TCATAGTTTT CAGGTTGGGC ACAGTGGNTC ATGCCTGTAA | 240 |
| TCCCAGCACT TTATGCGGCT GAGGCAGGCA GATCAGTTGA GGTCAGAAGT TTGAGACCAG | 300 |
| CCTGGGCAAT GTGGCAAAAC CTCATCTCCA CTAAAAATAC AAAAATTAGC CAGGCATGGT | 360 |

```
GGTGCACACA TGTTAATTCC CAGCTACTTG GGAGGNTTGA GACAGGAGGG TCGCTTGGNC    420

CTAGGAGGGA AGAAGTTGNA GGGANCTTAA TGTCACTGCA CTCTAGNTTG              470
```

(2) INFORMATION FOR SEQ ID NO: 78:

(i) SEQUENCE CHARACTERISTICS:
        (A) LENGTH: 445 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 78:

```
CACTCAATTC TGAATGCTGC CATCATGATC AGTGTCATTG TTGTCATGAC TANNCTCCTG    60

GTGGTTCTGT ATAAATACAG GTGCTATAAG GTGAGCATGA GACACAGATC TTTGNTTTCC   120

ACCCTGTTCT TCTTATGGTT GGGTATTCTT GTCACAGTAA CTTAACTGAT CTAGGAAAGA   180

AAAAATGTTT TGTCTTCTAG AGATAAGTTA ATTTTTAGTT TTCTTCCTCC TCACTGTGGA   240

ACATTCAAAA AATACAAAAA GGAAGCCAGG TGCATGTGTA ATGCCAGGCT CAGAGGCTGA   300

GGCAGGAGGA TCGCTTGGGC CCAGGAGTTC ACAAGCAGCT TGGGCAACGT AGCAAGACCC   360

TGCCTCTATT AAAGAAAACA AAAAACAAAT ATTGGAAGTA TTTTATATGC ATGGAATCTA   420

TATGTCATGA AAAAATTAGT GTAAA                                        445
```

(2) INFORMATION FOR SEQ ID NO: 79:

(i) SEQUENCE CHARACTERISTICS:
        (A) LENGTH: 496 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 79:

```
CCTGTATTTA TACTGAACCA CCAGGAGGAT AGTCATGACT ACAATGACNC TGATCATGAT    60

GGCAGCATTC AGAATTGAGT GCAGGGCTCT CTGGCCCACA GTCTCGGTAT CTTCTGTGAA   120

TGGGGTATAG ATTCTACAAT AAAACAAACA CAAAAGCCCT AGGTCAGTGT TAATGGAGAT   180

CACCAACCAC ATTACCACCT CCAACACAGA ATTTTCTTTT TCTTAATTCA ATTCGNATCT   240

TATAAGTCAC TTTTCCCCAA CTCACCAATN CTAGCTAAGA ATTTTTAACC TGAGAAAAAC   300

AGCTACACTC TAAAATTGCT TCAAAGAAAA TGTCTAACAT ATGGAAAGAA GGACTTAACA   360

TGTGAAGCAG ACACTGGCTC CATCTAGTGG GTGCTTTATA TTGAAATAAT TATAATACCT   420

CATCAAATTT TTTNGGGTAC AGNTTATTAG GAACTTGGTA TGGAACCAGA TTCTGCCACA   480

GAAACCACGN GGGCTG                                                  496
```

(2) INFORMATION FOR SEQ ID NO: 80:

(i) SEQUENCE CHARACTERISTICS:
        (A) LENGTH: 496 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 80:

```
CATTAGATAA TGGNTCAGGG TGGCCAAGGC TCCGTCTGTC GTTGTGCTCC TGCCGTTCTC    60
```

```
TATTGTCATT CTATAAGCAC AAGAAAAACA TTTTCAGTAA ATCAGATTCT CAGCAGAATC      120

AAGGTAACGG TTAGACCTGG GATTAACAAC AGACCCGTCA CTATGAGTTC TAAAAACCTG      180

AAGCAAGAAA AAACAATGTA CAGGAAGTAT GCAGTTTAAA AGTCTAGATT ATCTATCATT      240

GTTCACTGAA GGCATTCAGG TCCTCTCTTT TACCTGGGTC TTGGNTTGCT CCATTCTCTC      300

TGTTCATCCC AACATACACA ATTGTACTTA TCCTTTGAGA TGTACCTTAA ATACTGACAC      360

CTGCATGAAA ACTTGTTTAC TGGCTGCAGG TCCAAGCACC TTTTTCNAAA TTCAGCTTTC      420

TGTGATTTCA GACCACATAT GCAAGGAACT ATCTTACCTT AATTAATAAG ANTTTAAAAT      480

CCTTGTGTCA GAGGCG                                                     496
```

(2) INFORMATION FOR SEQ ID NO: 81:

(i) SEQUENCE CHARACTERISTICS:
        (A) LENGTH: 368 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 81:

```
AGGANCGCTT GGGCCCAGGA GTTCACAAGC AGCTTGGGCA ACGTAGCAAG ACCCTGCCTC       60

TATTAAAGAA AACAAAAAAC AAATATTGGA AGTATTTTAT ATGCATGGAA TCTATATGTC      120

ATGAAAAAAT TAGTGTAAAA TATATATATT ATGATTAGNT ATCAAGATTT AGTGATAATT      180

TATGTTATNN NGGGATTTCA ATGCCTTTTT AGGCCATTGT CTCAAAAAAT AAAAGCAGAA      240

AACAAAAAAA GTTGTAACTG AAAAATAAAC ATTTCCATAT AATAGCACAA TCTAAGTGGG      300

TTTTTGNTTG TTTGTTTGNT TGTTGAAGCA GGGCCTTGCC CTNCCACCCA GGNTGGAGTG      360

AAGTGCAG                                                              368
```

(2) INFORMATION FOR SEQ ID NO: 82:

(i) SEQUENCE CHARACTERISTICS:
        (A) LENGTH: 500 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 82:

```
GAATTCCTTT TTTTTTTTTT TTTTTTTTTT TTNCTCCTAA TGTTTTTATT GTNCCTTAGA       60

TAACTGGATA GNACAAAGTT NGNCTTNGTT TTTTACTTAA AAAACGTACT TTCCGCATAC      120

TGTNGCCCGT ATGACTTTCC TGTCCCATCG GAAACCAGAG TTTCCCCAGG TGAGCCCTTC      180

CTATCTGNGG NTACATGATT TAGCTAATTT AACAAGAAGA GAGTAATTCC TTNGGATTAT      240

TATCAACATG AAACTTGGAC TATGTCTCTA TAAGGGTGAA CACTGATTTT TTTTTTCTTT      300

TTAGAAACAA AAACCATCCA CTTATTAATC CAAACTACGG GATTGGATTT ACAACAATCA      360

TCGCATNAAC TGAACATACG AAGTTACCAC TCAAGGGAAT NACAGAAGAA CGTTGNACAA      420

TNTNTCTTAC GGGGTACGNG AATTCAAACA ATGTGGGGAN AGGAACTTCA NTCTACAAAN      480

TCTGACCATC GNTTCAGTAT                                                 500
```

(2) INFORMATION FOR SEQ ID NO: 83:

(i) SEQUENCE CHARACTERISTICS:
        (A) LENGTH: 450 base pairs (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 83:

GAATTCCTTT ACTCTTCTTT AATTCTACCG TCTTTGGGCA TACATCTCAT TTGNTGTGGA       60

AGAAGGTCTG ACAGNAGGGC TGACAGCACC GATTCATAAC ACATTCTTTT CATCATACAA      120

AGAGTAAGAC CCTAGAATAA TGGGACCATC TGCTACCACG ACAGAGCTGC CTTACTGGCT      180

GTAGAAAAAG ACTGCTTGTG TGGGAGAGAA GAATGAGGAC AGAGGAGGCA TCTGGGGCAA      240

GTGAGCGTAC AAGTATNTCT ACAAATTCAG AATTTGGTGG AAAATCCAAA TTTGNCTTCA      300

ACATGATAGA GAATTGATGA GAAAATAGCT GTNCTGTTTC CAAAATTTAC TGAATTTGGG      360

AACCTGAGGT TAAAACTTTT AGGATNAAGC AACTCAGGTT CAAGACTTNG NCTNGGGAAG      420

GAATGGAAAC ACAGACGGGA ATGAGTNTCA                                      450

(2) INFORMATION FOR SEQ ID NO: 84:

(i) SEQUENCE CHARACTERISTICS:
        (A) LENGTH: 450 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 84:

CAACTGTATT TATACAGNAA CCACCAGGAG GATAGTCATG ACAACAATGA CAAACTAGGA       60

ATAGCCCCCT TTCACTTCTG AGTCCCAGAG GTTACCCAAG GCACCCCTCT GACATCCGGC      120

CTGCTTCTTC TCACATGANA AAAACTAGCC CCCAGTNTGA TCCGCAGGTN GAGGAATNCC      180

CCGGGTCGAG GTTCGGATCC TGGATGACAG ACCCTCTCGC CCCTGAAGGN GATAACCGGG      240

TGTGGTACAT GGACGGNTAT CACAACAACC GCTTCGNACG TGAGTACAAG TCCATGGTTG      300

ACTTCATGAA CACGGACAAT TTCACCTCCC ACCGTCTCCC CCACCCCTGG TCGGGCACGG      360

GGNAGGTGGT CTNCAACGGT TCTTTCTNCT TCAACAAGTT CCAGAGCCAC ATCATCATCA      420

GGTTTGGACC TGAAGANAGA GAACATCCTC                                      450

(2) INFORMATION FOR SEQ ID NO: 85:

(i) SEQUENCE CHARACTERISTICS:
        (A) LENGTH: 500 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 85:

GGATCCCTCC CCTTTTTAGA CCATACAAGG TAACTTCCGG ACGTTGCCAT GGCATCTGTA       60

AACTGTCATG GTGTTGGCGG GGAGTGTCTT TTAGCATGCT AATGTATTAT AATTAGCGTA      120

TAGTGAGCAG TGAGGATAAC CAGAGGTCAC TCTCCTCACC ATCTTGGTTT TGGTGGGTTT      180

TGGCCAGCTT CTTTATTGCA ACCAGTTTTA TCAGCAAGAT CTTTATGAGC TGTATCTTGT      240

GCTGACTTCC TATCTCATCC CGTAACTAAG AGTACCTAAC CTCCTGCAAA TNGCAGCCCA      300

GTAGGTCTTG GNCTTATTTT ACCCAGCCCC TATTCAAGAT AGAGTTGCTC NTGGTCCAAA      360

CGCCTCTGAC ACAAGGATTT TAAAGTCTTA TTAATTAAGG TAAGATAGGT CCTTGGATAT      420

```
GTGGTCTGAA ATCACAGAAA GCTGAATTTG GAAAAAGGTG CTTGGAGCTG CAGCCAGTAA      480

ACAAGTTTTC ATGCAGGTGT                                                 500

(2) INFORMATION FOR SEQ ID NO: 86:

(i) SEQUENCE CHARACTERISTICS:
        (A) LENGTH: 500 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 86:

CTGCAGTGAG CCAAAATCGT GCCACTGCAC TTCACTCCAG CCTGGGTGAC AGGGCAAGGC       60

CCTGCTTCAA CAAACAAACA AACAAACAAA AACCCACTTA GATTGTGCTA TTATATGGAA      120

ATGTTTATTT TTCAGTTACA ACTTTTTTTG TTTTCTGCTT TTATTTGTTG AGACAATGGC      180

CTAAAAAGGC ATTGAAATNC CAAAATAACA TAAATTATCA CTAAATCTTG ATAACTAATC      240

ATAATATATA TATTTTACAC TAATTTTTTC ATGACATATA GATTCCATGC ATATAAAATA      300

CTTCCAATAT TTGTTTTTTG TTTTCTTTAA TAGAGGCAGG GTCTTGCTAC GTTGCCCAAG      360

CTGCTTGTGA ACTCCTGGGC CCAAGCGATC CTCCTGCCTC AGCCTCTGAG CCTGGCATTA      420

CACATGCACC TGGCTTCCTT TTTGTNTTTT TTGAATGTTC CACAGTGAGG AGGAAGAAAA      480

CTNAAAATTA ACTTATCTCT                                                 500

(2) INFORMATION FOR SEQ ID NO: 87:

(i) SEQUENCE CHARACTERISTICS:
        (A) LENGTH: 450 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 87:

CTGCAGATGA GAGGCACTAA TTATAAGCCA TATTACCTTT CTTCTGACAA CCACTTGTCA       60

GCCCACGTGG TTTCTGTGGC AGAATCTGGT TCTATAACAA GTTCCTAATA AGCTGTAGCC      120

AAAAAAATTT GATGAGGTAT TATAATTATT TCAATATAAA GCACCCACTA GATGGAGCCA      180

GTGTCTGCTT CACATGTTAA GTCCTTCTTT CCATATGTTA GACATTTTCT TTGAAGCAAT      240

TTTAGAGTGT AGCTGTTTTT CTCAGGTTAA AAATTCTTAG CTAGGATTGG TGAGTTGGGG      300

AAAAGTGACT TATAAGATAC GAATTGAATT AAGAAAAAGA AAATTCTGTG TTGGAGGTGG      360

TAATGTGGGT GGTGATCTTC ATTAACACTG ANCTAGGGNT TTGGGGTTTG GTTTATTGTA      420

GAATCTATAC CCCATTCANA GAAGATACCG                                      450

(2) INFORMATION FOR SEQ ID NO: 88:

(i) SEQUENCE CHARACTERISTICS:
        (A) LENGTH: 502 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 88:

CTGCAGCCAG TAAACAAGTT TTCATGCAGG TGTCAGTATT TAAGGTACAT CTCAAAGGAT       60
```

```
AAGTACAATT GTGTATGTTG GGATGAACAG AGAGAATGGA GCAAGCCAAG ACCCAGGTAA      120

AAGAGAGGAC CTGAATGCCT TCAGTGAACA ATGATAGATA ATCTAGACTT TTAAACTGCA      180

TACTTCCTGT ACATTGTTTT TTCTTGCTTC AGGTTTTTAG AACTCATAGT GACGGGTCTG      240

TTGTTAATCC CAGGTCTAAC CGTTACCTTG ATTCTGCTGA GAATCTGATT TACTGAAAAT      300

GTTTTTCTTG TGCTTATAGA ATGACAATAG AGAACGGCAG GAGCACAACG ACAGACGGAG      360

CCTTGGCCAC CCTGAGCCAT TATCTAATGG ACGACCCAGG GTAACTCCCG GCAGGTGGTG      420

GAGCAAGATG AGGAAGAAGA TGAGGAGCTG ACATTGAAAT ATGGCGGCNA GCATGTGATC      480

ATGCTCNTTG GCCCTGTGAN TC                                               502

(2) INFORMATION FOR SEQ ID NO: 89:

(i) SEQUENCE CHARACTERISTICS:
        (A) LENGTH: 499 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 89:

CTGCAGTGTT CCTTTTCTCC ACTTAAAACA TGAAGTAATA ACCCCTCGNT CTCTCAACTG       60

CTCCTGACCA TCACAGAGGA TGGGCTCTCC AGCTAAGTCA TGCCCCTTCA ATGNAGAGGC      120

CTTCAAGGTG ATGATGACAT GCTGTAAAGA AAAGCCACAC TGGGTTTGAG AATAATAAAA      180

CAAAACTCAT ACGTACAGCT GCCCATCCTT CCGGGTATAA AAGCTGACTG ACTTAATGGT      240

AGCCACGACC ACCACCATGC AGAGAGTCAC AGGGACAAAG AGCATGATCA CATGCTTGGC      300

GNCATATTTC AATGTCAGNT CCTCATCTTC TTCCTCATCT TGNTCCACCA CCTGCCGGGA      360

GTTACCNTGG GTCGTCCATT AGATAATGGG TCAGGGTGGC CAAGGCTCCG TCTGTCGTTG      420

TGCTCCTGCC GTTCTCTATT GTCATTCTAT AAGCACAAGA AAAACATTTN CAGTAAATCA      480

GATNCTCAGC AGAATCAAG                                                   499

(2) INFORMATION FOR SEQ ID NO: 90:

(i) SEQUENCE CHARACTERISTICS:
        (A) LENGTH: 500 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 90:

TAACTCCCAG GNTCAAGATN TCTNCCTGCG TTAGCCTCCT GAGTAGCTGG GACTATAGGT       60

ATGTGCCACT ATTCCTGAAA ACATAATCAG TTTTGAAGGT AGTGTCTGGG CTGGGCGCAG      120

TGGNTCACGC CTTCAATCCC AGCACTTTGG GAGGNCGAGG TGGGCGGATC ACCTGAGGTC      180

AGGAGTTCGA GACCAGCCTG ACCAACATGG GATAAGACTC CATCTCTACT AAAAATACAA      240

AAAATTAGCC AGGCATGGTG GNGCATGCCT GTAATCCCAG CTACTCAGGA GGNTGAGGNA      300

GGAGAATTGG TTGGAACCTA GGAAGCAGAG GCTGTGGTGG AGCCGAGATC GCACCATTGG      360

ACTCCAGGCT GGGNAACAAG AGTGAAAATC CNTCTTAAAA AAAAAAAAAA AAAGGTAGNG      420

TTTTGNCCGG NGCGGGGGGT CACGCCTGTA ATCCCAGNAT TGGGGANGGC AAGGNGGGGG      480

GTCANNANGN NAGNAGTCCG                                                  500
```

(2) INFORMATION FOR SEQ ID NO: 91:

(i) SEQUENCE CHARACTERISTICS:
        (A) LENGTH: 502 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 91:

```
GAATTCTGCT GACATGTCCT ATGTTCTTTT CTCCCCTACT CCTTCCTACT GTCAGNAATG      60
AAGGGTAGGG CTCCAGCCTG GACCCTGAAG TAAGCTAGAG GTTAGAAGCT AAAGAAGAAA     120
GAAGGAGATT GAGTCCTTNG ATGAACGTGA AGCCACCGTA CTAATCTGGA CTGCCTACCT     180
CTGCACTACT CTATGAGAGA GAAAGTATGT GCATTATTTA AACCAGTTGG GTTGATTTTC     240
TATTAACAAA GTCAGAAACA TCTCTGTAAA AAGCCAGACT GAATATTTTA AGCTCTATGG     300
GTCATATGGT CTCCAGGGCA AACACTCAAC TGTGCTACTG TAGTGTGAAA GCAGGCACAG     360
ACAATGTATT AACCAAGGAG GGTGGTCACT TTCCAATGAA AGTTTATCAC AAATTGGNGA     420
ATACTTGGTA TTACACCNNG GGGGAAGGTA GGAGAAGATC TTGCCTGTGG TTGTNGNTGG     480
CAATGTTGGT CTTTTATACG NG                                              502
```

(2) INFORMATION FOR SEQ ID NO: 92:

(i) SEQUENCE CHARACTERISTICS:
        (A) LENGTH: 495 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 92:

```
GAATTCTCTC CTTAGAAGTT CCATACACAA CACATCTCCC TAGAAGTCAT TGCCCTTACT      60
TGTTCTCATA GCCATCCTAA ATATAAGGGA GTCAGAAGTA AAGTCTGGNT GGCTGGGAAT     120
ATTGGCACCT GGAATAAAAA TGTTTTTCTG TGAATGAGAA ACAAGGGGAA GATGGATATG     180
TGACATTATC TTAAGACAAC TCCAGTTGCA ATTACTCTGC AGATGAGAGG CACTAATTAT     240
AAGCCATATT ACCTTTCTTC TGACAACCAC TTGTCAGCCC ACGTGGTTTC TGTGGCAGAA     300
TCTGGTTCTA TAACAAGTTC CTAATAAGCT GTAGCCAAAA AAATTTGATG AGGTATTATA     360
ATTATTTCAA TATAAAGCAC CCACTAGATG GAGCCAGTGT CTGCTTCACA TGTTAAGTCC     420
TTCTTTCCAT ATGTTAGACA TTTCTTTGAA GCAATTTTAG AGTGTAGCTG TTTCTCAGGT     480
TAAAATTCTT AGTAG                                                      495
```

(2) INFORMATION FOR SEQ ID NO: 93:

(i) SEQUENCE CHARACTERISTICS:
        (A) LENGTH: 500 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 93:

```
TATGGTTGCC TATTCTTGTC ACAGTAACTN AACTGATCTA GGAAAGAAAA AATGTTTTGT      60
CTTCTAGAGA TAAGTTAATT TTTAGTTTTC TTCCTCCTCA CTGTGGAACA TTCAAAAAAT     120
```

-continued

```
ACAAAAAGGA AGCCAGGTGC ATGTGTAATG CCAGGCTCAG AGGCTGAGGC AGGAGGATCG      180

CTTGGGCCCA GGAGTTCACA AGCAGCTTGG GCAACGTAGC AAGACCCTGC CTCTATTAAA      240

GAAAACAAAA AACAAATATT GGAAGTATTT TATATGCATG GAATCTATAT GTCATGAAAA      300

AATTAGTGTA AAATATATAT ATTATGATTA GTTATCAAGA TTTAGTGATA ATTTATGTTA      360

TTTTGGGATT TCAATGCCTT TTTAGGCCAT TGTCTCAAAA AAATAAAAGC AGGAAAACAA      420

AAAAAGTTGT AACTTGAAAA ATAAACATTT CCATATTTAT AGCCAACTAA GTGGGTTTNG      480

GGTNGGTTGG GTTGGTTGGT                                                 500
```

(2) INFORMATION FOR SEQ ID NO: 94:

(i) SEQUENCE CHARACTERISTICS:
        (A) LENGTH: 385 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 94:

```
TTATCATTAA CAGGTCCCAC AACCCTTAAA AAGTACAGAT TTTTTTTTTC TTNGTGGAGA       60

CAGGGTCTCA CTTGGTCGCC CAGACTGGAG TGCAGTGGCA CGATCTCAGT TCACCACAAC      120

CTCTGCCTCC TGGGTTCAAG CAATNCTCGT GCTTAAGCCT CCTGAGTAGG TGGAACCACG      180

CGTGCGCGCC ACCACGCTAG GTTNATTGTG GCTTTTTTAG TAGAGACAGG GTTTCGCCAT      240

GTTGCCCAGG CTGGTCTCAN ATTCCNGACC TCAAGTGATC CGNCCGCCTC AGACTCCCAA      300

AGTGNTGAGC ATTACAGNTG TGTACCACTA TGTCCCNGNC CNCATCTCTC TTTAAAACAN      360

CTTNCATTTA CCTAGTCCAC TCCTG                                           385
```

(2) INFORMATION FOR SEQ ID NO: 95:

(i) SEQUENCE CHARACTERISTICS:
        (A) LENGTH: 330 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 95:

```
GACCTAGAAA AGAAAGCATT TCAANNTAAT TAACAGGTCC CACAACCCTT AAAAAGTACA       60

GATTTTTTTT TTCTTTNNGG AGACAGGGTC TCACTTTGTC GCCCAGACTG GAGTGCAGTG      120

GCACGATCTC AGCTCACCAC ANCCTCTGCC TCCTGGGTTC AAGNANTTCT CGTGCTTANG      180

CCTCCTGAGT AGGTGGAACC ACGCGTGTGC GCCACCACGC TAGGCTACTT TNTGTATTTT      240

TAGTAGAGAC AGGGTTTCGC CATNTTGCCC AGGCTGNTCT CAAATTCCTG ACCCNCAAGT      300

GATCCCCCCN CCTTCAGTAC TCCCCATCAG                                      330
```

(2) INFORMATION FOR SEQ ID NO: 96:

(i) SEQUENCE CHARACTERISTICS:
        (A) LENGTH: 382 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 96:

```
GGTGGNCGTT CTAGAACTAG TGGCNCCCAA GGNAGAAGAA GTTTTCTTAG TACAGAACAA      60

AATGAAANGT CTCCCATGTC TACTTCTTTC TACACAGACA CGGCATCCAT CCGTTTTTCT     120

CANTCTTTCC NCCACCTTTC CCGTCTTTCT ATTCCACAAA GCCGNCATTG TCATCCTGGC     180

CCNTTCTCAA TGAGCTGTTG NNTACACCTC CCAGACGGCG TGGTGGNCGG TCAGAGGGGC     240

TCCTCACTTC CCAGTAGGGG TGGCCGNGCA GGNGGTGCCC CNCACCCCCC GGGCGGGGTG     300

GTTNGTCCNN CCGGNGGGNT GCACCNCCCC CACCCCTCCC CNCTCTNCTA CTGGCGGTCG     360

TNTATTNCAN NATCTTTAAG CA                                              382

(2) INFORMATION FOR SEQ ID NO: 97:

(i) SEQUENCE CHARACTERISTICS:
        (A) LENGTH: 360 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 97:

GGATCCAAAG GAAGTTAGAG GCCAGCTCAG TCTACACCTG CTACTGNTCA GTGCCCACCC      60

GGTCAAGGGA GACCAACACA TGGTAAAGGT CAAGGGCTTC TTGGAAGGCA GTCAGCAGCC     120

TGTGCAAGAT GTTCTCCACA CTGCTCAGNT TAAGGGGAGC TGGGGGCAGG ACCTCAGCTG     180

GNATCTCTGC TTCACCAGTG TCCAGGGGTT GCACAATTCT TGTTTACTCG TAGGATATTT     240

AATCTTGGNN GGTGCTATCA TAAATGGGAC TTATCCNCTN ATTATGTTTT CTTACTAGTT     300

GTTTATGTGA AGGTTATTGA TTTGGGTTTC ACTTTATTTN GTGGNAATGG AGTTTCACTC     360

(2) INFORMATION FOR SEQ ID NO: 98:

(i) SEQUENCE CHARACTERISTICS:
        (A) LENGTH: 208 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 98:

AATGTCACGG ATTCCTTTAG GTAGNTACAC CCATCAACCT TTTTGAGAAT AAAATGAATT      60

GAGAGTGTTA CAGTCTAATT CTATATCACA TGTAACTTTT ATTTGGATAT ATCAGTAATA     120

GTGCTTTTTT TTTTTTTTTT TTTTTTTTTT TTTTTTTTNG GNGANAGAGT CTCGCTCTGT     180

CGCCAGGTTG GAGTGNAATG GTGCGATC                                        208

(2) INFORMATION FOR SEQ ID NO: 99:

(i) SEQUENCE CHARACTERISTICS:
        (A) LENGTH: 470 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 99:

AACAAGGTTT CTCGGTCGGC GGTGAATATA CCGGGGCGTC GATATTTGTT GCGGAATACT      60

CCCCTGACCG TAAACGTGGC TTTATGGGCA GCTGGCTGGA CTTCGGTTCT ATTGCCGGGT     120

TTGTGCTGGG TGCGGGCGTG GTGGTGTTAA TTTCGACCAT TGTCGGCGAA GCGAACTTCC     180
```

```
TCGATTGGGG CTGGCGTATT CCGTTCTTTA TCGCTCTGCC GTTAGGGATT ATCGGGCTTT      240

ACCTGCGCCA TGCGCTGGAA GAGACTCCGG CGTTCCAGCA GNATGTCGAT AAACTGGAAC      300

AGGGCGACCG TGAAGGTTTG GAGGATGGCC CGAAAGTCTC GTTTAAAGAG ATTGGCACTA      360

AATACTGGNG CAGNCTGTTG AATGTTTGGG CTTGGTAATT GGCAACCAAC GTGATTACTA      420

NATGTTGGTG ACCTATATTG CCGAGTTATT GGCGGATAAC CTGAATTATC                 470
```

(2) INFORMATION FOR SEQ ID NO: 100:

(i) SEQUENCE CHARACTERISTICS:
        (A) LENGTH: 440 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 100:

```
TAATTATATT GAAATGCTTC TCNTCTAGGT CATCCATGNC TGGNTTATTA TATCATCTCT       60

ATTGNTGNTG CTCTTTTTTA CATNCATTTA CTTGGGGTAA GTTGTGAAAT TTGGGGTCTG      120

TCTTTCAGAA TTAACTACCT NNGTGCTGTG TAGCTATCAT TTAAAGCCAT GTACTTTGNT      180

GATGAATTAC TCTGAAGTTT TAATTGTNTC CACATATAGG TCATACTTGG TATATAAAAG      240

ACTAGNCAGT ATTACTAATT GAGACATTCT TCTGTNGCTC CTNGCTTATA ATAAGTAGAA      300

CTGAAAGNAA CTTAAGACTA CAGTTAATTC TAAGCCTTTG GGGAAGGATT ATATAGCCTT      360

CTAGTAGGAA GTCTTGTGCN ATCAGAATGT TTNTAAAGAA AGGGTNTCAA GGAATNGTAT      420

AAANACCAAA AATAATTGAT                                                  440
```

(2) INFORMATION FOR SEQ ID NO: 101:

(i) SEQUENCE CHARACTERISTICS:
        (A) LENGTH: 449 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 101:

```
AAAACAAAGC CTCTTGAGGT TCTGAAAAGG GAAAGAAAAA CAGAACTTTG TGCACTACAA       60

TTATACTGTT ATAAAAAACA CTTCCATAGA TTACATTAAG CAGAAACAAA CCTTTCTTTC      120

ATGTGTTCTC CTCCAGGCCA AGCTGTCTAA GGACCGCAAA GGCTGTTGTC ACTTGCAGGC      180

TCCCAGATTA GGTCTGAAAT AGGATTTCAC CAGGTCATCC ATTGTTAGTT AAATCCTAGT      240

AAATTCATTT ANACCAATCA AATACTTATA AGACCAATTT GTAAACCAGG AATGTATTAA      300

TTTGTCACGA CTTTCAACTA ACTGACAAAT TTACTATAAG CTCAAGGTAG GACTCTTTAG      360

CAATAAGTAG GAACCGCCTG AGACAACCAA ACATTTTCAA CCCACAAANG ATACTTTAAT      420

GACTTTCTGA TTTNCCAGCA AAAGGGGGG                                        449
```

(2) INFORMATION FOR SEQ ID NO: 102:

(i) SEQUENCE CHARACTERISTICS:
        (A) LENGTH: 425 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 102:

| | | |
|---|---|---|
| GGATCCGCCC TCCTCGGCCT CCCAAAGTGT TGGGATTACA GGCGTGAGCC ACCGCACCTG | 60 |
| GCTTTTTTTT TTTTTTTTTT TGGNGGAGAC AGAGTCTTAC TCTGTTGCCC AAGCTGGAGT | 120 |
| GCAGTGGTGC AATCTTGGTT CACTGNAACC TCCACCTCCA GAGTTCAAGC AATTCTCTGC | 180 |
| CTCAGTTTCT GGAGTAGCTG GGATTACAGG TGCCTGCCAT CACGCCTGGC TAAATTTGGN | 240 |
| ATTTTTTTTT AGTAGAGACA GGGTTTCACC ATGTTGGCCA GGCTGGTCTT GAACTCCTGA | 300 |
| CCTTGTGATC CACCAGCCTC GGCCTCCCAA ATTGNTGGGA TTACAGGCGT GAGCCACCAC | 360 |
| AACCAGGCTA AAGTTTTAAA ACATGCCAAG TGTATTTACA TAATGCGATA CGANTTATGT | 420 |
| ACATA | 425 |

(2) INFORMATION FOR SEQ ID NO: 103:

(i) SEQUENCE CHARACTERISTICS:
        (A) LENGTH: 386 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 103:

| | | |
|---|---|---|
| GGATCCGCCC GCCTTGGCCT CCCAAAGTGC TGGGATTACA GGCATGAGCC ACCGCTCCTG | 60 |
| GCTGAGTCTG CGATTTCTTG CCAGCTCTAC CCAGTTGTGT CATCTTAAGC AAGTCACTGA | 120 |
| ACTTCTCTGG ATTCCCTTCT CCTNTTGTAA AATAAGCATG TTATCTGTCC NNCCTGCCTT | 180 |
| GGGCATTGTG ATAAGGATAA GATGACATTA TAGAATNTNG CAAAATTAAA AGCGCTAGAC | 240 |
| AAATGATTTT ATGAAAATAT AAAGATTAGN TTGAGTTTGG GCCAGCATAG AAAAAGGAAT | 300 |
| GTTGAGAACA TTCCNTTAAG GATTACTCAA GCTCCCTTTG GTGTATATCA GNNGTCANNA | 360 |
| CNTATCTTNG GGGCTGAAAA ATGTTT | 386 |

(2) INFORMATION FOR SEQ ID NO: 104:

(i) SEQUENCE CHARACTERISTICS:
        (A) LENGTH: 224 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 104:

| | | |
|---|---|---|
| GAAAAGGGAA AGAAAAACAG AACTTTGTGC ACTACAATTA TACTGTTATA AAAAACACTT | 60 |
| CCATAGATTA CATTAAGCAG AAACAAACCT TTCTTTCATG TGTTCTCCTC CAGGCCAAGC | 120 |
| TGTCTAAGGA CCGCAAAGGC TGTTGTCACT TGCAGGCTCC CAGATTAGGT CTGAAATAGG | 180 |
| ATTTCACCAG GTCATCCATT GTTAGTTAAA TCCTAGTAAA TNCA | 224 |

(2) INFORMATION FOR SEQ ID NO: 105:

(i) SEQUENCE CHARACTERISTICS:
        (A) LENGTH: 440 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 105:

```
GGATCCGCCC TCCTCGGCCT CCCAAAGTGT TGGGATTACA GGCGTGAGCC ACCGCACCTG    60

GCTTTTTTTT TTTTTTTTTT TGGNGGAGAC AGAGTCTTAC TCTGTTGCCC AAGCTGGAGT   120

GCAGTGGTGC AATCTTGGTT CACTGCAACC TCCACCTCCA GAGTTCAAGC AATTCTCTGC   180

CTCAGTTTCT GGAGTAGCTG GGATTACAGG TGCCTGCCAT CACGCCTGGN TAAATTTGGG   240

ATTTTTTTTT AGTAGAGACA GGGTTTCANC ATGTTGGCCA GGNTGGTCTT GGACTCCTGA   300

CCTGGTGAAC CACCAGGCTC GGGCTCCAAA TTTGGTTGGG ATTACAGGGG GTNAANCAAC   360

CACAACCCAG NCTAAAGTTT TNAAAACATN CAAAGTGTTT TAAAATNATG NGATACGATT   420

TATTGTACAA TTAATTTTAT                                                440

(2) INFORMATION FOR SEQ ID NO: 106:

(i) SEQUENCE CHARACTERISTICS:
        (A) LENGTH: 448 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 106:

GTCTTTCCCA TCTTCTCCAC AGAGTTTGTG CCTTACATTA TTACTCCTTG CCATTTTCAA    60

GAAAGCATTG TCAGCTCTTC CAATCTCCAT CACCTTTGGG CTTGTTTTCT ACTTTGCCAC   120

AGATTATCTT GTACAGCCTT TTATGGACCA ATTAGCATTC CATCAATTTT ATATCTAGCA   180

TATTTGCGGN TAGAATCCCA TGGATGTTTC TTCTTTGACT ATAACAAAAT CTGGGGAGGA   240

CAAAGGTGAT TTTCCTGTGT CCACATCTAA CAAAGTCAAG ATCCCCGGCT GGACTTTTGG   300

AGGTTCCTTC CAAGTCTTCC TGACCACCTT GCACTATTGG ACTTTGGNAA GGAGGTGCCT   360

ATAGAAAACG ATTTTGGAAC ATACTTCATC GCAGGGGGAC TGTGTCCCCC GGTGGCAGAA   420

NCTACCAAGA TTTGCGGGNC GAGGTCAA                                       448

(2) INFORMATION FOR SEQ ID NO: 107:

(i) SEQUENCE CHARACTERISTICS:
        (A) LENGTH: 198 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 107:

GGATCCGCCC GCCTTGGCCT CCCAAAGTGC TGGGATTACA GGCATGAGCC ACCGCTCCTG    60

GCTGAGTCTG CGATTTCTTG CCAGCTCTAC CCAGTTGTGT CATCTTAAGC AAGTCACTGA   120

ACTTCTCTGG ATTCCCTTCT CCTTNAGTAA AATAAGNATG TTATCTGNCC GCCCTGCCTN   180

GGNNATTGNG ATAAGGAT                                                  198

(2) INFORMATION FOR SEQ ID NO: 108:

(i) SEQUENCE CHARACTERISTICS:
        (A) LENGTH: 500 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 108:
```

```
CTGCAGTGAG CCGTGATTGC ACCACTTTAC TCCAGCCTGG GCAACAAAAT GAGACCCTGG      60

CTCAAAAACA AAACAAAAA CAAAAAAAGA GTAAATTAAT TTAAAGGGAA GTATTAAATA       120

AATAATAGCA CAGTTGATAT AGGTTATGGT AAAATTATAA AGGTGGGATA TTAATATCTA      180

ATGTTTGGGA GCCATCACAT TATTCTAAAT AATGTNTTGG TGAAAATTAT TGTACATCTT     240

TTAAAATCTG TGTAATTTTT TTTCAGGGAA GTGTTTAAAA CCTATAACGT TGCTGTGGAC      300

TACATTACTG TTGCACTCCT GATCTGGAAT TTTGGGTGTG GTGGGAATGA TTTCCATTCA      360

CTGGAAAGGT CCACTTCGAC TCCAGCAGGC ATATCTCATT ATGATTAGTG CCTCATGGNC      420

CTGGTGTTTA TCAAAGTACC TCCCTGAATG GACTGCGTGG GTCATCTTGG NTGTGATTCA     480

GTATATGGTA AAACCCAAGA                                                  500
```

(2) INFORMATION FOR SEQ ID NO: 109:

(i) SEQUENCE CHARACTERISTICS:
        (A) LENGTH: 500 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 109:

```
CTGCAGCCTT GACCTCCTGG GATCAATCGA TCCTCCCACC TCAGCCTCCT AAGTAGCTGG      60

AACTACAGGT GTGCACCACC ATGCCCGGCT AATNGNTGTA TTTTCTGTAG ATACGAGGTN     120

TNGCCATGTT GCCCAGGCTG GTCTTGAACT CTGGGCTTAG GTGATCTGCC CGCCTCAGCC     180

TCCCAAAGTG CTAAGATTAC AGGCATGAGC TACCATGCCC AGCCGAAATC TTCAAATGAA     240

AAAGTTACTA TAGCTAATTA ATGATTTACT GAAGAGTTAT GGGATGTACA CGTTACCATT     300

TTCTCTAAAT CAAGATAAAG AGATGAGGAA AGAAAACACT CCAGTGGGGC ATTCCTGTNA      360

CAAAACAAAT TATCAGTCTT GGGGTTTNAC CATATACTGA AATCACAGGC AAGATGAGCC     420

ACGCAGTCCA TNCAGGGAGG TACTGGATAA CACCAGGGNC ATGAGGGACT AATCATAATG     480

AGATATGCTG CTGGAGTCGA                                                  500
```

(2) INFORMATION FOR SEQ ID NO: 110:

(i) SEQUENCE CHARACTERISTICS:
        (A) LENGTH: 550 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 110:

```
CTGCAGGATG AGAGCGATCT CTTNTTNCAT TTCCTGCGCT ACGCGCTGCG GGCGACCAAA      60

TTCTTTCGCC ATAATAAATT CTCCTGACNA AAAAGGGGCT GTTAGCCCCT TTTTAAAATT     120

AATTTCAGGT GGAAGGGCTG TTCACGTTGA CCTGATAAGA CGCGCCAGCG TCACATCAGG     180

CAATCCATGC CGGATGCAGC GTAAACGCCT TATCCCGCAT GGAACCCTAA AAACCTTAAG     240

CAATGGTACG TTGGATCTCG ATGATTTCGA ATACTTCGAT CACATCGNCA GTGCGGACGT     300

CGTTGTAGTT CTTAACGCCG ATACCACATT CCATACCGTT ACGGGACTTC GTTAACGTCA     360

TCTTTGGAAG CGGGGCAGGG ACTCCAGCTC GNCTTCGTAG ATAACCACGT TGGCACGCAG     420

GAACGCGGGT CGGGTTGTGA CGTTTAACAC AACTTCCGGG TAACCATACA GGCTGNGATG     480

GNACCAAATT TCGGGGATT TGGACAAGTC AAGAACTTCC CGCCAGACCG ATAATCTTGT      540
```

TGTTCAGTTC 550

(2) INFORMATION FOR SEQ ID NO: 111:

(i) SEQUENCE CHARACTERISTICS:
        (A) LENGTH: 541 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 111:

| | | | | | |
|---|---|---|---|---|---|
| CTGCAGCTTT | CCTTTAAACT | AGGAAGACTT | GTTCCTATAC | CCCAGTAACG | ATACACTGTA | 60 |
| CACTAAGCAA | ATAGCAGTCA | AACCCAAATG | AAATTTNTAC | AGATGTTCTG | TGTCATTTTA | 120 |
| TNTTGTTTAT | GTTGTCTCCC | CCACCCCCAC | CAGTTCACCT | GCCATTTATT | TCATATTCAT | 180 |
| TCAACGTCTN | NNTGTGTAAA | AAGAGACAAA | AAACATTAAA | CTTTTTTCCT | TCGTTAATTC | 240 |
| CTCCCTACCA | CCCATTTACA | AGTTTAGCCC | ATACATTTTA | TTAGATGTCT | TTTATGTTTT | 300 |
| TCTTTTNCTA | GATTTAGTGG | CTGNGTTGTG | TCCGAAAGGT | CCACTTCGTA | TTGCTGGTTG | 360 |
| AAACAGCTCA | GGAGAGAAAT | GAAACGCTTT | TTCCAGCTCT | CATTTACTCC | TGTAAGTATT | 420 |
| TGGAGAATGA | TATTGAATTA | GTAATCAGNG | TAGAATTTAT | CGGGAACTTG | AAGANATGTN | 480 |
| ACTATGGCAA | TTTCANGGNA | CTTGTCTCAT | CTTAAATGAN | AGNATCCCTG | GACTCCTGNA | 540 |
| G | | | | | | 541 |

(2) INFORMATION FOR SEQ ID NO: 112:

(i) SEQUENCE CHARACTERISTICS:
        (A) LENGTH: 241 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 112:

NNCCCNCNCN NNNNNNNTTN NTNTTGCCCG ATAACTATAG GGNGACTTGG AGATCCACCG     60

CGGTGGCGGN CGNTCTAGAA CTAGTGGATC CCCCGGGNTG CAGGACCCAA CGCTGCCCGA    120

GATGCGCCGC GTGCGGTTGC TGGAGATGGC GGACGCGATG GATATGTTCT GCCAAGGGTT    180

GGTTTGCGCA TTCACAGTTC TCCGCAAGAA TTGATTGGCT CCAATTCTTG GAGTGGTGAA    240

T                                                                   241

(2) INFORMATION FOR SEQ ID NO: 113:

(i) SEQUENCE CHARACTERISTICS:
        (A) LENGTH: 834 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 113:

CCCCCCCNCC NNNNNTTTTN NGCAGCCCGT AATTACCCTC ACTNCCGGGA ACAAAAGCTG     60

GGTACCGGGC CCCCCCTCGA GGTCGACGGT ATCGATAAGC TTGATATCGA ATTCCTGCAG    120

TGTTTAAAAA ATAAAATAAA CTAAAAGTTT ATTTATGAGG AGTACACTGC TTTCTTGTAA    180

ACACATGTAC AAGCCATATA ATAGAGTTCA TTTTTTACCC TAGTTACGGA AACACTAGAA    240

| | |
|---|---|
| AGTCTTCACC CGGCCAAGAT AACACATCTT TAGTAAAAAT AGCAAGAAAT ATTTTATGGG | 300 |
| TTGTTTACTT AAATCATAGT TTTCAGGTTG GGCACAGTGG NTCATGCCTG TAATCCCAGC | 360 |
| ACTTTATGCG GNTGAGGCAG GCAGATCAGT TGAGGTCAGA AGTTTGGAGA CCAGNCTGGG | 420 |
| CAATGTGGNA AAACCTCATC TCCACTAAAA ATACAAAAAT TAGNCAGGCA TGGTGGTGCA | 480 |
| CACATGTAAT TCCAGNTACT TGGGGAGGCT GAGACAGGAG GATCGNTTGA ACCTAGGGAG | 540 |
| GGAGGAGTTG GAGTGAGCTA ATGTCAATGC ACTCTTGGTT GGGGCGANAG AGCAAGATCT | 600 |
| TTCTTCCAAA AAAAAAAAAA AAAAAAAGC CAGGTGNGGN GGTCAAGGCT GTAATCCAGA | 660 |
| ATTNGGGAGG CCGNGGAGGN NATCANTGNG GNAGGNGTCA AGNGGGGCNG GCCACATGGG | 720 |
| GAACCCGTTN TTNTTAAATN AAAATTAGCC GGGGNGGGGG AGGACTNTAT CCNGTTCCGG | 780 |
| NGGTGNGGAG GATCNTTATT NTGGNGGAGG GTGGATGNNC CAGTTGACNC CCCC | 834 |

(2) INFORMATION FOR SEQ ID NO: 114:

(i) SEQUENCE CHARACTERISTICS:
        (A) LENGTH: 838 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 114:

| | |
|---|---|
| TTGGGCNCNC GCCCCTTAAN TTTTTATNGN TTNCTANAAA AANANNNGGC NCNNTAAAAT | 60 |
| ATATTTTTTN TTGTGACCCC TTTTAAAAGG GACCCNCTAA AAAATTTTNT GGTTNNTTTN | 120 |
| GATTTANGTG GGTGNTTTTN TTATATTTTT GGNGAGNNTC TGTAGTCNTC NCCCTCAAAC | 180 |
| ANNTCNTACN ATNGGNANCG TGACTCTGTC NTTNGTNANN NTCGNTNTCN NGTNATTCNA | 240 |
| GGNNCCTCGC GCNNCNCGGG CNNNGTTTTT TTTNNCNNTT TTTAAGCCNA ANNCTCAGTA | 300 |
| NCNTCCAACG GNGCTNNGAC ANNNGNNNCT NTCGNGGGTN CCCTCTNTNT NGNNCNNGGC | 360 |
| TNNNGNNNNC NGNCNGCNGN GCCNTGCGNN NNGNNNGNGG NNNGNTNNCA TANGGATNGN | 420 |
| GNTGCTCNNC NCNNGNGTNN TNAGTAGGNA NTTTTNTNNT ACTTGCCNNC NNNTNGCTGC | 480 |
| GAGNANAGCN ANNTNGNNGN AGNGNNGNTG CGCGGANNTT CCCCTGATNA NCTCGAGCNG | 540 |
| NTTACNGGNG CNNCCTNGAA NAAGNGNNGT ANNGTGCCGA GNCGCTANNC TGAGCCTGAG | 600 |
| TNTCGACNGG NATNGTGNNT CNTACNGTTA NGGGNNGCNN GANCGGGNTG ANTCNCCGGN | 660 |
| NGANCNAGCG ACTGCCTNTC ANGCGAANCG TNTCANGNNN GTAGAGCANA GGGTNANNNG | 720 |
| TCNNNNAAGC NTNNAGTGAN TGTCNTNACN NGTGANTTAC GGCNTAGNCT TGATNTNNAN | 780 |
| NCGAGGNNNN ATNNANNNTT GGANANTTNN TNNNNTCNCN TCGCGGNGNG NCNNGCCG | 838 |

(2) INFORMATION FOR SEQ ID NO: 115:

(i) SEQUENCE CHARACTERISTICS:
        (A) LENGTH: 803 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 115:

| | |
|---|---|
| ATTCGCGCGT AGCCCGATAA CTATAGGGCG ACNTGGAGNT CCACCGCGGT GGCGGCCGCT | 60 |
| CTAGNAACTA GTGGATCCCC CGGGCTGCAG GAATTCACGG ACTAATCCTC TACAGATCTT | 120 |

```
GCTGGAGTGG CCTTTCAGCC TTTTGTGACT GTTTGTAGTG AAATGTACAC ACAAGCCTAC      180

AAGGCAGCCC AGATGTACCA TAACTGTGGG AAAATTAAAA AAAAAAAAAC ACAGAACCTC      240

TCTATGTTGC CCATGCTGGA CTCAAACTCT TAGACAAGCA ATCCTCGTAC CTCAGCCTCC      300

TGAGTTCCTG AGTAGCTGGG ACTACAAGCA TGCACCACCA TGCCAGGCTA TGAGAAAGTT      360

CTTTTTATTG ATCCAGACCT TATTGCCTGG TAACTTCCAC CACTGTTCCT AGCTCTGNTC      420

TCTGGTCCTA ACAGAGGAAA ATCTTGACCC CACACCTAGT GCAACTGGAT AGCTTATNGT      480

TGGGCTNGTG TTTCCTCTAT TCTGGGTCCA CCCTAAAATC CNATAGATAC TCCAACTGCT      540

CANAGNAAAC CAAGCTCTCT CTCTNNCTTN CTTTCTTNNN CTCTATTNAT TNATGGGNNA      600

TNATTNATTN NGGGGATGGN GTTCGGTCGC CGCCCGGCTG GNGTGAAATG GGGGAGGCAA      660

TCAATTTAAC CCCACCCNGG GTCCAGGGAT CTCGTTNAAA CCGNNNNNNN NNNNNNNNNA      720

NGNNCNNCNC NNNCCNNTNN NNNGGTTTNN NNGNNNNGGG NNNCCNNNNN NANNNNNNTN      780

NNNCCNCCNA NNNTNCNNNN CCC                                             803
```

(2) INFORMATION FOR SEQ ID NO: 116:

(i) SEQUENCE CHARACTERISTICS:
        (A) LENGTH: 780 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 116:

```
CNNNNNNNCC CNNTNATTNT ACGCCAGCCG CGTAATTAAC CCTCACTAAA GGGAACAAAA       60

GCTGGGTACC GGGCCCCCCC TCGAGGTCGA CGGTATCGAT AAGCTTGATA TCGAATTCCA      120

ACTCCTCACT TGCCAGATGT GACCTTAAGC AAGTGAACTT CTGTGTGCCA CACTGTTTTC      180

ATCTGTAAAA GGATAAAGGG AATATCATAA ATTAGNTTGT TAAGCCTTAG TTTAATAATG      240

TCTCTAAGTT TTACATATAA GTAGACAGTG TCTTTCTTGT TTAGTGAATA ATCATTCTTA      300

TTATTTAATA GTATCTCTAC TAAATTTATT GTGTAAGATT ATACTAATCT TGTTTAGTGC      360

GTGGTAATCA CTTCTGCTCA TATTTAACCT ATAAGCATAA TATAGTTTAT TTATATACCA      420

NTTATTTATT TTATTTTATT TGNNGAGATG CAGCTTGTCT TTTNCAACCC AGGGNTGNGG      480

NGNAGNNGNG NAANCTTGNT TCACTGNAAC CNCCACCNCC CAGGTNCAAG NGATTCTCCT      540

GNTCAAGCCN CCTNAGNAGN TGGNATTACA GNACGANTAC ANNCCAGNTA NNNNGGNTNT      600

NNGNTNGNNA GGNNNCACAN NNGNCAGGTN NNTCGNCTCC NNGCCANTNA CTNNNNCCAN      660

CCCCNNNGNN NNNNATANAG NATNANCANN NNCCNCNNNN NCNNNNNNNG GNGGANNCCN      720

NNTNGCNGNN ANNGNNANNN NNTNNNNNNN NNGGNCNNNG NNNNNNNNCC NNNNNNCCCC      780
```

(2) INFORMATION FOR SEQ ID NO: 117:

(i) SEQUENCE CHARACTERISTICS:
        (A) LENGTH: 803 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 117:

```
NNNNNNNNNC CNNNNNNTTC GNNCGTAACN CGANTCACTA TAGGGCGACT TGGAGCTCCA       60

CCGCGGTGGC GGCCGCTCTA GAACTAGTGG ATCCCCCGGG CTGCAGGAAT TCGATATCAA      120
```

```
GCTTTNGTGT GTAAAAAGTA TTAGAATCTC ATGTTTTTGA ACAAGGTTGG CAGTGGGTTG      180

GGAGGAGGGA TTGGAGATTG ATGCGATAGG AATGTGAAGG GATAGCTTGG GGTGGATTTT      240

ATTTTTTAAT TTTAATTTTT ATTTNTTGAG ATGGAGTCTT GCTCTGTCTC CCAGGCTGGA      300

GTGCAGTGGT GTGATCTCAG CTCACGGGTT CAAGCGATTC TCCTGCTGCA GCCTCCCGAG      360

TAGCTGGGAT TACAGGAGCG CGCCACCACA CCCGGNTAAT TTNNTTGTAT TTTTAGTAGA      420

GACGGGGTTT CACCATGTTG GTTAGGCTGG TCTAGAACTC CCAACCTCAT GATCCGCCTG      480

CTTCGGCCTC CCAAAGTGCC GGAATTACAG GCGTGAGCGA CTGCACCCGG CCGCTTGGGG      540

GTGGATTTTT AAAGAAATTT AGAAGAATGT AACTTGGCCA GATACCATGT ACCCGTTAAT      600

TCATTTNCGG TTTTTTGGAT ACCCATTTTG NNATTCTCCC NCCACTGGAT AAATAAGGGN      660

GGTTCATTNT NGNTTAGTTT GGGTNTTTTT NAGTGTGGNT TCTGCTTATN ATTAGAATGG      720

NCTNCTTTNC CAANCTGGAA AGGGAGGAGT TAAAATCANT ACCAGAANCA GAAATTCTTT      780

TCANTTGTTG CNCNAGAAAT GCC                                             803
```

(2) INFORMATION FOR SEQ ID NO: 118:

(i) SEQUENCE CHARACTERISTICS:
  (A) LENGTH: 819 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO: 118:

```
TNCCNNNNCN NNNNNAATTT TNGCAGNCGC GTAATTAACC TCACTAAAGG GAACAAAAGC       60

TGGGTACCGG GCCCCCCCTC GAGGTCGACG GTATCGATAA GCTTCCCTCC CCTTCCTCAG      120

CTCTGGCGAC CCTGCGCTGT GGTGGTTCTC CAACCACACT CATTCCCTC AGCTGGCTCC      180

TTGCTCTTCT TCCACCCCCT CGTTGGAAGT GTTCCTAAGT GTTTGGCTTG GCCTCCTCTT     240

CCCCTTCCTT AGNTTAGACT TCTCCACTGC TCCAACATCA ACTGGAAATC TATGGAATTG     300

ATTCCTGTTT TCAGCTCCAG TCCTGTTCAC AGGGCATTTT CACCTGCTGG CACTTCCAAA     360

GTGACACTTC CAAACCACTT CCTCGCCCTC CTCTCTAAAC CAGGTCTTTC TTCCTAACTT     420

CCTTATTTCT GAGAATGTCT CTGNCATGTT CTAAACTGAA AACTCCTAGT CAACTNCACA     480

CTTTATTCCC TGGATCCTCA ATTGGGTTCC CATGTNCCGT TAGTGTTTCT TGGTAAGNCT     540

CTGCCANCAC CGNAGGATCG ACTCTAATCA CATCTCAACT GAATTATGGN AAAGTCAACT     600

CAATTCTCTC AACCATCCCA GGCTCCACTA TGGNTAATAT GCTAAGGAGA GCTGACCCAA     660

CGGGGAGAAG ATCTGNGGGG GAGGAGAGAA ACAAAGNTAA TGGAATNATT CTCGAAAAGC     720

CCACAAGGNG AAGGATAACC CNCTTCCNCT CGAAAGAGGG GGGATCGCCA GATNTCGCGC     780

CCGGAAAGAA ACCGGGGNGA GGGGGTTACA NTGTAAGNC                            819
```

(2) INFORMATION FOR SEQ ID NO: 119:

(i) SEQUENCE CHARACTERISTICS:
  (A) LENGTH: 796 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO: 119:

```
TNTTGGCTGG TACTGCTTGA GCAACTGGTG AAACTCCGCG CCTCACGCCC CGGGTGTGTC    60

CTTGTCCAGG GGCGACGAGC ATTCTGGGCG AAGTCCGCAC GCCTCTTGTT CGAGGCGGAA   120

GACGGGGTCT GATGCTTTCT CCTTGGTCGG GACTGTCTCG AGGCATGCAT GTCCAGTGAC   180

TCTTGTGTTT GCTGCTGCTT CCCTCTCAGA TTCTTCTCAC CGTTGTGGTC AGCTCTGCTT   240

TAGGCATATT AATCCATAGT GGAGGCTGGG ATGGGTGAGA GAATTGAGGT GACTTTTCCA   300

TAATTCAGGT GAGATGTGAT TAGAGTTCGA TCTGCGGTGG TGGCAGAGGC TTACAAGAAA   360

CACTAACGGG ACATGGAAC CAATTGAGGA TCAGGGAATA AAGTGTGAAG TTGACTAGGA    420

GGTTTTCAGT TTAGAACATG GCAGAGACAT TCTCAGAAAT AAGGAAGTTA GGAAGAAAGA   480

CTGGTTTAGA GAGGAGGGCG ANGAAGTGGT TTGGGAAGTG TCACTTTGGG AAGTGCCAGC   540

AGGTGAAAAT GCCTGTGACA GGATGGAGCT GAAAACAGGA TCAATTCCAT AGATTCCAGT   600

TGATGTNGGA GCAGGGGAGA AGTCTTAGCT AAGGAAGGGG AAGAGGAGGC CAAGGNAACA   660

CTTAGGACAA TTGNAACGAN GGGGGGGGAG AAGAGNAAGG GCCACTTAGG GGAATAATNT   720

GGTGGGGGAC CCCCAAGNNA GGGCGCANNN TTAGGAGGGG GGGANNTCAN AGGAAAGTGG   780

AAGNTTGGGT TTANCT                                                   796

(2) INFORMATION FOR SEQ ID NO: 120:

(i) SEQUENCE CHARACTERISTICS:
        (A) LENGTH: 802 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 120:

ATTCGTCGTA NCCCGATNAC TATAGGGCGA CTTGGAGCTC CACCGCGGTG GCGGNCGCGG    60

GCAGGGNCCG GNCCTTTGTG GCCGCCCGGG CCGCGAAGCC GGTGTCCTAA AAGATGAGGG   120

GCGGGGCGCG GNCGGTTGGG GCTGGGGAAC CCCGTGTGGG AAACCAGGAG GGGCGGCCCG   180

TTTCTCGGGC TTCGGGCGCG GCCGGGTGGA GAGAGATTCC GGGGAGCCTT GGTCCGGAAA   240

TGCTGTTTGC TCGAAGACGT CTCAGGGCGC AGGTGCCTTG GCCGGGATT AGTAGCCGTC    300

TGAACTGGAG TGGAGTAGGA GAAAGAGGAA GCGTCTTGGG CTGGGTCTGC TTGAGCAACT   360

GGTGAAACTC CGCGCCTCAC GCCCCGGGTG TGTCCTTGTC CAGGGGCGAC GAGCATTCTG   420

GGCGAAGTCC GCACGCCTCT TGTTCGAGGC GGAAGACGGG GTCTTGATGC TTTCTCCTTG   480

GGTCGGGGAC TGTCTCGAGG CATGCATGTC CAGTGACTCT TGTGTTTGGT GNTGCTTCCC   540

TCTCAGATCT TCTCACCGNG GTGGGCAACT CTGTTTAGGC ATATTATCCA TAGNGGAGGC   600

TGGATGGTTG AAANAATTGA GGTNATTTTC CATAATCAAG TGAAATTTGA TAGAGTCCGN   660

CTTTNGGGGT GNAAGGGTTA AAAAAAAATA ACGGAAATGG AACAATGAGG TCAAGGATTA   720

GTTGAGTTGN TAGNGGTTCA ATTAGANATG AAGGNATCTA AAATAGGAGT AGAGAANNNG   780

TTNAAAGAGG GAAAATTTTG CC                                            802

(2) INFORMATION FOR SEQ ID NO: 121:

(i) SEQUENCE CHARACTERISTICS:
        (A) LENGTH: 793 base pairs
        (B) TYPE: nucleic acid
        (C) STRANDEDNESS: single
        (D) TOPOLOGY: linear (ii) MOLECULE TYPE: DNA (genomic)
```

(xi) SEQUENCE DESCRIPTION: SEQ ID NO: 121:

| | |
|---|---|
| ATATGCAGCC GCGTAATTAA CCTCACTAAA GGGAACAAAA GCTGGGTACC GGGCCCCCCC | 60 |
| TCGAGGTCGA CGGTATCGAT AAGCTTGATA TCGAATTCCT GCAGCCCGGG GGATCCGCCC | 120 |
| CGCGGCCTCC CAAAGTGCTG GGATTACAGG CGTGAGCCAC CGCCCCGGGN CTCACATTTT | 180 |
| ATTTCTATTG GCTAGCGCTG CTCTAAATCT TCTGTTCCTT CTGCTACACC AGGCCTAACA | 240 |
| CTCAAAATCC CTGCCAACCT TTTCCTTCCT GAAGCTTCCC TCCCCTTCCT CAGCTCTGGC | 300 |
| GACCCTGCGC TGTGGTGGTT CTCCAACCAC ACTCATTCTC CTCAGCTGGC TCCTTGCTCT | 360 |
| TCTTCCACCC CCTCGNTGGA AGTGTTCCTA AGTGTTTGGC TTGGCCTCCT CTTCCCCTTC | 420 |
| CTTAGCTTAG ACTTCTCCAC TGCTCCAACA TCAACTGGAA ATCTATGGAA TTGATTCCTG | 480 |
| TTTCAGCTCC AGTCCTGTTC ACAGGGGATT TTCANCTGGT GGCATTTCCA AAGTGAAATT | 540 |
| CCAAACCACT TCCTCGGCCT CCTCTTCTAA ANCAGGTCTT TCTTCCTAAC TTCCTTATTC | 600 |
| TTGAGAATGT CTCTGCATGT TCTTAAANTG AAAACTCCTA GTCAAATTCA AATTTATCCC | 660 |
| TGATCCCAAA TGGTCCCATT CCCGTAGGGT TTNTGTAGCC TGCACACCGA GGTCGGANTT | 720 |
| TATNNATTCA CCGATTATGG AAAGTAACCA ATCTTNACCA NCCAGCTCAT TTGTTNTNTG | 780 |
| CTAAGAGGGT NCC | 793 |

(2) INFORMATION FOR SEQ ID NO: 122:

(i) SEQUENCE CHARACTERISTICS:
        (A) LENGTH: 440 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 122:

| | |
|---|---|
| AAAGTCATGG ATTCCTTTAG GTAGCTACAT TATCAACCTT TTTGAGAATA AAATGAATTG | 60 |
| AGAGTGTTAC AGTCTAATTC TATATCACAT GTAACTTTTA TTTGGATATA TCAGTAATAG | 120 |
| TGCTTTTTCN TTTTTTTTTT TTNTTTTTTT TNNTTTTNGG GGANAGAGTC TCGCTCTGTC | 180 |
| GCCAGGTTGG AGTGCAATGG TGCGATCTTG GCTCACTGAA AGCTCCACCN CCCGGGTTCA | 240 |
| AGTGATTCTC CTGCCTCAGC CNCCCAAGTA GNTGGGACTA CAGGGGTGCG CCACCACGCC | 300 |
| TGGGATAATT TTGGGNTTTT TAGTAGAGAT GGCGTTTCAC CANCTTGGNG CAGGCTGGTC | 360 |
| TTGGAACTCC TGANATCATG ATCTGCCTGC CTTAGCCTCC CCAAAGTGCT GGGATTNCAG | 420 |
| GGGTGAGCCA CTGTTCCTGG | 440 |

(2) INFORMATION FOR SEQ ID NO: 123:

(i) SEQUENCE CHARACTERISTICS:
        (A) LENGTH: 453 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 123:

| | |
|---|---|
| CTTAGTCTGT NTCGTAGTCA TATTAATTGT AAGTNTACAC TAATAAGAAT GTGTCAGAGC | 60 |
| TCTTAATGTC AAAACTTTGA TTACACAGTC CCTTTAAGGC AGTTCTGTTT TAACCCCAGG | 120 |
| TGGGTTAAAT ATTCCAGCTA TCTGAGGAGC TTTTNGATAA TTGGACCTCA CCTTAGTAGT | 180 |

```
TCTCTACCCT GGCCACACAT TAGAATCACT TGGGAGCTTT TAAAACTGTA AGCTCTGCCC    240

TGAGATATTC TTACTCAATT TAATTGTGTA GTTTTTAAAA TTCCCCAGGA AATTCTGGTA    300

TTTCTGTTTA GGAACCGCTG CCTCAAGCCT AGCAGNACAG ATATGTAGGA AATTAGCTCT    360

GTAAGGTTGG TCTTACAGGG GATAAACAGA TCCTTCCTTA GNCCCTGGGA CTTAATCACT    420

GAGAGTTTGG GTGGNGGTTT NGNATTTAAT GAC                                 453
```

(2) INFORMATION FOR SEQ ID NO: 124:

(i) SEQUENCE CHARACTERISTICS:
        (A) LENGTH: 369 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 124:

```
GACACACATT CACACATAAT TATGAAAGCA TTTTCAGGCA AAACTCAATC ACAAGTCTGG     60

GTTTTTAACA TAGTTAACTG AATATTTCCC TTGGGGGGTT AAATTTTAGA ACAGACGTNC    120

ATNCAATCTG GAAGAAGAGC TATGAAAAAA ACCTAGCTTG GGTNGGTTTC ATAGGGTNCA    180

TTATGNACAC ATTGTTATTT TATCCCTTAA TNCTAGTAAA GAAATAGAAT CTGAAAATAA    240

GTAAAACTAC TTGGAAAAAA NTTAAAGAT ACAGAAATTT CTATCTTAAA TGATGTGTGG     300

GCCNCTGTGA TTTTAGTNGG GNTGGTTAAA ANCCCAGAGG TGAAGAGNAT NCTCTATGCT    360

GTGNGGGGG                                                            369
```

(2) INFORMATION FOR SEQ ID NO: 125:

(i) SEQUENCE CHARACTERISTICS:
        (A) LENGTH: 516 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 125:

```
GCTCATCATG CTTCACGGGG GAGGCTGTGC GGGAAGAATG CTCCCACACA GNATAAAGAA     60

TGCTCCCGCA CAGGATAGAG AATGCCCCCG CACAGCATAG AGAAGCCCCC GCACAGCATA    120

GAGAATGCCC CCNCACAGCA TAGAGAAGCC CCCGCACAGC ATAGAGAATG CTCTTCACCT    180

CTGGGTTTTT AACCAGCCAA ACTAAAATCA CAGAGGSCMA CACATCATTT AAGATAGAAA    240

TTTCTGTATC TTTTAATTTY TTTCMAAGTA GTTTTACTTA TTTTCAGATT CTATTTCTTT    300

ACTAGAATTA AGGGATAAAA TAACAATGTG TGCATAATGA ACCCTATGAA ACMAACMMAA    360

GCTAGGTTTT TTTCATAGST CTTCTTCCAG ATTGAATGAA CGTCTGTTCT AAAATTTAAC    420

CCCCCAGGGA AATATTCAGT TAACTATGTT AAAAACCCAG ACTTGTGATT GAGTTTTGCC    480

TGAAAATGCT TTCATAATTA TGTGTGAATG TGTGTC                              516
```

(2) INFORMATION FOR SEQ ID NO: 126:

(i) SEQUENCE CHARACTERISTICS:
        (A) LENGTH: 121 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 126:

GTATAATGCA GGTGCTATAA GGTGAGCATG AGACACAGAT CTTTGCTTTC CACCCTGTTC    60

TTCTTATGGT TGGGTATTCT TGTCACAGTA ACTTAACTGA TCTAGGAAAG AAAAAATGTT   120

T    121

(2) INFORMATION FOR SEQ ID NO: 127:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 127:

TGGAGACTGG AACACAAC    18

(2) INFORMATION FOR SEQ ID NO: 128:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 128:

GTGTGGCCAG GGTAGAGAAC T    21

(2) INFORMATION FOR SEQ ID NO: 129:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 129:

ATCTCCGGCA GGCATATCT    19

(2) INFORMATION FOR SEQ ID NO: 130:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 130:

TGAAATCACA GCCAAGATGA G    21

(2) INFORMATION FOR SEQ ID NO: 131:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 131:

CCATAGCCTG TTTCGTAGC                                                    19

(2) INFORMATION FOR SEQ ID NO: 132:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 132:

CCATAGCCTA TTTCGTAGC                                                    19

(2) INFORMATION FOR SEQ ID NO: 133:

(i) SEQUENCE CHARACTERISTICS:
        (A) LENGTH: 2792 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 133:

```
TGGGACAGGC AGCTCCGGGG TCCGCGGTTT CACATCGGAA ACAAAACAGC GGCTGGTCTG      60
GAAGGAACCT GAGCTACGAG CCGCGGCGGC AGCGGGGCGG CGGGGAAGCG TATACCTAAT     120
CTGGGAGCCT GCAAGTGACA ACAGCCTTTG CGGTCCTTAG ACAGCTTGGC CTGGAGGAGA     180
ACACATGAAA GAAAGAACCT CAAGAGGCTT TGTTTTCTGT GAAACAGTAT TTCTATACAG     240
TTGCTCCAAT GACAGAGTTA CCTGCACCGT TGTCCTACTT CCAGAATGCA CAGATGTCTG     300
AGGACAACCA CCTGAGCAAT ACTGTACGTA GCCAGAATGA CAATAGAGAA CGGCAGGAGC     360
ACAACGACAG ACGGAGCCTT GGCCACCCTG AGCCATTATC TAATGGACGA CCCCAGGGTA     420
ACTCCCGGCA GGTGGTGGAG CAAGATGAGG AAGAAGATGA GGAGCTGACA TTGAAATATG     480
GCGCCAAGCA TGTGATCATG CTCTTTGTCC CTGTGACTCT CTGCATGGTG GTGGTCGTGG     540
CTACCATTAA GTCAGTCAGC TTTTATACCC GGAAGGATGG GCAGCTAATC TATACCCCAT     600
TCACAGAAGA TACCGAGACT GTGGGCCAGA GAGCCCTGCA CTCAATTCTG AATGCTGCCA     660
TCATGATCAG TGTCATTGTT GTCATGACTA TCCTCCTGGT GGTTCTGTAT AAATACAGGT     720
GCTATAAGGT CATCCATGCC TGGCTTATTA TATCATCTCT ATTGTTGCTG TTCTTTTTTT     780
CATTCATTTA CTTGGGGGAA GTGTTTAAAA CCTATAACGT TGCTGTGGAC TACATTACTG     840
TTGCACTCCT GATCTGGAAT TTTGGTGTGG TGGGAATGAT TTCCATTCAC TGGAAAGGTC     900
CACTTCGACT CCAGCAGGCA TATCTCATTA TGATTAGTGC CCTCATGGCC CTGGTGTTTA     960
TCAAGTACCT CCCTGAATGG ACTGCGTGGC TCATCTTGGC TGTGATTTCA GTATATGATT    1020
TAGTGGCTGT TTTGTGTCCG AAAGGTCCAC TTCGTATGCT GGTTGAAACA GCTCAGGAGA    1080
GAAATGAAAC GCTTTTTCCA GCTCTCATTT ACTCCTCAAC AATGGTGTGG TTGGTGAATA    1140
TGGCAGAAGG AGACCCGGAA GCTCAAAGGA GAGTATCCAA AAATTCCAAG TATAATGCAG    1200
AAAGCACAGA AAGGGAGTCA CAAGACACTG TTGCAGAGAA TGATGATGGC GGGTTCAGTG    1260
AGGAATGGGA AGCCCAGAGG GACAGTCATC TAGGGCCTCA TCGCTCTACA CCTGAGTCAC    1320
GAGCTGCTGT CCAGGAACTT TCCAGCAGTA TCCTCGCTGG TGAAGACCCA GAGGAAAGGG    1380
GAGTAAAACT TGGATTGGGA GATTTCATTT TCTACAGTGT TCTGGTTGGT AAAGCCTCAG    1440
```

-continued

```
CAACAGCCAG TGGAGACTGG AACACAACCA TAGCCTGTTT CGTAGCCATA TTAATTGGTT    1500

TGTGCCTTAC ATTATTACTC CTTGCCATTT TCAAGAAAGC ATTGCCAGCT CTTCCAATCT    1560

CCATCACCTT TGGGCTTGTT TTCTACTTTG CCACAGATTA TCTTGTACAG CCTTTTATGG    1620

ACCAATTAGC ATTCCATCAA TTTTATATCT AGCATATTTG CGGTTAGAAT CCCATGGATG    1680

TTTCTTCTTT GACTATAACC AAATCTGGGG AGGACAAAGG TGATTTTCCT GTGTCCACAT    1740

CTAACAAAGT CAAGATTCCC GGCTGGACTT TTGCAGCTTC CTTCCAAGTC TTCCTGACCA    1800

CCTTGCACTA TTGGACTTTG GAAGGAGGTG CCTATAGAAA ACGATTTTGA ACATACTTCA    1860

TCGCAGTGGA CTGTGTCCCT CGGTGCAGAA ACTACCAGAT TTGAGGGACG AGGTCAAGGA    1920

GATATGATAG GCCCGGAAGT TGCTGTGCCC CATCAGCAGC TTGACGCGTG GTCACAGGAC    1980

GATTTCACTG ACACTGCGAA CTCTCAGGAC TACCGGTTAC CAAGAGGTTA GGTGAAGTGG    2040

TTTAAACCAA ACGAACTCT TCATCTTAAA CTACACGTTG AAAATCAACC CAATAATTCT    2100

GTATTAACTG AATTCTGAAC TTTTCAGGAG GTACTGTGAG AAGAGCAGG CACCAGCAGC    2160

AGAATGGGGA ATGGAGAGGT GGGCAGGGGT TCCAGCTTCC CTTTGATTTT TTGCTGCAGA    2220

CTCATCCTTT TTAAATGAGA CTTGTTTTCC CCTCTCTTTG AGTCAAGTCA AATATGTAGA    2280

TTGCCTTTGG CAATTCTTCT TCTCAAGCAC TGACACTCAT TACCGTCTGT GATTGCCATT    2340

TCTTCCCAAG GCCAGTCTGA ACCTGAGGTT GCTTTATCCT AAAAGTTTTA ACCTCAGGTT    2400

CCAAATTCAG TAAATTTTGG AAACAGTACA GCTATTTCTC ATCAATTCTC TATCATGTTG    2460

AAGTCAAATT TGGATTTTCC ACCAAATTCT GAATTTGTAG ACATACTTGT ACGCTCACTT    2520

GCCCCCAGAT GCCTCCTCTG TCCTCATTCT TCTCTCCCAC ACAAGCAGTC TTTTTCTACA    2580

GCCAGTAAGG CAGCTCTGTC RTGGTAGCAG ATGGTCCCAT TATTCTAGGG TCTTACTCTT    2640

TGTATGATGA AAAGAATGTG TTATGAATCG GTGCTGTCAG CCCTGCTGTC AGACCTTCTT    2700

CCACAGCAAA TGAGATGTAT GCCCAAAGCG GTAGAATTAA AGAAGAGTAA AATGGCTGTT    2760

GAAGCAAAAA AAAAAAAAAA AAAAAAAAAA AA                                 2792
```

(2) INFORMATION FOR SEQ ID NO: 134:

(i) SEQUENCE CHARACTERISTICS:
        (A) LENGTH: 467 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 134:

```
Met Thr Glu Leu Pro Ala Pro Leu Ser Tyr Phe Gln Asn Ala Gln Met
1               5                   10                  15

Ser Glu Asp Asn His Leu Ser Asn Thr Val Arg Ser Gln Asn Asp Asn
            20                  25                  30

Arg Glu Arg Gln Glu His Asn Asp Arg Arg Ser Leu Gly His Pro Glu
        35                  40                  45

Pro Leu Ser Asn Gly Arg Pro Gln Gly Asn Ser Arg Gln Val Val Glu
    50                  55                  60

Gln Asp Glu Glu Asp Glu Glu Leu Thr Leu Lys Tyr Gly Ala Lys
65                  70                  75                  80

His Val Ile Met Leu Phe Val Pro Val Thr Leu Cys Met Val Val Val
                85                  90                  95

Val Ala Thr Ile Lys Ser Val Ser Phe Tyr Thr Arg Lys Asp Gly Gln
```

```
            100                 105                 110
Leu Ile Tyr Thr Pro Phe Thr Glu Asp Thr Glu Thr Val Gly Gln Arg
            115                 120                 125

Ala Leu His Ser Ile Leu Asn Ala Ala Ile Met Ile Ser Val Ile Val
            130                 135                 140

Val Met Thr Ile Leu Leu Val Val Leu Tyr Lys Tyr Arg Cys Tyr Lys
145                 150                 155                 160

Val Ile His Ala Trp Leu Ile Ile Ser Ser Leu Leu Leu Leu Phe Phe
                    165                 170                 175

Phe Ser Phe Ile Tyr Leu Gly Glu Val Phe Lys Thr Tyr Asn Val Ala
                180                 185                 190

Val Asp Tyr Ile Thr Val Ala Leu Leu Ile Trp Asn Phe Gly Val Val
            195                 200                 205

Gly Met Ile Ser Ile His Trp Lys Gly Pro Leu Arg Leu Gln Gln Ala
            210                 215                 220

Tyr Leu Ile Met Ile Ser Ala Leu Met Ala Leu Val Phe Ile Lys Tyr
225                 230                 235                 240

Leu Pro Glu Trp Thr Ala Trp Leu Ile Leu Ala Val Ile Ser Val Tyr
                    245                 250                 255

Asp Leu Val Ala Val Leu Cys Pro Lys Gly Pro Leu Arg Met Leu Val
                260                 265                 270

Glu Thr Ala Gln Glu Arg Asn Glu Thr Leu Phe Pro Ala Leu Ile Tyr
            275                 280                 285

Ser Ser Thr Met Val Trp Leu Val Asn Met Ala Glu Gly Asp Pro Glu
            290                 295                 300

Ala Gln Arg Arg Val Ser Lys Asn Ser Lys Tyr Asn Ala Glu Ser Thr
305                 310                 315                 320

Glu Arg Glu Ser Gln Asp Thr Val Ala Glu Asn Asp Asp Gly Gly Phe
                    325                 330                 335

Ser Glu Glu Trp Glu Ala Gln Arg Asp Ser His Leu Gly Pro His Arg
                340                 345                 350

Ser Thr Pro Glu Ser Arg Ala Ala Val Gln Glu Leu Ser Ser Ser Ile
            355                 360                 365

Leu Ala Gly Glu Asp Pro Glu Glu Arg Gly Val Lys Leu Gly Leu Gly
            370                 375                 380

Asp Phe Ile Phe Tyr Ser Val Leu Val Gly Lys Ala Ser Ala Thr Ala
385                 390                 395                 400

Ser Gly Asp Trp Asn Thr Thr Ile Ala Cys Phe Val Ala Ile Leu Ile
                    405                 410                 415

Gly Leu Cys Leu Thr Leu Leu Leu Ala Ile Phe Lys Lys Ala Leu
                420                 425                 430

Pro Ala Leu Pro Ile Ser Ile Thr Phe Gly Leu Val Phe Tyr Phe Ala
            435                 440                 445

Thr Asp Tyr Leu Val Gln Pro Phe Met Asp Gln Leu Ala Phe His Gln
450                 455                 460

Phe Tyr Ile
465

(2) INFORMATION FOR SEQ ID NO: 135:

(i) SEQUENCE CHARACTERISTICS:
        (A) LENGTH: 1964 base pairs
        (B) TYPE: nucleic acid
        (C) STRANDEDNESS: single
        (D) TOPOLOGY: linear
```

(ii) MOLECULE TYPE: cDNA (xi) SEQUENCE DESCRIPTION: SEQ ID NO: 135:

```
ACCANACANC GGCAGCTGAG GCGGAAACCT AGGCTGCGAG CCGGCCGCCC GGGCGCGGAG      60
AGAGAAGGAA CCAACACAAG ACAGCAGCCC TTCGAGGTCT TTAGGCAGCT TGGAGGAGAA     120
CACATGAGAG AAAGAATCCC AAGAGGTTTT GTTTTCTTTG AGAAGGTATT TCTGTCCAGC     180
TGCTCCAATG ACAGAGATAC CTGCACCTTT GTCCTACTTC CAGAATGCCC AGATGTCTGA     240
GGACAGCCAC TCCAGCAGCG CCATCCGGAG CCAGAATGAC AGCCAAGAAC GGCAGCAGCA     300
GCATGACAGG CAGAGACTTG ACAACCCTGA GCCAATATCT AATGGGCGGC CCAGAGTAA      360
CTCAAGACAG GTGGTGGAAC AAGATGAGGA GGAAGACGAA GAGCTGACAT TGAAATATGG     420
AGCCAAGCAT GTCATCATGC TCTTTGTCCC CGTGACCCTC TGCATGGTCG TCGTCGTGGC     480
CACCATCAAA TCAGTCAGCT TCTATACCCG AAGGACGGT CAGCTAATCT ACACCCCATT      540
CACAGAAGAC ACTGAGACTG TAGGCCAAAG AGCCCTGCAC TCGATCCTGA ATGCGGCCAT     600
CATGATCAGT GTCATTGTCA TTATGACCAT CCTCCTGGTG GTCCTGTATA AATACAGGTG     660
CTACAAGGTC ATCCACGCCT GGCTTATTAT TTCATCTCTG TTGTTGCTGT TCTTTTTTTC     720
GTTCATTTAC TTAGGGGAAG TATTTAAGAC CTACAATGTC GCCGTGGACT ACGTTACAGT     780
AGCACTCCTA ATCTGGAATT TTGGTGTGGT CGGGATGATT GCCATCCACT GGAAAGGCCC     840
CCTTCGACTG CAGCAGGCGT ATCTCATTAT GATCAGTGCC CTCATGGCCC TGGTATTTAT     900
CAAGTACCTC CCCGAATGGA CCGCATGGCT CATCTTGGCT GTGATTTCAG TATATGATTT     960
GGTGGCTGTT TTATGTCCCA AAGGCCCACT TCGTATGCTG GTTGAAACAG CTCAGGAAAG    1020
AAATGAGACT CTCTTTCCAG CTCTTATCTA TTCCTCAACA ATGGTGTGGT TGGTGAATAT    1080
GGCTGAAGGA GACCCAGAAG CCCAAAGGAG GGTACCCAAG AACCCCAAGT ATAACACACA    1140
AAGAGCGGAG AGAGAGACAC AGGACAGTGG TTCTGGGAAC GATGATGGTG GCTTCAGTGA    1200
GGAGTGGGAG GCCCAAAGAG ACAGTCACCT GGGGCCTCAT CGCTCCACTC CCGAGTCAAG    1260
AGCTGCTGTC CAGGAACTTT CTGGGAGCAT TCTAACGAGT GAAGACCCGG AGGAAAGAGG    1320
AGTAAAACTT GGACTGGGAG ATTTCATTTT CTACAGTGTT CTGGTTGGTA AGGCCTCAGC    1380
AACCGCCAGT GGAGACTGGA ACACAACCAT AGCCTGCTTT GTAGCCATAC TGATCGGCCT    1440
GTGCCTTACA TTACTCCTGC TCGCCATTTT CAAGAAAGCG TTGCCAGCCC TCCCCATCTC    1500
CATCACCTTC GGGCTCGTGT TCTACTTCGC CACGGATTAC CTTGTGCAGC CCTTCATGGA    1560
CCAACTTGCA TTCCATCAGT TTTATATCTA GCCTTTCTGC AGTTAGAACA TGGATGTTTC    1620
TTCTTTGATT ATCAAAAACA CAAAAACAGA GAGCAAGCCC GAGGAGGAGA CTGGTGACTT    1680
TCCTGTGTCC TCAGCTAACA AAGGCAGGAC TCCAGCTGGA CTTCTGCAGC TTCCTTCCGA    1740
GTCTCCCTAG CCACCCGCAC TACTGGACTG TGGAAGGAAG CGTCTACAGA GGAACGGTTT    1800
CCAACATCCA TCGCTGCAGC AGACGGTGTC CCTCAGTGAC TTGAGAGACA AGGACAAGGA    1860
AATGTGCTGG GCCAAGGAGC TGCCGTGCTC TGCTAGCTTT GACCGTGGGC ATGGAGATTT    1920
ACCCGCACTG TGAACTCTCT AAGGTAAACA AAGTGAGGTG AACC                     1964
```

(2) INFORMATION FOR SEQ ID NO: 136:

(i) SEQUENCE CHARACTERISTICS:
        (A) LENGTH: 467 amino acids
        (B) TYPE: amino acid
        (D) TOPOLOGY: linear (ii) MOLECULE TYPE: protein (xi) SEQUENCE DESCRIPTION: SEQ ID NO: 136:

```
Met Thr Glu Ile Pro Ala Pro Leu Ser Tyr Phe Gln Asn Ala Gln Met
  1               5                  10                  15

Ser Glu Asp Ser His Ser Ser Ala Ile Arg Ser Gln Asn Asp Ser
             20                  25                  30

Gln Glu Arg Gln Gln Gln His Asp Arg Gln Arg Leu Asp Asn Pro Glu
         35                  40                  45

Pro Ile Ser Asn Gly Arg Pro Gln Ser Asn Ser Arg Gln Val Val Glu
     50                  55                  60

Gln Asp Glu Glu Asp Glu Glu Leu Thr Leu Lys Tyr Gly Ala Lys
 65              70                  75                  80

His Val Ile Met Leu Phe Val Pro Val Thr Leu Cys Met Val Val
                 85                  90                  95

Val Ala Thr Ile Lys Ser Val Ser Phe Tyr Thr Arg Lys Asp Gly Gln
                100                 105                 110

Leu Ile Tyr Thr Pro Phe Thr Glu Asp Thr Glu Thr Val Gly Gln Arg
             115                 120                 125

Ala Leu His Ser Ile Leu Asn Ala Ala Ile Met Ile Ser Val Ile Val
        130                 135                 140

Ile Met Thr Ile Leu Leu Val Val Leu Tyr Lys Tyr Arg Cys Tyr Lys
145                 150                 155                 160

Val Ile His Ala Trp Leu Ile Ile Ser Ser Leu Leu Leu Leu Phe Phe
                165                 170                 175

Phe Ser Phe Ile Tyr Leu Gly Glu Val Phe Lys Thr Tyr Asn Val Ala
                180                 185                 190

Val Asp Tyr Val Thr Val Ala Leu Leu Ile Trp Asn Phe Gly Val Val
                195                 200                 205

Gly Met Ile Ala Ile His Trp Lys Gly Pro Leu Arg Leu Gln Gln Ala
        210                 215                 220

Tyr Leu Ile Met Ile Ser Ala Leu Met Ala Leu Val Phe Ile Lys Tyr
225                 230                 235                 240

Leu Pro Glu Trp Thr Ala Trp Leu Ile Leu Ala Val Ile Ser Val Tyr
                245                 250                 255

Asp Leu Val Ala Val Leu Cys Pro Lys Gly Pro Leu Arg Met Leu Val
                260                 265                 270

Glu Thr Ala Gln Glu Arg Asn Glu Thr Leu Phe Pro Ala Leu Ile Tyr
        275                 280                 285

Ser Ser Thr Met Val Trp Leu Val Asn Met Ala Glu Gly Asp Pro Glu
    290                 295                 300

Ala Gln Arg Arg Val Pro Lys Asn Pro Lys Tyr Asn Thr Gln Arg Ala
305                 310                 315                 320

Glu Arg Glu Thr Gln Asp Ser Gly Ser Gly Asn Asp Asp Gly Gly Phe
                325                 330                 335

Ser Glu Glu Trp Glu Ala Gln Arg Asp Ser His Leu Gly Pro His Arg
            340                 345                 350

Ser Thr Pro Glu Ser Arg Ala Ala Val Gln Glu Leu Ser Gly Ser Ile
        355                 360                 365

Leu Thr Ser Glu Asp Pro Glu Glu Arg Gly Val Lys Leu Gly Leu Gly
    370                 375                 380

Asp Phe Ile Phe Tyr Ser Val Leu Val Gly Lys Ala Ser Ala Thr Ala
385                 390                 395                 400
```

```
Ser Gly Asp Trp Asn Thr Thr Ile Ala Cys Phe Val Ala Ile Leu Ile
            405                 410                 415

Gly Leu Cys Leu Thr Leu Leu Leu Ala Ile Phe Lys Lys Ala Leu
        420                 425                 430

Pro Ala Leu Pro Ile Ser Ile Thr Phe Gly Leu Val Phe Tyr Phe Ala
            435                 440                 445

Thr Asp Tyr Leu Val Gln Pro Phe Met Asp Gln Leu Ala Phe His Gln
    450                 455                 460

Phe Tyr Ile
465

(2) INFORMATION FOR SEQ ID NO: 137:

(i) SEQUENCE CHARACTERISTICS:
        (A) LENGTH: 2296 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 137:
```

| | |
|---|---|
| GAATTCGGCA CGAGGGCATT TCCAGCAGTG AGGAGACAGC CAGAAGCAAG CTTTNGGAGC | 60 |
| TGAAGGAACC TGAGACAGAA GCTAGTCCCC CCTCTGAATT TTACTGATGA AGAAACTGAG | 120 |
| GCCACAGAGC TAAAGTGACT TTTCCCAAGG TCGCCCAGCG AGGACGTGGN ACTTCTCAGA | 180 |
| CGTCAGGAGA GTGATGTGAG GGAGCTGTGT NACCATAGAA AGTGACGTGT TAAAAACCAG | 240 |
| CGCTGCCCTC TTTGGAAAGC CAGGGAGCAT CATTCAATTT AGCCTGCTGA AGAAGAAA | 300 |
| CCAAGTGTCC GGGATTCAAG ACCTCTCTTG CGSCCCCAAG TGTTCCGTGG GTGCTTCCAG | 360 |
| AGGNAGGGYT ATGTCACATT CATGCCTCTG ACAGSGAGGA AGAAGTGTGT GATGAGCGGA | 420 |
| CGTCCCTAAT GTCGGCCGAG AGCCCCACGC CGCGCTCCTG CCAGGAGGGC AGGCAGGGCC | 480 |
| CAGAGGATGG AGAGAATACT NCCCAGTGGA GAASCCAGGA GAACGAGGAG GACGGTGAGG | 540 |
| AGGACCCTGA CCGCTATGTC TGTAGTGGGG TTCCCGGGCG SCCGCCAGGC CTGGAGGAAG | 600 |
| AGCTGACCCT CAAATACGGA GCGAAGCATG TGATCATGCT GTTTGTGCCT GTCACTCTGT | 660 |
| GCATGATCGT GGTGGTAGCC ACCATCAAGT CTGTGCGCTT CTACACAGAG AAGAATGGAC | 720 |
| AGCTCATCTA CACGCCATTC ACTGAGGACA CACCCTCGGT GGGCCAGCGC CTCCTCAACT | 780 |
| CCGTGCTGAA CACCCTCATC ATGATCAGCG TCATCGTGGT TATGACCATC TTCTTGGTGG | 840 |
| TGCTCTACAA GTACCGCTGC TACAAGTTCA TCCATGGCTG GTTGATCATG TCTTCACTGA | 900 |
| TGCTGCTGTT CCTCTTCACC TATATCTACC TTGGGGAAGT GCTCAAGACC TACAATGTGG | 960 |
| CCATGGACTA CCCCACCCTC TTGCTGACTG TCTGGAACTT CGGGGCAGTG GGCATGGTGT | 1020 |
| GCATCCACTG GAAGGGCCCT CTGGTGCTGC AGCAGGCCTA CCTCATCATG ATCAGTGCGC | 1080 |
| TCATGGCCCT AGTGTTCATC AAGTACCTCC CAGAGTGGTC CGCGTGGGTC ATCCTGGGCG | 1140 |
| CCATCTCTGT GTATGATCTC GTGGCTGTGC TGTGTCCCAA AGGGCCTCTG AGAATGCTGG | 1200 |
| TAGAAACTGC CCAGGAGAGA AATGAGCCCA TATTCCCTGC CCTGATATAC TCATCTGCCA | 1260 |
| TGGTGTGGAC GGTTGGCATG GCGAAGCTGG ACCCCTCCTC TCAGGGTGCC CTCCAGCTCC | 1320 |
| CCTACGACCC GGAGATGGAA GAAGACTCCT ATGACAGTTT TGGGGAGCCT TCATACCCCG | 1380 |
| AAGTCTTTGA GCCTCCCTTG ACTGGCTACC CAGGGGAGGA GCTGGAGGAA GAGGAGGAAA | 1440 |
| GGGGCGTGAA GCTTGGCCTC GGGGACTTCA TCTTCTACAG TGTGCTGGTG GGCAAGGCGG | 1500 |
| CTGCCACGGG CAGCGGGGAC TGGAATACCA CGCTGGCCTG CTTCGTGGCC ATCCTCATTG | 1560 |

```
GCTTGTGTCT GACCCTCCTG CTGCTTGCTG TGTTCAAGAA GGCGCTGCCC GCCCTCCCCA    1620

TCTCCATCAC GTTCGGGCTC ATCTTTTACT TCTCCACGGA CAACCTGGTG CGGCCGTTCA    1680

TGGACACCCT GGCCTCCCAT CAGCTCTACA TCTGAGGGAC ATGGTGTGCC ACAGGCTGCA    1740

AGCTGCAGGG AATTTTCATT GGATGCAGTT GTATAGTTTT ACAYTCTAGT GCCATATATT    1800

TTTAAGACTT TTCTTTCCTT AAAAAATAAA GTACGTGTTT ACTTGGTGAG GAGGAGGCAG    1860

AACCAGCTCT TTGGTGCCAG CTGTTTCATC ACCAGACTTT GGCTCCCGCT TTGGGGAGCG    1920

CCTCGCTTCA CGGACAGGAA GCACAGCAGG TTTATCCAGA TGAACTGAGA AGGTCAGATT    1980

AGGGTGGGGA GAAGAGCATC CGGCATGAGG GCTGAGATGC SCAAAGAGTG TGCTCGGGAG    2040

TGGCCCCTGG CACCTGGGTG CTCTGGCTGG AGAGGAAAAG CCAGTTCCCT ACGAGGAGTG    2100

TTCCCAATGC TTTNNTCCNT NNTKNCCTTK TTAWNTTANT KCCYTTARAA ACTNANNCCT    2160

KTTNTTKTTW CGGNARNCAC MCNNCNGGGR NGNGGNNTWA NARTNAWANC CAAWAAATAN    2220

NTNANTCCTK TTAANAAAAA AAAAAAAAAA AAAAAAAAAA AAAAAAAAAA AAAAAAAAAA    2280

AAAAAAAAAR GAATTC                                                    2296

(2) INFORMATION FOR SEQ ID NO: 138:

(i) SEQUENCE CHARACTERISTICS:
        (A) LENGTH: 372 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 138:

Glu Glu Leu Thr Leu Lys Tyr Gly Ala Lys His Val Ile Met Leu Phe
1               5                   10                  15

Val Pro Val Thr Leu Cys Met Ile Val Val Ala Thr Ile Lys Ser
            20                  25                  30

Val Arg Phe Tyr Thr Glu Lys Asn Gly Gln Leu Ile Tyr Thr Pro Phe
        35                  40                  45

Thr Glu Asp Thr Pro Ser Val Gly Gln Arg Leu Leu Asn Ser Val Leu
    50                  55                  60

Asn Thr Leu Ile Met Ile Ser Val Ile Val Val Met Thr Ile Phe Leu
65                  70                  75                  80

Val Val Leu Tyr Lys Tyr Arg Cys Tyr Lys Phe Ile His Gly Trp Leu
                85                  90                  95

Ile Met Ser Ser Leu Met Leu Leu Phe Leu Phe Thr Tyr Ile Tyr Leu
                100                 105                 110

Gly Glu Val Leu Lys Thr Tyr Asn Val Ala Met Asp Tyr Pro Thr Leu
            115                 120                 125

Leu Leu Thr Val Trp Asn Phe Gly Ala Val Gly Met Val Cys Ile His
    130                 135                 140

Trp Lys Gly Pro Leu Val Leu Gln Gln Ala Tyr Leu Ile Met Ile Ser
145                 150                 155                 160

Ala Leu Met Ala Leu Val Phe Ile Lys Tyr Leu Pro Glu Trp Ser Ala
                165                 170                 175

Trp Val Ile Leu Gly Ala Ile Ser Val Tyr Asp Leu Val Ala Val Leu
                180                 185                 190

Cys Pro Lys Gly Pro Leu Arg Met Leu Val Glu Thr Ala Gln Glu Arg
            195                 200                 205
```

```
Asn Glu Pro Ile Phe Pro Ala Leu Ile Tyr Ser Ser Ala Met Val Trp
210                 215                 220
Thr Val Gly Met Ala Lys Leu Asp Pro Ser Ser Gln Gly Ala Leu Gln
225                 230                 235                 240
Leu Pro Tyr Asp Pro Glu Met Glu Glu Asp Ser Tyr Asp Ser Phe Gly
                245                 250                 255
Glu Pro Ser Tyr Pro Glu Val Phe Glu Pro Pro Leu Thr Gly Tyr Pro
                260                 265                 270
Gly Glu Glu Leu Glu Glu Glu Glu Arg Gly Val Lys Leu Gly Leu
                275                 280                 285
Gly Asp Phe Ile Phe Tyr Ser Val Leu Val Gly Lys Ala Ala Ala Thr
290                 295                 300
Gly Ser Gly Asp Trp Asn Thr Thr Leu Ala Cys Phe Val Ala Ile Leu
305                 310                 315                 320
Ile Gly Leu Cys Leu Thr Leu Leu Leu Leu Ala Val Phe Lys Lys Ala
                325                 330                 335
Leu Pro Ala Leu Pro Ile Ser Ile Thr Phe Gly Leu Ile Phe Tyr Phe
                340                 345                 350
Ser Thr Asp Asn Leu Val Arg Pro Phe Met Asp Thr Leu Ala Ser His
                355                 360                 365
Gln Leu Tyr Ile
        370

(2) INFORMATION FOR SEQ ID NO: 139:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 139:

GGTACCGCCA CCATGACAGA GGTACCTGCA C                                    31

(2) INFORMATION FOR SEQ ID NO: 140:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 140:

GAATTCACTG GCTGTAGAAA AAGAC                                           25

(2) INFORMATION FOR SEQ ID NO: 141:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 141:
```

GGATCCGGTC CACTTCGTAT GCTG                                              24

(2) INFORMATION FOR SEQ ID NO: 142:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 142:

TTTTTTGAAT TCTTAGGCTA TGGTTGTGTT CCA                                    33

(2) INFORMATION FOR SEQ ID NO: 143:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 143:

GATTAGTGGT TGTTTTGTG                                                    19

(2) INFORMATION FOR SEQ ID NO: 144:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 144:

GATTAGTGGC TGTTTTGTG                                                    19

(2) INFORMATION FOR SEQ ID NO: 145:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 145:

TTTTTCCAGC TCTCATTTA                                                    19

(2) INFORMATION FOR SEQ ID NO: 146:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 146:

```
TTTTTCCAGT TCTCATTTA                                                      19

(2) INFORMATION FOR SEQ ID NO: 147:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 147:

TACAGTGTTC TGGTTGGTA                                                      19

(2) INFORMATION FOR SEQ ID NO: 148:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 148:

TACAGTGTTC TGGTTGGTA                                                      19

(2) INFORMATION FOR SEQ ID NO: 149:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 149:

TACAGTGTTG TGGTTGGTA                                                      19

(2) INFORMATION FOR SEQ ID NO: 150:

(i) SEQUENCE CHARACTERISTICS:
        (A) LENGTH: 1092 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 150:

GTCTAGATAA GNCAACATTC AGGGGTAGAA GGGGACTGTT TATTTTTTCC TTTAGTCTCT          60

CTTAAAGAGT GAGAAAAATT TTCCCAGGAA TCCCGGTGGA CTTTGCTTCA CCACTCATAG         120

GTTCATACCA AGTTACAACC CCACAACCTT AGAGCTTTTG TTAGGAAGAG GCTTGGTGGG         180

ATTACCGTGC TTGGCTTGGC TTGGTCAGGA TTCACCACCA GAGTCATGTG GGAGGGGGTG         240

GGAACCCAAA CAATTCAGGA TTCTGCCCTC AGGAAATAAA GGAGAAAATA GCTGTTGGAT         300

AAACTACCAG CAGGCACTGC TACAGCCCAT GCTTTGTGGT TTAAGGGCCA GCTAGTTACA         360

ATGACAGCTA GTTACTGTTT CCATGTAATT TTCTTAAAGG TATTAAATTT TTCTAAATAT         420

TAGAGCTGTA ACTTCCACTT TCTCTTGAAG GCACAGWAAG GGAGTCACAA GACACTGTTG         480
```

```
CAGAGAATGA TGATGGCGGG TTCAGTGAGG AATGGGAASC CCAGRGGGAC ANTCATCTAG      540

GGCCTCATCG CTCTACACCT GAGTCACGAG CTKCTNTCCA GGRACTTTCC ANCAGTATCC      600

TCGCTGGTGA AGACCCAGAG GAAAGNATGT TCANTTCTCC ATNTTTCAAA GTCATGGATT      660

CCTTTAGGTA GCTACATTAT CAACCTTTTT GAGAATAAAA TGAATTGAGA GTGTTACAGT      720

CTAATTCTAT ATCACATGTA ACTTTTATTT GGATATATCA GTAATAGTGC TTTTTYNTTT      780

TTTTTTTTTT TTTTTTTTTT TTTTNGGNGA NAGAGTCTCG CTCTGTCGCC AGGTTGGAGT      840

GCAATGGTGC GATCTTGGCT CACTGAAAGC TCCACCNCCC GGGTTCAAGT GATTCTCCTG      900

CCTCAGCCNC CCAAGTAGNT GGGACTACAG GGGTGCGCCA CCACGCCTGG GATAATTTTG      960

GGNTTTTTAG TAGAGATGGC GTTTCACCAN CTTGGNGCAG GCTGGTCTTG GAACTCCTGA     1020

NATCATGATC TGCCTGCCTT AGCCTCCCCA AAGTGCTGGG ATTNCAGGGG TGAGCCACTG     1080

TTCCTGGGCC TC                                                         1092
```

(2) INFORMATION FOR SEQ ID NO: 151:

(i) SEQUENCE CHARACTERISTICS:
        (A) LENGTH: 1003 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 151:

```
CTGCAGTGAG CCGAGATCAT GCTGCTGTAC TCCAGCCTGG GCCACAGAGC CAAACTCCAT       60

CTCCCAAAAA AAAAAAATAT TAATTAATAT GATNAAATGA TGCCTATCTC AGAATTCTTG      120

TAAGGATTTC TTAGKACAAG TGCTGGGTAT AAACTATANA TTCRATAGAT GNCGATTATT      180

ACTTAYTATT GTTATTGATA AATAACAGCA GCATCTACAG TTAAGACTCC AGAGTCAGTC      240

ACATAGAATC TGGNACTCCT ATTGTAGNAA ACCCCNMMAG AAAGAAAACA CAGCTGAAGC      300

CTAATTTTGT ATATCATTTA CTGACTTCTC TCATTCATTG TGGGGTTGAG TAGGGCAGTG      360

ATATTTTTGA ATTGTGAAAT CATANCAAAG AGTGACCAAC TTTTTAATAT TTGTAACCTT      420

TCCTTTTTAG GGGGAGTAAA ACTTGGATTG GGAGATTTCA TTTTCTACAG TGTTCTGGTT      480

GGTAAAGCCT CAGCAACAGC CAGTGGAGAC TGGAACACAA CCATAGCCTG TTTCGTAGCC      540

ATATTAATTG TMMSTATACA CTAATAAGAA TGTGTCAGAG CTCTTAATGT CMAAACTTTG      600

ATTACACAGT CCCTTTAAGG CAGTTCTGTT TTAACCCCAG GTGGGTTAAA TATTCCAGCT      660

ATCTGAGGAG CTTTTNGATA ATTGGACCTC ACCTTAGTAG TTCTCTACCC TGGCCACACA      720

TTAGAATCAC TTGGGAGCTT TTAAAACTGT AAGCTCTGCC CTGAGATATT CTTACTCAAT      780

TTAATTGTGT AGTTTTTAAA ATTCCCCAGG AAATTCTGGT ATTTCTGTTT AGGAACCGCT      840

GCCTCAAGCC TAGCAGCACA GATATGTAGG AAATTAGCTC TGTAAGGTTG GTCTTACAGG      900

GATAAACAGA TCCTTCCTTA GTCCCTGGAC TTAATCACTG AGAGTTTGGG TGGTGGTTTT      960

GGATTTAATG ACACAACCTG TAGCATGCAG TGTTACTTAA GAC                      1003
```

(2) INFORMATION FOR SEQ ID NO: 152:

(i) SEQUENCE CHARACTERISTICS:
        (A) LENGTH: 1726 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 152:

| | | | | | |
|---|---|---|---|---|---|
| GGATCCCTCC | CCTTTTTAGA | CCATACAAGG | TAACTTCCGG | ACGTTGCCAT | GGCATCTGTA | 60 |
| AACTGTCATG | GTGTTGGCGG | GGAGTGTCTT | TTAGCATGCT | AATGTATTAT | AATTAGCGTA | 120 |
| TAGTGAGCAG | TGAGGATAAC | CAGAGGTCAC | TCTCCTCACC | ATCTTGGTTT | TGGTGGGTTT | 180 |
| TGGCCAGCTT | CTTTATTGCA | ACCAGTTTTA | TCAGCAAGAT | CTTTATGAGC | TGTATCTTGT | 240 |
| GCTGACTTCC | TATCTCATCC | CGNAACTAAG | AGTACCTAAC | CTCCTGCAAA | TTGMAGNCCA | 300 |
| GNAGGTCTTG | GNCTTATTTN | ACCCAGCCCC | TATTCAARAT | AGAGTNGYTC | TTGGNCCAAA | 360 |
| CGCCYCTGAC | ACAAGGATTT | TAAAGTCTTA | TTAATTAAGG | TAAGATAGKT | CCTTGSATAT | 420 |
| GTGGTCTGAA | ATCACAGAAA | GCTGAATTTG | GAAAAAGGTG | CTTGGASCTG | CAGCCAGTAA | 480 |
| ACAAGTTTTC | ATGCAGGTGT | CAGTATTTAA | GGTACATCTC | AAAGGATAAG | TACAATTGTG | 540 |
| TATGTTGGGA | TGAACAGAGA | GAATGGAGCA | ANCCAAGACC | CAGGTAAAAG | AGAGGACCTG | 600 |
| AATGCCTTCA | GTGAACAATG | ATAGATAATC | TAGACTTTTA | AACTGCATAC | TTCCTGTACA | 660 |
| TTGTTTTTTC | TTGCTTCAGG | TTTTTAGAAC | TCATAGTGAC | GGGTCTGTTG | TTAATCCCAG | 720 |
| GTCTAACCGT | TACCTTGATT | CTGCTGAGAA | TCTGATTTAC | TGAAAATGTT | TTTCTTGTGC | 780 |
| TTATAGAATG | ACAATAGAGA | ACGGCAGGAG | CACAACGACA | GACGGAGCCT | TGGCCACCCT | 840 |
| GANCCATTAT | CTAATGGACG | ACCCAGGGTA | ACTCCCGGCA | GGTGGTGGAN | CAAGATGAGG | 900 |
| AAGAAGATGA | GGANCTGACA | TTGAAATATG | NCGSCAAGCA | TGTGATCATG | CTCTTTGKCC | 960 |
| CTGTGACTCT | CTGCATGGTG | GTGGTCGTGG | NTACCATTAA | GTCAGTCAGC | TTTTATACCC | 1020 |
| GGAAGGATGG | GCAGCTGTAC | GTATGAGTTT | KGTTTTATTA | TTCTCAAASC | CAGTGTGGCT | 1080 |
| TTTCTTTACA | GCATGTCATC | ATCACCTTGA | AGGCCTCTNC | ATTGAAGGGG | CATGACTTAG | 1140 |
| CTGGAGAGCC | CATCCTCTGT | GATGGTCAGG | AGCAGTTGAG | AGANCGAGGG | GTTATTACTT | 1200 |
| CATGTTTTAA | GTGGAGAAAA | GGAACACTGC | AGAAGTATGT | TTCCTGTATG | GTATTACTGG | 1260 |
| ATAGGGCTGA | AGTTATGCTG | AATTGAACAC | ATAAATTCTT | TTCCACCTCA | GGGNCATTGG | 1320 |
| GCGCCCATTG | NTCTTCTGCC | TAGAATATTC | TTTCCTTTNC | TNACTTKGGN | GGATTAAATT | 1380 |
| CCTGTCATCC | CCCTCCTCTT | GGTGTTATAT | ATAAAGTNTT | GGTGCCGCAA | AAGAAGTAGC | 1440 |
| ACTCGAATAT | AAAATTTTCC | TTTTAATTCT | CAGCAAGGNA | AGTTACTTCT | ATATAGAAGG | 1500 |
| GTGCACCCNT | ACAGATGGAA | CAATGGCAAG | CGCACATTTG | GGACAAGGGA | GGGGAAAGGG | 1560 |
| TTCTTATCCC | TGACACACGT | GGTCCCNGCT | GNTGTGTNCT | NCCCCCACTG | ANTAGGGTTA | 1620 |
| GACTGGACAG | GCTTAAACTA | ATTCCAATTG | GNTAATTTAA | AGAGAATNAT | GGGGTGAATG | 1680 |
| CTTTGGGAGG | AGTCAAGGAA | GAGNAGGTAG | NAGGTAACTT | GAATGA | | 1726 |

(2) INFORMATION FOR SEQ ID NO: 153:

(i) SEQUENCE CHARACTERISTICS:
        (A) LENGTH: 1883 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 153:

| | | | | | |
|---|---|---|---|---|---|
| CNCGTATAAA | AGACCAACAT | TGCCANCNAC | AACCACAGGC | AAGATCTTCT | CCTACCTTCC | 60 |
| CCCNNGGTGT | AATACCAAGT | ATTCNCCAAT | TTGTGATAAA | CTTTCATTGG | AAAGTGACCA | 120 |

| | | | | |
|---|---|---|---|---|
|CCCTCCTTGG|TTAATACATT|GTCTGTGCCT|GCTTTCACAC|TACAGTAGCA CAGTTGAGTG|180|
|TTTGCCCTGG|AGACCATATG|ACCCATAGAG|CTTAAAATAT|TCAGTCTGGC TTTTTACAGA|240|
|GATGTTTCTG|ACTTTGTTAA|TAGAAAATCA|ACCCAACTGG|TTTAAATAAT GCACATACTT|300|
|TCTCTCTCAT|AGAGTAGTGC|AGAGGTAGNC|AGTCCAGATT|AGTASGGTGG CTTCACGTTC|360|
|ATCCAAGGAC|TCAATCTCCT|TCTTTCTTCT|TTAGCTTCTA|ACCTCTAGCT TACTTCAGGG|420|
|TCCAGGCTGG|AGCCCTASCC|TTCATTTCTG|ACAGTAGGAA|GGAGTAGGGG AGAAAAGAAC|480|
|ATAGGACATG|TCAGCAGAAT|TCTCTCCTTA|GAAGTTCCAT|ACACAACACA TCTCCCTAGA|540|
|AGTCATTGCC|CTTACTTGTT|CTCATAGCCA|TCCTAAATAT|AAGGGAGTCA GAAGTAAAGT|600|
|CTKKNTGGCT|GGGAATATTG|GCACCTGGAA|TAAAAATGTT|TTTCTGTGAA TGAGAAACAA|660|
|GGGGAAGATG|GATATGTGAC|ATTATCTTAA|GACAACTCCA|GTTGCAATTA CTCTGCAGAT|720|
|GAGAGGCACT|AATTATAAGC|CATATTACCT|TTCTTCTGAC|AACCACTTGT CAGCCCNCGT|780|
|GGTTTCTGTG|GCAGAATCTG|GTTCYATAMC|AAGTTCCTAA|TAANCTGTAS CCNAAAAAAT|840|
|TTGATGAGGT|ATTATAATTA|TTTCAATATA|AAGCACCCAC|TAGATGGAGC CAGTGTCTGC|900|
|TTCACATGTT|AAGTCCTTCT|TTCCATATGT|TAGACATTTT|CTTTGAAGCA ATTTTAGAGT|960|
|GTAGCTGTTT|TTCTCAGGTT|AAAAATTCTT|AGCTAGGATT|GGTGAGTTGG GGAAAAGTGA|1020|
|CTTATAAGAT|NCGAATTGAA|TTAAGAAAAA|GAAAATTCTG|TGTTGGAGGT GGTAATGTGG|1080|
|KTGGTGATCT|YCATTAACAC|TGANCTAGGG|CTTTKGKGTT|TGKTTTATTG TAGAATCTAT|1140|
|ACCCCATTCA|NAGAAGATAC|CGAGACTGTG|GGCCAGAGAG|CCCTGCACTC AATTCTGAAT|1200|
|GCTGCCATCA|TGATCAGNGT|CATTGTWGTC|ATGACTANNC|TCCTGGTGGT TCWGTATAAA|1260|
|TACAGGTGCT|ATAAGGTGAG|CATGAGACAC|AGATCTTTGN|TTTCCACCCT GTTCTTCTTA|1320|
|TGGTTGGGTA|TTCTTGTCAC|AGTAACTTAA|CTGATCTAGG|AAAGAAAAAA TGTTTTGTCT|1380|
|TCTAGAGATA|AGTTAATTTT|TAGTTTTCTT|CCTCCTCACT|GTGGAACATT CAAAAAATAC|1440|
|AAAAAGGAAG|CCAGGTGCAT|GTGTAATGCC|AGGCTCAGAG|GCTGAGGCAG GAGGATCGCT|1500|
|TGGGCCCAGG|AGTTCACAAG|CAGCTTGGGC|AACGTAGCAA|GACCCTGCCT CTATTAAAGA|1560|
|AAACAAAAAA|CAAATATTGG|AAGTATTTTA|TATGCATGGA|ATCTATATGT CATGAAAAAA|1620|
|TTAGTGTAAA|ATATATATAT|TATGATTAGN|TATCAAGATT|TAGTGATAAT TTATGTTATT|1680|
|TTGGGATTTC|AATGCCTTTT|TAGGCCATTG|TCTCAAMAAA|TAAAAGCAGA AAACAAAAAA|1740|
|AGTTGTAACT|GAAAAATAAA|CATTTCCATA|TAATAGCACA|ATCTAAGTGG GTTTTTGNTT|1800|
|GTTTGTTTGN|TTGTTGAAGC|AGGGCCTTGC|CCTNYCACCC|AGGNTGGAGT GAAGTGCAGT|1860|
|GGCACGATTT|TGGCTCACTG|CAG| | |1883|

(2) INFORMATION FOR SEQ ID NO: 154:

(i) SEQUENCE CHARACTERISTICS:
        (A) LENGTH: 1990 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 154:

| | | | | |
|---|---|---|---|---|
|ATGTTTGACA|ATTTCTCCGT|TCCACCCTTG|ATTAAATAAG|GTAGTATTCA TTTTTTAAGT|60|
|TTTAGCTTTT|GGATATATGT|GTAAGTGTGG|TATGCTGTCT|AATGAATTAA GACAATTGGT|120|
|NCTKTCTTTA|CCCMACANCT|GGACMAAGAG|CAGGCAAGAT|NCAANAATCA AGTGACCCAG|180|

-continued

```
NCAAACCAGA CACATTTTCT GCTCTCAGCT AGCTTGCCAC CTAGAAAGAC TGGTTGTCNA      240

AGTTGGAGTC CAAGAATCGC GGAGGATGTT TAAAATGCAG TTTCTCAGGT TCTCNCCACC      300

CACCAGAAGT TTTGATTCAT TGAGTGGTGG GAGAGGGCA AGATATTTGC GATTTTAACA       360

GCATTCTCTT GATTGTGATG CAGCTGGTTC SCAAATAGGT ACCCTAAAGA AATGACAGGT      420

GTTAAATTTA GGATGGCCAT CGCTTGTATG CCGGGAGAAG CACACGCTGG GCCCAATTTA      480

TATAGGGGCT TTCGTCCTCA GCTCGAGCAR CCTCAGAACC CCGACAACCY ACGCCAGCKC      540

TCTGGGCGGA TTCCRTCAGK TGGGGAAGSC CAGGTGGAGC TCTGGKTTCT CCCCGCAATC      600

GTTTCTCCAG GCCGGAGGCC CCGCCCCCTT CCTCCTGGCT CCTCCCCTCC TCCGTGGGCC      660

GNCCGCCAAC GACGCCAGAG CCGGAAATGA CGACAACGGT GAGGGTTCTC GGGCGGGGCC      720

TGGGACAGGC AGCTCCGGGG TCCNCGNNWT NACATCGGAA ACAAAACAGC GGCTGGTCTG      780

GAAGGAACCT GAKCTACGAC CCGCGGCGGC AGCGGGGCGG CGGGGAAGCG TATGTGCGTG      840

ATGGGGAGTC CGGGCAAGCC AGGAAGGCAC CGCGGACATG GGCGGCCGCG GGCAGGGNCC      900

GGNCCTTTGT GGCCGCCCGG GCCGCGAAGC CGGTGTCCTA AAAGATGAGG GGCGGGCGC       960

GGCCGGTTGG GGCTGGGGAA CCCCGTGTGG GAAACCAGGA GGGGCGGCCC GTTTCTCGGG     1020

CTTCGGGCGC GGCCGGGTGG AGAGAGATTC CGGGAGCCT TGGTCCGGAA ATGCTGTTTG      1080

CTCGAAGACG TCTCAGGGCG CAGGTGCCTT GGGCCGGGAT TAGTAGCCGT CTGAACTGGA     1140

GTGGAGTAGG AGAAAGAGGA AGCGTCTTGG GCTGGGTCTG CTTGAGCAAC TGGTGAAACT     1200

CCGCGCCTCA CGCCCCGGGT GTGTCCTTGT CCAGGGGCGA CGAGCATTCT GGGCGAAGTC     1260

CGCACGCCTC TTGTTCGAGG CGGAAGACGG GGTCTTGATG CTTTCTCCTT GGTCGGGACT     1320

GTCTCGAGGC ATGCATGTCC AGTGACTCTT GTGTTTGCTG CTGCTTCCCT CTCAGATTCT     1380

TCTCACCGTT GTGGTCAGCT CTGCTTTAGG CATATTAATC CATAGTGGAG CTGGGATGG      1440

GTGAGAGAAT TGAGGTGACT TTTCCATAAT TCAGGTGAGA TGTGATTAGA GTYCGGATCC     1500

TNCGGTGGTG GCAGAGGCTT ACCAAGAAAC ACTAACGGGA CATGGGAACC AATTGAGGAT     1560

CCAGGGAATA AAGTGTGAAG TTGACTAGGA GGTTTTCAGT TTAAGAACAT GGCAGAGACA     1620

TTCTCAGAAA TAAGGAAGTT AGGAAGAAAG ACCTGGTTTA GAGAGGAGGG CGAGGAAGTG     1680

GTTTGGAAGT GTCACTTTGG AAGTGCCAGC AGGTGAAAAT GCCCTGTGAA CAGGACTGGA     1740

GCTGAAAACA GGAATCAATT CCATAGATTT CCAGTTGATG TTGGAGCAGT GGAGAAGTCT     1800

AANCTAAGGA AGGGAAGAG GAGGCCAAGC CAAACACTTA GGAACACTTN CNACGAGGGG      1860

GTGGAAGAAG AGCAAGGAGC CAGCTGAGGA GAATGAGTGT GGTTGGAGAA CCACCACAGC     1920

NCAGGGTCGC CAGANCTGAG GAAGGGGAGG GAAGCTTATC GAGKAMSGWC RACMKCGAGT     1980

TGGCAGGGAT                                                            1990
```

(2) INFORMATION FOR SEQ ID NO: 155:

(i) SEQUENCE CHARACTERISTICS:
        (A) LENGTH: 736 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 155:

```
GTCTTTCCCA TCTTCTCCAC AGAGTTTGTG CCTTACATTA TTACTCCTTG CCATTTTCAA       60

GAAAGCATTG TCAGCTCTTC CAATCTCCAT CACCTTTGGG CTTGTTTTCT ACTTTGCCAC      120
```

-continued

```
AGATTATCTT GTACAGCCTT TTATGGACCA ATTAGCATTC CATCAATTTT ATATCTAGCA        180

TATTTGCGGT TAGAATCCCA TGGATGTTTC TTCTTTGACT ATAACAAAAT CTGGGGAGGA        240

CAAAGGTGAT TTCCTGTGTC CACATCTAAC AAATCAAGAT CCCCGGCTGG ACTTTTGGAG        300

GTTCCTTCCA AGTCTTCCTG ACCACCTTGC ACTATTGGAC TTTGAAGGA GGTGCCTATA         360

GAAAACGATT TGAACATAC TTCATCGCAG TGGACTGTGT CCTCGGTGCA GAAACTACCA         420

GATTTGAGGG ACGAGGTCAA GGAGATATGA TAGGCCCGGA AGTTGCTGTG CCCCATCAGC        480

AGCTTGACGC GTGGTCACAG GACGATTTTC ACTGACACTG CGAACTCTCA GGACTACCGT        540

TACCAAGAGG TTAGGTGAAG TGGTTTAAAC CAAACGGAAC TCTTCATCTT AAACTACACG        600

TTGAAAATCA ACCCAATAAT TCTGTATTAA CTGAATTCTG AACTTTTCAG GAGGTACTGT        660

GAGGAAGAGC AGGCACCACC AGCAGAATGG GGAATGGAGA GGTGGGCAGG GGTTCCAGCT        720

TCCCTTTGAT TTTTTG                                                       736
```

(2) INFORMATION FOR SEQ ID NO: 156:

(i) SEQUENCE CHARACTERISTICS:
        (A) LENGTH: 1117 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 156:

```
GGATCCGCCC GCCTTGGCCT CCCAAAGTGC TGGGATTACA GGCATGAGCC ACCGCTCCTG         60

GCTGAGTCTG CGATTTCTTG CCAGCTCTAC CCAGTTGTGT CATCTTAAGC AAGTCACTGA        120

ACTTCTCTGG ATTCCCTTCT CCTNNWGTAA AATAAGNATG TTATCTGNCC NNCCTGCCTT        180

GGGCATTGTG ATAAGGATAA GATGACATTA TAGAATNTNG CAAAATTAAA AGCGCTAGAC        240

AAATGATTTT ATGAAAATAT AAAGATTAGN TTGAGTTTGG GCCAGCATAG AAAAAGGAAT        300

GTTGAGAACA TTCCNTTAAG GATTACTCAA GCYCCCCTTT TGSTGKNWAA TCAGANNGTC        360

ATNNAMNTAT CNTNTGTGGG YTGAAAATGT TTGGTTGTCT CAGGCGGTTC CTACTTATTG        420

CTAAAGAGTC CTACCTTGAG CTTATAGTAA ATTTGTCAGT TAGTTGAAAG TCGTGACAAA        480

TTAATACATT CCTGGTTTAC AAATTGGTCT TATAAGTATT TGATTGGTNT AAATGNATTT        540

ACTAGGATTT AACTAACAAT GGATGACCTG GTGAAATCCT ATTTCAGACC TAATCTGGGA        600

GCCTGCAAGT GACAACAGCC TTTGCGGTCC TTAGACAGCT TGGCCTGGAG GAGAACACAT        660

GAAAGAMMGG TTTGWNTCTG NTTAWTGTAA TCTATGRAAG TGTTTTTWAT MACAGTATAA        720

TTGTMTGMAC AAAGTTCTGT TTTTCTTTCC CTTTNCAGAA CCTCAAGAGG CTTTGTTTTC        780

TGTGAAACAG TATTTCTATA CAGNTGCTCC AATGACAGAG TNACCTGCAC CGTTGTCCTA        840

CTTCCAGAAT GCACAGATGT CTGAGGACAA CCACCTGAGC AATACTGTAC GTAGCCAGGT        900

ACAGCGTCAG TYTCTNAAAC TGCCTYYGNC AGACTGGATT CACTTATCAT CTCCCCTCAC        960

CTCTGAGAAA TGCTGAGGGG GSTAGGNAGG GCTTTCTCTA CTTNACCACA TTTNATAATT       1020

ATTTTTGGGT GACCTTCAGC TGATCGCTGG GAGGGACACA GGGCTTNTTT AACACATAGG       1080

GTGTTGGATA CAGNCCCTCC CTAATTCACA TTTCANC                                1117
```

(2) INFORMATION FOR SEQ ID NO: 157:

(i) SEQUENCE CHARACTERISTICS:
        (A) LENGTH: 540 base pairs
        (B) TYPE: nucleic acid (C) STRANDEDNESS: single
        (D) TOPOLOGY: linear (ii) MOLECULE TYPE: cDNA (xi) SEQUENCE DESCRIPTION: SEQ ID NO: 157:

```
CTGCAGCTTT CCTTTAAACT AGGAAGACTT GTTCCTATAC CCCAGTAACG ATACACTGTA      60

CACTAAGCAA ATAGCAGTCA AACCCAAATG AAATTTNTAC AGATGTTCTG TGTCATTTTA     120

TNTTGTTTAT GTTGTCTCCC CCACCCCCAC CAGTTCACCT GCCATTTATT TCATATTCAT     180

TCAACGTCTN NNTGTGTAAA AAGAGACAAA AAACATTAAA CTTTTTTCCT TCGTTAATTC     240

CTCCCTACCA CCCATTTACA AGTTTAGCCC ATACATTTTA TTAGATGTCT TTTATGTTTT     300

TCTTTTNCTA GATTTAGTGG CTGTTTNGTG TCCGAAAGGT CCACTTCGTA TGCTGGTTGA     360

AACAGCTCAG GAGAGAAATG AAACGCTTTT TCCAGCTCTC ATTTACTCCT GTAAGTATTT     420

GGAGAATGAT ATTGAATTAG TAATCAGNGT AGAATTTATC GGGAACTTGA AGANATGTNA     480

CTATGGCAAT TTCANGGNAC TTGTCTCATC TTAAATGANA GNATCCCTGG ACTCCTGNAG     540
```

(2) INFORMATION FOR SEQ ID NO: 158:

(i) SEQUENCE CHARACTERISTICS:
        (A) LENGTH: 509 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 158:

```
CCCCGTCNAT GCATACTTTG TGTGTCCAGT GCTTACCTGG AATCCNGTCT TTCCCAACAG      60

CAACAATGGT GTGGTTGGTG AATATGGCAG AAGGAGACCC GGAAGCTCAA AGGAGAGTAT     120

CCAAAAATTC CAAGTATAAT GCAGAAAGTA GGTAACTYYY NTTAGATAMN ATCTTGATTT     180

TNCAGGGTCA CTGTTATAAG CTAACAGTAT AGNAATGTTT TTATCGTCTT TCTNKGGNCA     240

TAGACTCCTN KGAGAATCTC TTGAGAACTA TGATAATGCC CAGTAAATAC NCAGATAAGT     300

ATTTAAGGAG TNCAGATACT CAAANCCCAA CAATACNGTC AAAGCATCCT AGGTTAAGAC     360

AMCNCCCATT AAATACAGAA TACCAGCATG GAAAGGTTCA GGCTGAGGTT ATGATTGGGT     420

TTGGGTTTTG GGNNNGTTTT TTATAAGTCA TGATTTTAAA AAGAAAAAAT AAACTCTCTC     480

CAAACATGTA AAGTAAGAA TCTCCTAAA                                        509
```

(2) INFORMATION FOR SEQ ID NO: 159:

(i) SEQUENCE CHARACTERISTICS:
        (A) LENGTH: 823 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 159:

```
CAGGAGTGGA CTAGGTAAAT GNAAGNTGTT TTAAAGAGAG ATGNGGNCNG GGACATAGTG      60

GTACACANCT GTAATGCTCA NCACTKATGG GGAGTACTGA AGGNGGNSGG ATCACTTGNG     120

GGTCNGGAAT NTGAGANCAG CCTGGGCAAN ATGGCGAAAC CCTGTCTCTA CTAAAAATAG     180

CCANAAWNWA GCCTAGCGTG GTGGCGCRCA CGCGTGGTTC CACCTACTCA GGAGGCNTAA     240

GCACGAGNAN TNCTTGAACC CAGGAGGCAG AGGNTGTGGT GARCTGAGAT CGTGCCACTG     300
```

```
CACTCCAGTC TGGGCGACMA AGTGAGACCC TGTCTCCNNN AAGAAAAAAA AAATCTGTAC    360

TTTTTAAGGG TTGTGGGACC TGTTAATTAT ATTGAAATGC TTCTYTTCTA GGTCATCCAT    420

GCCTGGCTTA TTTATATCATC TCTATTGTTG CTGCTCTTTT TTACATTCAT TTACTTGGGG   480

TAAGTTGTGA AATTTGGGGT CTGTCTTTCA GAATTAACTA CCTNNGTGCT GTGTAGCTAT    540

CATTTAAAGC CATGTACTTT GNTGATGAAT TACTCTGAAG TTTTAATTGT NTCCACATAT    600

AGGTCATACT TGGTATATAA AAGACTAGNC AGTATTACTA ATTGAGACAT TCTTCTGTNG    660

CTCCTNGCTT ATAATAAGTA GAACTGAAAG NAACTTAAGA CTACAGTTAA TTCTAAGCCT    720

TTGGGGAAGG ATTATATAGC CTTCTAGTAG GAAGTCTTGT GCNATCAGAA TGTTTNTAAA    780

GAAAGGGTNT CAAGGAATNG TATAAANACC AAAAATAATT GAT                     823

(2) INFORMATION FOR SEQ ID NO: 160:

(i) SEQUENCE CHARACTERISTICS:
        (A) LENGTH: 945 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 160:

GTTNTCCNAA CCAACTTAGG AGNTTGGACC TGGGRAAGAC CNACNTGATC TCCGGGAGGN     60

AAAGACTNCA GTTGAGCCGT GATTGCACCC ACTTTACTCC AAGCCTGGGC AACCAAAATG    120

AGACACTGGC TCCAAACACA AAAACAAAAA CAAAAAAAGA GTAAATTAAT TTANAGGGAA    180

GNATTAAATA AATAATAGCA CAGTTGATAT AGGTTATGGT AAAATTATAA AGGTGGGANA    240

TTAATATCTA ATGTTTGGGA GCCATCACAT TATTCTAAAT AATGTTTTGG TGGAAATTAT    300

TGTACATCTT TTAAAATCTG TGTAATTTTT TTTCAGGGAA GTGTTTAAAA CCTATAACGT    360

TGCTGTGGAC TACATTACTG TTNCACTCCT GATCTGGAAT TTTGGTGTGG TGGGAATGAT    420

TTCCATTCAC TGGAAAGGTC CACTTCGACT CCAGCAGGCA TATCTCATTA TGATTAGTGC    480

CCTCATGNCC CTGKTGTTTA TCAAGTACCT CCCTGAATGG ACTGNGTGGC TCATCTTGGC    540

TGTGATTTCA GTATATGGTA AAACCCAAGA CTGATAATTT GTTTGTCACA GGAATGCCCC    600

ACTGGAGTGT TTTCTTTCCT CATCTCTTTA TCTTGATTTA GAGAAAATGG TAACGTGTAC    660

ATCCCATAAC TCTTCAGTAA ATCATTAATT AGCTATAGTA ACTTTTTCAT TTGAAGATTT    720

CGGCTGGGCA TGGTAGCTCA TGCCTGTAAT CTTAGCACTT TGGGAGGCTG AGGCGGGCAG    780

ATCACCTAAG CCCAGAGTTC AAGACCAGCC TGGGCAACAT GGCAAAACCT CGTATCTACA    840

GAAAATACAA AAATTAGCCG GGCATGGTGG TGCACACCTG TAGTTCCAGC TACTTAGGAG    900

GCTGAGGTGG GAGGATCGAT TGATCCCAGG AGGTCAAGNC TGCAG                   945

(2) INFORMATION FOR SEQ ID NO: 161:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 161:

Tyr Thr Pro Phe
1
```

(2) INFORMATION FOR SEQ ID NO: 162:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 162:

```
Ser Thr Pro Glu
1
```

(2) INFORMATION FOR SEQ ID NO: 163:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 163:

```
AAACTTGGAT TGGGAGAT                                              18
```

(2) INFORMATION FOR SEQ ID NO: 164:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 164:

```
Asn Asp Asn Arg Glu Arg Gln Glu His Asn Asp Arg Arg Ser Leu
1               5                   10                  15
```

(2) INFORMATION FOR SEQ ID NO: 165:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 165:

```
Lys Asp Gly Gln Leu Ile Tyr Thr Pro Phe Thr Glu Asp Thr Glu
1               5                   10                  15
```

(2) INFORMATION FOR SEQ ID NO: 166:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 166:

```
Glu Ala Gln Arg Arg Val Ser Lys Asn Ser Lys Tyr Asn Ala Glu
1               5                   10                  15
```

(2) INFORMATION FOR SEQ ID NO: 167:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 167:

```
Ser His Leu Gly Pro His Arg Ser Thr Pro Glu Ser Arg Ala Ala
1               5                   10                  15
```

(2) INFORMATION FOR SEQ ID NO: 168:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 168:

TCACAGAAGA TACCGAGACT                                        20

(2) INFORMATION FOR SEQ ID NO: 169:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 169:

CCCAACCATA AGAAGAACAG                                        20

(2) INFORMATION FOR SEQ ID NO: 170:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 170:

TCTGTACTTT TTAAGGGTTG TG                                     22

(2) INFORMATION FOR SEQ ID NO: 171:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 171:

-continued

ACTTCAGAGT AATTCATCAN CA                                                22

(2) INFORMATION FOR SEQ ID NO: 172:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 172:

GACTCCAGCA GGCATATCT                                                    19

(2) INFORMATION FOR SEQ ID NO: 173:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 173:

GATGAGACAA GTNCCNTGAA                                                   20

(2) INFORMATION FOR SEQ ID NO: 174:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 174:

TTAGTGGCTG TTTNGTGTCC                                                   20

(2) INFORMATION FOR SEQ ID NO: 175:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 175:

CACCCATTTA CAAGTTTAGC                                                   20

GENETIC SEQUENCES AND PROTEINS RELATED TO ALZHEIMER'S DISEASE

RELATED APPLICATIONS

This is a Continuation-In-Part of U.S. application Ser. No. 08/431,048, filed Apr. 28, 1995 which is currently pending in the U.S. Patent Office.

FIELD OF THE INVENTION

The present invention relates generally to the field of neurological and physiological dysfunctions associated with Alzheimer's Disease. More particularly, the invention is concerned with the identification, isolation and cloning of the gene which when mutated is associated with Alzheimer's Disease as well as its transcript, gene products and associated sequence information and neighbouring genes. The present invention also relates to methods of diagnosing for and detection of carriers of the gene, Alzheimer's Disease diagnosis, gene therapy using recombinant technologies and therapy using the information derived from the DNA, protein, and the metabolic function of the protein.

BACKGROUND OF THE INVENTION

In order to facilitate reference to various journal articles, a listing of the articles is provided at the end of this specification.

Alzheimer's Disease (AD) is a degenerative disorder of the human central nervous system characterized by progressive memory impairment and cognitive and intellectual decline during mid to late adult life (Katzman, 1986). The disease is accompanied by a constellation of neuropathologic features principal amongst which are the presence of extracellular amyloid or senile plaques and the neurofibrillary degeneration of neurons. The etiology of this disease is complex, although in some families it appears to be inherited as an autosomal dominant trait. However, even amongst these inherited forms of AD, there are at least three different genes which confer inherited susceptibility to this disease (St George-Hyslop et al., 1990). The ∈4 (Cys112Arg) allelic polymorphism of the Apolipoprotein E (ApoE) gene has been associated with AD in a significant proportion of cases with onset late in life (Saunders et al., 1993; Strittmatter et al., 1993). Similarly, a very small proportion of familial cases with onset before age 65 years have been associated with mutations in the β-amyloid precursor protein (APP) gene (Chartier-Harlin et al., 1991; Goate et al., 1991; Murrell et al., 1991; Karlinsky et al., 1992; Mullan et al., 1992). A third locus (AD3) associated with a larger proportion of cases with early onset AD has recently been mapped to chromosome 14q24.3 (Schellenberg et al., 1992; St George-Hyslop et al., 1992; Van Broeckhoven et al., 1992).

Although chromosome 14q carries several genes which could be regarded as candidate genes for the site of mutations associated with AD3 (e.g. cFOS, alpha-1-antichymotrypsin, and cathepsin G), most of these candidate genes have been excluded on the basis of their physical location outside the AD3 region and/or the absence of mutations in their respective open reading frames (Schellenberg, GD et al., 1992; Van Broeckhoven, C et al., 1992; Rogaev et al., 1993; Wong et al., 1993).

There have been several developments and commercial directions in respect of treatment of Alzheimer's Disease and diagnosis thereof. Published PCT application WO 94 23049 describes transfection of high molecular weight YAC DNA into specific mouse cells. This method is used to analyze large gene complexes, for example the transgenic mice may have increased amyloid precursor protein gene dosage, which mimics the trisomic condition that prevails in Downs Syndrome and the generation of animal models with β-amyloidosis prevalent in individuals with Alzheimer's Disease. Published international application WO 94 00569 describes transgenic non-human animals harbouring large trans genes such as the trans gene comprising a human amyloid precursor protein gene. Such animal models can provide useful models of human genetic diseases such as Alzheimer's Disease.

Canadian Patent application 2096911 describes a nucleic acid coding for amyloid precursor protein-cleaving protease, which is associated with Alzheimer's Disease and Down's syndrome. The genetic information may be used to diagnose Alzheimer's disease. The genetic information was isolated from chromosome 19. Canadian patent application 2071105, describes detection and treatment of inherited or acquired Alzheimer's disease by the use of YAC nucleotide sequences. The YACs are identified by the numbers 23CB10, 28CA12 and 26FF3.

U.S. Pat. No. 5,297,562, describes detection of Alzheimer's Disease having two or more copies of chromosome 21. Treatment involves methods for reducing the proliferation of chromosome 21 trisomy. Canadian Patent application 2054302, describes monoclonal antibodies which recognize human brain cell nucleus protein encoded by chromosome 21 and are used to detect changes or expression due to Alzheimer's Disease or Down's Syndrome. The monoclonal antibody is specific to a protein encoded by human chromosome 21 and is linked to large pyramidal cells of human brain tissue.

By extensive effort and a unique approach to investigating the AD3 region of chromosome 14q, the Alzheimer's related membrane protein (ARMP) gene has been isolated, cloned and sequenced from within the AD3 region on chromosome 14q24.3. In addition, direct sequencing of RT-PCR products spanning this 3.0 kb cDNA transcript isolated from affected members of at least eight large pedigrees linked to chromosome 14, has led to the discovery of missense mutations in each of these different pedigrees. These mutations are absent in normal chromosomes. It has now been established that the ARMP gene is causative of familial Alzheimer's Disease type AD3. In realizing this link, it is understood that mutations in this gene can be associated with other cognitive, intellectual, or psychological diseases such as cerebral hemorrhage, schizophrenia, depression, mental retardation and epilepsy. These phenotypes are present in these AD families and these phenotypes have been seen in mutations of the APP protein gene. The Amyloid Precursor Protein (APP) gene is also associated with inherited Alzheimer's Disease. The identification of both normal and mutant forms of the ARMP gene and gene products has allowed for the development of screening and diagnostic tests for ARMP utilizing nucleic acid probes and antibodies to the gene product. Through interaction with the defective gene product and the pathway in which this gene product is involved, gene therapy, manipulation and delivery are now made possible.

SUMMARY OF THE INVENTION

Various aspects of the invention are summarized as follows. In accordance with a first aspect of the invention, a purified mammalian polynucleotide is provided which codes for Alzheimer's related membrane protein (ARMP). The polynucleotide has a sequence which is the functional equivalent of the DNA sequence of ATCC deposit 97124, deposited Apr. 28, 1995. The mammalian polynucleotide may be in the form of DNA, genomic DNA, cDNA, mRNA and various fragments and portions of the gene sequence encoding ARMP. The mammalian DNA is conserved in many species, including humans and rodents, example mice. The mouse sequence encoding ARMP has greater than 95% homology with the human sequence encoding the same protein.

Purified human nucleotide sequences which encode mutant ARMP have mutations at nucleotide position i) 685, A→C ii) 737, A→G iii) 986, C→A, iv) 1105, C→G, v) 1478, G→A, vi) 1027, C→T, vii) 1102, C→T and viii) 1422, C→G of Sequence ID No: 1 as well as in the cDNA sequence of a further human clone of a sequence identified by ID NO:133.

The nucleotide sequences encoding ARMP have an alternative splice form in the genes open reading frame. The human cDNA sequence which codes for ARMP has sequence ID No. 1 as well as sequence ID NO:133 as sequenced in a another human clone. The mouse sequence which encodes ARMP has sequence ID No. 3, as well as SEQ ID NO:135 derived from a further clone containing the entire coding region. Various DNA and RNA probes and primers may be made from appropriate polynucleotide lengths selected from the sequences. Portions of the sequence also encode antigenic determinants of the ARMP.

Suitable expression vectors comprising the nucleotide sequences are provided along with suitable host cells transfected with such expression vectors.

In accordance with another aspect of the invention, purified mammalian Alzheimer's related membrane protein is provided. The purified protein has an amino acid sequence encoded by polynucleotide sequence as identified above which for the human is SEQ ID NO:2 and SEQ ID NO:134 (derived from another clone). The mouse amino acid sequence is defined by SEQ ID No.4 and SEQ ID No. 136, the later being translated from another clone containing the entire coding region. The purified protein may have substitution mutations selected from the group consisting of positions identified in SEQ ID No: 2 and Sequence ID NO:134.

| | |
|---|---|
| i) | M 146L |
| ii) | H 163R |
| iii) | A 246E |
| iv) | L 286V |
| v) | C 410Y |
| vi) | A 260V |
| vii) | A 285V |
| viii) | L 392V |

In accordance with another aspect of the invention, are polyclonal antibodies raised to specific predicted sequences of the ARMP protein. Polypeptides of at least six amino acid residues are provided. The polypeptides of six or greater amino acid residues may define antigenic epitopes of the ARMP. Monoclonal antibodies having suitably specific binding affinity for the antigenic regions of the ARMP are prepared by use of corresponding hybridoma cell lines. In addition, other polyclonal antibodies may be prepared by inoculation of animals with suitable peptides or holoprotein which add suitable specific binding affinities for antigenic regions of the ARMP.

In accordance with another aspect of the invention, a purified mammalian polynucleotide is provided which codes for a homologue of the ARMP gene. This homologue bears substantial nucleotide homology to the ARMP gene and is identified by SEQ ID NO:137. A plasmid including this nucleic acid was deposited with the ATCC under the terms of the Budapest Treaty on Jun. 28, 1995 and has been assigned ATCC accession number 97214.

In accordance with another aspect of the invention, a partial protein sequence of the mammalian ARMP gene homologue is provided. This partial sequence bears substantial amino acid homology to the ARMP protein and is identified by SEQ ID NO:138.

In accordance with another aspect of the invention a bioassay is provided for determining if a subject has a normal or mutant ARMP, where the bioassay comprises providing a biological sample from the subject conducting a biological assay on the sample to detect a normal or mutant gene sequence coding for ARMP, a normal or mutant ARMP amino acid sequence, or a normal or defective protein function.

In accordance with another aspect of the invention, a process is provided for producing ARMP comprising culturing one of the above described transfected host cells under suitable condition, to produce the ARMP by expressing the DNA sequence. Alternatively, ARMP may be isolated from mammalian cells in which the ARMP is normally expressed.

In accordance with another aspect of the invention, is a therapeutic composition comprising ARMP and a pharmaceutically acceptable carrier.

In accordance with another aspect of the invention, a recombinant vector for transforming a mammalian tissue cell to express therapeutically effective amounts of ARMP in the cells is provided. The vector is normally delivered to the cells by a suitable vehicle. Suitable vehicles include vaccinia virus, adenovirus, adeno associated virus, retrovirus, liposome transport, neuraltropic viruses, Herpes simplex virus and other vector systems.

In accordance with another aspect of the invention, a method of treating a patient deficient in normal ARMP comprising administering to the patient a therapeutically effective amount of the protein targeted at a variety of patient cells which normally express ARMP. The extent of administration of normal ARMP being sufficient to override any effect the presence of the mutant ARMP may have on the patient. As an alternative to protein, suitable ligands and therapeutic agents such as small molecules and other drug agents may be suitable for drug therapy designed to replace the protein and defective ARMP, displace mutant ARMP, or to suppress its formation.

In accordance with another aspect of the invention an immuno therapy for treating a patient having Alzheimer's Disease comprises treating the patient with antibodies specific to the mutant ARMP to reduce biological levels or activity of the mutant ARMP in the patient. To facilitate such amino acid therapy, a vaccine composition may be provided for evoking an immune response in a patient of Alzheimer's Disease where the composition comprises a mutant ARMP and a pharmaceutically acceptable carrier with or without a suitable excipient. The antibodies developed specific to the mutant ARMP could be used to target appropriately encapsulated drugs/molecules, specific cellular/tissue sites. Therapies utilizing specific ligands which bind to normal or wild type ARMP or either mutant or wild type and which augments normal function of ARMP in membranes and/or cells or inhibits the deleterious effect of the mutant protein are also made possible.

In accordance with another aspect of the invention, a transgenic animal model for Alzheimer's Disease which has the mammalian polynucleotide sequence with at least one mutation which when expressed results in mutant ARMP in the animal cells and thereby manifests a phenotype. For example, the human Prion gene when over-expressed in rodent peripheral nervous system and muscle cells causes a quite different response in the animal than the human. The animal may be a rodent and is preferably a mouse, but may also be other animals including rat, pig, Irosophila melanogaster, C. elegans (nematode), all of which are used for transgenic models. Yeast cells can also be used in which the ARMP Sequence is expressed from an artificial vector.

In accordance with another aspect of the invention a transgenic mouse model for Alzheimer's Disease has the mouse gene encoding ARMP human or murine homologues mutated to manifest the symptoms. The transgenic mouse may exhibit symptoms of cognitive memory or behavioural disturbances. In addition or alternatively, the symptoms may appear as another cellular tissue disorders such as in mouse liver, kidney spleen or bone marrow and other organs in which the ARMP gene product is normally expressed.

In accordance with another aspect of the invention, the protein can be used as a starting point for rationale drug design to provide ligands, therapeutic drugs or other types of small chemical molecules.

BRIEF DESCRIPTION OF THE DRAWINGS

Various aspects of the invention are described hereinafter with respect to the drawings wherein:

FIG. 1a. Genomic physical and transcriptional map of the AD3 region of chromosome 14. Genetic map inter-marker genetic distances averaged for male and female meiosis are indicated in centiMorgans.

FIG. 1c. Regions of interest within the constructed physical contig map. FIG. 1d. Transcriptional map illustrating physical locations of the 19 independent longer cDNA clones.

| |
|---|
| (a) Met 146 Leu |
| (b) His 163 Arg |
| (c) Ala 246 Glu |
| (d) Leu 286 Val |
| (e) Cys 410 Tyr |

Figure 3A:
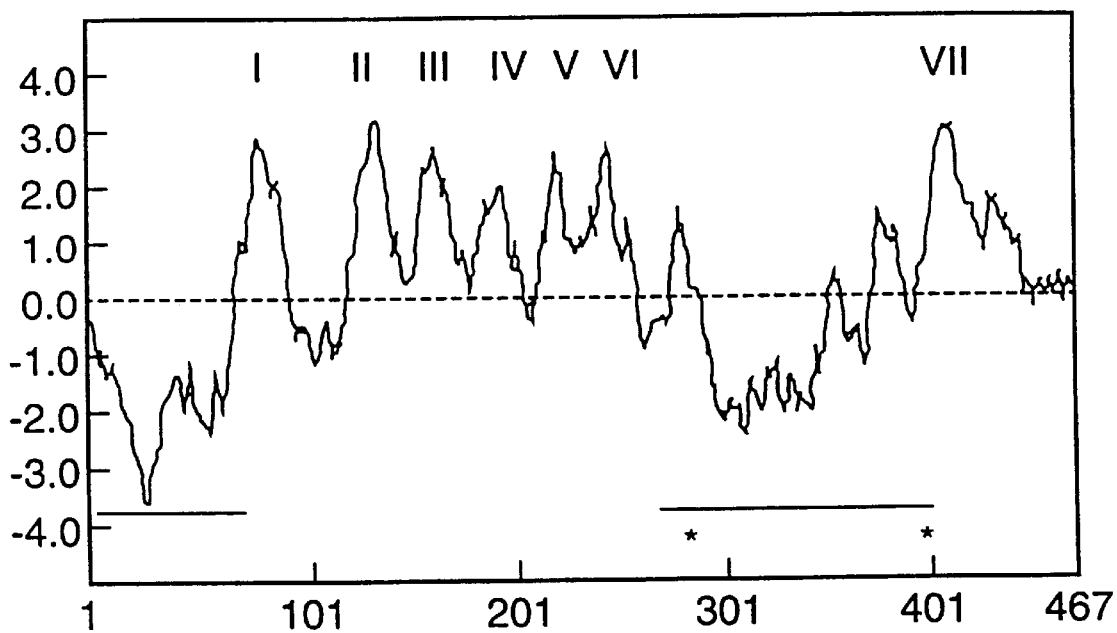

FIG. 3A. Hydropathy plot of the putative ARMP protein.

Figure 3B:
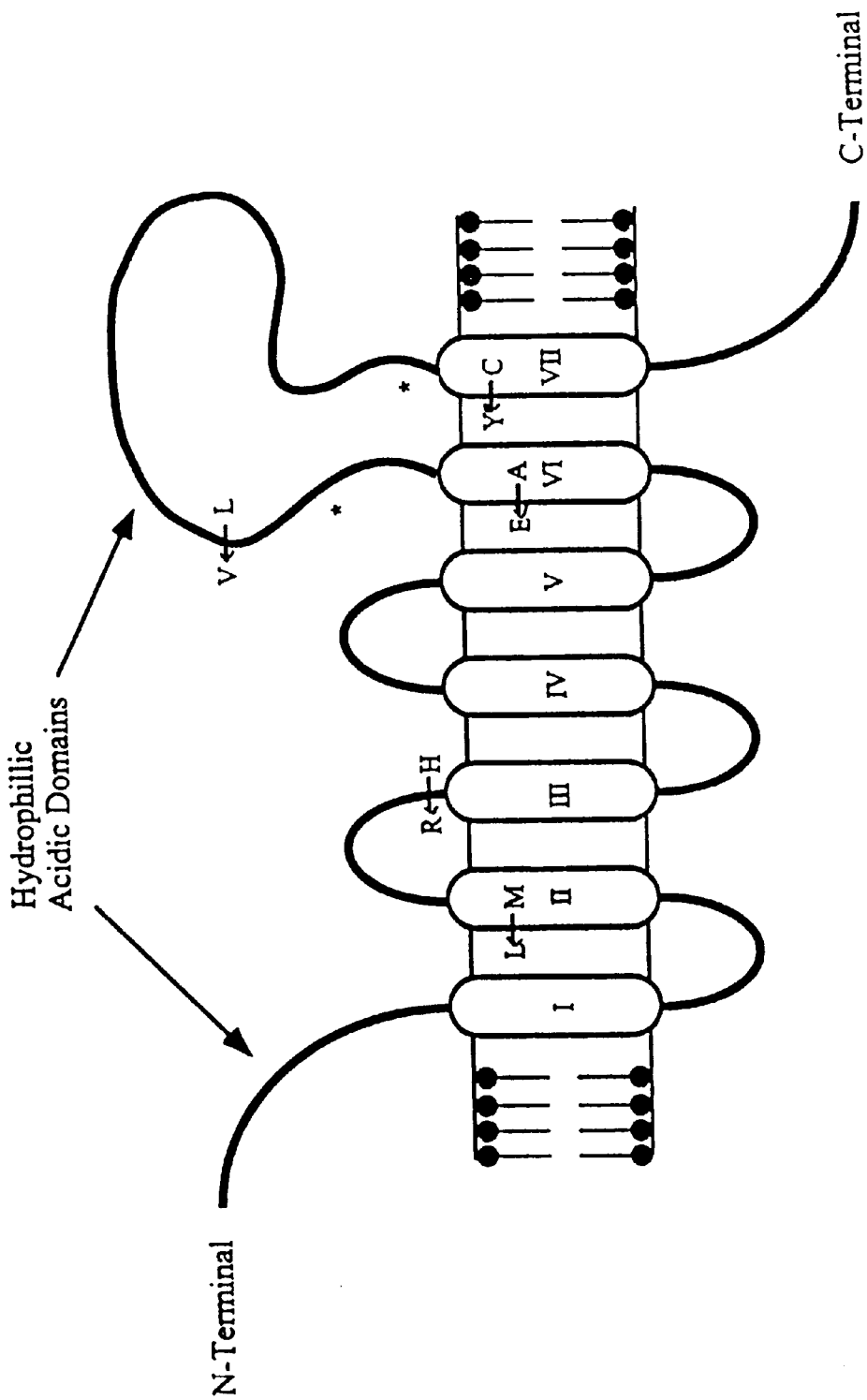

FIG. 3B. A model for the structural organization of the putative ARMP protein. Roman numerals depict the transmembrane domains. Putative glycosylation sites are indicated as asterisks and most of the phosphorylation sites are located on the same membrane face as the two acidic hydrophillic loops. The MAP kinase site is present at residue 115 and the PKC site at residue 114. FAD mutation sites are indicated by horizontal arrows.

DETAILED DESCRIPTION OF PREFERRED EMBODIMENTS

In order to facilitate review of the various embodiments of the invention and an understanding of various elements and constituents used in making the invention and using same, the following definition of terms used in the invention description is as follows:

Alzheimer Related Membrane Protein gene (ARMP gene)—the gene which when mutated is associated with familial Alzheimer's Disease and/or other inheritable disease phenotypes (eg. cerebral hemorrhage, mental retardation, schizophrenia, psychosis, and depression). This definition is understood to include the various sequence polymorphisms that exist, wherein nucleotide substitutions in the gene sequence do not affect the essential function of the gene product, as well as functional equivalents of the nucleotide sequences of SEQ ID No. 1, SEQ ID NO:183, SEQ ID No: 3 and SEQ ID NO:135. This term primarily relates to an isolated coding sequence, but can also include some or all of the flanking regulatory elements and/or introns. The term ARMP gene includes the gene in other species analogous to the human gene which when mutated is associated with Alzheimer's disease.

Alzheimer Related Membrane Protein (ARMP)—the protein encoded by the ARMP gene. The preferred source of protein is the mammalian protein as isolated from humans or animals. Alternatively, functionally equivalent proteins may exist in plants, insects and invertebrates (such as C. elegans). The protein may be produced by recombinant organisms, or chemically or enzymatically synthesized. This definition is understood to include functional variants such as the various polymorphic forms of the protein wherein amino acid substitutions or deletions within the amino acid sequence do not affect the essential functioning of the protein, or its structure. It also includes functional fragments of ARMP.

Mutant ARMP gene—The ARMP gene containing one or more mutations which lead to Alzheimer's Disease and/or other inheritable disease phenotypes (eg. cerebral hemorrhage, mental retardation, schizophrenia, psychosis, and depression). This definition is understood to include the various mutations that exist, wherein nucleotide substitutions in the gene sequence affect the essential function of the gene product, as well as mutations of functional equivalents of the nucleotide sequences of SEQ ID No. 1, SEQ ID NO:133, SEQ ID No:3, and SEQ ID NO: 135 (the corresponding amino acid sequences). This term primarily relates to an isolated coding sequence, but can also include some or all of the flanking regulatory elements and/or introns.

Mutant ARMP—a mammalian protein that is highly analogous to ARMP in terms of primary structure, but wherein one or more amino acid deletions and/or substitutions result in impairment of its essential function, so that mammals, especially humans, whose ARMP producing cells express mutant ARMP rather than the normal ARMP, demonstrate the symptoms of Alzheimer's Disease and/or other relevant inheritable phenotypes (eg. cerebral hemorrhage, mental retardation, schizophrenia, psychosis, and depression).

mARMP gene—mouse gene analogous to the human ARMP gene. Functional equivalent as used in describing gene sequences and amino acid sequences means that a recited sequence need not be identical to the definitive sequence of the Sequence ID Nos but need only provide a sequence which functions biologically and/or chemically the equivalent of the definitive sequence. Hence sequences which correspond to a definitive sequence may also be considered as functionally equivalent sequence.

mARMP—mouse Alzheimer related membrane protein, analogous to the human ARMP, encoded by the mARMP gene. This definition is understood to include the various polymorphic forms of the protein wherein amino acid substitutions or deletions of the sequence does not affect the essential functioning of the protein, or its structure.

Mutant mARMP—a mouse protein which is highly analogous to mARMP in terms of primary structure, but wherein one or more amino acid deletions and/or substitutions result in impairment of its essential function, so that mice, whose mARMP producing cells express mutant mARMP rather than the normal mARMP demonstrate the symptoms of Alzheimer's Disease and/or other relevant inheritable phenotypes, or other phenotypes and behaviours as manifested in mice.

ARMP carrier—a mammal in apparent good health whose chromosomes contain a mutant ARMP gene that may be transmitted to the offspring and who will develop Alzheimer's Disease in mid to late adult life.

Missense mutation—A mutation of nucleic acid sequence which alters a codon to that of another amino acid, causing an altered translation product to be made.

Pedigree—In human genetics, a diagram showing the ancestral relationships and transmission of genetic traits over several generations in a family.

E5-1 gene —a homologue of the ARMP gene which encodes E5-1 homologue protein.

E5-1 homologue protein—a mammalian protein with substantial homology to ARMP. This term includes the protein of SEQ ID NO:138 and functional variants such as polymorphic forms of the protein wherein amino acid substitutions or deletions within the amino acid sequence do not affect the functioning of the protein.

Linkage analysis—Analysis of co-segregation of a disease trait or disease gene with polymorphic genetic markers of defined chromosomal location.

hARMP gene—human ARMP gene

ORF—open reading frame.

PCR—polymerase chain reaction.

contig—continuous cloned regions

YAC—yeast artificial chromosome

RT-PCR—reverse transcription polymerase chain reaction.

SSR—Simple sequence repeat polymorphism.

The present invention is concerned with the identification and sequencing of the mammalian ARMP gene in order to gain insight into the cause and etiology of familial Alzheimer's Disease. From this information, screening methods and therapies for the diagnosis and treatment of the disease can be developed. The gene has been identified, cDNA isolated and cloned, and its transcripts and gene products identified and sequenced. During such identification of the gene, considerable sequence information has also been developed on intron information in the ARMP gene, flanking untranslated information and signal information and information involving neighbouring genes in the AD3 chromosome region. Direct sequencing of overlapping RT-PCR products spanning the human gene isolated from affected members of large pedigrees linked to chromosome 14 has led to the discovery of missense mutations which co-segregate with the disease.

Although it is generally understood that Alzheimer's Disease is a neurological disorder, most likely in the brain, expression of ARMP has been found in varieties of human tissue such as heart, brain, placenta, lung, liver, skeletal muscle, kidney and pancreas. Although this gene is expressed widely, the clinically apparent phenotype exists in brain although it is conceivable that biochemical phenotypes may exist in these other tissues. As with other genetic diseases such as Huntington's Disease and APP-Alzheimer's, the clinical disease manifestation may reflect different biochemistries of different cell types and tissues (which stem from genetics and the protein). Such findings suggest that AD may not be solely a neurological disorder but may also be a systemic disorder, hence requiring alternative therapeutic strategies which may be targeted to other tissues or organs or generally in addition or separately from neuronal or brain tissues.

The mutations identified have been related to Alzheimer disease pathology. With the identification of sequencing of the gene and the gene product, probes and antibodies raised to the gene product can be used in a variety of hybridization and immunological assays to screen for and detect the presence of either a normal or mutated gene or gene product.

Patient therapy through removal or blocking of the mutant gene product, as well as supplementation with the normal gene product by amplification, by genetic and recombinant techniques or by immunotherapy can now be achieved. Correction or modification of the defective gene product by protein treatment immunotherapy (using antibodies to the defective protein) or knock-out of the mutated gene is now also possible. Familial Alzheimer's Disease could also be controlled by gene therapy in which the gene defect is corrected in situ or by the use of recombinant or other vehicles to deliver a DNA sequence capable of expressing the normal gene product, or a deliberately mutated version of the gene product whose effect counter balances the deleterious consequences of the disease mutation to the affected cells of the patient.

Isolating the Human ARMP Gene

Genetic mapping of the AD3 locus.

After the initial regional mapping of the AD3 gene locus to 14q24.3 near the anonymous microsatellite markers D14S43 and D14S53 (Schellenberg, G D et al., 1992; St George-Hyslop, P et al., 1992; Van Broeckhoven, C et al., 1992), twenty one pedigrees were used to segregate AD as a putative autosomal dominant trait (St George-Hyslop, P et al., 1992) and to investigate the segregation of 18 additional genetic markers from the 14q24.3 region which had been organized into a high density genetic linkage map (FIG. 1b) (Weissenbach et al., 1992; Gyapay et al., 1994). Pairwise maximum likelihood analyses previously published confirmed substantial cumulative evidence for linkage between FAD and all of these markers (Table 1). However, much of the genetic data supporting linkage to these markers were derived from six large early onset pedigrees FAD1 (Nee et al., 1983), FAD2 (Frommelt et al., 1991), FAD3 (Goudsmit et al., 1981; Pollen, 1993) , FAD4 (Foncin et al., 1985), TOR1.1 (Bergamini, 1991) and 603 (Pericak-Vance et al., 1988) each of which provide at least one anonymous genetic marker from 14q24.3 (St. George-Hyslop, P. et al 1992).

In order to more precisely define the location of the AD3 gene relative to the known locations of the genetic markers from 14q24.3, recombinational landmarks were sought by direct inspection of the raw haplotype data only from genotyped affected members of the six pedigrees showing definitive linkage to chromosome 14. This selective strategy in this particular instance necessarily discards data from the reconstructed genotypes of deceased affected members as well as from elderly asymptomatic members of the large pedigrees, and takes no account of the smaller pedigrees of uncertain linkage status. However, this strategy is very sound because it also avoids the acquisition of potentially misleading genotype data acquired either through errors in the reconstructed genotypes of deceased affected members arising from non-paternity or sampling errors or from the inclusion of unlinked pedigrees.

Upon inspection of the haplotype data for affected subjects, members of the six large pedigrees whose genotypes were directly determined revealed obligate recombinants at D14S48 and D14S53, and at D14S258 and D14S63. The single recombinant at D14S53, which depicts a telomeric boundary for the FAD region, occurred in the same AD affected subject of the FAD1 pedigree who had previously been found to be recombinant at several other markers located telomeric to D14S53 including D14S48 (St George-Hyslop, P et al., 1992). Conversely, the single recombinant at D14S258, which marks a centromeric boundary of the FAD region, occurred in an affected member of the FAD3 pedigree who was also recombinant at several other markers centromeric to D14S258 including D14S63. Both recombinant subjects had unequivocal evidence of Alzheimer's disease confirmed through standard clinical tests for the illness in other affected members of their families, and the genotype of both recombinant subjects was informative and co-segregating at multiple loci within the interval centromeric to D14S53 and telomeric to D14S258.

When the haplotype analyses were enlarged to include the reconstructed genotypes of deceased affected members of the six large pedigrees as well as data from the remaining fifteen pedigrees with probabilities for linkage of less than 0.95, several additional recombinants were detected at one or more marker loci within the interval between D14S53 and D14S258. Thus, one additional recombinant was detected in the reconstructed genotype of a deceased affected member of each of three of the larger FAD pedigrees (FAD1, FAD2 and other related families), and eight additional recombinants were detected in affected members of five smaller FAD pedigrees. However, while some of these recombinants might have correctly placed the AD3 gene within a more defined target region, we were forced to regarded these potentially closer "internal recombinants" as unreliable not only for the reasons discussed earlier, but also because they provided mutually inconsistent locations for the AD3 gene within the D14S53–D14S258 interval.

Construction of a physical contig spanning the AD3 region.

Figure 1B:
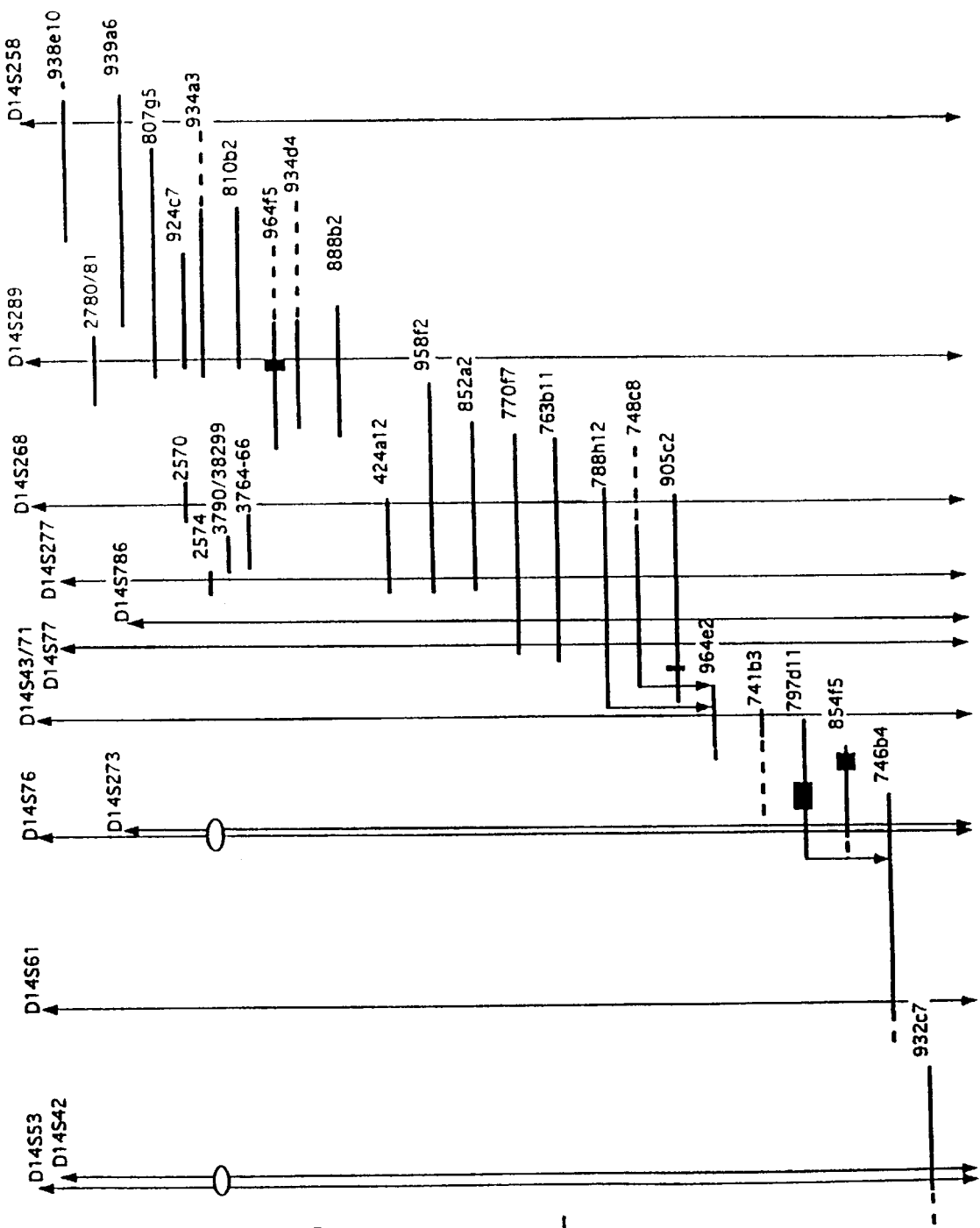
FIG. 1b. Is the constructed physical contig map of overlapping genomic DNA fragments cloned into YACs spanning a FAD locus on chromosome 14q.
Figure 2A:
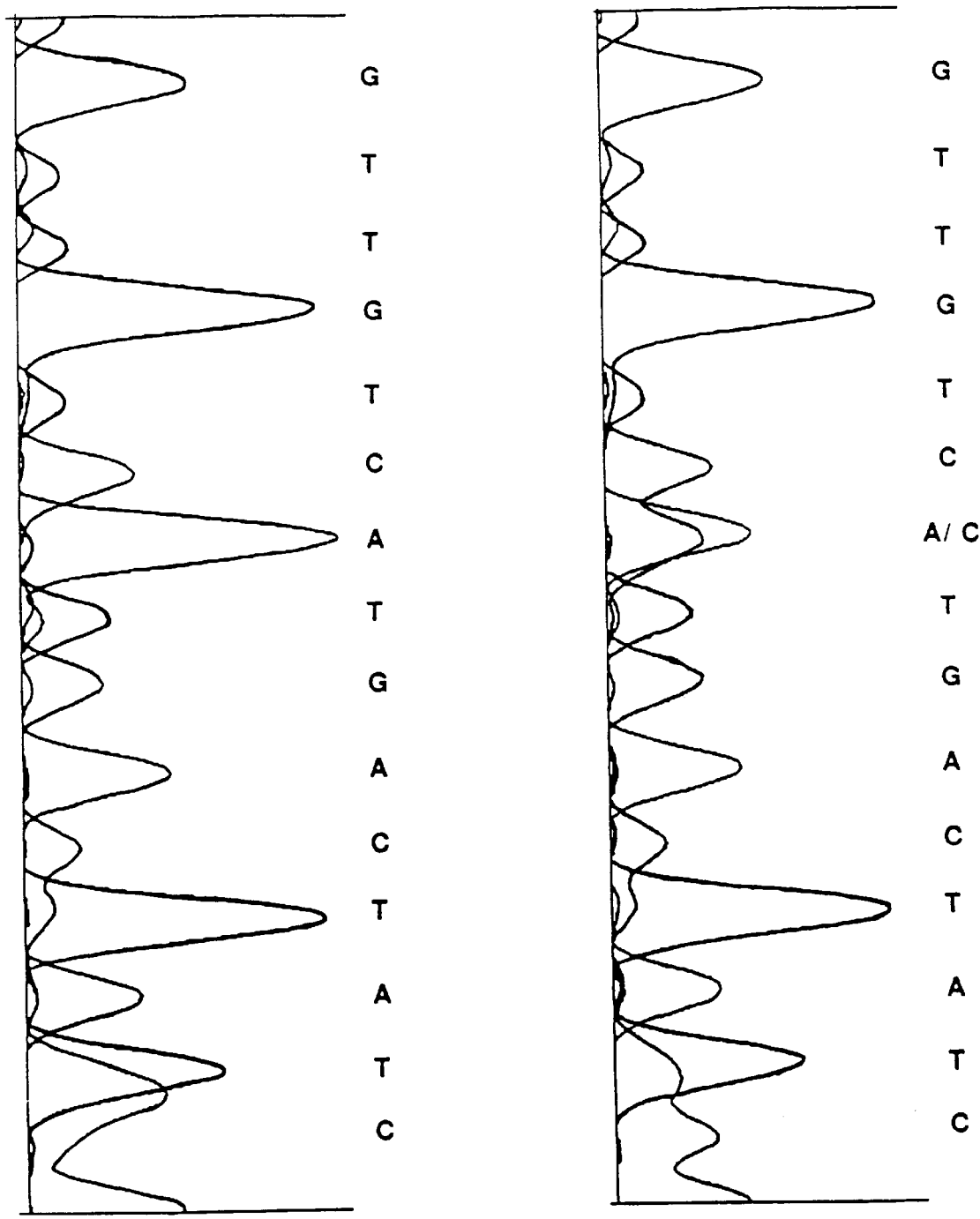
FIGS. 2(a–e). Automated fluorescent chromatograms representing the change in nucleic acids which direct (by the codon) the amino acid sequence of the gene.
Figure 2B:
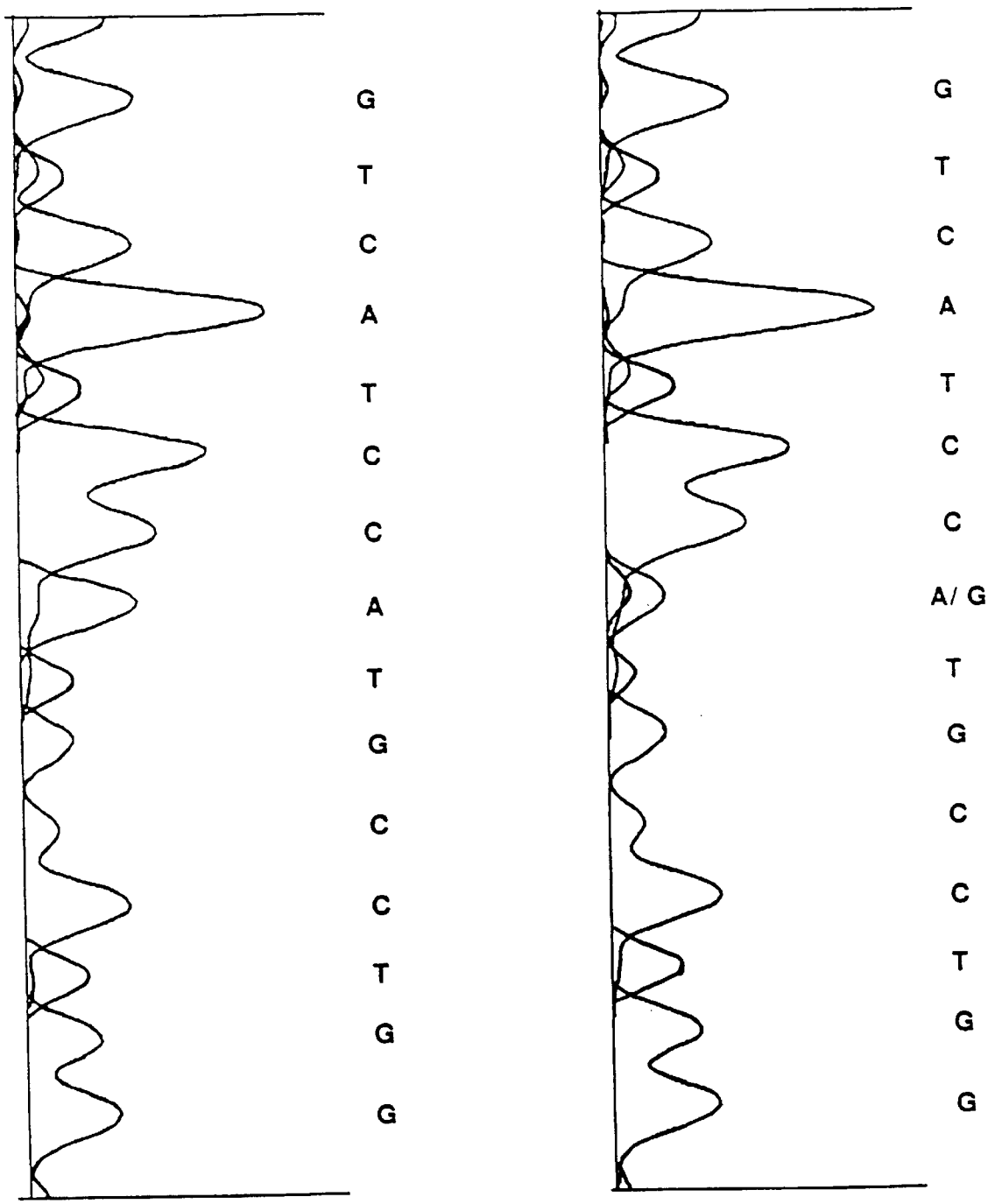
Figure 2C:
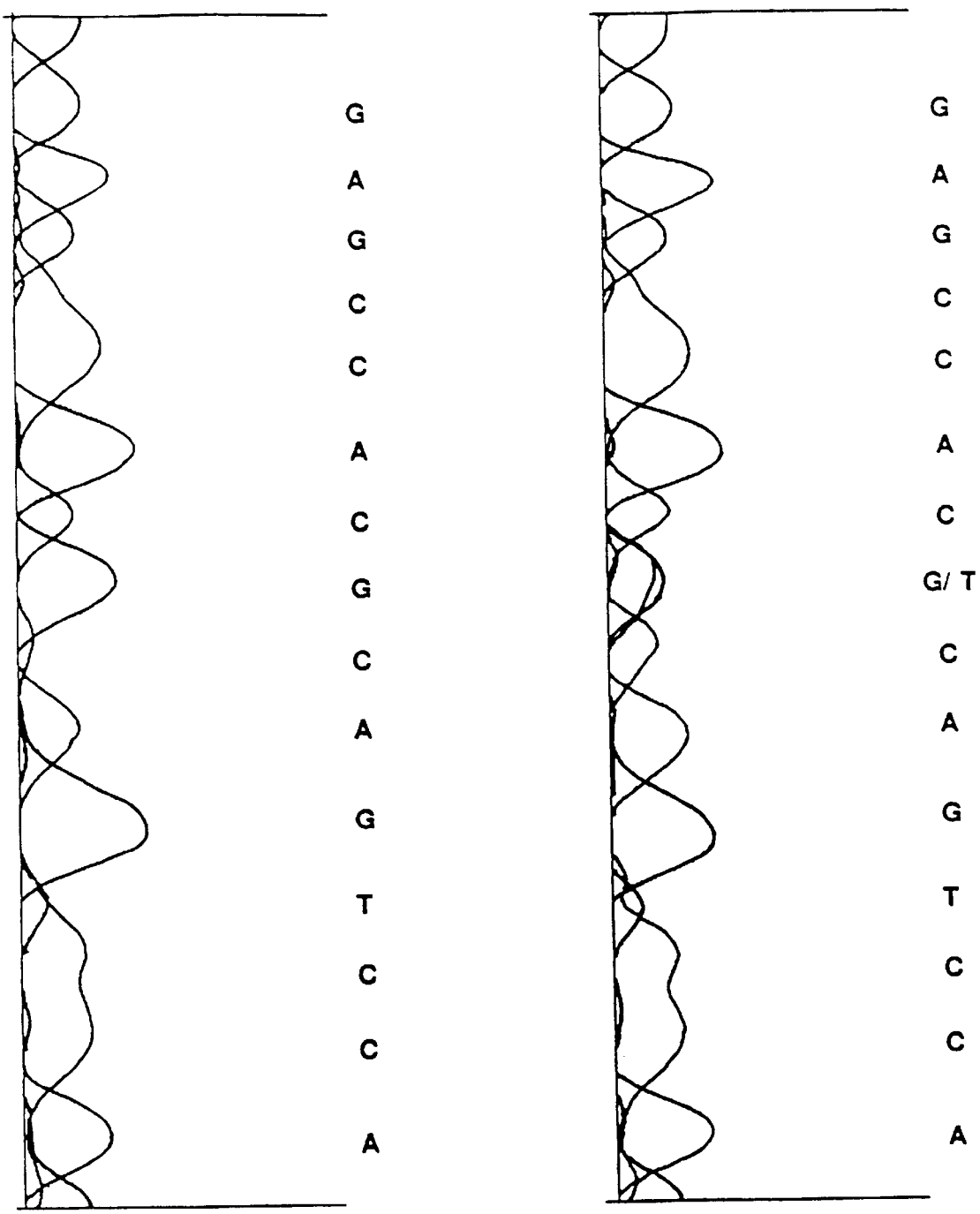
Figure 2D:
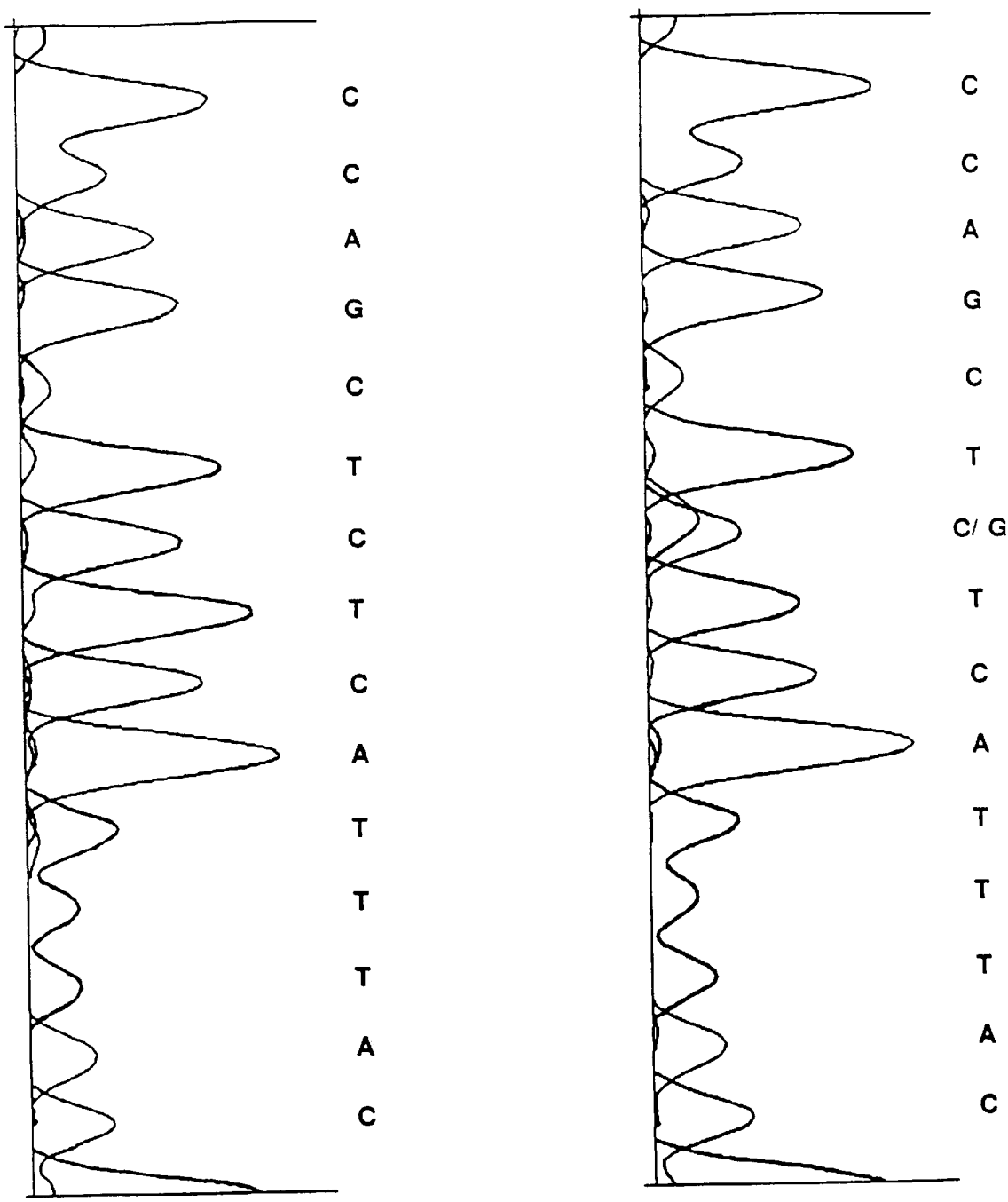
Figure 2E:
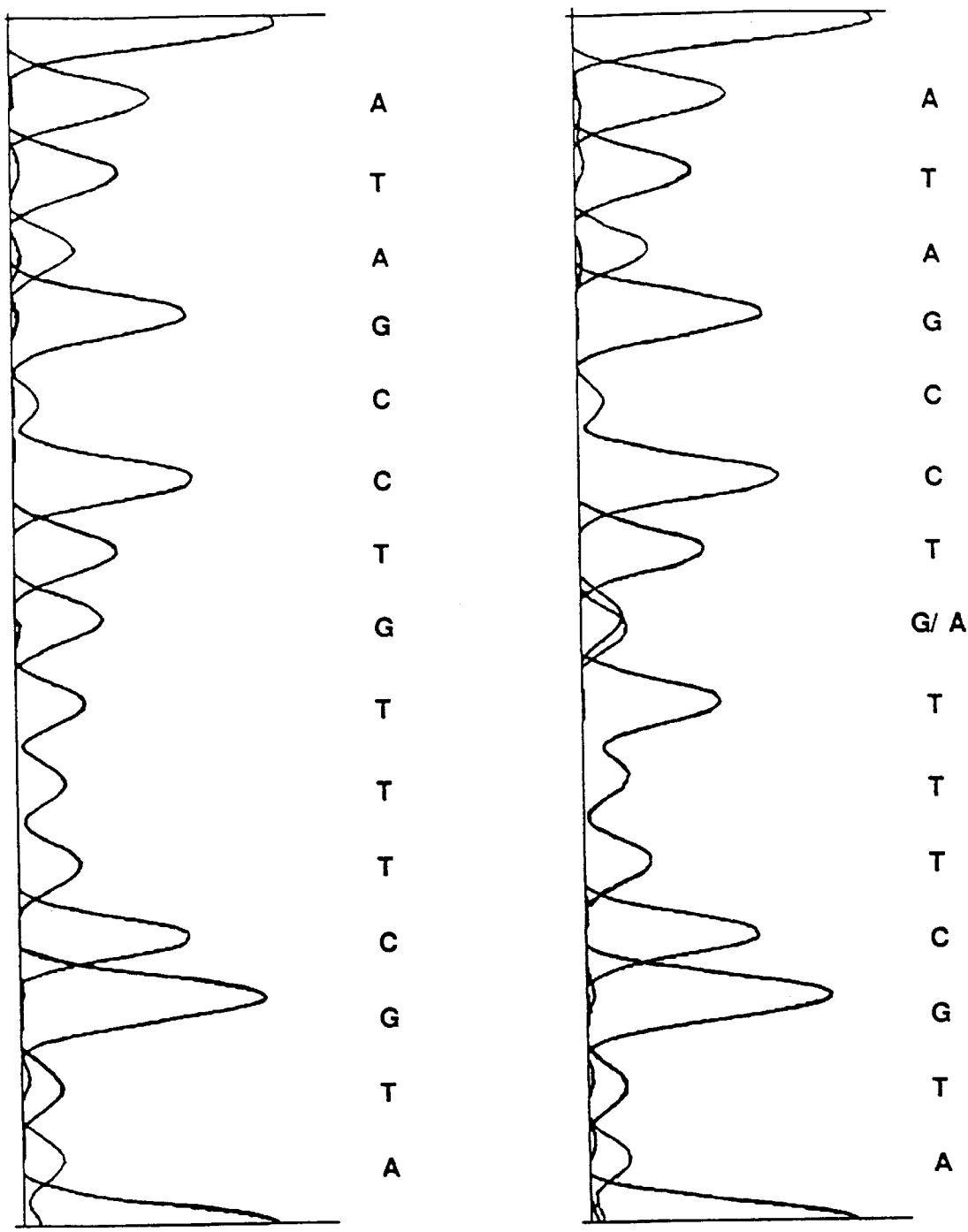

As an initial step toward cloning the AD3 gene a contig of overlapping genomic DNA fragments cloned into yeast artificial chromosome vectors, phage artificial chromosome vectors and cosmid vectors was constructed (FIG. 1b). FISH mapping studies using cosmids derived from the YAC clones 932c7 and 964f5 suggested that the interval most likely to carry the AD3 gene was at least five megabases in size. Because the large size of this minimal co-segregating region would make positional cloning strategies intractable, additional genetic pointers were sought which focused the search for the AD3 gene to one or more subregions within the interval flanked by D14S53 and D14S258. Haplotype analyses at the markers between D14S53 and D14S258 failed to detect statistically significant evidence for linkage disequilibrium and/or allelic association between the FAD trait and alleles at any of these markers, irrespective of whether the analyses were restricted to those pedigrees with early onset forms of FAD, or were generalized to include all pedigrees. This result was not unexpected given the diverse ethnic origins of our pedigrees. However, when pedigrees of similar ethnic descent were collated, direct inspection of the haplotypes observed on the disease bearing chromosome segregating in different pedigrees of similar ethnic origin revealed two clusters of marker loci (Table 2). The first of these clusters located centromeric to D14S77 (D14S786, D14S277 and D14S268) and spanned the 0.95 Mb physical interval contained in YAC 78842 (depicted as region B in FIG. 1c). The second cluster was located telomeric to D14S77 (D14S43, D14S273, and D14S76) and spanned the ~1 Mb physical interval included within the overlapping YAC clones 964c2, 74163, 797d11 and part of 854f5 (depicted as region A in FIG. 1c). Identical alleles were observed in at least two pedigrees from the same ethnic origin (Table 2). As part the strategy, it was reasoned that the presence of shared alleles at one of these groups of physically clustered marker loci might reflect the co-inheritance of a small physical region surrounding the ARMP gene on the original founder chromosome in each ethnic population. Significantly, each of the shared extended haplotypes were rare in normal caucasian populations and allele sharing was not observed at other groups of markers spanning similar genetic intervals elsewhere on chromosome 14q24.3.

Transcription mapping and preliminary analysis of candidate genes

To isolate expressed sequences encoded within both critical intervals, a direct selection strategy was used involving immobilized, cloned, human genomic DNA as the hybridization target to recover transcribed sequences from primary complementary DNA pools derived from human brain mRNA (Rommens et al., 1993). Approximately 900 putative cDNA fragments of size 100 to 600 base pairs were recovered from regions A and B in FIG. 1c. These fragments were hybridized to Southern blots containing genomic DNAs from each of the overlapping YAC clones and genomic DNAs from humans and other mammals. This identified a subset of 151 clones which showed evidence for evolutionary conservation and/or for a complex structure which suggested that they were derived from spliced mRNA. The clones within this subset were collated on the basis of physical map location, cross-hybridization and nucleotide sequence, and were used to screen conventional human brain cDNA libraries for longer cDNAs. At least 19 independent cDNA clones over 1 kb in length were isolated and then aligned into a partial transcription map of the AD3 region (FIG. 1d). Only three of these transcripts corresponded to known characterized genes (cFOS, dihydrolipoamide succinyl transferase and latent transforming growth factor binding protein 2).

Recovery of Potential Candidate Genes

Each of the open reading frame portions of the candidate genes were recovered by RT-PCR from mRNA isolated from post-mortem brain tissue of normal control subjects and from either post-mortem brain tissue or cultured fibroblast cell lines of affected members of six pedigrees definitively linked to chromosome 14. The RT-PCR products were then screened for mutations using chemical cleavage and restriction endonuclease fingerprinting single-strand sequence conformational polymorphism methods (Saleeba and Cotton, 1993; Liu and Sommer, 1995), and by direct nucleotide sequencing. With one exception, all of the genes examined, although of interest, were not unique to affected subjects, and did not co-segregate with the disease. The single exception was the candidate gene represented by clone S182 which contained a series of nucleotide changes not observed in normal subjects, but which altered the predicted amino acid sequence in affected subjects. Although nucleotide sequence differences were also observed in some of the other genes, most were in the 3' untranslated regions and none were unique to AD-affected subjects.

The remaining sequences, a subset of which are mapped in FIG. 1b together with additional putative transcriptional sequences not identified in FIG. 1c, are identified in the sequence listings as 14 through 43. The SEQ ID Nos: 14 to 43 represent neighbouring genes or fragments of neighbouring genes adjacent the hARMP gene or possibly additional coding fragments arising from alternative splicing of the hARMP. SEQ ID Nos: 44–126, and SEQ ID Nos: 150–160 represent neighboring genomic fragments containing both exon and intron information. Such sequences are useful for creating primers, for creating diagnostic tests, creating altered regulatory sequences and use of adjacent genomic sequences to create better animal models.

Characterization of the hARMP gene

Hybridization of the S182 clone to northern blots identified a transcript expressed widely in many areas of brain and peripheral tissues as a major 3.0 kb transcript and a minor transcript of 7.0 kb. Although the identity of the ~7.0 kb transcript is unclear, two observations suggest that the ~3.0 kb transcript represents an active product of the gene. Hybridization of the S182 clone to northern blots containing mRNA from a variety of murine tissues, including brain, identifies only a single transcript identical in size to the ~3.0 kb human transcript. All of the longer cDNA clones recovered to date (2.6–2.8 kb), which include both 5' and 3' UTRs and which account for the ~3.0 kb band on the northern blot, have mapped exclusively to the same physical region of chromosome 14. From these experiments the ~7.0 kb transcript could represent either a rare alternately spliced or polyadenylated isoform of the ~3.0 kb transcript or could represent another gene with homology to S182.

The nucleotide sequence of the major transcript was determined from the consensus of eleven independent longer cDNA clones and from 3 independent clones recovered by standard 5' rapid amplification of cDNA ends and bears no significant homology to other human genes. The cDNA of the sequenced transcript is provided in SEQ ID No: 1 and the predicted amino acid sequence is provided in SEQ ID No: 2. The cDNA sequence of another sequenced human clone is also provided as SEQ ID NO:133 and its predicted amino acid sequence is provide in SEQ ID NO:134.

Analysis of the 5' end of multiple cDNA clones and RT-PCR products as well as corresponding genomic clones indicates that the 5' UTR is contained within at least two exons and that transcription either begins from two different start sites and/or that one of the early 5' untranslated exons is alternatively spliced (Table 6). The longest predicted open reading frame contains 467 amino acids with a small alternatively spliced exon of 4 amino acids at 25 codons from the putative start codon (Table 3). This putative start codon is the first in phase ATG located 63 bp downstream of a TGA stop codon and lacks a classical Kozak consensus sequences around the first two in-phase ATG sequences (Rogaer et al, in preparation). Like other genes lacking classical 'strong' start codons, the putative 5' UTR of the human transcripts are rich in GC.

Comparison of the nucleic acid and predicted amino acid sequences with available databases using the BLAST alignment paradigms revealed modest amino acid similarity with the C. elegans sperm integral membrane protein SPE-4 ($p=1.5e^{-25}$, 24–37% identity over three groups of at least fifty residues) and weaker similarity to portions of several other membrane spanning proteins including mammalian chromogranin A and alpha subunit of mammalian voltage dependent calcium channels (Altschul et al., 1990). This clearly established that they are not the same gene. The amino-acid sequence similarities across putative transmembrane domains may occasionally yield alignment that simply arises from the limited number of hydrophobic amino acids, but there is also extended sequence alignment between S182 protein and SPE-4 at several hydrophillic domains. Both the putative S182 protein and SPE-4 are predicted to be of comparable size (467 and 465 residues, respectively) and to contain at least seven transmembrane domains with a large acidic domain preceding the final predicted transmembrane domain. The S182 protein does have a longer predicted hydrophillic region at the N terminus.

Further investigation of the hARMP has revealed a host of sequence fragments which form the hARMP gene and include intron sequence information, 5' end untranslated sequence information and 3' end untranslated sequence information (Table 6). Such sequence fragments are identified in SEQ ID Nos. 6–13.

Mutations in the S182 transcript

Direct sequencing of overlapping RT-PCR products spanning the 3.0 kb S182 transcript isolated from affected members of the six large pedigrees linked to chromosome 14 led to the discovery of eight missense mutations in each of the six pedigrees (Table 7, FIG. 2). Each of these mutations co-segregated with the disease in the respective pedigrees [FIGS. 3(a)(b)(c)(d)(e)], and were absent from 142 unrelated neurologically normal subjects drawn from the same ethnic origins as the FAD pedigrees (284 unrelated chromosomes).

The location of the gene within the physical interval segregating with AD3 trait, the presence of eight different missense mutations which co-segregate with the disease trait in six pedigrees definitively linked to chromosome 14, and the absence of these mutations in 284 independent normal chromosomes cumulatively confirms that the hARMP gene is the AD3 locus. Further biologic support for this hypothesis arises both from the fact that the residues mutated in FAD kindreds are conserved in evolution (Table 3) and occur in domains of the protein which are also highly conserved, and from the fact that the S182 gene product is expressed at high levels in most regions of the brain including the most severely affected with AD.

The DNA sequence for the hARMP gene as cloned has been incorporated into a plasmid Bluescript. This stable vector has been deposited at ATCC under accession number 97124 on Apr. 28, 1995.

Several mutations in the hARMP gene have been identified which cause a severe type of familial Alzheimer's Disease. One, or a combination of these mutations may be responsible for this form of Alzheimer's Disease as well as several other neurological disorders. The mutations may be any form of nucleotide sequence alteration or substitution. Specific disease causing mutations in the form of nucleotide and/or amino acid substitutions have been located, although we anticipate additional mutations will be found in other families. Each of these nucleotide substitutions occurred within the putative ORF of the S182 transcript, and would be predicted to change the encoded amino acid at the following positions, numbering from the first putative initiation codon. The mutations are listed in respect of their nucleotide locations in SEQ ID No: 1 and SEQ ID NO:133 (an additional human clone) and amino acid locations in SEQ ID No: 2 and SEQ ID NO:134 (the additional human clone).

| i)   | 685, A→C  | Met | 146 | Leu |
| ii)  | 737, A→G  | His | 163 | Arg |
| iii) | 986, C→A  | Ala | 246 | Glu |
| iv)  | 1105, C→G | Leu | 286 | Val |

-continued

| | | | | |
|---|---|---|---|---|
| v) | 1478, G→A | Cys | 410 | Tyr |
| vi) | 1027, C→T | Ala | 260 | Val |
| vii) | 1102, C→T | Ala | 285 | Val |
| viii) | 1422, C→G | Leu | 392 | Val |

The Met146Leu, Ala246Glu and Cys410Tyr mutations have not been detected in the genomic DNA of affected members of the eight remaining small early onset autosomal dominant FAD pedigrees or six additional families in our collection which express late FAD onset. We predict that such mutations would not commonly occur in late onset FAD which has been excluded by genetic linkage studies from the more aggressive form of AD linked to chromosome 14q24.3 (St George-Hyslop, P et al., 1992; Schellenberg et al., 1993). The His163Arg mutation has been found in the genomic DNA of affected members of one additional FAD pedigree for which positive but significant statistical evidence for linkage to 14 becomes established. Age of onset of affected members was consistent with affected individuals from families linked to chromosome 14.

Mutations Ala269Val, Ala285Val, and Leu392Val all occur within the acidic hydrophilic loop between putative transmembrane 6 (TM6) and transmembrane (TM7) (FIG. 3). Two of the mutations (A260V; A285V) and the L286V mutation are also located in the alternative spliced domain.

All eight of the mutations can be assayed by a variety of strategies (direct nucleotide sequencing, allele specific oligos, ligation polymerase chain reaction, SSCP, RFLPs etc.) using RT-PCR products representing the mature mRNA/cDNA sequence or genomic DNA. Allele specific oligos were chosen for assaying the mutations. For the A260V and the A285V mutations, genomic DNA carrying the exon was amplified using the same PCR primers and methods as for the L286V mutation. PCR products were then denatured and slot blotted to duplicate nylon membranes using the slot blot protocol described for the C410T mutation.

Of all of the nucleotide substitutions co-segregated with the disease in their respective pedigrees, none were seen in asymptomatic family members aged more than two standard deviations beyond the mean age of onset, and none were present on 284 chromosomes from unrelated neurologically normal subjects drawn from comparable ethnic origins.

Identification of an Alternative Splice Form of the ARMP Gene Product

During sequencing studies of RT-PCR products for the ARMP gene recovered from a variety of tissues, it was discovered that some peripheral tissues (principally white blood cells) demonstrated two alternative splice forms of the ARMP gene. One form is identical to the (putatively 467 amino acid) isoform constitutatively expressed in all brain regions. The alternative splice form results from the exclusion of the segment of the cDNA between base pairs 1018 to 1116 inclusive, and results in a truncated isoform of the ARMP protein wherein the hydrophobic part of the hydrophilic acidically-charged loop immediately C-terminal to TM6 is removed. This alternatively spliced isoform therefore is characterized by preservation of the sequence N-terminal to and including the tyrosine at position 256, changing of the aspartate at 257 to alanine, and splicing on to the C-terminal part of the protein from and including tyrosine 291. Such splicing differences are often associated with important functional domains of the proteins. This argues that this hydrophilic loop (and consequently the N-terminal hydrophillic loop with similar amino acid charge) is/are active functional domains of the ARMP product and thus sites for therapeutic targeting.

ARMP Protein

With respect to DNA SEQ ID NO. 1 and DNA SEQ ID NO: 133, analysis of the sequence of overlapping cDNA clones predicted an ORF protein of 467 amino acids when read from the first in phase ATG start codon and a molecular mass of approximately 52.6 kDa as later described, due to either polymorphisms in the protein or alternate splicing of the transcript, the molecular weight of the protein can vary due to possible substitutions or deletions of amino acids.

The analysis of predicted amino acid sequence using the Hopp and Woods algorithm suggested that the protein product is a multispanning integral membrane protein such as a receptor, a channel protein, or a structural membrane protein. The absence of recognizable signal peptide and the paucity of glycosylation sites are noteworthy, and the hydropathy profile suggests that the protein is less likely to be a soluble protein with a highly compact three-dimensional structure.

The protein may be a cellular protein with a highly compact three dimensional structure in which respect is may be similar to APOE which is also related to Alzheimer's Disease. In light of this putative functional role, it is proposed that this protein be labelled as the Alzheimer Related Membrane Protein (ARMP). The protein also contains a number of potential phosphorylation sites, one of which is the consensus site for MAPkinase which is also involved in the hyperphosphorylation of tau during the conversion of normal tau to neurofibrillary tangles. This consensus sequence may provide a common putative pathway linking this protein and other known biochemical aspects of Alzheimer's Disease and would represent a likely therapeutic target. Review of the protein structure reveals two sequences YTPF (residues 115–119) SEQ NO:161 and STPE (residues 353–356) SEQ ID NO:162 which represent the 5/T-P motif which is the MAP kinase consensus sequence. Several other phosphorylation sites exist with concensus sequences for Protein Kinase C activity. Because protein kinase C activity is associated with differences in the metabolism of APP which are relevant to Alzheimer's Disease, these sites on the ARMP protein and homologues are sites for therapeutic targetting.

The N-terminal is characterized by a highly hydrophilic acidic charged domain with several potential phosphorylation domains, followed sequentially by a hydrophobic membrane spanning domain of 19 residues; a charged hydrophilic loop, then five additional hydrophobic membrane spanning domains interspersed with short (5–20 residue) hydrophilic domains; an additional larger acidic hydrophilic charged loop, and then at least one and possibly two other hydrophobic potentially membrane spanning domains culminating in a polar domain at the C-terminus (Table 4 and FIG. 3B). The presence of seven membrane spanning domains is characteristic of several classes of G-coupled receptor proteins but is also observed with other proteins including channel proteins.

Comparison of the nucleic acid and predicted amino acid sequences with available databases using the BLAST alignment paradigms revealed amino acid similarity with the *C. elegans* sperm integral membrane protein spe-4 and a similarity to several other membrane spanning proteins including mammalian chromogranin A and the α-subunit of mammalian voltage dependent calcium channels.

The similarity between the putative products of the spe-4 and ARMP genes implies that they may have similar activities. The SPE-4 protein of *C. elegans* appears to be involved in the formation and stabilization of the fibrous body-membrane organelle (FBMO) complex during spermatogenesis. The FBMO is a specialized Golgi-derived organelle, consisting of a membrane bound vesicle attached to and partly surrounding a complex of parallel protein fibers and may be involved in the transport and storage of soluble and membrane-bound polypeptides. Mutations in spe-4 disrupt the FBMO complexes and arrest spermatogenesis. Therefor the physiologic function of spe-4 may be either to stabilize interactions between integral membrane budding and fusion events, or to stabilize interactions between the membrane and fibrillary proteins during the intracellular transport of the FBMO complex during spermatogenesis. Comparable function could be envisaged for the ARMP. The ARMP could be involved either in the docking of other membrane-bound proteins such as βAPP, or the axonal transport and fusion budding of membrane-bound vesicles during protein transport such as in the golgi apparatus or endosome-lysosome system. If correct, then mutations might be expected to result in aberrant transport and processing of βAPP and/or abnormal interactions with cytoskeletal proteins such as the microtubule-associated protein Tau. Abnormalities in the intracellular and in the extracellular disposition of both βAPP and Tau are in fact an integral part of the neuropathologic features of Alzheimer's Disease. Although the location of the ARMP mutations in highly conserved residues within conserved domains of the putative proteins suggests that they are pathogenic, at least three of these mutations are conservative which is commensurate with the onset of disease in adult life. Because none of the mutations observed so far are deletions or nonsense mutations that would be expected to cause a loss of function, we cannot predict whether these mutations will have a dominant gain-of-function effect and promote aberrant processing of βAPP or a dominant loss-of-function effect causing arrest of normal βAPP processing.

An alternative possibility is that the ARMP gene product may represent a receptor or channel protein. Mutations of such proteins have been causally related to several other dominant neurological disorders in both vertebrate (eg. Malignant hyperthermia, hyperkalemic periodic paralysis in humans) and in invertebrate organisms (deg-1(d) mutants in *C. elegans*). Although the pathology of these other disorders does not resemble that of Alzheimer's Disease there is evidence for functional abnormalities in ion channels in Alzheimer's Disease. For example, anomalies have been reported in the tetra-ethylammonium-sensitive 113pS potassium channel and in calcium homeostasis. Perturbations in transmembrane calcium fluxes might be especially relevant in view of the weak homology between S182 and the α-ID subunit of voltage-dependent calcium channels and the observations that increases in intracellular calcium in cultured cells can replicate some of the biochemical features of Alzheimer's Disease such as alteration in the phosphorylation of Tau-microtubule-associated protein and increased production of Aβ peptides.

As mentioned purified normal ARMP protein is characterized by a molecular weight of 52.6 kDa. the normal ARMP protein, substantially free of other proteins, is encoded by the aforementioned SEQ. ID NO: 1 and SEQ ID NO: 133. As will be later discussed, the ARMP protein and fragments thereof may be made by a variety of methods. Purified mutant ARMP protein is characterized by FAD—associated phenotype (necrotic death, apoptic death, granulovascular degeneration. neurofibrillary degeneration, abnormalities or changes in the metabolism of APP, and $Ca^{2+}$, $K^+$, and glucose, and mitochondrial function and energy metabolism neurotrasmitter metabolism, all of which have been found to be abnormal in human brain, and/or peripheral tissue cells in subjects with Alzheimer's Disease) in a variety of cells. The mutant ARMP, free of other proteins, is encoded by the mutant DNA sequence.

Description of a Homologous Gene

A gene (E5-1 homologue) with substantial nucleotide and amino acid homology to the ARMP gene was identified by using the nucleotide sequence of the cDNA for ARMP to search date bases using the BLASTN paradigm of Altschul et al. 1990. This gene is identified as SEQ ID NO: 137 and its corresponding amino acid sequence is SEQ ID NO: 138. Three expressed sequence tagged sites (ESTs) identified by accession numbers T03796, R14600, and R05907 were discovered which had substantial homology ($p<1.0$ $e^{-100}$, greater than 97% identity over at least 100 contiguous base pairs). Oligonucleotide primers were produced from these sequences and used to generate PCR products b reverse transcriptase PCR (RT-PCR). these short RT-PCR products were partially sequenced to confirm their identity with the sequences within the data base and were then used as hybridization probes to screen full-length cDNA libraries. Several different cDNA's were recovered from a cancer cell cDNA library (CaCo-2) and from a human brain cDNA library (E5-1, G1-1, cc54, cc32-13). Hybridization of these cDNA's to Northern Blots detected an ~2.4 kilobase mRNA band in many tissues including brain, as well as a ~2.6 Kb mRNA band in muscle, cardiac muscle and pancreas. Nucleotide sequencing of the recovered clones, which partially overlapped with each other, inferred an open reading frame (ORF) which showed approximately 70% amino acid similarity to the ARMP gene. Table 8 shows a comparison of structure and sequence of E5-1 homologue protein and ARMP. The similarity was greatest in several domains of the protein corresponding to the intervals between transmembrane domain 1 (TM1) and TM6, and from TM7 to the C-terminus fo the ARMP gene. The main differences with the ARMP gene is a difference in the size and amino acid sequence of the acidically-charged hydrophilic loop in the position equivalent to the hydrophilic loop between transmembrane domains TM6 and TM7 in the ARMP protein and in the sequence of the N-terminal hydrophilic domains. This argues for similar functions, but with specificity of function being conferred in part by these two domains.

This amino acid similarity to ARMP suggest that the E5-1 homologue protein may be related to Alzheimer's Disease. Due to its structural similarity with the ARMP protein, the E5-1 homologue protein ay be used for the development of probes, peptides, or antibodies to various peptides which may recognize both the E5-1 and the ARMP gene and gene product, respectively. As a protein homologue for ARMP, the E5-1 homologue protein may be used as a replacement for a defective ARMP gene product. It may also be used to elucidate functions of the ARMP gene in tissue culture. A plasmid including this nucleic acid was deposited with the ATCC under the terms of the Budapest Treaty on Jun. 28, 1995 and has been assigned ATCC accession number 97214.

Functional Domains of the ARMP Protein and Defined by Splicing Sites and Similarities within Other Members of a Gene Family The ARMP protein is a member of a novel class of transmembrane proteins which share substantial amino acid homology. The homology is sufficient that certain nucleotide probes and antibodies raised against one can identify other members of this gene family. The major difference between members of this family reside in the amino acid and nucleotide sequence homologous to the hydrophilic acid loop domain between putative transmembrane 6 and transmembrane 7 domains of the ARMP gene and gene product. This region is alternatively spliced in some non-neural tissues, and is also the site of several pathogenic disease-causing mutations in the ARMP gene. The variable splicing of this hydrophilic loop, the presence of a high-density of pathogenic mutations within this loop, and the fact that the amino acid sequences of the loop differs between members of the gene family suggest that this loop is an important functional domain of the protein and may confer some specificity to the physiologic and pathogenic interactions which the ARMP gene product undergoes because the N-terminal hydrophilic domain shares the same acidic charge and same orientation with respect to the membrane, it is very likely that these two domains share functionality either in a coordinated (together) or independent fashion (eg. different ligands or functional properties). As a result everything said about the hydrophilic loop shall apply also to the N-terminal hydrophilic domain.

Knowledge of the specificity of the loop can be used to identify ligands and functional properties of the ARMP gene product (eg. sites fo interactions with APP, cytosolic proteins such as kinases, Tau, and MAP, etc.). Soluble recombinant fusion proteins can be made or the nucleotide sequence coding for amino acids within the loop or parts of the loop can be expressed in suitable vectors (yeast-2-hybrid, baculovirus, and phage—display systems for instance), and used to identify other proteins which interact with ARMP in the pathogenesis fo Alzheimer's disease and other neurological and psychiatric diseases. Therapies can be designed to modulate these interactions and thus to modulate Alzheimer's disease and the other conditions associated with acquired or inherited abnormalities of the ARMP gene or its gene products. The potential efficacy of these therapies can be tested by analyzing the affinity and function of these interactions after exposure to the therapeutic agent by standard pharmacokinetic measurements of affinity (Kd and Vmax etc) using synthetic peptides or recombinant proteins corresponding to functional domains of the ARMP gene (or its homologues). An alternate method for assaying the effect of any interactions involving functional domains such as the hydrophilic loop is to monitor changes in the intracellular trafficking and post-translational modification of the ARMP gene by in-situ hybridization, immunohistochemistry, Western blotting and metabolic pulse-chase labelling studies in the presence of and in the absence of the therapeutic agents. A third way is to monitor the effects of "downstream" events including (i) changes in the intracellular metabolism, trafficking and targeting of APP and its products; (ii) changes in second messenger event eg. cAMP, intracellular Ca++ protein kinase activities, etc..

Isolation and Purification of the ARMP Protein

The ARMP protein may be isolated and purified by methods selected on the basis of properties revealed by its sequence. Since the protein possesses properties of am membrane-spanning protein, a membrane fraction of cells in which the protein is highly expressed (eg. central nervous system cells or cells from other tissues) would be isolated and the proteins removed by extraction and the proteins solubilized using a detergent.

Purification can be achieved using protein purification procedures such as chromatography methods (gel-filtration, ion-exchange and immunoaffinity), by high-performance liquid chromatography (RP-HPLC, ion-exchange HPLC, size-exclusion HPLC, high-performance chromatofocusing and hydrophobic interaction chromatography) or by precipitation (immunoprecipitation). Polyacrylamide gel electrophoresis can also be use to isolate the ARMP protein based on its molecular weight, charge properties and hydrophobicity.

Similar procedures to those just mentioned could be used to purify the protein from cells transfected with vectors containing the ARMP gene (eg. baculovirus systems, yeast expression systems. eukaryotic expression systems).

Purified protein can be used in further biochemical analyses to establish secondary and tertiary structure which may aid in the design of pharmaceuticals to interact with the protein, alter protein charge configuration or charge interaction with other proteins, lipid or saccharide moities, alter its function in membranes as a transporter channel or receptor and/or in cells as an enzyme or structural protein and treat the disease.

The protein can also be purified by creating a fusion protein by legating the ARMP cDNA sequence to a vector which contains sequence for another peptide (eg. GST—glutathione succinyl transferase). The fusion protein is expressed and recovered from prokaryotic (eg. bacterial or baculovirus) or eukaryotic cells. The fusion protein can then be purified by affinity chromatography based upon the fusion vector sequence. The ARMP protein can then be further purified from the fusion protein by enzymatic cleavage of the fusion protein.

Isolating mouse ARMP gene

In order to characterize the physiological significance of the normal and mutant hARMP gene and gene products in a transgenic mouse model it was necessary to recover a mouse homologue of the hARMP gene. We recovered a murine homologue for the hARMP gene by screening a mouse cDNA library with a labelled human DNA probe and in this manner recovered a 2 kb partial transcript (representing the 3+ end of the gene) and several RT-PCR products representing the 5'end. Sequencing of the concensus cDNA transcript of the murine homologue revealed substantial amino acid identity. The sequence cDNA is identified in SEQ ID NO: 3 and the predicted amino acid Sequence is provided in SEQ ID NO; 4. Further sequencing of the mouse cDNA transcript has provided the sequence for the complete coding sequence identified as SEQ ID NO: 135 and the predicted amino acid sequence from this sequence is provide din SEQ ID NO: 136. More importantly, all of the amino acids that were mutated in the FAD pedigrees wee conserved between the murine homologue and the normal human variant (Table 3). This conservation of the ARMP gene as is shown in table 3, indicates that an orthologous gene exists in the mouse (mARMP), and it is now possible to clone mouse genomic libraries using human ARMP probes. This will also make it possible to identify and characterize the ARMP gene in other species. This also provides evidence of animals with various disease states or disorders currently known or yet to be elucidated.

Transgenic Mouse Model

The creation of a mouse model for Alzheimer's Disease is important to the understanding of the disease and for the testing of possible therapies. Currently no unambiguous viable animal model for Alzheimer's Disease exists.

There are several ways in which to create an animal model for Alzheimer's Disease. Generation of a specific mutation in the mouse gene such as the identified hARMP gene mutations is one strategy. Secondly, we could insert a wild type human gene and/or humanize the murine gene by homologous recombination. Thirdly, it is also possible to insert a mutant (single or multiple) human gene as genomic or minigene cDNA constructs using wild type or mutant or artificial promoter elements. Fourthly, knock-out of the endogenous murine genes may be accomplished by the insertion of artificially modified fragments of the endogenous gene by homologous recombination. The modifications include insertion of mutant stop codons, the deletion of DNA sequences, or the inclusion of recombination elements (Icx p sites) recognized by enzymes such as Cre recombinanse.

To inactivate the mARMP gene chemical or x-ray mutagenesis of mouse gametes, followed by fertilization, can be applied. Heterozygous offspring can then be identified by Southern blotting to demonstrate loss of one allele by dosage or failure to inherit one parental allele using RFLP markers.

To create a transgenic mouse a mutant version of hARMP or mARMP can be inserted onto a mouse germ line using standard techniques of oocyte microinjection or transfection or microinjection into stem cells. Alternatively, if it is desired to inactivate or replace the endogenous mARMP gene, homologous recombination using embryonic stem cells may be applied.

For oocyte injection, one or more copies of the mutant or wild type ARMP gene can be inserted into the pronucleus of a just-fertilized mouse oocyte. This oocyte is then reimplanted into a pseudo-pregnant foster mother. The liveborn mice can then be screened for integrants using analysis of tail DNA for the presence of human ARMP gene sequences. The transgene can be either a complete genomic sequence injected as a YAC, BAC, PAC or other chromosome DNA fragment, a cDNA with either the natural promoter or a heterologous promoter, or a minigene containing all of the coding region and other elements found to be necessary for optimum expression.

Retroviral infection of early embryos can also be done to insert the mutant or wild type hARMP. In this method, the mutant or wild type hARMP is inserted into a retroviral vector which is used to directly infect mouse embryos during the early stages fo development to generate a chimera, some of which will lead to germline transmission. Similar experiments can be conducted in the cause of mutant proteins, using mutant murine or other animal ARMP gene sequences.

Homologous recombination using stem cells allows for the screening of gene transfer cells to identify the rate homologous recombination events. Once identified, these can be used to generate chimeras by injection of mouse blastocysts, and a proportion of the resulting mice will show germline transmission from the recombinant line. This methodology is especially useful fi inactivation of the mARMP gene is desired. For example, inactivation of the mARMP gene can be done by designing a DNA fragment which contains sequences from a mARMP exon flanking a selectable marker. Homologous recombination leads to the insertion of the marker sequences in the middle of an exon, inactivating the mARMP gene. DNA analysis of individual clones can then be used to recognize the homologous recombination events.

It is also possible to create mutations in the mouse germline by injecting oligonucleotides containing the mutation of interest and screening the resulting cells by PCR.

This embodiment of the invention has the most significant commercial value as a mouse model for Alzheimer's Disease. Because of the high percentage of sequence conservation between human and mouse it is contemplated that an orthologous gene will exist also in many other species. It is thus contemplated that it will be possible to generate other animal models using similar technology.

Screening and Diagnosis for Alzheimer's Disease General Diagnostic Uses of the ARMP Gene and Gene Product The ARMP gene and gene products will be useful for diagnosis of Alzheimer's disease, presenile and senile dementias, psychiatric diseases such as schizophrenia, depression, etc., and neurologic disease such as stroke and cerebral hemorrhage—all of which are seen to a greater or lesser extent in symptomatic subjects bearing mutations in the ARMP gene or in the APP gene. Diagnosis of inherited cases of these diseases can be accomplished by analysis of the nucleotide sequence (including genomic and cDNA sequences included in this patent). Diagnosis can also be achieved by monitoring alterations in the electrophoretic mobility and by the reaction with specific antibodies to mutant or wild-type ARMP gene products, and by functional assays demonstrating altered function of the ARMP gene product. In addition, the ARMP gene and ARMP gene products can be used to search for inherited anomalies in the gene and/or its products (as well as those of the homologous gene) and can also be used for diagnosis in the same way as they can be used for diagnosis of non-genetic cases.

Diagnosis of non-inherited cases can be made by observation of alterations in the ARMP transcription, translation, and post-translational modification and processing as well as alterations in the intracellular and extracellular trafficking of ARMP gene products in the brain and peripheral cells. Such changes will include alterations in the amount of ARMP messenger RNA and/or protein, alteration in phosphorylation state, abnormal intercellular location/distribution, abnormal extracellular distribution, etc. Such assays will include: Northern Blots (with ARMP-specific and ARMP-non-specific nucleotide probes which also cross-react with other members of the gene family), and Western blots and enzyme-linked immunosorbent assays (ELISA) (with antibodies raised specifically to ARMP; to various functional domains of ARMP; to other members of the homologous gene family; and to various post-translational modification states including glycosylated and phosphorylated isoforms). Theses assays can be performed on peripheral tissues (eg. blood cells, plasma, cultured or other fibroblast tissues, etc.) as well as on biopsies of CNS tissues obtained antimortem or postmortem, and upon cerebrospinal fluid. Such assays might also include in-situ hybridization and immunohistochemistry (to localized messenger RNA and protein to specific subcellular compartments and/or within neuropathological structures associated with these disease such as neurofibrillary tangles and amyloid plaques).

Screening for Alzheimer's Disease

Screening for Alzheimer's Disease as linked to chromosome 14 may now be readily carried out because of the knowledge of the mutations in the gene.

People with a high risk for Alzheimer's Disease (present in family pedigree) or, individuals not previously known to be at risk, or people in general may be screened routinely using probes to detect the presence of a mutant ARMP gene by a variety of techniques. Genomic DNA used for the diagnosis may be obtained from body cells, such as those present in the blood, tissue biopsy, surgical specimen, or autopsy material. The DNA may be isolated and used directly for detection of a specific sequence or may be PCR amplified prior to analysis. RNA or cDNA may also be used. To detect a specific DNA sequence hybridization using specific oligonucleotides, direct DNA sequencing, restriction enzyme digest, RNase protection, chemical cleavage, and ligase-mediated detection are all methods which can be utilized. Oligonucleotides specific to mutant sequences can be chemically synthesized and labelled radioactively with isotopes, or non-radioactively using biotin tags, and hybridized to individual DNA samples immobilized on membranes or other solid-supports by dot-blot or transfer from gels after electrophoresis. The presence or absence of these mutant sequences are then visualized using methods such as autoradiography, fluorometry, or colorimetric reaction. Examples of suitable PCR primers which are useful for example in amplifying portions of the subject sequence containing the aforementioned mutations are set out in Table 5. This table also sets out the change in enzyme site to provide a useful diagnostic pool as defined herein.

Direct DNA sequencing reveals sequence differences between normal and mutant ARMP DNA. Cloned DNA segments may be used as probes to detect specific DNA segments. PCR can be used to enhance the sensitivity of this method. PCR is an enzymatic amplification directed by sequence -specific primers, and involves repeated cycles of heat denaturation of the DNA, annealing of the complementary primers and extension of the annealed primer with a DNA polymerase. This results in an exponential increase of the target DNA.

Other nucleotide sequence amplification techniques may be used such as ligation-mediated PCR, anchored PCR and enzymatic amplification as would be understood by those skilled in the art.

Sequence alterations may also generate fortuitous restriction enzyme recognition sites which are revealed by the use of appropriate enzyme digestion followed by gel-blot hybridization. DNA fragments carrying the site (normal or mutant) are detected by their increase or reduction in size, or by the increase or decrease of corresponding restriction fragment numbers. Genomic DNA samples may also be amplified by PCR prior to treatment with the appropriate restriction enzyme and the fragments of different sizes are visualized under UV light in the presence of ethidium bromide after gel electrophoresis.

Genetic testing base don DNA sequence differences may be achieved by detection of alteration in electrophoretic mobility of DNA fragments in gels. Small sequence deletions and insertions can be visualized by high resolution gel electrophoresis. Small deletions may also be detected as changes in the migration pattern of DNA heteroduplexes in non-denaturing gel electrophoresis. Alternatively, a single base substitution mutation may be detected based on differential PCR product length in PCR. The PCR products fo the normal and mutant gene could be differentially detected in acrylamide gels.

Nuclease protection assays (S1 or ligase-mediated) also reveal sequence changes at specific locations.

Alternatively, to confirm or detect a polymorphism restriction mapping changes ligated PCR, ASO, REF-SSCP chemical cleavage, endonuclease cleavage at mismatch sites and SSCP may be used. Both REF-SSCP and SSCP are mobility shift assays which are based upon the change in conformation due to mutations.

DNA fragments may also be visualized by methods in which the individual DNA samples are not immobilized on membranes. The probe and target sequences may be in solution or the probe sequence may be immobilized. Autoradiography, radioactive, decay, spectrophotometry, and fluorometry may also be used to identify specific individual genotypes. Finally, mutations can be detected by direct nucleotide sequencing.

According to an embodiment of the invention, the portion of the cDNA or genomic DNA segment that is informative for a mutation, can be amplified using PCR. For example, the DNA segment immediately surrounding the C410Y mutation acquired from peripheral blood samples from an individual can be screened using the oligonucleotide primers 885 (tggagactggaacacaac) SEQ ID NO: 127 and 893 (gtgtggccagggtagagaact) SEQ ID NO: 128. This region would then be amplied by PCR, the products separated b electrophoresis, and transferred to membrane. Labelled oligonucleotide probes are then hybridized to the DNA fragments and autoradiography performed.

ARMP Expression

As an embodiment of the present invention, AMRP protein may be expressed using eukaryotic and prokaryotic expression systems. Eukaryotic expression systems can be used for many studies of the ARMP gene and gene product including determination of proper expression and porttranslational modifications for full biological activity, identifying regulatory elements located in the 5' region of the large amounts of the normal and mutant protein for isolation and purification, to use cells expressing the ARMP protein as a functional assay system for antibodies generated against the protein or to test effectiveness of pharmacological agents, or as a component of a signal transduction system, to study the function of the normal complete protein, specific portions of the protein, or of naturally occurring and artificially produced mutant proteins.

Eukaryotic and prokaryotic expression systems were generated using two different classes of ARMP nucleotide cDNA sequence inserts. In the first class, termed full-length constructs, the entire ARMP cDNA sequence is inserted into the expression plasmid in the correct orientation, and includes both the natural 5' UTR and 3' UTR sequences as well as the entire open reading frame. The open reading frames bear a nucleotide sequence cassette which allows either the wild type open reading frame to be included in the expression system or alternatively, single or a combination of double mutations can be inserted into the open reading frame. This was accomplished by removing a restriction fragment from the wild type open reading frame using the enzymes NarI and PflmI and replacing it with a similar fragment generated by reverse transcriptase PCR and which bears the nucleotide sequence encoding either the Met146Leu mutation or the Hys163Arg mutation. A second restriction fragment was removed from the wild type normal nucleotide sequence for the open reading frame by cleavage with the enzymes PflmI and NcoI and replaced with restriction fragments bearing either the nucleotide sequence encoding the Ala246Glu mutation, or the Ala260Val mutation or the Ala285Val mutation or the Leu286Val mutation, or the Leu392Val mutation or the Cys410Tyr mutation. Finally, a third variant bearing combinations of either the Mel146Leu or His163Arg mutations in tandem with the remaining mutation, was made by linking the NarI-PflmI fragment bearing these mutations and the PflmI-NcoI fragments bearing the remaining mutations.

A second variant of cDNA inserts bearing wild type or mutant cDNA sequences was constructed by removing from the full-length cDNA the 5' UTR and part of the 3' UTR sequences. The 5' UTR sequence was replaced with a synthetic oligonucleotide containing a KpnI restriction site and a Kozak initiation site (oligonucleotide 969: ggtaccgccaccatgacagaggtacctgcac, SEQ ID NO: 139). The 3' UTR was replaced with an oligonucleotide corresponding to position 2566 of the cDNA and bears an artificial EcoRI site (oligonucleotide 970:gaattcactggctgtagaaaaagac, SEQ ID NO: 140). Mutant variants of this construct were then made b inserting the same mutant sequences described above at the NarI-PflmI fragment, and at the PsImI-NcoI sites describe above.

For eukaryotic expressions, these various cDNA constructs bearing wild type and mutant sequences described above were cloned into the expression vector pZeoSV (invitrogen). for prokaryotic expression, two constructs have been made using the glutathione S-transferase fusion vector pGEX-kg. The inserts which have been attached to the GST fusion nucleotide sequence are the same nucleotide sequence described above (generated with the oligonucleotide primers 969, SEQ ID NO: 139 and 970, SEQ ID NO: 140) bearing either the normal open reading frame nucleotide sequence, or bearing a combination of single and double mutation as described above. This construct allows expression of the full-length protein in mutant and wild type variants in prokaryotic cell systems as a GST fusion protein which allows purification of the full-length protein followed by removal of the GST fusion product by thrombin digestion. The second prokaryotic cDNA construct was generated to created a fusion protein with the same vector, and allows the production of the amino acid sequence corresponding to the hydrophilic acidic loop domain between TM6 and TM7 of the full-length protein, as either a wild type nucleotide sequence (thus a wild type amino acid sequence for fusion proteins) or as a mutant sequence bearing either the Ala285Val mutation, or the Leu286Val mutation, or the Leu392Val mutation. This was accomplished by recovering wild type or mutant sequence from appropriate sources of RNA using the oligonucleotide primers 989: ggatccggtccacttcgtatgctg, SEQ ID NO: 141, and 990:tttttgaattcttaggctatggttgtgttcca, SEQ ID NO; 142. This allows cloning of the appropriate mutant or wild type nucleotide sequence corresponding to the hydrophilic acid loop domain at the BamHI and the EcoRI sites within the pGEX-KG vector.

These prokaryotic expression systems allow the holo-protein or various important functional domains of the protein to be recovered as fusion proteins and then used for binding studies, structural studies, functional studies, and for the generation of appropriated antibodies.

Expression of the ARMP gene in heterologous cell systems can be used to demonstrates structure-function relationships. Ligating the ARMP DNA sequence into a plasmid expression vector to transfect cells is useful method to test the proteins influence on various cellular biochemical parameters. Plasmid expression vectors containing either the entire, normal or mutant human or mouse ARMP sequence or portions thereof, can be used in in vitro mutagenesis experiments which will identify portions of the protein crucial for regulatory function.

The DNA sequence can be manipulated in studies to understand the expression of the gene and its product, to achieve production of large quantities of the protein for functional analysis, for antibody production, and for patient therapy. The changes in the sequence may or may not alter the expression pattern in terms of relative quantities, tissue-specificity and functional properties. Partial or full-length DNA sequences which encode for the ARMP protein, modified or unmodified, may be ligated to bacterial expression vectors. *E Coli* can be used using a variety of expression vector system eg. the T7 RNA polymerase/promoter system using two plasmids or by labeling of plasmid-encoded proteins, or by expression by infection with M13 Phage mGPI-2. *E. Coli* vectors can also be used with Phage lamba regulatory sequence, by fusion and by glutathione-S-transferase fusion proteins, etc., all of which together with many other prokaryotic expression systems are widely available commercially.

Alternatively, the ARMP protein can be expressed in insect cells using baculoviral vectors, or in mammalian cells using vaccinia virus or specialised eukaryotic expression vectors. For expression in mammalian cells, the cDNA sequence may be ligated to heterologous promoters, such as the simian virus (SV40) promoter in the pSV2 vector and other similar vectors and introduced into cultured eukaryotic cells, such as COS cells to achieve transient or long-term expression. The stable integration of the chimeric gene construct may be maintained in mammalian cells by biochemical selection, such as neomycin and mycophoenolic acid.

The ARMP DNA sequence can be altered using procedures such as restriction enzyme digestion, full-in with DNA polymerase, deletion by exonuclease, extension by terminal deoxynucleotide transferase, ligation of synthetic or cloned DNA sequences and site-directed sequence alteration with the use of specific oligonucleotides together with PCR.

The cDNA sequence or portions thereof, or a mini gene consisting of a cDNA with an intron and its own promoter, is introduced into eukaryotic expression vectors by conventional techniques. These vectors permit the transcription of the cDNA in eukaryotic cells by providing regulatory sequences that initiate and enhance the transcription of the cDNA and ensure its proper splicing and polyadenylation. The endogenous ARMP gene promoter can also be sued. Different promoters within vectors have different activities which alters the level of expression of the cDNA. In addition, certain promoters can also modulate function such as the glucocorticoid-responsive promoter from the mouse mammary tumor virus.

Some of the vectors listed contain selectable markers or neo bacteria genes that permit isolation of cells by chemical selection. Stable long-term vectors can be maintained in cells as episomal, freely replicating entities by using regulatory elements of viruses. Cell lines can also be produced which have integrated the vector into the genomic DNA. In this manner, the gene, product is produced on a continuous basis.

Vectors are introduced into recipient cells by various methods including calcium phosphate, storntium phosphate, electroporation, lipofection, DEAE dextran, microinjection, or by protoplast fusion. Alternatively, the cDNA can be introduced by infection using viral vectors.

Using the techniques mentioned, the expression vectors containing the ARMP gene or portions thereof can be introduced into a variety of mammalian cells from other species or into non-mammalian cells.

The recombinant cloning vector, according to this invention, comprises the selected DNA of the DNA sequences of this invention for expression in a suitable host. The DNA is operatively linked in the vector to an expression control sequence in the recombinant DNA molecule so that normal and mutant ARMP protein can be expressed. The expression control sequence may be selected from the group consisting of sequences that control the expression of genes of prokaryotic or eukaryotic cells and their viruses and combinations therefore. The expression control sequence may be selected from the group consisting of the lac system, the trp system, the tac system, the trc system, major operator and promoter regions of phage lambda, the control region of the fd coat protein, early and late promoters of SE40, promoters derived from polyoma, adenovirus, baculovirus, simian virus, 3- phosphoglycerate kinase promoter, yeast acid phosphatase promoters, yeast alphamating factors and combinations thereof.

The host cell which may be transfected with the vector of this invention may be selected from the group consisting of *E. Coli, pseudomonas, bacillus subtillus, bacillus stearothermophilus*, or other bacili; other bacteria, yeast, fungi, insect, mouse or other animal, plant hosts, or human tissue cells.

For the mutant ARMP DNA sequence similar systems are employed to express and the produce the mutant protein.

Antibodies to Detect ARMP

Antibodies to epitopes with the ARMP protein can be raised to provide information on the characteristics of the proteins. Generation of antibodies would enable the visualization of the protein in cells and tissues using Western blotting. In this technique, proteins are run on polyacrylamide gel and then transferred onto nitrocellulose membranes. These membranes are then incubated in the presence of the antibody (primary), then following washing are incubated to a secondary antibody which is used for detection of the protein-primary antibody complex. Following repeated washing, the entire complex is visualized using colourimetric or chemiluminescent methods.

Antibodies to the ARMP protein also allow for the use of immunocytochemistry and immunofluorescence techniques in which the proteins can be visualized directly in cells and tissues. This is most helpful in order to establish the subcellular location of the protein and the tissue specificity of the protein.

In order to prepare polyclonal antibodies, fusion proteins containing defined portions or all of the ARMP protein can be synthesized in bacteria by expression of corresponding DNA sequences in a suitable cloning vehicle. The protein can then be purified, coupled to a carrier protein and mixed with Freund's adjuvant (to help stimulate the antigenic response by the rabbits) and injected into rabbits or other laboratory animals. Alternatively, protein can be isolated from cultured cells expressing the protein. Following booster injections at bi-weekly intervals, the rabbits or other laboratory animals are then bled and the sera isolated. The sera can be used directly or purified prior to use, by various methods including affinity chromatography, Protein A-Sepharose, Antigen Sepharose, Anti-mouse-Ig-Sepharose. The sera can then be used to probe protein extracts run on a polyacrylamide gel to identify the ARMP protein. Alternatively, synthetic peptides can be made to the antigenic portions of the protein and used to innoculate the animals.

To produce monoclonal ARMP antibodies, cells actively expressing the protein are cultured or isolated from tissues and the cell membranes isolated. The membranes, extracts, or recombinant protein extracts, containing the ARMP protein, are injected in Freund's adjuvant into mice. After being injected 9 times over a three week period, the mice spleens are removed and resuspended in phosphate buffered saline (PSB). The spleen cells serve as a source of lymphocytes, some of which are producing antibody of the appropriate specificity. These are then fused with a permanently growing myeloma partner cell, and the products of the fusion are plated into a number of tissue culture wells in the presence of a selective agent such as HAT. The wells are then screened to identify those containing cells making useful antibody by ELISA. These are then freshly plated. After a period of growth, these wells are again screened to identify antibody-producing cells. Several cloning procedures are carried out until over 90% of the wells contain single clones which are positive for antibody production. From this procedure a stable line of clones is established which produce the antibody. The monoclonal antibody can then be purified by affinity chromatography using Protein A Sepharose, ion-exchange chromatography, as well as variations and combinations of these techniques.

In situ hybridization is another method used to detect the expression of ARMP protein. In situ hybridization relies upon the hybridization of a specifically labelled nucleic acid probe to the cellular RNA in individual cells or tissues. Therefore, it allows the identification of mRNA within intact tissues, such as the brain. In this method, oligonucleotides corresponding to unique portions of the ARMP gene are used to detect specific mRNA species in the brain.

In this method a rat is anesthetized and transcardially perfused with cold PBS, followed by perfusion with a formaldehyde solution. The brain or other tissues is then removed, frozen in liquid nitrogen, and cut into thin micron sections. The sections are placed on slides and incubated in proteinase K. Following rinsing in DEP, water and ethanol, the slides are placed in prehybridization buffer. A radioactive probe corresponding to the primer is made by nick translation and incubated with the sectioned brain tissue. After incubation and air drying, the labeled areas are visualized by autoradiography. Dark spots on the tissue sample indicate hybridization of the probe with brain mRNA which demonstrates the expression of the protein.

Antibodies may also be used coupled to compounds for diagnostic and/or therapeutic uses such as radionuclides for imaging and therapy and liposomes for the targeting of compounds to a specific tissue location.

Therapies

An important aspect of the biochemical studies using the genetic information of this invention is the development of therapies to circumvent or overcome the ARMP gene defect, and thus prevent, treat, control serious symptoms or cure the disease. In view of expression of the ARMP gene in a variety of tissues, one has to recognize the Alzheimer's Disease may not be restricted to the brain. Alzheimer's Disease manifests itself as a neurological disorder which in one of its forms is caused by a mutation in the ARMP gene, but such manifest may be caused by the mutations in other organ tissues, such as the liver, releasing factors which affect the brain activity and ultimately cause Alzheimer's Disease. Hence, in considering various therapies, it is understood that such therapies may be targeted at tissue other than the brain, such as heart, placenta, lung, liver, skeletal muscle, kidney and pancreas. where ARMP is also expressed.

Rationale for Therapeutic, Diagnostic, and Investigational Applications of the ARMP Gene and Gene Products as They Relate to the Amyloid Precursor Protein The Aβ peptide derivatives of APP are neurotoxic (Selkoe et al, 1994). APP is metabolized by passages through the Golgi network and then to secretory pathways via clathrin-coated vesicles with subsequent passage to the plasma membrane where the mature APP is cleaved by α-secretase to a soluble fraction (Protease Nexin II) plus a non-amyloidogenic C-terminal peptide (Selkoe et al. 1995, Gandy et al. 1993). Alternatively, mature APP can be directed to the endosome-lysosome pathway where it undergoes beta and gamma secretase cleavage to produce the Aβ peptides. The phosphorylation state of the cell determines the relative balance of α-secretase (non-amyloidogenic) or Aβ pathways (amyloidogenic pathway) (Gandy et al. 1993). The phosphorylation state of the cell can be modified pharmacologically by phorbol esters, muscarinic agonists and other agents, and appears to be mediated by cytosolic factors (especially protein kinase C) acting upon an integral membrane protein in the Golgi network, which we propose to be the ARMP, and members of the homologous family (all of which carry several phosphorylation consensus sequences for protein kineaseC). Mutations in the ARMP gene will cause alterations in the structure and function of the ARMP gene product leading to defective interactions with regulatory elements (eg. protein kinase C) or with APP, thereby promoting APP to be directed to the amyloidogenic endosome-lysosome pathway. Environmental factors (viruses, toxins, and aging etc) may also have similar effects on ARMP. To treat Alzheimer's disease, the phosphorylation state of ARMP can be altered by chemical and biochemical agents (eg. drugs, peptides and other compounds) which alter the activity of protein kinase C and other protein kinases, or which alter the activity of protein phosphatases, or which modify the availability of ARMP to be postranslationally modified. The interactions between kinases and phosphatases with the ARMP gene products (and the products of its homologues), and the interactions of the ARMP gene products with other proteins involved in the trafficking of APP within the Golgi network can be modulated to decrease trafficking of Golgi vesicles to the endosomelysosome pathway thereby promoting Aβ peptide production. Such compounds will include: peptide analogues of APP, ARMP, and homologues of ARMP as well as other interacting proteins, lipids, sugars, and agents which promote differential glycosylation of ARMP and its homologues; agents which alter the biologic half-life of messenger RNA or protein of ARMP and homologues including antibodies and antisense oligonucleotides; and agents which act upon ARMP transcription.

The effect of these agents in cell lines and whole animals can be monitored by monitoring: transcription; translation; post-translational modification of ARMP (eg phosphorylation or glycosylation); and intracellular trafficking of ARMP and its homologues through various intracellular and extracellular compartments. Methods for these studies include Western and Northern blots; immunoprecipitation after metabolic labelling (pulse-chase) with radio-labelled methionine and ATP, and immunochistochemistry. The effect of these agents can also be monitored using studies which examine the relative binding affinities and relative amounts of ARMP gene products involved in interactions with protein kineace C and/or APP using either standard binding affinity assays or co-precipitation and Western blots using antibodies to protein kinease C, APP or ARMP and its homologues. The effect of these agents can also be monitored by assessing the production of Aβ peptides by ELISA before and after exposure to the putative therapeutic agent (Huang et al. 1993). The effect can also be monitored by assessing the viability of cell lines after exposure to aluminum salts and to Aβ peptides which are thought to be neurotoxic in Alzheimer's disease. Finally, the effect of these agents can be monitored by assessing the cognitive function of animals bearing: their normal genotype at APP or ARMP homologues; or bearing human APP transgenes (with or without mutations); or bearing human ARMP transgenes (with or without mutations); or a combination of all of these.

Rationale for Therapeutic, Diagnostic, and Investigational Applications of the ARMP Gene and Its Products Based Upon its Putative Function as a Channel Protein or Receptor The ARMP gene product and especially the gene product for the E5-1 homologue have amino acid sequence homology to human ion channel proteins and receptors. For instance, the E5-1 homologue shows substantial homology to the human sodium channel α-subunit (E=0.18, P=0.16, identities=22–27% over two regions of at least 35 amino acid residues) using the BLASTP paradigm of Altschul et al. 1990. Other diseases (such as malignant hyperthermia and hyperkalemic periodic paralysis in humans and the neurodegenerative of mechanosensory neurons in *C. elegans*) arise through mutations in ion channels or receptor proteins. Mutation of the ARMP gene and/or mutations in homologues could affect similar functions and lead to Alzheimer's disease and other psychiatric and neurological diseases. Based upon this, a test for Alzheimer's disease can be produced to detect an abnormal receptor or an abnormal ion channel function related to abnormalities that are acquired or inherited in the ARMP gene and its product, or in one of the homologous genes and their products. This test can be accomplished either in vivo or in vitro by measurements of ion channel fluxes and/or transmembrane voltage or current fluxes using patch clamp, voltage clamp and fluorescent dyes sensitive to intracellular calcium or transmembrane voltage. Defective ion channel or receptor function can also be assayed by measurements of activation of second messengers such as cyclic AMP, cGMP tyrosine kinases, phosphates, increases in intracellular $Ca^{2+}$ levels, etc. Recombinantly made proteins may also be reconstructed in artificial membrane systems to study ion channel conductance. Therapies which affect Alzheimer's disease (due to acquired/inherited defects in the ARMP gene; due to defects in other pathways leading to this disease such as mutations in APP; and due to environmental agents) can be tested by analysis of their ability to modify an abnormal ion channel or receptor function induced by mutation in the ARMP gene or in one of its homologues. Therapies could also be tested by their ability to modify the normal function of an ion channel or receptor capacity of the ARMP gene products and its homologues. Such assays can be performed on cultured cells expressing endogenous normal or mutant ARMP genes/gene products (or its homologues). Such studies can be performed in addition on cells transfected with vectors capable of expressing ARMP, parts of the ARMP gene and gene product, mutant ARMP, or one its homologues (in normal or mutant form). Therapies for Alzheimer's disease can be devised to modify an abnormal ion channel or receptor function of the ARMP gene or its homologue. Such therapies can be conventional drugs, peptides, sugars, or lipids, as well as antibodies or other ligands which affect the properties of the ARMP gene product. Such therapies can also be performed by direct replacement of the ARMP gene and/or its homologue by gene therapy. In the case of an ion channel, the gene therapy could be performed using either mini-genes (cDNA plus a promoter) or genomic constructs bearing genomic DNA sequences for parts or all of the ARMP gene. Mutant ARMP or homologous gene sequences might also be used to counter the effect of the inherited or acquired abnormalities of the ARMP gene as has recently been done for replacement of the mec 4 and deg 1 in *C. elegans* (Huang and Chalfie, 1994). The therapy might also be directed at augmenting the receptor or ion channel function of the homologous genes such as the E5-1 homologue, in order that it may potentially take over the functions of the ARMP gene rendered defective by acquired or inherited defects. Therapy using antisense oligonucleotides to block the expression of the mutant ARMP gene, coordinated with gene replacement with normal ARMP or a homologous gene can also be applied using standard techniques of either gene therapy or protein replacement therapy.
Protein Therapy Treatment of Alzheimer's Disease can be performed by replacing the mutant protein with normal protein, or by modulating the function of the mutant protein. Once the biological pathway of the ARMP protein has been completely understood, it may also be possible to modify the pathophysiologic pathway (eg. a signal transduction pathway) in which the protein participates in order to correct the physiological defect.

To replace the mutant protein with normal protein, or with a protein bearing a deliberate counterbalancing mutation it is necessary to obtain large amounts of pure ARMP protein from cultured cell systems which can express the protein. Delivery of the protein to the affected brain areas or other tissues can then be accomplished using appropriate packaging or administrating systems.

Gene Therapy

Gene therapy is another potential therapeutic approach in which normal copies of the ARMP gene are introduced into patients to successfully code for normal protein in several different affected cell types. The gene must be delivered to those cells in a form in which it can be taken up and code for sufficient protein to provide effective function. Alternatively, in some neurologic mutants it has been possible to prevent disease by introducing another copy of the homologous gene bearing a second mutation in that gene or to alter the mutation, or use another gene to block its effect.

Retroviral vectors can be used for somatic cell gene therapy especially because of their high efficiency of infection and stable integration and expression. The targeted cells however must be able to divide and the expression of the levels of normal protein should be high because the disease is a dominant one. The full length ARMP gene can be cloned into a retroviral vector and driven from its endogenous promoter or from the retroviral long terminal repeat or from a promoter specific for the target cell type of interest (such as neurons).

Other viral vectors which can be used include adeno-associated virus, vaccinia virus, bovine papilloma virus, or a herpesvirus such as Epstein-Barr virus.

Gene transfer could also be achieved using non-viral means requiring infection in vitro. This would include calcium phosphate, DEAE dextran, electroporation, and protoplast fusion. Liposomes may also be potentially beneficial for delivery of DNA into a cell. Although these methods are available, many of these are lower efficiency.

Antisense based strategies can be employed to explore ARMP gene function and as a basis for therapeutic drug design. The principle is based on the hypothesis that sequence-specific suppression of gene expression can be achieved by intracellular hybridization between mRNA and a complementary antisense species. The formation of a hybrid RNA duplex may then interfere with the processing/transport/translation and/or stability of the target ARMP mRNA. Hybridization is required for the antisense effect to occur, however the efficiency of intracellular hybridization is low and therefore the consequences or such an event may not be very successful. Antisense strategies may use a variety of approaches including the use of antisense oligonucleotides, injection of antisense RNA and transfection of antisense RNA expression vectors. Antisense effects can be induced by control (sense) sequences, however, the extent of phenotypic changes are highly variable. Phenotypic effects induced by antisense effects are based on changes in criteria such as protein levels, protein activity measurement, and target mRNA levels. Multidrug resistance is a useful model to study molecular events associated with phenotypic changes due to antisense effects, since the multidrug resistance phenotype can be established by expression of a single gene mdr1(MDR gene) encoding for P-glycoprotein.

Transplantation of normal genes into the affected area of the patient can also be useful therapy for Alzheimer's Disease. In this procedure, a normal hARMP protein is transferred into a cultivatable cell type such as glial cells, either exogenously or endogenously to the patient. These cells are then injected serotologically into the disease affected tissue(s). This is a known treatment for Parkinson's disease.

Immunotherapy is also possible for Alzheimer's Disease. Antibodies can be raised to a mutant ARMP protein (or portion thereof) and then be administered to bind or block the mutant protein and its deleterious effects. Simultaneously, expression of the normal protein product could be encouraged. Administration could be in the form of a one time immunogenic preparation or vaccine immunization. An immunogenic composition may be prepared as injectables, as liquid solutions or emulsions. The ARMP protein may be mixed with pharmaceutically acceptable excipients compatible with the protein. Such excipients may include water, saline, dextrose, glycerol, ethanol and combinations thereof. The immunogenic composition and vaccine may further contain auxiliary substances such as emulsifying agents or adjuvants to enhance effectiveness. Immunogenic compositions and vaccines may be administered parenterally by injection subcutaneously or intramuscularly.

The immunogenic preparations and vaccines are administered in such amount as will be therapeutically effective, protective and immunogenic. Dosage depends on the route of administration and will vary according to the size of the host.

The above disclosure generally describes the present invention. A more complete understanding can be obtained by reference to the following specific examples. These examples are described solely for purposes of illustration and are not intended to limit the scope of the invention. Changes in the form and substitution of equivalents are contemplated as circumstances may suggest or render expedient. Although specific terms have been employed herein, such terms are intended in a descriptive sense and not for purposes of limitations.

EXAMPLE 1

Development of the Genetic, Physical "Contig" and Transcriptional Map of the Minimal Co-segregating Region The CEPH Mega YAC and the RPCI PAC human total genomic DNA libraries were searched for clones genomic DNA fragments from the AD3 region of chromosome 14q24.3 using oligonucleotide probes for each of the ##SSR marker loci used in the genetic linkage studies as well as ## additional markers depicted in FIG. 1a (Albertsen et el., 1990; Chumakov et al., 1992; Toannu et al., 1994). The genetic map distances between each marker are depicted above the contig, and are derived from published data (NIH/CEPH Collaborative Mapping Group, 1992; Wang, 1992; Weissenbach, J et al., 1992; Gyapay, G et al., 1994). Clones recovered for each of the initial marker loci were arranged into an ordered series of partially overlapping clones ("contig") using four independent methods. First, sequences representing the ends of the YAC insert were isolated by inverse PCR (Riley et al., 1990), and hybridized to Southern blot panels containing restriction digests of DNA from all of the YAC clones recovered for all of the initial loci in order to identify other YAC clones bearing overlapping sequences. Second, inter-Alu PCR was performed on each YAC, and the resultant band patterns were compared across the pool of recovered YAC clones in order to identify other clones bearing overlapping sequences (Bellamne-Chartelot et al., 1992; Chumakov et al., 1992). Third, to improve the specificity of the Alu-PCR fingerprinting, we restricted the YAC DNA with HaeIII or RsaI, amplified the restriction products with both Alu and L1H consensus primers, and resolved the products by polyacrylamide gel electrophoresis. Finally, as additional STSs were generated during the search for transcribed sequences, these STSs were also used to identify overlaps. The resultant contig was complete except for a single discontinuity between YAC932C7 bearing D14S53 and YAC746B4 containing D14S61. The physical map order of the STSs within the contig was largely in accordance with the genetic linkage map for this region (NIH/CEPH Collaborative Mapping Group, 1992; Wang, Z, Weber, J. L., 1992; Weissenbach, J et al., 1992; Gyapay, G et al., 1994). However, as with the genetic maps, we were unable to unambiguously resolve the relative order of the loci within the D14S43/D14S71 cluster and the D14S76/D14S273 cluster. PAC1 clones suggest that D14S277 is telomeric to D14S268, whereas genetic maps have suggested the reverse order. Furthermore, a few STS probes failed to detect hybridization patterns in at least one YAC clone which, on the basis of the most parsimonious consensus physical map and from the genetic map, would have been predicted to contain that STS. For instance, the D14S268 (AFM265) and RSCAT7 STSs are absent from YAC788H12. Because these results were reproducible, and occurred with several different STS markers, these results most likely reflect the presence of small interstitial deletions within one of the YAC clones.

EXAMPLE 2

Cumulative Two-point Lod Scores for Chromosome 14q24.3 Markers

Genotypes at each polymorphic microsatellite marker locus were determined by PCR from 100 ng of genomic DNA of all available affected and unaffected pedigree members as previously described (St George-Hyslop, P et al., 1992) using primer sequences specific for each microsatellite locus (Weissenbach, J et al., 1992; Gyapay, G et al., 1994). The normal population frequency of each allele was determined using spouses and other neurologically normal subjects from the same ethnic groups, but did not differ significantly from those established for mixed Caucasian populations (Weissenbach, J et al., 1992; Gyapay, G et al., 1994). The maximum likelihood calculations assumed an age of onset correction, marker allele frequencies derived from published series of mixed Caucasian subjects, and an estimated allele frequency for the AD3 mutation of 1:1000 as previously described (St George-Hyslop, P et al., 1992). The analyses were repeated using equal marker allele frequencies, and using phenotype information only from affected pedigree members as previously described to ensure that inaccuracies in the estimated parameters used in the maximum likelihood calculations did not misdirect the analyses (St George-Hyslop, P et al., 1992). These supplemental analyses did not significantly alter either the evidence supporting linkage, or the discovery of recombination events.

EXAMPLE 3

Haplotypes Between Flanking Markers Segregated with AD3 in FAD Pedigrees

Extended haplotypes between the centromeric and telomeric flanking markers on the parental copy of chromosome 14 segregating with AD3 in fourteen early onset FAD pedigrees (pedigrees NIH2, MGH1, Tor1.1, FAD4, FAD1, MEX1, and FAD2 show pedigree specific lod scores≧+3.00 with at least one marker between D14S258 and D14S53). Identical partial haplotypes (boxed) are observed in two regions of the disease bearing chromosome segregating in several pedigrees of similar ethnic origin. In region A, shared alleles are seen at D14S268 ("B": allele size=126 bp, allele frequency in normal Caucasians=0.04; "C"; size=124 bp, frequency=0.38); D14S277 ("B": size=156 bp, frequency=0.19; "C": size=154 bp, frequency=0.33); and RSCAT6 ("D": size=111 bp, frequency 0.25; "E": size=109 bp, frequency=0.20; "F": size=107 bp, frequency=0.47). In region B, alleles of identical size are observed at D14S43 ("A": size=193 bp, frequency=0.01; "D": size=187 bp, frequency=0.12; "E": size=185 bp, frequency=0.26; "I": size=160 bp, frequency=0.38); D14S273 ("3": size=193 bp, frequency=0.34; "6": size=187 bp, frequency=0.02) and D14S76 ("1": size=bp, frequency=0.01; "5": size=bp, frequency=0.38; "6": size=bp, frequency=0.07; "9": size= bp, frequency=0.38). The ethnic origins of each pedigree are abbreviated as: Ashk=Ashkenazi Jewish, Ital=Southern Italian; Angl=Anglo-Saxon-Celt; FrCan=French Canadian; Jpn=Japanese; Mex=Mexican Caucasian; Ger=German; Am=American Caucasian. The type of mutation detected is depicted by the amino acid substitution and putative codon number or by ND where no mutation has been detected because a comprehensive survey has not been undertaken due to the absence of a source of mRNA for RT-PCR studies.

EXAMPLE 4

Recovery of Transcribed Sequences from the AD3 Interval

Putative transcribed sequences encoded in the AD3 interval were recovered using either a direct hybridization method in which short cDNA fragments generated from human brain mRNA were hybridized to immobilized cloned genomic DNA fragments (Rommens, JM et al., 1993). The resultant short putatively transcribed sequences were used as probes to recover longer transcripts from human brain cDNA libraries (Stratagene, La Jolla). The physical location of the original short clone and of the subsequently acquired longer cDNA clones were established by analysis of the hybridization pattern generated by hybridizing the probe to Southern blots containing a panel of EcoRI digested total DNA samples isolated from individual YAC clones within the contig. The nucleotide sequence of each of the longer cDNA clones was determined by automated cycle sequencing (Applied Biosystems Inc., CA), and compared to other sequences in nucleotide and protein databases using the blast algorithm (Altschul, SF et al., 1990). Accession numbers for the transcribed sequences in this report are: L40391, L40392, L40393, L40394, L40395, L40396, L40397, L40398, L40399, L40400, L40401, L40402, and L40403.

EXAMPLE 5

Locating Mutations in the ARMP Gene Using Restriction Enzymes

The presence of Ala 246 Glu mutation which creates a Dde1 restriction site was assayed in genomic DNA by PCR using the end labelled primer 849 (5'-atctccggcaggcatatct-3') SEQ ID NO: 129 and the unlabelled primer 892 (5'-tgaaatcacagccaagatgag-3') SEQ ID NO: 130 to amplify an 84 bp genomic exon fragment using 100 ng of genomic DNA template, 2 mM $MgCl_2$, 10 pMoles of each primer, 0.5 U Taq polymerase, 250 uM dNTPs for 30 cycles of 95° C.×20 seconds, 60° C.×20 seconds, 72° C.×5 seconds. The products were incubated with an excess of DdeI for 2 hours according to the manufacturing protocol, and the resulting restriction fragments were resolved on a 6% nondenaturing polyacrylamide gel and visualized by autoradiography. The presence of the mutation was inferred from the cleavage of the 84 bp fragment to due to the presence of a DdeI restriction site. All affected members of the FAD1 pedigree (filled symbols) and several at-risk members ("R") carried the DdeI site. None of the obligate escapees (those individuals who do not get the disease, age>70 years), and none of the normal controls carried the DdeI mutation.

EXAMPLE 6

Locating Mutation in the ARMP Gene Using Allele Specific Oligonucleotides

The presence of the Cys 410 Tyr mutation was assayed using allele specific oligonucleotides 100 ng of genomic DNA was amplified with the exonic sequence primer 885 (5'-tggagactggaacacaac-3') SEQ ID NO: 127 and the opposing intronic sequence primer 893 (5'-gtgtggccagggtagagaact-3') SEQ ID NO: 128 using the above reaction conditions except 2.5 mM MgCl$_2$, and cycle conditions of 94° C.×20 seconds, 58° C.×20 seconds, and 72° C. for 10 seconds). The resultant 216 bp genomic fragment was denatured by 10-fold dilution in 0.4 M NaOH, 25 mM EDTA, and was vacuum slot-botted to duplicate nylon membranes. The end-labelled "wild type" primer 890 (5'-ccatagcctgtttcgtagc-3') SEQ ID NO: 131 and the end-labelled "mutant" primer 891 (5'-ccatagcctAtttcgtagc-3') SEQ ID NO: 132 were hybridized to separate copies of the slot-blot filters in 5×SSC, 5×Denhardt's, 0.5% SDS for 1 hour at 48° C., and then washed successively in 2×SSC at 23° C. and 2×SSC, 0.1% SDS at 50° C. and then exposed to X-ray film. All testable affected members as well as some at-risk members of the AD3 (shown) and NIH2 pedigrees (not shown) possessed the Cys 410 Tyr mutation. Attempts to detect the Cys 410 Tyr mutation by SSCP revealed that a common intronic sequence polymorphism migrated with the same SSCP pattern.

EXAMPLE 7

Northern Hybridization Demonstrating the Expression of ARMP Protein mRNA in a Variety of Tissues Total cytoplasmic RNA was isolated from various tissue samples (including heart, brain and different regions of, placenta, lung, liver, skeletal muscle, kidney and pancreas) obtained from surgical pathology using standard procedures such as CsCl purification. The RNA was then electrophoresed on a formaldehyde gel to permit size fractionation. The nitrocellulose membrane was prepared and the RNA was then transferred onto the membrane. $^{32}$P-labelled cDNA probes were prepared and added to the membrane in order for hybridization between the probe the RNA to occur. After washing, the membrane was wrapped in plastic film and placed into imaging cassettes containing X-ray film. The autoradiographs were then allowed to develop for one to several days. The positions of the 28S and 18S rRNA bands are indicated. Sizing was established by comparison to standard RNA markers. Analysis of the autoradiographs revealed a prominent band at 3.0 kb in size. These northern blots demonstrated the ARMP gene is expressed in all of the tissues examined.

EXAMPLE 8

Eukaryotic and Prokaryotic Expression Vector Systems

Eukaryotic and prokaryotic expression systems have been generated using two different classes of ARMP nucleotide cDNA sequence inserts. In the first class, termed full-length constructs, the entire ARMP cDNA sequence was inserted into the expression plasmid in the correct orientation, and included both the natural 5' UTR and 3' UTR sequences as well as the entire open reading frame. The open reading frames bear a nucleotide sequence cassette which allows either the wild type open reading frame to be included in the expression system or alternatively, single or a combination of double mutations can be inserted into the open reading frame. This was accomplished by removing a restriction fragment from the wild type open reading frame using the enzymes NarI and PflmI and replacing it with a similar fragment generated by reverse transcriptase PCR and which bears the nucleotide sequence encoding either the Met146Leu mutation or the Hys163Arg mutation. A second restriction fragment was removed from the wild type normal nucleotide sequence for the open reading frame by cleavage with the enzymes PflmI and NcoI and replaced with restriction fragments bearing wither the nucleotide sequence encoding the Ala246Glu mutation, or the Ala260Val mutation or the Ala285Val mutation or the Leu286Val mutation, or the Leu392Val mutation, or the Cys410Tyr mutation. Finally, a third variant bearing combinations of either the Met146Leu or His163Arg mutations in tandem with the remaining mutations by linking the NarI-PflmI fragment bearing those mutations and the PflmI-NcoI fragments bearing the remaining mutations.

A second variant of cDNA inserts bearing wild type or mutant cDNA sequences was constructed by removing from the full-length cDNA the 5' UTR and part of the 3' UTR sequences. The 5' UTR sequence was replaced with a synthetic oligonucleotide containing a KpnI restriction site and a Kozak initiation site (oligonucleotide 969; ggtaccgccaccatgacagaggtacctgcac) SEQ ID NO: 139. The 3' UTR was replaced with an oligonucleotide corresponding to position 2566 of the cDNA and bears an artificial EcoRI site (oligonucleotide 970:gaattcactggctgtagaaaaagac) SEQ ID NO: 140. Mutant variants of this construct were then made by inserting the same mutant sequences described above at the NarI-PflmI fragment, and at the PsImI-NcoI sites described above.

For eukaryotic expressions, these various cDNA constructs bearing wild type and mutant sequences were cloned into the expression vector pZeoSV (invitrogen). For prokaryotic expression, two constructs were made using the glutathione S-transferase fusion vector pGEX-kg. The inserts which have been attached to the GST fusion nucleotide sequence are the same nucleotide sequence described above generated with the oligonucleotide primers 969, Sequence ID NO: 139 and 970, Sequence ID NO: 140, bearing either the normal open reading frame nucleotide sequence or bearing a combination of single and double mutations as described above. This construct allows expression of the full-length protein in mutant and wild type variants in prokaryotic cell systems as a GST fusion protein which will allow purification of the full-length protein followed by removal of the GST fusion product by thrombin digestion. The second prokaryotic cDNA construct was generated to create a fusion protein with the same vector, and allows the production of the amino acid sequence corresponding to the hydrophillic acidic loop domain between TM6 and TM7 of the full-length protein, as either a wild type nucleotide sequence (thus a wild type amino acid sequence for fusion proteins) or as a mutant sequence bearing either the Ala285Val mutation, or the Leu286Val mutation, or the Leu392Val mutation. This was accomplished by recovering wild type or mutant sequence from appropriate sources of RNA using the oligonucleotide primers 989:ggatccggtccacttcgtatgctg SEQ ID NO: 141, and 990:tttttgaattcttaggctatggttgtgttcca SEQ ID NO: 142. This allows cloning of the appropriate mutant or wild type nucleotide sequence corresponding to the hydrophillic acid loop domain at the BamHI and the EcoRI sites within the pGEX-KG vector.

These prokaryotic expression systems allow the holoprotein or various important functional domains of the protein to be recovered as fusion proteins and then used for binding studies, structural studies, functional studies, and for the generation of appropriate antibodies.

EXAMPLE 9

Identification of Three New Mutations in the ARMP Gene

Three novel mutations have been identified in subjects affected with early onset Alzheimer's disease. All of these mutations co-segregate with the disease, and are absent from at least 200 normal chromosomes. The three mutations are as follows: a substitution of C by T at position 1027 which results in the substitution of alanine 260 for valine; substitution of C by T at position 1102, which results in the substitution of alanine at 285 by valine; and substitution of C by G at position 1422 which results in the substitution of leucine 392 by valine. Significantly, all of these mutations occur within the acidic hydrophillic loop between putative TM6 and TM7. Two of the mutations (A260V; A285V) and the L286V mutation are also located in the alternative spliced domain.

The three new mutations, like the other mutations, can be assayed by a variety of strategies (direct nucleotide sequencing, Allele specific oligos, ligation polymerase chain reaction, SSCP, RFLPs) using RT-PCR products representing the mature mRNA/cDNA sequence or genomic DNA. We have chosen allele specific oligos. For the A260V and the A285V mutations, genomic DNA carrying the exon can be amplified using the same PCR primers and methods as for the L286V mutation. PCR products were then denatured and slot blotted to duplicate nylon membranes using the slot blot protocol described for the C410T mutation.

The Ala260Val mutation was scored on these blots by using hybridization with end-labeled allele-specific oligonucleotides corresponding to the wild type sequence (994:gattagtggttgttttgtg) SEQ ID NO: 143 or the mutant sequence (995:gattagtggctgttttgtg) SEQ ID NO: 144 by hybridization at 48° C. followed by a wash at 52° C. in 3×SSC buffer containing 0.1% SDS. The Ala285Val mutation was scored on these slot blots as described above but using instead the allele-specific oligonucleotides for the wild type sequence (1003:tttttccagctctcattta) SEQ ID NO 145, or the mutant primer (1004:tttttccagttctcattta) SEQ ID NO: 146 at 48° C. followed by washing at 52° C. as above except that the wash solution was 2×SSC.

The Leu392Val mutation was scored by amplification of the exon from genomic DNA using primers 996 (aaacttggattgggagat) SEQ ID NO: 148 and 893 (gtgtggccagggtagagaact) SEQ ID NO: 128 using standard PCR buffer conditions excepting that the magnesium concentration was 2 mM and cycle conditions were 94° C. time 10 seconds, 56° C. times 20 seconds, and 72° C. for 10 seconds. The result 200 based pair genomic fragment was denatured as described for the Cys410Tyr mutation and slot-blotted in duplicate to nylon membranes. The presence or absence of the mutation was then scored by differential hybridization to either a wild type end-labelled oligonucleotide (999:tacagtgttctggttggta) SEQ ID NO: 147 or with an end-labeled mutant primer (100:tacagtgttgtggttggta) SEQ ID NO: 149 by hybridization at 45° C. and then successive washing in 2×SSC at 23° C. and then at 68° C.

EXAMPLE 10

Polyclonal Antibody Production

Peptide antigens were synthesized by solid-phase techniques and purified by reverse phase high pressure liquid chromatography. Peptides were covalently linked to keyhole limpet hematoxylin (KLH) via disulfide linkages that were made possible by the addition of a cystein residue at the peptide C-terminus. This additional residue does not appear normally in the protein sequence and was included only to facilitate linkage to the KLH molecule. A total of three rabbits were immunized with peptide-KLH complexes for each peptide antigen and were then subsequently given booster injections at seven day intervals. Antisera were collected for each peptide and pooled and IgG precipitated with ammonium sulfate. Antibodies were then affinity purified with Sulfo-link agarose (Pierce) coupled with the appropriate peptide. This final purification is required to remove non-specific interactions of other antibodies present in either the pre- or post-immune system.

The specific sequences to which we have raised antibodies are;

Polyclonal antibody 1: NDNRERQDHNDRRSL (C)—residues 30–45 SEQ ID NO: 164

Polyclonal antibody 2: KDGQLIYTPFTEDTE (C)—residues 109–120 SEQ ID NO: 165

Polyclonal antibody 3: EAQRRVSKNSKYNAE (C)—residues 304–319 SEQ ID NO: 166

Polyclonal antibody 4: SHLGPHRSTPESRAA (C)—residues 346–360 SEQ ID NO: 167

The non-native cysteine residue is indicated at the C-terminal by (C). These sequences are contained within various predicted domains of the protein. For example, antibodies 1, 3, and 4 are located in potentially functional domains that are exposed to the aqueous media and may be involved in binding to other proteins critical for the development of the disease phenotype. Antibody 2 corresponds to a short linking region situated between the predicated first and second transmembrane helices.

Although preferred embodiments of the invention have been described herein in detail, it will be understood by those skilled in the art that variations may be made thereto without departing from the spirit of the invention or the scope of the appended claims.

TABLE 1

| LOCUS | RECOMBINATION FRACTION (θ) | | | | | | |
|---|---|---|---|---|---|---|---|
| | 0.00 | 0.05 | 0.10 | 0.15 | 0.20 | 0.30 | 0.40 |
| D14S63 | −∞ | 1.54 | 3.90 | 4.38 | 4.13 | 2.71 | 1.08 |
| D14S258 | +∞ | 21.60 | 19.64 | 17.19 | 14.50 | 8.97 | 3.81 |
| D14S77 | −∞ | 15.18 | 15.53 | 14.35 | 12.50 | 7.82 | 2.92 |
| D14S71 | −∞ | 15.63 | 14.14 | 12.19 | 10.10 | 5.98 | 2.39 |
| D14S43 | −∞ | 19.36 | 17.51 | 15.27 | 12.84 | 7.80 | 3.11 |
| D14S273 | −∞ | 12.30 | 11.52 | 10.12 | 8.48 | 5.04 | 1.91 |
| D14S61 | −∞ | 26.90 | 24.92 | 22.14 | 18.98 | 12.05 | 5.07 |
| D14S53 | +∞ | 11.52 | 11.41 | 10.39 | 8.99 | 5.73 | 2.51 |
| D14S48 | −∞ | 0.50 | 1.05 | 1.14 | 1.04 | 0.60 | 0.18 |

TABLE 2

| LOCUS | NLB2 | FAD3 | TUR1.1 | FAD4 | RB | FAD1 | MG12 | BOW | COOK | 603 | Ter42 | QUE | MEX1 | FAD2 |
|---|---|---|---|---|---|---|---|---|---|---|---|---|---|---|
| D14S63 | 1 | 4 | 7 | 4 |  | 5 |  |  |  |  |  |  | 9 | 2 |
| D14S258 | 6 | 6 | 8 | 7 | 4 | 5 | 5 | 6 | 6 |  | 7 | 6 | 7 | 6 |
| D14S268 | C | C | B | B | C | C | C | C | C | C | C | B | C | C |
| D14S277 | C | C | C | C | C | C | C | C | C | A | A | C | B | B |
| D14S786 | D | D | E | E | K | E | E | D/F | E | E | E | E | F | D |
| D14S73 | Y | Y | K | S | P | P | P | K | H |  | C | U | F | A |
| D14S71 | 7 | 7 | 1 | 5 | 7 | 7 |  | 6 | 7 |  | 3 | 7 | 2 | 6 |
| D14S43 | A | A | 1 | 1 | 1 | E | D | I | I |  | C | 1 | D | C |
| D14S273 | 6 | 6 | 5 | 5 | 5 | 4 | 4 | 4 | 6 |  | 6 | 6 | 5 | 3 |
| D14S76 | 5 | 5 | 5 | 5 | 5 | 6 | 9 | 9 |  |  | 9 | 1 | 5 | 5 |
| D14S61 | E | E | G | F |  | I |  |  |  |  | D |  | L | F |
| D14S53 | F | F | C | F | F | J | C | F | E |  | J | D | F | F |
| ETHNIC ORIGIN | Ashk | Ashk | Ital | Ital | Iml | Angl | Angl | Angl | Angl | Amer | FrCan | FrCan | Mex | Ger |
| MUTATION | C401Y | C410Y | M146L | M146L | ND | A246E | ND | ND | ND | H163R | H163R | ND | ND | L286V |

TABLE 3

| No. | Target File | Ray | Target | Overlap | Match | Similarities Percentage |
|---|---|---|---|---|---|---|
| 1 | narmp.con/long[Frame 1] | 1 | 1 | 467 | 465 | 99.57% |

```
             1         10        20        30        40        50        60        70
HUMAN N- MTELPAPLSYFQNAQMSEDNHLSNTVRSQNDNRERQEHNDRRSLGHPEPLSNQRPQGNSRQVVEQDEERD
         ****************************  ****** *** ** *** *** ***** *******
MOUSE N- MTEIPAPLSYFQNAQMSEDSHSSSAIRSQNDSQERQQQHDRQRLDNPEPISNGRPQSNSRQVVEQQEEED
             1         10        20        30        40        50        60        70

71        80        90       100       110       120       130       140
         EELTLKYGAKHVIHLFVPVTLCMVVVVATIKSTSFYTAKDGQLIYTPFTEDTETVGQRALHSILNAAIMI
         ************* *******************  *** ****************** *********
         EELTLKYGAKHVIMLFVPVTLCMVVVVATIKSVSFYTRKDGQLIYTPFTEDTETVGQRALASILNAAIMI
            71        80        90       100       110       120       130       140

141       150       160       170       180       190       200       210
         SVIVVMTILLVVLYKYRCYKVIHAWLIISSLLLLFFFSFIYLGTVFRTYNYXVDYVTVALLIWNWGVVGM
         ***** *************** ** ********** ********** ****** **************
         SVIVIMTILLVVLYKYRCYKBIHAMLIISSLLLLFFFSFIYLGKBFRTYNVXVDYVTVALLIWNWGVVGM
           141       150       160       170       180       190       200       210

211       220       230       240       250       260       270       280
         ISIHWKGPLRLQQAYLIMISALMALVFIKYLFIMTAWLILAVISVYDLVAVLCPKGPLKMLVPTAQERMR
         * ***** ******** ************ **** ************** ******* *** *****
         IAIHWKCPLRLQQAVLIMISALMALVFTKYLPIWTAWLILAVISVYDLVAVLCPKGFLDMLVETAQERNE
           211       220       230       240       250       260       270       280

281       290       300       310       320       330       340       350
         TLFPALIYSSTMVWLVNMAEQDPEAQRRVSKNSKYNAESTERESQDTVAEMICGGPSKEWEACRDSHLGP
         **************** * ** ********* *** ** ** **    *    *   *  *  ****
         TLFPALIYSSTMVWLVNMAEGDPEAQRRVPKNPKYNTCRAERETQDEGSGNCCGGRSETWEAQRTSHLGF
           281       290       300       310       320       330       340       350

351       360       370       380       390       400       410       420
         HRSTPESRAAVQELSSSILAGEDPEERGVKLGLGDFIFYBVLVGKASATASGDWNTTIACFBAILIGLCL
         *************** *  **************** *  **************** ***********
         HRSTPESRAAVQELSGSILTSEDPEERGVKLGLGDFIPYSVLVGKASATASGDWNTTIACXVAILIGLCL
           351       360       370       380       390       400       410       420

421       430       440       450       460
         TLLLLAIFKKALPALPISITFGLVFYFATDYLVQFFMDQLAFHQFYI -C (SEQ ID NO:2)
         ***** ** **  * ********* *  ****************** -C
         XLLLLAIYKKGXPAXPISITFGFVFKXFATDYLVQFMDQLAFHQFYI -C (SEQ ID NO:4)
           421       430       440       450       460
```

TABLE 4

HUMAN ARMP FUNCTIONAL DOMAINS

| Domains (Amino Acid Residue) | Functional Characteristic |
|---|---|
| 82–100 AA | Hydrophobic |
| 132–154 AA | Hydrophobic |
| 164–183 AA | Hydrophobic |
| 195–213 AA | Hydrophobic |
| 221–238 AA | Hydrophobic |
| 244–256 AA | Hydrophobic |
| 281–299 AA | Hydrophobic |
| 404–428 AA | Hydrophobic |
| 431–449 AA | Hydrophobic |
| 115–119 AA (YTPF) | Phosphorylation Site |
| 353–356 AA (STPC) | Phosphorylation Site |
| 300–385 AA | Acid Rich Domain |
|  | Possible Metal Binding Domain |

TABLE 4-continued

HUMAN ARMP FUNCTIONAL DOMAINS

| Domains (Amino Acid Residue) | Functional Characteristic |
|---|---|
| ANTIGENIC SITES INCLUDING AMINO ACID RESIDUES | |
| 27–44 | |
| 46–48 | |
| 50–60 | |
| 66–67 | |
| 107–111 | |
| 120–121 | |
| 125–126 | |
| 155–160 | |
| 185–189 | |
| 214–223 | |
| 220–230 | |
| 240–245 | |
| 267–269 | |
| 273–282 | |
| 300–370 | |
| 400–420 | |

TABLE 5

| | | | | |
|---|---|---|---|---|
| M14SLEU | Bsph1 (destroy) | 910 (170-S182 F) TCACAGAAGATA CCGAGACT (SEQ ID NO:68) | 911 (170-S182) R CCCAACCATAAGA AGAACAG (SEQ ID NO:69) | |
| MIS 163 Ary | Nla III (destroy) | 927 (intronic) TCTGTACTTTTT AAGGGTTGTG (SEQ ID NO:70) | 928 ACTTCAGAGTAATT CATCANCA (SEQ ID NO:71) | |
| Ala 246 | Dlc I (create) | 849* GACTCCAGCAGG CATATCT (SEQ ID NO:172) | 892 TGAAATCACAGCC AAGATGAG (SEQ ID NO:130) | |
| Leu 286 Val. | Pvu II (create) | 952 GATGAGACAAGT NCCNTGAA (SEQ ID NO:173) 945 TTAGTGGCTGTT TNGTGTCC (SEQ ID NO:174) | 951 CACCCATTTACAAG TTTAGC (SEQ ID NO:175) | |
| Cys 410 Tys | Allele specific iligo | 893 GTGTGGCCAGGG TAGAGAACT (SEQ ID NO:128) | 885 TGGAGACTGGAAC ACAAC (SEQ ID NO:127) | CCATAGCCTGTTTCGTAGC 890 = WT (SEQ ID NO:131) CCATAGCCTATTTCGTAGC 891 = MUT (SEQ ID NO:132) |

TABLE 6

POSITION OF EXONS AND INTRON-EXON BOUNDARIES OF ARMP GENE

| cDNA/mRNA SEQUENCE | | CORRESPONDING GENOMIC SEQUENCE | |
|---|---|---|---|
| ARMP (917 ver) | Transcript ID CC44 ver | Genomic sequence file ID & position of exon | Comments |
| 1–113bp | N/A | 917–936.gen @ 731–834bp | Alternate 5'UTR |
| N/A | 1–422bp | 917–936.gen @ 1067–1475bp | Alternate 5'UTR |
| 114–195bp | 423–500bp | 932–943.gen @ 589–671bp | |
| 196–335bp | 501–632bp | 932–943.gen @ 759–899bp | 12bp Variably spliced |
| 337–586bp | 633–883bp | 901–912.gen @ 787–1037bp | |

TABLE 6-continued

POSITION OF EXONS AND INTRON-EXON BOUNDARIES OF ARMP GENE

| cDNA/mRNA SEQUENCE | | CORRESPONDING GENOMIC SEQUENCE | |
|---|---|---|---|
| ARMP (917 ver) | Transcript ID CC44 ver | Genomic sequence file ID & position of exon | Comments |
| 587–730bp | 884–1026bp | 910–915.gen @ 1134–1278bp | M146L mutation |
| 731–795bp | 1027–1092bp | 925–913.gen @ 413–478bp | H163R mutation |
| 796–1017bp | 1093–1314bp | 849–892.gen @ 336–558bp | A246E mutation |
| 1018–1116bp | 1315–1413bp | 951–952.gen @ 312–412bp | L286V mutation, variable spl |
| 1117–1204bp | 1414–1501bp | 983–1011.gen @ 61–149bp | |
| 1205–1377bp | 1502–1674bp | 874–984.gen @ 452–625bp | |
| 1378–1497bp | 1674–1794bp | 885–1012.gen @ 431–550bp | C410Y mutation |
| 1498–2760bp | 1795–3060bp | 930–919.gen @ ~10bp-end | last AA, STOP, 3'UTR |

TABLE 7

MUTATIONS POLYMORPHISMS IN THE ARMP

| Nucleotide # in ARMP.UPD | Amino acid # in ARMP.PRO | Comment |
|---|---|---|
| A→$C_{684}$ | Met146Leu | Pathogenic, Unique to AD affected. |
| A→$G_{730}$ | His163Arg | " |
| C→$A_{985}$ | Ala246Glu | " |
| C→$T_{1027}$ | Ala260Val | " |
| C→$G_{1102}$ | Ala285Val | " |
| C→$G_{1104}$ | Leu286Val | " |
| C→$G_{1422}$ | Leu392Val | " |
| G→$A_{1477}$ | Cys410Tyr | " |
| G→$T_{863}$ | Phe205Leu | Polymorphism in normals |
| C→$A_{1700}$ | non-coding | 3'UTR polymorphism |
| G→$A_{2601}$ | non-coding | " |
| del$C_{2620}$ | non-coding | " |

TABLE 8

COMPARISON OF STRUCTURE AND SEQUENCE OF HOMOLOGUE ES-1 (TOP) AND ARMP (BOTTOM)
Matching Percentage (Total Window: 61%, Alignment Window: 72%)

```
 -69 ................................................   -20
   1 MTELPAPLSYFQNAQMSEDNHLSNTVRSQNDNRERQEHNDRRSLGHPEPL    50

-19 ....................EELTLKYGAKHVIMLFVPVTLCMIVVVATI    30
                         ||||||||||||||||| |||||||||||
  51 SNGRPQGNSRQVVEQDEEEDEELTLKYGAKHVIMLFVPVTLCMVVVVATI   100
                                          TM1

31 KSVRFYTEKNGQLIYTPFTEDTPSVGQRLLNSVLNTLIMISVIVVMTIFL    80
     ||| |||  |  ||||||||||||  |||| | ||| |||||||||| |
 101 KSVSFYTRKDGQLIYTPFTEDTETVGQRALHSILNAAIMISVIVVMTILL   150
                                                   TM2

81 VVLYKYPCYKFIHGWLIMSSLMLLFLFRYIYLGEVLKTYNVAMDYPTL-L   130
     |||||||| ||| ||| ||| |||   ||||||| |||||| |  | |
 151 VVLYKYRCYKVIHAWLIISSLLLLFFFSFIYLGEVFKTYNVAVDYITVAL   200
            TM2                     TM3

131 LTVWNFGAVGMVCIHWKGPLVLQQAYLIMISALMALVFIKYLPEWSAWVI   180
     |  ||  ||| |||||||||| ||||||||||||||||||||| ||| ||
 201 LI-WNLGVVGMISIHWEFPLRLQQAYLIMISALMALVFIXYLPEWTAWLI   250
              TM4                    TM5         TM6

181 LGA-ISVYDLVAVLCPKGPLFMLVETAQERNEPIFPALIYSSAMVWTBGM   230
     | | |||||||||||||||||||||||||||| |||||||| |||| | |
 251 L-AVISVYDLVAVLCPKGPLRMLVETAQERNETLFPALIYSSTMVWLVNM   300
                     TM6
```

TABLE 8-continued

COMPARISON OF STRUCTURE AND SEQUENCE OF HOMOLOGUE ES-1 (TOP) AND ARMP (BOTTOM)
Matching Percentage (Total Window: 61%, Alignment Window: 72%)

```
231 AKLDP......G..SQG.AL......QLPY...DP....EME-EDSYDSF   280  ⎫
    |  ||     |   |  |        |       |     |||   ||         ⎪ LARGE
301 AEGDPEAQRRVSKNSKYNAESTERESQDTVAENDDGGFSE-EWEAQRDSH   350  ⎬ ACIDIC
                                                              ⎪ HYDROPHILIC
281 -GEP--SYPE----VFEPPLTGYP--GEELEEEEERGVKLGLGDFIFYSV   330  ⎪ LOOP
    |  |  ||     |  |   |      ||  ||  ||||||||||||||        ⎪
351 LG-PHRSTPESRAAVQE--LSSSILAGEDPEE---RGBKLGLGDFIFYSV   400  ⎭

331 LVGKAAATGSGDWNTTLACFVAILIGLCLTLLLLAVFKKALPALPISITF   380
    |||||  || |||||||| ||||||||||||||||| ||||||||||||||
401 LVGKASATASGDWNTTIACFVAILIGLCLTLLLLAIFKKALPALPISITF   450
                    TM7

381 GLIFYFSTDNLVRPFMDTLASHQLYI*.................     430  (SEQ ID NO:138)
    || ||| || || |||| || || ||
451 GLVFYFATDYLVQPFMDQLAFHQFYT..................     500  (SEQ ID NO:2)
```

---

We claim:

1. An isolated polynucleotide encoding a human Alzheimer's Related Membrane Protein (ARMP) comprising the amino acid sequence shown in SEQ ID NO: 134 or a complement of said polynucleotide.

2. The polynucleotide of claim 1, comprising the nucleic acid sequence shown in SEQ ID NO: 133.

3. A recombinant vector comprising the polynucleotide of claim 1.

4. A host cell comprising the recombinant vector of claim 3.

5. A process for producing a human ARMP, comprising culturing the host cell of claim 4 under conditions whereby the polynucleotide encoding the human ARMP is expressed.

6. An isolated polynucleotide encoding a mouse ARMP, said polynucleotide comprising the nucleic acid sequence shown in SEQ ID NO: 135.

7. An isolated polynucleotide which encodes a mutant ARMP comprising the amino acid sequence shown in SEQ ID NO: 2, SEQ ID NO: 4, SEQ ID NO: 134 or SEQ ID NO: 136, which has an amino acid substitution at position 260, 285 and/or 392 of said sequence.

8. The polynucleotide of claim 7, which encodes a mutant ARMP having an amino acid substitution at position 260 of SEQ ID NO: 2, SEQ ID NO: 4, SEQ ID NO: 134 or SEQ ID NO: 136.

9. The polynucleotide of claim 8, in which the Ala residue at position 260 is substituted by Val.

10. The polynucleotide of claim 7, which encodes a mutant ARMP having an amino acid substitution at position 285 of SEQ ID NO: 2, SEQ ID NO: 4, SEQ ID NO: 134 or SEQ ID NO: 136.

11. The polynucleotide of claim 10, in which the Ala residue at position 285 is substituted by Val.

12. The polynucleotide of claim 7, which encodes a mutant ARMP having an amino acid substitution at position 392 of SEQ ID NO: 2, SEQ ID NO: 4, SEQ ID NO: 134 or SEQ ID NO: 136.

13. The polynucleotide of claim 12, in which the Leu residue at position 392 is substituted by Val.

14. A recombinant vector comprising the polynucleotide of claim 7.

15. A host cell comprising the recombinant vector of claim 14.

16. A process for producing a human ARMP, comprising culturing the host cell of claim 15 under conditions whereby the polynucleotide encoding the human ARMP is expressed.

17. An isolated polynucleotide which encodes a mutant ARMP comprising the amino acid sequence shown in SEQ ID NO: 134, which has an amino acid substitution at position 146, 163, 246, 286 and/or 410 of said sequence.

18. The polynucleotide of claim 17, which encodes a mutant ARMP having an amino acid substitutions at position 146 of SEQ ID NO: 134.

19. The polynucleotide of claim 18, which encodes a mutant ARMP in which the Met residue at position 146 of SEQ ID NO: 134 is substituted by Leu.

20. The polynucleotide of claim 17, which encodes a mutant ARMP having an amino acid substitution at position 163 of SEQ ID NO: 134.

21. The polynucleotide of claim 20, which encodes a mutant ARMP in which the His residue at position 163 of SEQ ID NO: 134 is substituted by Arg.

22. The polynucleotide of claim 17, which encodes a mutant ARMP having an amino acid substitution at position 246 of SEQ ID NO: 134.

23. The polynucleotide of claim 22, which encodes a mutant ARMP in which the Ala residue at position 246 of SEQ ID NO: 134 is substituted by Glu.

24. The polynucleotide of claim 17, which encodes a mutant ARMP having an amino acid substitution at position 286 of SEQ ID NO: 134.

25. The polynucleotide of claim 24, which encodes a mutant ARMP in which the Leu residue at position 286 of SEQ ID NO: 134 is substituted by Val.

26. The polynucleotide of claim 17, which encodes a mutant ARMP having an amino acid substitution at position 410 of SEQ ID NO: 134.

27. The polynucleotide of claim 26, which encodes a mutant ARMP in which the Cys residue at position 410 of SEQ ID NO: 2 is substituted by Tyr.

28. A recombinant vector comprising the polynucleotide of claim 17.

29. A host cell comprising the recombinant vector of claim 28.

30. A process for producing a mouse ARMP, comprising culturing the host cell of claim 29 under conditions whereby the polynucleotide encoding the mouse ARMP is expressed.

\* \* \* \* \*

UNITED STATES PATENT AND TRADEMARK OFFICE
CERTIFICATE OF CORRECTION

PATENT NO. : 6,210,919 B1
DATED : April 3, 2001
INVENTOR(S) : Paul E. Fraser et al.

It is certified that error appears in the above-identified patent and that said Letters Patent is hereby corrected as shown below:

<u>Title page,</u>
Item [73], Assignee, add -- The Governing Council of the University of Toronto --

Signed and Sealed this

Thirtieth Day of December, 2003

JAMES E. ROGAN
*Director of the United States Patent and Trademark Office*